US012503713B1

(12) United States Patent
Thomas et al.

(10) Patent No.: US 12,503,713 B1
(45) Date of Patent: Dec. 23, 2025

(54) STABILIZATION OF TRYPTAMINES BY DENATURING ENZYMES, OPTIMIZING IONIZATION STATES, AND CONTROLLING CONFOUNDING VARIABLES

(71) Applicant: Convergent Health Sciences LLC, Boulder, CO (US)

(72) Inventors: C. Russell Thomas, Boulder, CO (US); Douglas G. Metcalf, Boulder, CO (US)

(73) Assignee: Convergent Health Sciences LLC, Boulder, CO (US)

( * ) Notice: Subject to any disclaimer, the term of this patent is extended or adjusted under 35 U.S.C. 154(b) by 0 days.

(21) Appl. No.: 19/212,289

(22) Filed: May 19, 2025

(51) Int. Cl.
*C12P 17/10* (2006.01)
*C12N 9/02* (2006.01)

(52) U.S. Cl.
CPC ............ *C12P 17/10* (2013.01); *C12N 9/0061* (2013.01); *C12Y 110/03002* (2013.01)

(58) Field of Classification Search
None
See application file for complete search history.

(56) References Cited

U.S. PATENT DOCUMENTS 3,183,172 A 5/1965 Heim
3,192,111 A 6/1965 Hofmann

FOREIGN PATENT DOCUMENTS

WO 2021/253123 A1 12/2021
WO 2021/253124 A1 12/2021

OTHER PUBLICATIONS

Casale, "An Aqueous-Organic Extraction Method for the Isolation and Identification of Psilocin from Hallucinogenic Mushrooms," Journal of Forensic Sciences, 1985, 30(1):247-250.

Galdino et al., "Extraction Yields of Psilocybin and Psilocin: A Short Review of Current Methods and Their Implications," Pharmaceuticals, 2025, 18:380 (28 pages).

Kargbo et al., "Psilocybin: Characterization of the Metastable Zone Width (MSZW), Control of Anhydrous Polymorphs, and Particle Size Distribution (PSD)," ACS Omega, 2022, 7(6):1c06708 (8 pages).

Laboratory Services Bureau record for Psilocyn/Psilocybin (4 pages; unknown publication date).

Abdel-Rahman et al., Caenorhabditis elegans as a model to study the impact of exposure to light emitting diode (LED) domestic lighting, Journal of Environmental Science & Health, Part A, 2017, 52(5):433-439.

Andersson et al., Occurrence and use of hallucinogenic mushrooms containing psilocybin alkaloids, 2009, 121 pages.

Beug & Bigwood, Quantitative analysis of psilocybin and psilocin in Psilocybe baeocystis (Singer and Smith) by high-performance liquid chromatography and by thin-layer chromatography, Journal of Chromatography, 1981, 207:379-385.

Blaschko & Levine, A comparative study of hydroxyindole oxidases, British Journal of Pharmacology, 1960, 15:625-633.

Christiansen & Rasmussen, Analysis of indole alkaloids in Norwegian Psilocybe semilanceata using high-performance liquid chromatography and mass spectrometry, Journal of Chromatography A, 1982, 244(2):357-364.

Daâssi et al., Purification and biochemical characterization of a new alkali-stable laccase from *Trametes* sp. isolated in Tunisia: role of the enzyme in olive mill waste water treatment, 2013, World Journal of Microbiology and Biotechnology, 2013, 29:2145-255.

Daya et al., The effect of variations in pH and temperature on stability of melatonin in aqueous solution, Journal of Pineal Research, 2001, 31:155-158.

Esteves et al., Combining FTIR-ATR and OPLS-DA methods for magic mushrooms discrimination, Forensic Chemistry, 2022, 29:100421 (11 pages).

Gartz, Magic Mushrooms Around the World, (Taake ed. 1997), 134 pages.

Gotvaldová et al., Extensive collection of psychotropic mushrooms with determination of their tryptamine alkaloids, International Journal of Molecular Sciences, 2022, 23:14068 (16 pages).

Gotvaldová et al., Stability of psilocybin and its four analogs in the biomass of the psychotropic mushroom Psilocybe cubensis, Drug Testing & Analysis, 2020, 13:439-446.

Huang & Kissinger, Liquid chromatographic determination of serotonin in homogenized dog intestine and rat brain tissue using a 2 mm i.d. Peek column Current Separations, 1996, 14(3/4): 114-119.

Kysilka & Wurst, A novel extraction procedure for psilocybin and psilocin determination in mushroom samples, Planta Medica, 1990, 56:327-328.

Lenz et al., Injury-triggered blueing reactions of Psilocybe "magic" mushrooms, Angewandte Chemie, 2020, 59:1450-1454 & Supplement.

Paul et al., Investigation of the structure, stability, and relative solubility of psilocybin in water and pure organic solvents: a molecular simulation study, Journal of Molecular Liquids, 2023, 392:123479 (17 pages).

Pranil et al., Influence of pH, temperature, and light on the stability of melatonin in aqueous solutions and fruit juices, Heliyon, 2020, 6:e03648 (7 pages).

Nagy & Veress, HPLC Analysis of hallucinogenic mushroom alkaloids (psilocin and psilocybin) applying hydrophilic interaction chromatography (HILIC), Journal of Forensic Research, 2016, 7(6):1000356 (6 pages).

(Continued)

*Primary Examiner* — Suzanne M Noakes
*Assistant Examiner* — Jae W Lee
(74) *Attorney, Agent, or Firm* — Douglas G. Metcalf

(57) ABSTRACT

Various aspects of this disclosure relate to the discovery that phosphatase and laccase enzymes confound the extraction and quantification of psilocybin and other tryptamines during the preparation of psilocybin-containing products from mushrooms. Various aspects of this disclosure relate to the discovery that ionization states of phosphoryloxytryptamines affect the extraction and quantification of psilocybin and other tryptamine. This disclosure describes methods to denature enzymes, optimize ionization states, and control for other variables to improve extraction yields of tryptamines from mushrooms, manufacturing intermediates, and tryptamine-containing products and to improve the accuracy of methods to quantify tryptamines.

12 Claims, No Drawings

Specification includes a Sequence Listing.

(56) References Cited

OTHER PUBLICATIONS

Waldbillig et al., Exploring *Psilocybe* spp. Mycelium and fruiting body chemistry for potential therapeutic compounds, Frontiers in Fungal Biology, 2023, 4:1295223 (10 pages).

STABILIZATION OF TRYPTAMINES BY DENATURING ENZYMES, OPTIMIZING IONIZATION STATES, AND CONTROLLING CONFOUNDING VARIABLES

SEQUENCE LISTING

This disclosure includes a sequence listing, which has file name "2025-05-19-Sequence_Listing_ConvergentUS0-279," which was created on May 19, 2025, which has a file size of 110,952 bytes, and which is incorporated by reference in its entirety.

BACKGROUND

The strict regulation of psilocybin-producing mushrooms has long impeded the commercial development of psilocybin-containing products. State laws are nevertheless beginning to change. Oregon legalized psilocybin-assisted therapy in 2021, Colorado legalized psilocybin in 2022, and a majority of other states have pending or enacted legislation to fund research into psilocybin, study frameworks to scale back regulations, and/or decriminalize or legalize psilocybin. Texas and Utah both enacted legislation to evaluate the therapeutic potential of psilocybin, for example, and various other Republican-controlled jurisdictions including Georgia, Indiana, Iowa, and Montana are considering similar or even more expansive measures. Additionally, the Secretary of Health and Human Services Robert F. Kennedy, Jr., who oversees the Food and Drug Administration (FDA), National Institutes of Health, and Substance Abuse and Mental Health Services Administration, announced that he will prioritize the deregulation of psychedelics. See, e.g., Shayla Love, *The Horseshoe Theory of Psychedelics: Donald Trump's* 2024 *Campaign has Cemented the Right's Romance with Hallucinogenic Drugs*, The Atlantic, Nov. 1, 2024.

While Oregon and Colorado legalized the possession and use of psilocybin, they declined to legalize the retail sale of psilocybin mushrooms and products derived therefrom. Oregon enacted regulations, for example, that allow the manufacture—but not the sale—of psilocybin-containing products. Laws that restrict commercial production and sale may nevertheless disappear as mainstream acceptance of psychedelics grows, possibly following a similar trajectory as the legalization of marijuana or an even more rapid trajectory in view of the policy goals of Secretary Kennedy.

The lobbying groups that succeeded in deregulating marijuana, for example, shifted their focus to psychedelics, and they are becoming increasingly sophisticated, well-funded, and emboldened in view of past success and the contemporary political landscape. The historically liberal political actors who spearheaded the deregulation of marijuana are now also joined by conservative lobbyists and politicians, who view psychedelics as a promising intervention to treat post-traumatic stress disorder and related conditions that lack effective FDA-approved therapies and that afflict large numbers of military veterans and first responders.

Psychedelics are uniquely effective for two reasons. First, they desynchronize the default-mode network, which recalls and replays deleterious thought patterns. See, e.g., Joshua S. Siegel et al., *Psilocybin Desynchronizes the Human Brain*, Nature, 2024, 1037:1. Second, they promote neuroplasticity, which allows the brain to rewire itself to attenuate harmful memories and behaviors and to build positive thought patterns See, e.g., id.

Psilocybin is a member of the tryptamine class of compounds. Psychedelic tryptamines each bind 5-hydroxytryptamine (5-HT) receptors generally and 5-HT receptor 2A (5HT2A) specifically. 5HT2A is widespread in the central nervous system including the hippocampus, which is responsible for recalling memories, forming new memories, and imagining the future. Psychedelic tryptamines are notably 5HT2A agonists in contrast with many FDA-approved pharmaceuticals that antagonize 5HT2A including the antidepressant trazodone (DESYREL®, over twenty million prescriptions per year in the United States), the muscle relaxer cyclobenzaprine (FLEXERIL®, over ten million prescriptions per year), the antipsychotic quetiapine (SEROQUEL®, over ten million prescriptions per year), the antipsychotic aripiprazole (ABILIFY®, over five million prescriptions per year) the antipsychotic risperidone (RISPERDAL®, over four million prescriptions per year), the antidepressant mirtazapine (REMERON®, over four million prescriptions per year), and the antipsychotic olanzapine (ZYPREXA®, over three million prescriptions per year) as well as most other tricyclic antidepressants, tetracyclic antidepressants, and antipsychotics. Psychedelic tryptamines modulate a strikingly-important drug target in a strikingly-unique way.

Several factors confound the manufacture of mushroom-derived, psilocybin-containing products including the heterogeneity, stability, and quantification of naturally-occurring tryptamines. Psychedelic mushrooms generally produce psilocybin, which is a phosphorylated prodrug of the psychoactive tryptamine psilocin. Mushrooms synthesize psilocybin from psilocin and synthesize psilocin from dimethyltryptamine (DMT), which is also psychoactive. Psilocybin, psilocin, and DMT each comprise a tertiary amine containing two nitrogen-bound methyl groups (hence the name dimethyltryptamine). Incomplete methylation results in the psilocybin analog baeocystin, which is a secondary amine, and norbaeocystin, which is a primary amine. Additional methylation results in the psilocybin analog aeruginascin, which is a quaternary amine. Baeocystin, norbaeocystin, and aeruginascin can be dephosphorylated into the psychoactive compounds norpsilocin, 4-hydroxytryptamine (4-HT), and dephosphorylaeruginascin (also known as 2-(4-hydroxy-1H-indol-3-yl)ethyl-trimethylindium; 4-hydroxy-TMT), respectively. 4-HT is a structural isomer of the neurotransmitter serotonin, which is also known as 5-hydroxytryptamine (5-HT; 5-HT receptors are serotonin receptors). Each of the foregoing compounds falls within the tryptamine class of molecules, which comprise the same indolamine backbone structure as the amino acid tryptophan, but which lack the α-carboxylate group of tryptophan. The phosphorylated hydroxytryptamines psilocybin, baeocystin, norbaeocystin, and aeruginascin are susceptible to dephosphorylation, and their dephosphorylated counterparts psilocin, norpsilocin, 4-HT, and 4-hydroxy-TMT are susceptible to oxidation, which ultimately results in dimers and higher-order oligomers that absorb visible light to result in the characteristic blue coloration indicative of tryptamine-containing fungi. Tryptamine heterogeneity and stability make them challenging to quantify, for example, because dephosphorylation and oxidation may occur during extraction and because phosphorylated and dephosphorylated tryptamines display markedly-different solubilities in commonly-used solvents, which stymies their simultaneous extraction. As a result, quantitative extraction protocols do not presently exist. The measured tryptamine concentrations of contemporary mushroom-derived products are therefore wildly inaccurate. Such products are instead dosed by dry weight of the mushroom rather than by tryptamine content.

Sandoz AG reported the first preparative purifications of psilocybin and psilocin from mushrooms in a 1958 patent application that matured into U.S. Pat. Nos. 3,183,172 and 3,192,111. Sandoz chemist Albert Hofmann gained insight into psychedelic mushrooms from mycologist Roger Heim and ethnomycology enthusiast R. Gordon Wasson, a former executive at J.P. Morgan & Co. Wasson attended a Mazatec mushroom ritual in Mexico in 1955 and published an article about his experience in LIFE magazine in 1957, which first introduced psychedelic mushrooms into popular culture. Wasson, R. Gordon, *Seeking the Magic Mushroom*, LIFE, 1957, 49(19):100. The CIA notably funded Wasson and Heim to collect mushroom specimens through its infamous mind control program Project MKUltra, which allegedly conducted experiments with lysergic acid diethylamide (LSD) on Unabomber Ted Kaczynski, cult leader Charles Manson, mob boss James "Whitey" Bulger, and Palestinian Sirhan Sirhan, who was convicted of assassinating Secretary Kennedy's father (although Secretary Kennedy recently stated, "I don't believe that Sirhan's bullets ever hit my father, and neither did the coroner." *Robert F Kennedy Jr Names 2nd Shooter Who Killed His Father with Sirhan Sirhan (Part 7)*, YOUTUBE (Nov. 12, 2023), www.youtube.com/watch?v=tBxU2qNSaWQ). Heim ultimately delivered the mushroom specimens to Hofmann, who had famously synthesized LSD and identified its psychedelic properties by unintentionally self-administering a dose.

The Sandoz patents protected the manufacture and therapeutic use of crystalline forms of psilocybin and psilocin, which Sandoz marketed as tranquilizers. Sandoz did not purport to develop methods to quantify the tryptamine content of mushrooms. Secondary accounts of the research nevertheless confuse extraction yields with the tryptamine content of mushrooms, which erroneously presumes 100 percent extraction efficiency. Sandoz reported neither the tryptamine content of a mushroom nor any method to quantify tryptamine content.

The Sandoz purification strategy, in general, (1) extracts tryptamines from dried fungal material with methanol or ethanol, (2) washes lipids from the extracts with petroleum ether and chloroform, (3) iteratively dissolves the tryptamines in water to remove aqueous precipitates and then precipitates the tryptamines with ethanol or acetone to remove residual hydrophobic solutes, (4) chromatographically separates the tryptamines on a cellulose column with a water-in-butanol mobile phase, (5) precipitates halogens with silver cation, and (6) crystallizes purified psilocin or psilocybin from either water or methanol.

Throughout the 1960s, Sandoz marketed purified psilocybin to physicians, and the counterculture movement popularized the recreational and spiritual use of psychedelic mushrooms in parallel. No methods were developed, however, to quantify the tryptamine content of a mushroom. Research instead focused upon simply identifying mushrooms that produce psychedelic tryptamines as well as relative concentrations, which might aid in the selection of species and strains for further study.

The Nixon administration then passed the Comprehensive Drug Abuse Prevention of Control Act of 1970, which classified psilocybin and psilocin as schedule I controlled substances that lacked any accepted medical use, and President Nixon commenced the "war on drugs" declaring drug abuse "public enemy number one," a label previously reserved for gangsters such as Al Capone. Much of the world followed suit when the United Nations enacted the Convention on Psychotropic Substance the following year. The United States statute and international treaty attenuated research that might actually quantify the tryptamine content of various fungi, and research instead focused upon the forensic analysis of seized mushrooms to simply detect the presence or absence of psilocybin or psilocin. Forensic labs simply adopted portions of the Sandoz preparative extraction method by extracting psilocybin and psilocin with methanol.

Two Czech microbiologists then identified that conventional methanol extractions recover less than 80 percent of psilocybin and less than 10 percent of psilocin. Roman Kysilka & Milan Wurst, *A Novel Extraction Procedure for Psilocybin and Psilocin Determination in Mushroom Samples*, PLANTA MED., 1990, 56:327. They also identified that water was unable to extract either psilocybin or psilocin, which was surprising because both are more soluble in water than methanol. They instead identified that saturated potassium nitrate solutions containing 75 percent methanol and 25 percent water displayed superior psilocybin-extraction efficiency relative to other concentrations of methanol and water, solutions lacking potassium nitrate, and conventional extraction protocols. They failed to explain the role of potassium nitrate in their extractions, and they found that the methanol/water/potassium nitrate solution was ineffective at extracting psilocin. Few advances to improve extraction efficiency have published since.

In view of their promising therapeutic potential and the advent of regulatory change, improved methods to manufacture tryptamine-containing products and to quantify tryptamine content are desirable.

SUMMARY

Various aspects of this disclosure relate to the discovery that conventional methods to extract tryptamines from mushrooms are qualitative and not quantitative. No method therefore previously existed that could accurately quantify the amount of psilocybin or psilocin in a mushroom, and this disclosure identifies improved methods for accurate quantification. The stabilization of tryptamines against dephosphorylation and oxidation as well as the preparation of partially-purified tryptamine extracts that may be useful to manufacture tryptamine-containing products present related issues, and this disclosure also identifies improved methods to both stabilize tryptamines and prepare partially-purified tryptamine extracts for use in commercial products.

The inventors believe they identified various defects in the prior art extractions of psilocybin and psilocin as well as improved methods to extract tryptamines from mushrooms. First, the prior art teaches contradictory findings that (1) room-temperature methanol is a superior extraction solvent for mushroom-derived tryptamines, but that (2) mushroom-derived tryptamines are only soluble in boiling methanol. See, e.g., U.S. Pat. No. 3,183,172. Without limiting this disclosure or any patent claim that matures from this disclosure, the inventors believe that either (a) methanol disrupts cell membranes, which frees tryptamines from intracellular compartments, (b) methanol denatures or otherwise neutralizes enzymes that act upon tryptamines such as phosphatases and esterases that convert psilocybin (and other phosphoryloxytryptamines) into psilocin (and other hydroxytryptamines) and laccases that convert psilocin (and other hydroxytryptamines) into inactive oligomers, (c) methanol, methoxide, and methyloxonium ion are less reactive toward tryptamines than water, hydroxide, and hydronium ion, (d) reactive oxygen species, metal ions, and other reactive species such as those that might be released by lysing mitochondria are less reactive toward tryptamines in methanol than in water and/or less soluble in methanol than in water, or (e) two, three, or each of (a), (b), (c), and (d). In other words, methanol improves extraction yields not because methanol is an appropriate extraction solvent but because methanol lyses the cell membranes that sequester tryptamines, and, once methanol lyses the cell membranes, it attenuates the ability of both (1) intracellular enzymes and reactive species in different cellular compartments from degrading the tryptamines and (2) extracellular enzymes and extracellular reactive species from similarly degrading the tryptamines. Without limiting this disclosure or any patent claim that matures from this disclosure, the inventors describe additional methods to (a) disrupt cell membranes such as with a surfactant, acid, base, solvent, chaotrope, heating, freezing, sonicating, or lyophilizing, (b) denature or otherwise neutralize enzymes such as with a surfactant, acid, base, solvent, chaotrope, chelator, heating, freezing, sonicating, or lyophilizing, (c) reduce water, hydroxide, and hydronium ion content during extraction such as by using a solvent other than water, and (d) limit the effects of reactive oxygen species, metal ions, and other reactive species such as by introducing an antioxidant and/or chelator into an extraction mixture. For example, fungi may be initially treated with methanol (for example, for quantification) or ethanol (for example, for preparative purification) to disrupt cell membranes, denature enzymes, and attenuate unproductive chemical reactions, and then the methanol or ethanol may be diluted with water to dissolve the tryptamines.

Second, the prior art largely overlooks the ionization states of tryptamines generally and phosphoryloxytryptamines specifically. Each of the Chemical Abstracts Service Registry (CAS Number 520-52-5), National Library of Medicine PubChem database (CID 10624), National Cancer Institute (Thesaurus Code C62529), FDA Global Substance Registration System (UNII 2RV7212BP0), Kyoto Encyclopedia of Genes and Genomes (KEGG Entry D12881), Chemical Database of the European Molecular Biology Laboratory (ChEMBL ID CHEMBL194378), Chemical Entities of Biological Interest database (ChEBI ID 8614), Merck Index (Monograph ID M9305), DrugBank (Accession Number DB11664), ChemSpider (ID 10178), CompTox Chemicals Dashboard (ID DTXSID0048898), and Wikipedia, for example, identifies psilocybin as {3-[2-(dimethylamino)ethyl]-1H-indol-4-yl} dihydrogen phosphate as an artifact of International Union of Pure and Applied Chemistry (IUPAC) nomenclature. This species of molecular psilocybin is rare because the dihydrogen phosphate of psilocybin has a pKa of about 1.3 whereas the azanium of psilocybin, which is the conjugate acid of the amino, has a pKa of about 10.4, and thus, deprotonating the azanium without deprotonating the dihydrogen phosphate presents challenging thermodynamics. The Henderson-Hasselbalch equation suggests that one molecule of molecular psilocybin would theoretically exist per every two billion ions of psilocybin in aqueous solutions at a pH of 2 to 10. When psilocybin is dissolved in water, then any deprotonated amino would form a hydrogen bond with a proton of a solvating water molecule, and any fully-protonated phosphate would form a hydrogen bond with an oxygen of a solvating water molecule, but characterizing these bonds as hydrogen bonds instead of covalent bonds is arbitrary because the solvating water would rapidly convert the two hydrogen bonds into covalent bonds. Any molecular psilocybin would have an ephemeral existence at least in water and other protic polar solvents. Molecular psilocybin might nevertheless exist in the event that psilocybin partitions into a hydrophobic solvent or a lipid bilayer, but molecular psilocybin is not particularly relevant to the extraction of psilocybin from (a) mushrooms to prepare tryptamine-containing products and (b) mushrooms, manufacturing intermediates, and products derived therefrom to quantify their tryptamine concentrations. Psilocybin likely instead exists predominantly as anionic [2-(4-phosphonatooxy-1H-indol-3-yl)ethyl]-dimethylazanium (which is a synonym of {3-[2-(dimethylazaniumyl)ethyl]-1H-indol-4-yl}phosphate) with a lesser amount of zwitterionic [2-(4-phosphonooxy-1H-indol-3-yl)ethyl]-dimethylazanium (which is a synonym of {3-[2-(dimethylazaniumyl)ethyl]-1H-indol-4-yl} hydrogen phosphate). Various aspects of this disclosure relate to the discovery that anionic, zwitterionic, and other ionization states of phosphoryloxytryptamines result in strikingly-different properties that affect their solubilities and chemical stabilities. Optimizing the ionization states of phosphoryloxytryptamines upends the prior art paradigms for their extraction, formulation, and quantification to allow increased extraction yields, more stable formulations, and more accurate quantification. Psilocin and other hydroxytryptamines can analogously exist as cationic, molecular, and anionic species, which again display strikingly-different properties that affect their solubilities and chemical stabilities.

The solubility of psilocybin and other phosphoryloxytryptamines in methanol, other alcohols, and aprotic solvents depends upon whether the psilocybin and other phosphoryloxytryptamines exist as anionic, zwitterionic, or cationic species. Without limiting this disclosure or any patent claim that matures from this disclosure, the anionic forms of psilocybin and other phosphoryloxytryptamines are less soluble in aprotic solvents such as chloroform, acetone, and ethers, which lack any ability to hydrogen bond to the phosphate oxygen atoms. Without limiting this disclosure or any patent claim that matures from this disclosure, the anionic forms are similarly less soluble in alcohols, especially higher alcohols, because hydrogen bonding between the phosphate oxygen atoms and solvent results in large entropic penalties. Without limiting this disclosure or any patent claim that matures from this disclosure, the zwitterionic forms of psilocybin and other phosphoryloxytryptamines are more soluble in aprotic solvents and alcohols than anionic forms, for example, because the phosphate oxygen atoms can participate in an intramolecular hydrogen bond with the azanium proton, which more fully neutralizes the electrostatic charge of the phosphate in zwitterionic forms than in anionic forms such that the entropic penalty is not as severe for orienting solvent around the zwitterionic forms. C f. Alexander M. Sherwood et al., Psilocybin: *Crystal Structure Solutions Enable Phase Analysis of Prior Art and Recently Patented Examples*, Structural Chemistry, 2022, C78:36. Additionally, both the protonated oxygen of the monoanionic phosphate and the azanium proton of zwitterionic forms of psilocybin and other phosphoryloxytryptamines can participate in hydrogen-bonding interactions with polar solvents, which increases the solubility of the zwitterionic forms in alcohols and polar aprotic solvents relative to anionic forms. Without limiting this disclosure or any patent claim that matures from this disclosure, the cationic forms of psilocybin and other phosphoryloxytryptamines are more soluble in polar aprotic solvents such as chloroform, acetone, and ethers than anionic forms because polar aprotic solvents can hydrogen bond with both of the two protonated oxygens of the phosphate as well as the azanium proton.

The phosphate of psilocybin has two pKa values of about 1.3 and 6.5, and the phosphates of other phosphoryloxytryptamines have pKa values that are about the same as psilocybin. The azanium of psilocybin has a pKa of about 10.4, and other phosphoryloxytryptamines display azanium pKa values that vary depending upon the nature of their azaniums (e.g., whether they are primary, secondary, or tertiary amines). Psilocybin and other phosphoryloxytryptamines exist in aqueous solutions having a pH of about 1.3 to about 6.5 predominantly in zwitterionic forms and in aqueous solutions having a pH of about 6.5 to about 10.4 predominantly in monoanionic forms. Certain aspects of this disclosure relate to the discovery that the extraction of tryptamines from fungal material with alcohols without accounting for the ionization state of phosphoryloxytryptamines-which Albert Hofmann ignored and no prior art appreciates to date—is inefficient because a substantial portion of the phosphoryloxytryptamines will exist in anionic forms that lack robust solubility in alcohols. C f. Roman Kysilka & Milan Wurst, A *Novel Extraction Procedure for Psilocybin and Psilocin Determination in Mushroom Samples*, Planta Med., 1990, 56:327. A Brønsted acid may be introduced during an alcohol extraction protocol, for example, to favor conversion of anionic forms to zwitterionic forms and to thereby increase the solubility of phosphoryloxytryptamines in alcohols. Acidification is important not only for the extraction of phosphoryloxytryptamines from fungal material, but also for the extraction of phosphoryloxytryptamines from manufacturing intermediates and final products, for example, to accurately quantify tryptamines for quality control. Too much acidification may nevertheless be problematic, however, because the cationic forms of psilocybin and other phosphoryloxytryptamines become susceptible to spontaneous dephosphorylation in the presence of water. Conversely, alkaline conditions also increase spontaneous dephosphorylation in the presence of water. Appropriate buffers can favor zwitterionic forms over cationic and anionic forms, and the Detailed Description that follows describes appropriate buffers in greater detail.

The term "pKa" as used herein has its art-recognized definition, which is the negative logarithm, base ten, of an acid dissociation constant. The skilled person will recognize that the relationship between aqueous pKa values and pH lacks appreciable significance for solvents other than water, and thus, the Detailed Description generally teaches ratios of various ionization states for dissolved and solid-phase phosphoryloxytryptamines.

Third, the prior art presents a paradox that tryptamine monomers absorb ultraviolet light—and do not absorb appreciable amounts of visible light—but that tryptamines are nevertheless light-sensitive. Neither psilocybin nor psilocin absorbs an appreciable amount of light above 300 nanometers. Conventional light bulbs including incandescent, fluorescent, and LED bulbs do not emit ultraviolet light, which might tend to suggest that ambient ultraviolet light such as from windows might be responsible for the light sensitivity of tryptamines. Without limiting this disclosure or any patent claim that matures from this disclosure, the inventors propose that one or both of (a) two-photon absorption and (b) the production of reactive species (such as reactive oxygen species) from visible light results in tryptamine light sensitivity. In particular, blue light increases reactive oxygen species in living organisms and may also contribute to the light-sensitivity of tryptamines in fungal material. C f. Fawzia Abdel-Rahman et al., *Caenorhabditis elegans as a Model to Study the Impact of Exposure to Light Emitting Diode (LED) Domestic Lighting*, Journal of Environmental Science & Health, Part A, 2017, 52(5):433. The inventors therefore propose that fungal material should be processed at a color temperature of less than 4000 K and/or with an illuminance of no greater than 300 lux. In particular, white LED lighting generally displays a strong blue emission at about 380-450 nanometers from either gallium nitride (GaN) or indium gallium nitride (InGaN) LEDs. When fungal material is processed, the inventors propose that either (1) GaN and InGaN LED emissions should be reduced or eliminated, and higher wavelengths should be favored such as those from cerium-doped yttrium aluminum garnet phosphor (Ce:YAG) LEDs or manganese(IV)-doped potassium fluorosilicate (PFS) LEDs, or (2) luminous flux at greater than 500 nanometers should exceed luminous flux at less than 500 nanometers. Tryptamines may be further protected by storage and/or processing in containers that are opaque to blue light such as containers that transmit no greater than 20 percent of light at wavelengths less than 500 nanometers. Fungi is generally opaque to blue light, which inhibits the light-related degradation of tryptamines that are, for example, greater than one centimeter from a light-exposed surface. Storage in containers that are opaque to blue light is therefore particularly important after fungal material is either (1) mechanically processed to a greater surface-area-to-volume ratio such as by grinding dried fungal material into a powder or (2) chemically processed to lyse membranes such as by treating the fungal material with a solvent, surfactant, or chaotrope. Additionally, sacrificial antioxidants such as ascorbate, erythorbate, or propyl gallate may be added to liquid compositions to favor the oxidation of the sacrificial antioxidants over the oxidation of tryptamines. Finished products may also contain sacrificial antioxidants such as a tocopherol, tocotrienol, or ascorbyl palmitate.

Fourth, contemporary methods to quantify dissolved tryptamines utilize high-performance liquid chromatography (HPLC), which is typically performed under acidic conditions because HPLC typically utilizes an alkaline-labile stationary phase. Alkaline conditions degrade conventional HPLC columns. Separations therefore generally utilize a mobile phase comprising either 0.1 percent trifluoroacetic acid, which results in a pH of about 2, or 0.1 percent formic acid, which results in a pH of about 2.7 at least in an aqueous mobile phase. Acidic conditions risk hydrolyzing the phosphate groups of psilocybin, baeocystin, norbaeocystin, and aeruginascin into psilocin, norpsilocin, 4-HT, and 4-hydroxy-TMT, however, which impairs the accurate quantification of tryptamines.

The hydrolysis of phosphate groups results in under-reporting psilocybin, baeocystin, norbaeocystin, and aeruginascin concentrations and potentially over-reporting psilocin, norpsilocin, 4-HT, and 4-hydroxy-TMT concentrations. The phosphate group of psilocybin, for example, has pKa values of about 1.3 and 6.5. Without limiting this disclosure or any patent claim that matures from this disclosure, a significant amount of psilocybin will exist as cationic psilocybin (about 17 percent) at a pH of 2, which is more susceptible to spontaneous dephosphorylation than zwitterionic psilocybin. A significant amount of psilocybin will also exist as cationic psilocybin (about 4 percent) at a pH of 2.7, which is again more susceptible to spontaneous dephosphorylation than zwitterionic psilocybin. Without limiting this disclosure or any patent claim that matures from this disclosure, cationic psilocybin is more susceptible to dephosphorylation by nucleophilic attack by water molecules particularly because the psilocybin amine can hydrogen bond with the phosphate to create a partial positive charge that attracts nucleophiles. Independent of the mechanism, spontaneous dephosphorylation presents a thermodynamic sink that drives the equilibrium of psilocybin towards dephosphorylation and confounds accurate quantification. Without limiting this disclosure or any patent claim that matures from this disclosure, the probability of such dephosphorylation decreases with increasing pH, and a pH of at least 3 and no greater than 8 may therefore result in more accurate quantification of tryptamines.

Exemplary methods of this disclosure follow, and the Detailed Description provides variations upon these methods. In a first method, fungal material is grown, for example, in the dark (such as at less than 10 lux) at room temperature or slightly above room temperature (about 21 to 27 degrees Celsius) in aqueous or gel culture comprising a carbon source (such as malt extract and agar), and which culture is optionally supplemented with minerals including one or more of sodium cation (such as about 0.05 to 50 millimolar), potassium cation (such as about 0.01 to 10 millimolar), calcium cation (such as about 0.01 to 10 millimolar), magnesium cation (such as about 0.01 to 10 millimolar), iron cation (such as about 0.1 to 100 micromolar), zinc cation (such as about 0.01 to about 10 micromolar), and copper cation (such as about 0.005 to about 5 micromolar). The fungal material is grown to favor the development of mycelium and sclerotium and to disfavor the development of fruiting bodies. Without limiting this disclosure or any patent claim that matures from this disclosure, the development of fruiting bodies increases the production of oxidoreductase enzymes generally, which can oxidize tryptamines, and laccase enzymes specifically, which can convert psychedelic tryptamines into inactive oligomers. The production of oxidoreductases is disfavored, and thus, fruiting bodies are disfavored in certain embodiments. Contra Adam Waldbillig et al., Exploring *Psilocybe* spp. *mycelium* and *fruiting body chemistry for potential therapeutic compounds*, Frontiers in Fungal Biology, 2023, 4:1295223. Growing the fungal material in the dark in media containing 4 to 10 percent dry malt extract and a minimal amount of agar (such as about 2 percent), for example, favors mycelium and sclerotium and disfavors fruiting bodies and laccase enzymes. Fruiting bodies are nevertheless compatible with the methods of this disclosure, which improve the stability, extraction, and quantification of tryptamines regardless of whether tryptamine-containing fungal material contains mycelium, sclerotium, or fruiting bodies.

Upon maturation of the mycelium and sclerotium, the fungal material may be dehydrated. Maturation depends upon many different factors including the composition of the culture, temperature, and the relative amount and nature of the inoculant. Fungal material should be harvested after the rate of tryptamine production has peaked. When a culture is inoculated with fresh mycelium, then fungal material may be harvested, for example, two-to-ten weeks following inoculation. Upon harvest, aqueous media is first mechanically separated from fungal material such as by filtering, pressing, or centrifuging the culture, and the wet fungal material is then dried, for example, under vacuum optionally by lyophilization. When the fungal material is lyophilized, then it may be rapidly frozen in a cooling bath such as in a liquid nitrogen bath or a dry-ice-in-acetone bath to minimize the enzymatic degradation of tryptamines by phosphatases, esterases, oxidoreductases, laccases, other enzymes, and reactive species as ice crystals lyse cell membranes to allow intracellular compartments to mix with each other and with the extracellular space. The wet fungal material may be initially separated from the liquid media by centrifugation, for example, and fungal pellets may be frozen in a cooling bath immediately after decanting the supernatant. Freezing by conduction in a cooling bath may result in improved tryptamine yields relative to freezing by convection, for example, in a freezer, because the rate of freezing directly correlates with tryptamine stability.

Prior to any dehydration or purification step, the enzymes (e.g., phosphatases, esterases, oxidoreductases, laccases) of the fungal material may be inactivated, for example, by denaturing the enzymes with heat. Various methods of heat-inactivation are described in the Detailed Description and include heating with an autoclave, a dehydrator, a convection oven, a pasteurization apparatus, a heating bath, infrared radiation, or microwave radiation. The heating method, temperature, and time may be co-optimized to control the magnitude of heat transfer and strike an appropriate balance between denaturing enzymes and undesirable thermal degradation of tryptamines. Suitable temperature ranges and periods of time are described in the Detailed Description that follows. Heat-inactivated fungal material may be rapidly cooled following the heating to minimize undesirable thermal degradation of tryptamines. Heat-inactivated fungal material may be frozen following heating, for example, and then lyophilized to dehydrate the heat-inactivated fungal material.

Following any heating or dehydration step, the dried fungal material may be powdered and homogenized, for example, using a mortar and pestle, mill, or grinder. The powdered, dried fungal material may then be stored in an opaque container in a desiccator or under partial vacuum in the dark such as at less than 10 lux.

A first method to quantify tryptamines comprises lysing a 500-milligram portion of the powdered, dried fungal material and denaturing enzymes, for example, by vortexing or sonicating with about 10 milliliters of 6 molar guanidinium chloride or 8 molar urea in water buffered to a pH of about 4.5 to 6.5 with 50 millimolar phosphate buffer or other suitable buffer and containing 500 millimolar ethylenediamine tetraacetate (EDTA) or other chelator and either 50 millimolar ascorbate, erythorbate, or other sacrificial antioxidant. Guanidinium and urea are chaotropes that lyse membranes and denature proteins including phosphatases and oxidoreductases (of which laccases are an example). EDTA sequesters metal ions including iron cations (which can directly or indirectly oxidize tryptamines), copper cations (which laccases require as a cofactor), and other divalent metal cations such as magnesium, manganese, zinc, and calcium (which various phosphatases, esterases, and oxidoreductases require as cofactors). Ascorbate and erythorbate are sacrificial antioxidants that can neutralize reactive species. The mixture is then centrifuged, and the supernatant is collected. The tryptamine content of the supernatant is quantified against psilocybin, psilocin, baeocystin, norpsilocin, norbaeocystin, 4-HT, aeruginascin, 4-hydroxy-TMT, and DMT standards by HPLC (for example, as described further in the Detailed Description) with a water and methanol gradient or other suitable mobile phase buffered to a pH of about 3.0 to 6.5, for example, with 50 millimolar citrate buffer or other suitable buffer. Tryptamine concentrations may be quantified, for example, by monitoring the absorbance of eluates at about 215-230 nanometers or at about 260-290 nanometers.

A second method to quantify tryptamines comprises lysing a 500-milligram portion of the powdered, dried fungal material, for example, by vortexing or sonicating with about 10 milliliters of methanol containing 50 millimolar ascorbate, erythorbate, tert-butylhydroquinone (TBHQ), butylated hydroxytoluene (BHT), butylated hydroxyanisole (BHA), or other sacrificial antioxidant. Because tryptamines lack robust solubility in methanol, the methanol is then diluted with 10 milliliters of water buffered to a pH of about 4.5 to 6.5 with 50 millimolar phosphate buffer or other suitable buffer and containing 5 millimolar pentetic acid (DTPA) or other chelator and 50 millimolar ascorbate or other sacrificial antioxidant. The mixture is then centrifuged, and the supernatant is collected. The tryptamine content of the supernatant is quantified against psilocybin, psilocin, baeocystin, norpsilocin, norbaeocystin, 4-HT, aeruginascin, 4-hydroxy-TMT, and DMT standards by HPLC with a water and methanol gradient or other suitable mobile phase and buffered to a pH of about 3.0 to 6.5.

A third method to quantify tryptamines comprises lysing a 500-milligram portion of the powdered, dried fungal material and denaturing enzymes, for example, by vortexing or sonicating with 10 milliliters of either 2 percent Triton X-100 (polyethylene glycol 4-(2,4,4-trimethylpent-2-yl) phenyl ether) or 2 percent CHAPS (3-{dimethyl[3-(3α,7α,12α-trihydroxy-5β-cholan-24-amido)propyl]azaniumyl}propylsulfonate) in water buffered to a pH of about 4.5 to 6.5 with 50 millimolar bicarbonate buffer or other suitable buffer and containing 500 millimolar egtazic acid (EGTA) or other chelator and 10 millimolar propyl gallate or other sacrificial antioxidant. Triton X-100 and CHAPS are surfactants that lyse membranes and denature proteins. EGTA sequesters metal ions including both iron and copper cations. Propyl gallate presents a sacrificial antioxidant that can neutralize reactive species. The mixture is then centrifuged, and the supernatant is collected. The tryptamine content of the supernatant is quantified against psilocybin, psilocin, baeocystin, norpsilocin, norbaeocystin, 4-HT, aeruginascin, 4-hydroxy-TMT, and DMT standards by HPLC with a water and methanol gradient or other suitable mobile phase.

As an alternative to drying and powdering the fungal material, the wet fungal material is introduced into ethanol at a temperature of about 50 to 60 degrees Celsius at about 20 milliliters of ethanol per gram of the wet fungal material, homogenized, sonicated, and vigorously stirred to lyse the cells and denature enzymes. After about 10 minutes, the mixture is cooled on ice and then centrifuged to produce a first supernatant and a first pellet. The first supernatant is concentrated under vacuum, for example, such as in a rotary evaporator in a cold room at about 4 degrees Celsius to a residual volume of about 500 microliters per gram of original starting material, to which 500 microliters of water is added per gram of the original starting material. The mixture is then centrifuged to produce a second supernatant, which is lyophilized to produce a first powder. Additionally, tryptamines are extracted by suspending the first pellet in 500 microliters of water per gram of the original starting material and centrifuging the suspension to produce a third supernatant, which is lyophilized to produce a second powder. Portions of the first powder and the second powder are each independently dissolved in water to quantify tryptamines against psilocybin, psilocin, baeocystin, norpsilocin, norbaeocystin, 4-HT, aeruginascin, 4-hydroxy-TMT, and DMT standards by HPLC with a water and methanol gradient or other suitable mobile phase.

As a second method to process wet fungal material, the wet fungal material is introduced into boiling water (about 100 degrees Celsius at sea level) at about 20 milliliters of water per gram of the wet fungal material and vigorously stirred to lyse the cells and denature enzymes. After about 10 minutes, the mixture is cooled on ice and then centrifuged to produce a supernatant, which is lyophilized to produce a powder. A portion of the powder is dissolved in water to quantify tryptamines against psilocybin, psilocin, baeocystin, norpsilocin, norbaeocystin, 4-HT, aeruginascin, 4-hydroxy-TMT, and DMT standards by HPLC with a water and methanol gradient or other suitable mobile phase.

As a third method to process wet fungal material, the wet fungal material is cooled to a temperature of about 4 degrees Celsius and then introduced into 20 milliliters of glacial acetic acid (also at about 4 degrees Celsius) per gram of the wet fungal material, homogenized, and sonicated to lyse the cells and denature enzymes. The supernatant is separated from solids, for example, by centrifugation and decanting. The solids are dried under vacuum, for example, by lyophilization. The acetic acid is removed from the supernatant by fractional freezing (which allows recovery and recycling of the acetic acid) and/or under vacuum, for example, by lyophilization. The dried solids and the material recovered from the supernatant are powdered and homogenized, for example, using a mortar and pestle either after recombining the solids and recovered material or in parallel. The powdered, dried fungal material may then be stored in an opaque container in a desiccator and/or under vacuum in the dark. A portion of the powdered, dried fungal material is dissolved in water and then centrifuged, and the supernatant is used to quantify tryptamines against psilocybin, psilocin, baeocystin, norpsilocin, norbaeocystin, 4-HT, aeruginascin, 4-hydroxy-TMT, and DMT standards by HPLC with a water and methanol gradient or other suitable mobile phase.

The pKa of acetic acid is about 4.8, which is greater than the lowest pKa of psilocybin, which is about 1.3. Depending upon the amount of water and inherent buffer (for example, the carboxylic acid groups of aspartate and glutamate) in the wet fungal material as well as chemical reactions that consume protons upon combining the wet fungal material with acetic acid, the pH of the supernatant of the preceding paragraph may range from about 2 to about 4. As discussed above, acidic conditions risk hydrolyzing the phosphate groups of psilocybin, baeocystin, norbaeocystin, and aeruginascin into psilocin, norpsilocin, 4-HT, and 4-hydroxy-TMT. Gentler methods may therefore be used to extract tryptamines from fungal material with acetic acid, an example of which is set forth in the following paragraph.

As a fourth method to process wet fungal material, the wet fungal material is cooled to a temperature of about 4 degrees Celsius and then introduced into 10 milliliters of 1 molar acetic acid (also at 4 degrees Celsius) per gram of the wet fungal material, homogenized, and sonicated to lyse the cells and denature enzymes. The mixture is adjusted to a pH in the range of 4.5 to 6.5 with glacial acetic acid and then diluted to 20 total milliliters with deionized water. The supernatant is separated from solids, for example, by centrifugation and decanting. The solids are dried under vacuum, for example, by lyophilization. The acetic acid is removed from the supernatant by fractional freezing (which allows recovery and recycling of the acetic acid) and/or under vacuum, for example, by lyophilization. The dried solids and the material recovered from the supernatant are powdered and homogenized, for example, using a mortar and pestle either after recombining the solids and recovered material or in parallel. The powdered, dried fungal material may then be stored in an opaque container in a desiccator or under vacuum in the dark. A portion of the powdered, dried fungal material is dissolved in water, centrifuged, and the supernatant is used to quantify tryptamines against psilocybin, psilocin, baeocystin, norpsilocin, norbaeocystin, 4-HT, aeruginascin, 4-hydroxy-TMT, and DMT standards by HPLC with a water and methanol gradient or other suitable mobile phase.

As a fifth method to process wet fungal material, the wet fungal material is cooled to a temperature of about 4 degrees Celsius and then introduced into 10 milliliters of food-grade white vinegar (also at 4 degrees Celsius) per gram of the wet fungal material, homogenized, and sonicated to lyse the cells and denature enzymes. The supernatant is separated from solids, for example, by centrifugation and decanting. The solids are dried under vacuum, for example, by lyophilization. Volatiles are removed from the supernatant under vacuum, for example, by lyophilization. The dried solids and the material recovered from the supernatant are powdered and homogenized, for example, using a mortar and pestle either after recombining the solids and recovered material or in parallel. The powdered, dried fungal material may then be stored in an opaque container in a desiccator or under vacuum in the dark. A portion of the powdered, dried fungal material is dissolved in water and then centrifuged, and the supernatant is used to quantify tryptamines against psilocybin, psilocin, baeocystin, norpsilocin, norbaeocystin, 4-HT, aeruginascin, 4-hydroxy-TMT, and DMT standards by HPLC with a water and methanol gradient or other suitable mobile phase.

Unlike culinary fungi such as *Agaricus bisporus*, which produces both button and portobello mushrooms, fungi that contain psychedelic tryptamines generally have not been bred to select against the production of proteins, polysaccharides, phenolic compounds, indoles other than tryptamines, and mycotoxins that can cause gastrointestinal distress and other undesirable effects in humans. In comparison, domesticated *A. bisporus* mushrooms produce relatively low amounts of the polysaccharides beta-glucan and chitin (of which Albert Hofmann determined the chemical structure in 1929, for his doctoral thesis) compared to wild mushrooms. Mushrooms that contain psychedelic tryptamines notably also contain indole-3-acetic acid, which is an immunotoxin, and tryptophol, which is the sedative that is also produced by the *Trypanosoma* parasite that results in African sleeping sickness. As a result of polysaccharides, indole-3-acetic acid, tryptophol, and other compounds, individuals who consume mushrooms that contain psychedelic tryptamines may experience one or more side effects such as drowsiness, bloating, gas, cramping, nausea, vomiting, diarrhea, headaches, and fever. Additionally, the same species of mushroom may be cultivated differently to produce different concentrations of proteins, polysaccharides, phenolic compounds, indoles, and mycotoxins. White button mushrooms and portobello mushrooms are both *A. bisporus*, for example, but white button mushrooms are bred and grown to minimize the production of laccase enzymes and other oxidoreductases that synthesize melanin-like pigments and to minimize the phenolic and indolic precursors to melanin-like pigments. Portobello mushrooms also have greater concentrations of beta-glucan, chitin, and the mycotoxin agaritine than white button mushrooms. Without limiting this disclosure or any patent claim that matures from this disclosure, preparing tryptamine-containing compositions from fungal material that contains relatively high amounts of mycelium and/or sclerotium and relatively low amounts of fruiting bodies as described herein can reduce the concentration of proteins, polysaccharides, phenolic compounds, indoles other than tryptamines, and/or mycotoxins that cause gastrointestinal distress and other undesirable side effects per dose of the psychedelic tryptamines. Without limiting this disclosure or any patent claim that matures from this disclosure, growing fungal material under low light conditions inhibits the production of laccase enzymes that synthesize melanin-like pigments and phenolic and indolic precursors to melanin-like pigments, which both reduces the risk of laccase-mediated degradation of tryptamines and reduces the risk that phenolic and indoles other than tryptamines will cause undesirable side effects, respectively. Without limiting this disclosure or any patent claim that matures from this disclosure, heating fungal material as described herein can denature proteins and/or degrade other compounds that cause gastrointestinal distress and other undesirable side effects associated with prior art mushroom preparations. Without limiting this disclosure or any patent claim that matures from this disclosure, partially purifying psychedelic tryptamines as described herein can reduce the concentration of proteins, polysaccharides, phenolic compounds, indoles other than tryptamines, and mycotoxins that cause gastrointestinal distress and other undesirable side effects per dose of the psychedelic tryptamines.

In some embodiments, a tryptamine-containing composition is sufficiently purified as described herein such that the composition comprises a combined concentration of psilocybin and psilocin of at least 40 milligrams and no greater than 950 milligrams by dry weight. In some specific embodiments, the tryptamine-containing composition comprises a combined concentration of psilocybin and psilocin of at least 80 milligrams and no greater than 950 milligrams by dry weight. In some very specific embodiments, the tryptamine-containing composition comprises a combined concentration of psilocybin and psilocin of at least 120 milligrams and no greater than 950 milligrams by dry weight.

In some embodiments, a tryptamine-containing composition comprises a combined concentration by dry weight of psilocybin and psilocin and a concentration by dry weight of protein, and the composition is sufficiently purified as described herein such that the combined concentration by dry weight of psilocybin and psilocin is greater than the concentration by dry weight of protein. In some specific embodiments, the tryptamine-containing composition comprises a combined concentration by dry weight of psilocybin and psilocin of at least 80 milligrams and no greater than 950 milligrams and a concentration by dry weight of protein of less than 40 milligrams per gram of the composition.

In some embodiments, a tryptamine-containing composition is sufficiently purified as described herein such that the composition comprises a combined concentration by dry weight of psilocybin and psilocin of at least 40 milligrams and no greater than 950 milligrams, and the composition comprises a combined concentration by dry weight of beta-glucan and chitin of less than 500 milligrams. In some specific embodiments, the tryptamine-containing composition comprises a combined concentration by dry weight of psilocybin and psilocin of at least 40 milligrams and no greater than 950 milligrams, and the composition comprises a combined concentration by dry weight of beta-glucan and chitin of less than 200 milligrams. In some very specific embodiments, the tryptamine-containing composition comprises a combined concentration by dry weight of psilocybin and psilocin and a combined concentration by dry weight of beta-glucan and chitin, and the tryptamine-containing composition is sufficiently purified as described herein such that the combined concentration by dry weight of psilocybin and psilocin is greater than the combined concentration by dry weight of beta-glucan and chitin.

In some embodiments, a tryptamine-containing composition is sufficiently purified as described herein such that the tryptamine-containing composition comprises a mole ratio of psilocybin to indole-3-acetic acid of at least 10:1. In some specific embodiments, the tryptamine-containing composition comprises a mole ratio of psilocybin to indole-3-acetic acid of at least 100:1. In some very specific embodiments, the tryptamine-containing composition comprises a mole ratio of psilocybin to indole-3-acetic acid of at least 1000:1.

In some embodiments, a tryptamine-containing composition is sufficiently purified as described herein such that the tryptamine-containing composition comprises a combined concentration by dry weight of psilocybin and psilocin of at least 40 milligrams and no greater than 950 milligrams and no greater than 1000 parts per million indole-3-acetic acid by dry weight. In some specific embodiments, the tryptamine-containing composition comprises no greater than 100 parts per million indole-3-acetic acid by dry weight. In some very specific embodiments, the tryptamine-containing composition comprises no greater than 10 parts per million indole-3-acetic acid by dry weight.

In some embodiments, a tryptamine-containing composition is sufficiently purified as described herein such that the tryptamine-containing composition comprises a mole ratio of psilocybin to tryptophol of at least 10:1. In some specific embodiments, the tryptamine-containing composition comprises a mole ratio of psilocybin to tryptophol of at least 100:1. In some very specific embodiments, the tryptamine-containing composition comprises a mole ratio of psilocybin to tryptophol of at least 1000:1.

In some embodiments, a tryptamine-containing composition is sufficiently purified as described herein such that the tryptamine-containing composition comprises a combined concentration by dry weight of psilocybin and psilocin of at least 40 milligrams and no greater than 950 milligrams and no greater than 1000 parts per million tryptophol by dry weight. In some specific embodiments, the tryptamine-containing composition comprises no greater than 100 parts per million tryptophol by dry weight. In some very specific embodiments, the tryptamine-containing composition comprises no greater than 10 parts per million tryptophol by dry weight.

After a tryptamine-containing composition is produced and tryptamines are quantified, the tryptamine-containing composition may optionally be adjusted to a standard concentration of one or more tryptamines, for example, with one or more fillers (e.g., methylcellulose, sodium carboxymethyl cellulose (NaCMC)), sweeteners (e.g., sucrose, sucralose, one or more steviol glycosides, aspartame, saccharin, xylitol, erythritol, sorbitol), anticaking agents (e.g., sodium aluminosilicate, tricalcium silicate), preservatives (e.g., a sulfite salt, a bisulfite salt, a metabisulfite salt, a sorbate salt, sorbic acid, an ascorbate salt, ascorbic acid, a tocopherol, a tocotrienol), sequestrants (e.g., an EDTA salt, a phosphate salt, a pyrophosphate salt, a tripolyphosphate salt, a metaphosphate salt, a hexametaphosphate salt, a diacetate salt, a gluconate salt), nutrients (e.g., a zinc salt, a calcium salt), other permitted or GRAS food additives (e.g., as set forth in Title 21, Part 172 or Part 182 of the United States Code of Federal Regulations), a less-concentrated or more-concentrated tryptamine-containing composition, and/or a different mushroom composition that lacks psychoactive tryptamines (e.g., portobello, lion's mane, reishi, and/or cordyceps). The standard concentration may be, for example, 10 milligrams of psilocybin per gram, 10 milligrams of psilocybin and psilocin combined per gram, 10 milligrams of potential psilocin per gram (which equals the sum of (i) psilocybin divided by its molecular weight of 284.25 and multiplied by the molecular weight of psilocin of 204.27 and (ii) psilocin), 10 milligrams of psilocybin equivalents per gram (which equals the sum of (i) psilocybin and (ii) psilocin divided by its molecular weight of 204.27 and multiplied by the molecular weight of psilocybin of 284.25), 10 milligrams of psilocybin, psilocin, baeocystin, and norpsilocin combined per gram, 10 milligrams of potential psychoactive tryptamines per gram (which equals approximately the sum of (i) psilocybin divided by its molecular weight of 284.25 and multiplied by the molecular weight of psilocin of 204.27, (ii) psilocin, (iii) baeocystin divided by its molecular weight of 270.22 and multiplied by the molecular weight of norpsilocin of 190.25, and (iv) norpsilocin), or other standard concentration of one or more tryptamines per gram. The tryptamine-containing composition may optionally be a powder when the tryptamine-containing composition is adjusted to a standard concentration of one or more tryptamines, or the tryptamine-composition composition may be a liquid or a colloidal suspension.

The phosphoryloxytryptamines of a tryptamine-containing powder may exist as a salt as described herein, e.g., as a sodium salt, potassium salt, chloride salt, and/or acetate salt, etc., which are further described in the Detailed Description that follows. The salt may comprise an anion that can buffer acidity (e.g., acetate), which can advantageously inhibit acid-driven dephosphorylation of the phosphoryloxytryptamines when the salt is dissolved in a solvent. The phosphoryloxytryptamines of a tryptamine-containing powder may also advantageous exist at a zwitterionic phosphoryloxytryptamine to anionic phosphoryloxytryptamine mole ratio and/or zwitterionic phosphoryloxytryptamine to cationic phosphoryloxytryptamine mole ratio as described herein to inhibit dephosphorylation during the manufacture of the powder and/or to inhibit dephosphorylation in the powder form.

A tryptamine-containing composition may then be used to prepare products for human consumption such as edibles, teas, pills, or the composition itself, e.g., in a hermetically-sealed container. The composition itself may be loaded into single-serving containers (such as mylar bags) that contain a known amount of one or more tryptamines (such as 10, 15, 20, or 25 milligrams and/or as described in the preceding paragraph). The composition may instead be loaded into capsules or pressed into pills, which are then packaged in a container. Suitable pill capsule sizes include 000, 00, 0, 1, 2, and 3. Pill capsules may advantageously be colored to inhibit the transmittance of light generally and wavelengths of less than 500 nanometers specifically and/or the pill capsules may inhibit fluid communication (or be hermetically sealed) to inhibit oxygen and/or water vapor from entering the capsules and oxidizing and/or dephosphorylating the tryptamines within. Suitable binders for pressing pills include polyvinylpyrrolidone (povidone, PVP), hydroxypropylcellulose (HPC), hydroxypropyl methyl cellulose (hypromellose, HPMC), microcrystalline cellulose (MC), NaCMC, polyethylene glycol (PEG), gelatin, starch, carbomers, and combinations of the foregoing. Pressed pills may advantageously be coated with one or more excipients that inhibit the transmittance of light generally and wavelengths of less than 500 nanometers specifically and/or with one or more excipients that inhibit fluid communication (or that hermetically-seal the pressed pills) to inhibit oxygen and/or water vapor from entering the pressed pills and oxidizing and/or dephosphorylating the tryptamines within. A container that contains pill capsules or pressed pills may be opaque to the transmittance of light generally and wavelengths of less than 500 nanometers specifically and/or inhibit fluid communication (or be hermetically sealed) to inhibit oxygen and/or water vapor from entering the container and oxidizing and/or dephosphorylating the tryptamines within. A container may also contain an oxygen-absorbing agent (such as a packet containing iron powder) and/or a desiccant (such as a packet containing silica, bentonite, activated carbon, or calcium oxide) to inhibit the oxidation and/or dephosphorylation of the tryptamines within the container. A tryptamine-containing composition may also be formulated into an "edible" product such as a chocolate as described infra. The phosphoryloxytryptamines of a tryptamine-containing edible product may exist as a salt as described herein, e.g., as a sodium salt, potassium salt, chloride salt, and/or acetate salt, etc., which are further described in the Detailed Description that follows. The phosphoryloxytryptamines of a tryptamine-containing edible product may also advantageous exist at a zwitterionic phosphoryloxytryptamine to anionic phosphoryloxytryptamine mole ratio and/or zwitterionic phosphoryloxytryptamine to cationic phosphoryloxytryptamine mole ratio as described herein to inhibit dephosphorylation during the manufacture of the tryptamine-containing edible product and/or to inhibit dephosphorylation in the product format.

Chocolate presents an appropriate vehicle to stabilize tryptamines because chocolate can be formulated at neutral or alkaline pH, as opaque, and to inhibit the permeability of gasses (e.g., oxygen and/or water vapor). A chocolate product may be formulated with a pH of about 4.5 to about 8.0, which can inhibit acid-degradation of tryptamines. A chocolate product may also be formulated with a surface-area-to-volume ratio of less than 10 per meter, which can inhibit gas permeability. A chocolate product can also be formulated with an internal core comprising the tryptamines and a protective outer layer to inhibit gas permeability. An internal core may optionally comprise a mixture of a tryptamine-containing composition and a confection or a lipid-based filling such as a bonbon filling. Lipid-based fillings (especially fat-based fillings) are relatively inert because they inhibit acid/base and redox chemistry that can degrade tryptamines relative to aqueous-phase fillings. A tryptamine-containing composition may be combined, for example, with cocoa butter and/or coconut oil and optionally one or more flavorings and/or sweeteners to produce a suitable filling. The outer layer may comprise, for example, a layer of hard chocolate (e.g., of the type found in a chocolate bar or the outer layer of a bonbon) and/or a candy shell (e.g., of the type that coats a dragée or comfit). The outer layer may advantageously be thick enough to inhibit the transmission of light and/or to inhibit the permeability of gasses, for example, such as at least 2 millimeters. Other confections may nevertheless be suitable for stabilizing tryptamines to increase the shelf life of an edible product including dragées and comfits. A binder such as arabinogalactan (e.g., from gum arabic) may be used, for example, to solidify a tryptamine-containing composition (or a mixture of a tryptamine-containing composition and other ingredients) and/or to seal the tryptamine-containing composition to inhibit interactions with other ingredients of a confection and/or to inhibit gas permeability.

Tryptamine compositions may also be stabilized as an ingredient for incorporation into other edible products, for example, to manufacture gummies, chips, and other snack foods. A tryptamine-containing composition, for example, may be spray dried or otherwise formulated into a stabilized composition with a binder (e.g., arabinogalactan, microcrystalline cellulose, ethylcellulose, methyl ethyl cellulose, HPC, HPMC, starch, modified food starch, etc.) that protects the tryptamines from chemical interactions with other ingredients. A tryptamine-containing composition may also be formulated as nonpareils (also known as "sugar pearls"), in which the tryptamine-containing composition is combined with one or more sweeteners (e.g., sucrose, fructose, glucose, lactose, mannitol) and/or binders (e.g., starch, cellulose) and solidified into the nonpareils. Nonpareil-like particles have previously been used to formulate pharmaceuticals, but prior-art formulations comprise an inert core coated with an active agent that increases the surface area of the active agent to allow for rapid release (optionally after the dissolution of a protective outer layer, e.g., such as the NONPAREIL™ branded products offered by Freund Corporation, Japan). The stabilized compositions and nonpareils of this disclosure differ from the prior art because they reduce the surface area of the active agent to inhibit interactions with other ingredients by sequestering tryptamines within the core of a particle instead of within an outer-layer of a particle. Any particle may have, for example, a diameter ranging from about 10 microns to about 2 millimeters depending upon the application.

Tryptamines may promote neuroplasticity independent from their psychedelic effects, which has resulted in attempts by contemporary scientists (e.g., David E. Olson of the University of California, Davis) to develop synthetic "psychoplastogens" that display similar neuroplastic effects as naturally-occurring psychedelics, but that display muted or absent psychedelic effects. Certain aspects of this disclosure relate to the discovery that extended-release formulations of psychedelic tryptamines attenuate psychedelic side effects while nevertheless retaining psychoplastic effects. Without limiting this disclosure or any patent claim that matures from this disclosure, tachyphylaxis attenuates the psychedelic effects of tryptamines on the order of hours without eliminating neuroplastic effects, and extended-release formulations can therefore exploit tachyphylaxis to minimize psychedelic effects while retaining neuroplastic effects. For example, either purified tryptamines or a tryptamine-containing composition may be combined with excipients that favor extended release of the tryptamines such as (1) hydrophilic polymers that inhibit the release of the tryptamines when dry, but that gradually hydrate and swell in the gastrointestinal tract to allow for extended release (e.g., HPC, HPMC, methylcellulose, NaCMC, polyacrylic acid (e.g., CARBOPOL®), polyethylene oxide (PEO), guar gum, xanthan gum); (2) hydrophobic polymers that inhibit the release of tryptamines (e.g., ethylcellulose, cellulose acetate, cellulose acetate phthalate, PVP, polyvinyl acetate (PVA), poly(methyl methacrylate), poly(methacrylic acid, methyl methacrylate) (e.g., EUDRAGIT® S, EUDRAGIT® L 100), poly(methacrylic acid, ethyl acrylate) (e.g., Acryl-EZE, EUDRAGIT® L 100-55, Eastacryl 30D, KOLLICOAT® MAE), poly(ethyl acrylate, methyl methacrylate) (e.g., EUDRAGIT® NE, EUDRAGIT® NM), poly(methyl acrylate, methyl methacrylate, methacrylic acid) (e.g., EUDRAGIT® FS), poly(ethyl acrylate, methyl methacrylate, 2-trimethylammonioethyl methacrylate chloride) (e.g., EUDRAGIT® RL, EUDRAGIT® RS), and poly(butyl methacrylate, (2-dimethylaminoethyl)methacrylate, methyl methacrylate) (e.g., EUDRAGIT® E); (3) combined hydrophilic and hydrophobic polymers (e.g., HPMC and ethylcellulose); (4) waxes and lipids that dissolve and/or melt in the gastrointestinal tract (e.g., beeswax, carnauba wax, hydrogenated vegetable oil, paraffin wax, stearyl alcohol, steric acid, lecithin); and/or (5) ion exchange resins that bind either the phosphate of the anionic forms of psilocybin, baeocystin, norbaeocystin, and/or aeruginascin (anion exchange) or the protonated amine of psilocin, norpsilocin, 4-HT, 4-hydroxy-TMT, and/or DMT (cation exchange) and that release their tryptamine payloads as an anionic payload exchanges for anions of the gastrointestinal tract (e.g., chloride anion) and/or as a cationic payload exchanges for cations of the gastrointestinal tract (e.g., sodium cation, potassium cation). Compositions and methods for formulating extended-release embodiments are described, for example, in REMINGTON: THE SCIENCE AND PRACTICE OF PHARMACY, 22nd edition (Allen Jr, Loyd V., editor) Pharmaceutical Press, 2012, which is incorporated by reference in its entirety. In some embodiments, an extended-release formulation displays a time-to-peak concentration (Tmax) for psilocin of at least six hours. Repeated administration of a psychedelic tryptamine formulation such as at least twice per week, daily, or twice daily may also exploit tachyphylaxis to minimize psychedelic effects while retaining neuroplastic effects. Extended-release formulations and/or repeated administration may also be used to attenuate psychedelic effects while nevertheless retaining the neuroplastic effects of other naturally-occurring and synthetic psychoplastogens including other tryptamines (e.g., bufotenin, 5-methoxy-dimethyltryptamine (5-MeO-DMT)), psychedelic phenylethylamines (e.g., mescaline, 4-halo-2,5-dimethoxyphenethylamines), psychedelic lysergamides (e.g., LSD), and psychedelic indole alkaloids (e.g., ibogaine, noribogaine).

The substituent "halo" as used in chemical formula may refer to any one of fluoro, chloro, bromo, and iodo. In some very specific embodiments, halo is fluoro. In some embodiments, halo is selected from chloro, bromo, and iodo. In some very specific embodiments, halo is chloro. In some specific embodiments, halo is selected from bromo and iodo. In some very specific embodiments, halo is bromo. In some very specific embodiments, halo is iodo.

Many variations of the foregoing compositions and methods result in improved stability, extraction, quantification, and pharmacokinetics of tryptamines, and the Detailed Description that follows contains additional variations. The skilled person will immediately recognize numerous other combinations of the disclosures contained herein, and neither the foregoing Background and Summary nor the Abstract nor the following Detailed Description shall limit any patent claim that matures from this disclosure, which patent claim(s) shall instead be construed in view of the language of the claim(s) as well as their claim dependency and, if any ambiguity remains, then in accordance with the conventional canons of claim construction.

DETAILED DESCRIPTION

Fungal material that produces psychedelic tryptamines is first grown and separated from its growth media. The nature of the fungal material and the growth media is not particularly limiting.

The term "wet fungal material" as used in this disclosure refers to harvested fungal material that has undergone either no further processing or minimal further processing (such as by separating the wet fungal material from growth media and/or mechanically processing the wet fungal material), and which has not been either frozen, dried, or extracted.

The term "tryptamine" as used in this disclosure refers to a compound that comprises the heavy-atom connectivity of 2-(1H-indol-3-yl)ethylazanium, in which various protons are substituted by various substituents. Tryptamines include phosphoryloxytryptamines and hydroxytryptamines. The heavy atoms of tryptamines consist of (1) at least nine carbon atoms, (2) at least two nitrogen atoms, (3) optionally one or more oxygen atoms (e.g., phosphoryloxytryptamines, hydroxytryptamines), (4) optionally one phosphorous atom (e.g., phosphoryloxytryptamines), (5) in some instances one sulfur atom (e.g., bufoviridine, 5-methylthio-N,N-dimethyltryptamine), and (6) in some instances one, two, or three halogen atoms (e.g., convolutindole A, desformylflustrabromine, 5-bromo-N,N-dimethyltryptamine). Naturally-occurring tryptamines include compounds in which (1) one or more amine protons are substituted by methyl, and (2) the proton bound to the 4-carbon or 5-carbon of the indole benzene ring is substituted by phosphonooxy or hydroxy. DMT (dimethyltryptamine), for example, is a naturally-occurring tryptamine in which two amine protons are substituted by methyl. Other substituents found in naturally-occurring tryptamines include, without limitation, methoxy (e.g., convolutindole A, melatonin), acetyl (e.g., melatonin), sulfooxy (e.g., bufoviridine), halogens (e.g., convolutindole A, desformylflustrabromine, 5-bromo-N,N-dimethyltryptamine), and branched, unsaturated hydrocarbons (e.g., desformylflustrabromine). Many artificial tryptamines have also been synthesized.

The term "phosphoryloxytryptamine" as used in this disclosure refers to a compound that comprises the heavy-atom connectivity of 2-(1H-indol-3-yl)ethylazanium, in which a proton of the benzene ring of the indole is substituted by phosphonooxy and in which various other protons are optionally substituted by various other substituents (typically hydrocarbon substituents such as methyl). Naturally-occurring phosphoryloxytryptamines include compounds in which the proton bound to the 4-carbon or 5-carbon of the indole benzene ring is substituted by phosphonooxy. Psilocybin is a phosphoryloxytryptamine, for example, in which two amine protons are substituted by methyl and the proton bound to the 4-carbon is substituted by phosphonooxy. The phosphonooxy substituent is typically ionized, i.e., the phosphonooxy is monoanionic phosphonooxy (and the phosphoryloxytryptamine is a zwitterion) or dianionic phosphonatooxy (and the phosphoryloxytryptamine is a monoanion). Ionization of the phosphonooxy substituent allows for an intramolecular interaction between the negatively-charged phosphonooxy and the positively-charged amine. C f. Alexander M. Sherwood et al., *Psilocybin: Crystal Structure Solutions Enable Phase Analysis of Prior Art and Recently Patented Examples*, STRUCTURAL CHEMISTRY, 2022, C78:36. Naturally-occurring phosphoryloxytryptamines include psilocybin, baeocystin, norbaeocystin, and aeruginascin.

The term "hydroxytryptamine" as used in this disclosure refers to a compound that comprises the heavy-atom connectivity of 2-(1H-indol-3-yl)ethylazanium, in which a proton of the benzene ring of the indole is substituted by hydroxy and in which various other protons are optionally substituted by various other substituents (typically hydrocarbon substituents such as methyl). Naturally-occurring hydroxytryptamines include compounds in which the proton bound to the 4-carbon or 5-carbon of the indole benzene ring is substituted by hydroxy. Psilocin and bufotenin are hydroxytryptamines, for example, in which two amine protons are substituted by methyl and the proton bound to the 4-carbon (psilocin) or 5-carbon (bufotenin) is substituted by hydroxy. Serotonin is a hydroxytryptamine, for example, in which the proton bound to the 5-carbon is substituted by hydroxy. 6-Hydroxymelatonin is an example of a hydroxytryptamine in which the proton bound to the 6-carbon is substituted by hydroxy, the proton bound to the 5-carbon is substituted by methoxy, and an amine proton is substituted by acetyl. Other naturally-occurring hydroxytryptamines include norpsilocin, 4-HT, 4-hydroxy-TMT, and N-acetylserotonin.

In some embodiments, the fungal material is selected from a species of *Amanita, Conocybe, Copelandia, Galerina, Gerronema, Gymnopilus, Hypholoma, Inocybe,*

*Panaeolina, Panaeolus, Pholiotina, Pluteus, Psilocybe, Russula*, and *Stropharia*, which species biosynthetically produces one or more tryptamines. In some specific embodiments, the fungal material is a species of *Inocybe, Panaeolus, Pholiotina, Psilocybe*, or *Stropharia*, which species biosynthetically produces one or more tryptamines. In some very specific embodiments, the fungal material is selected from *Inocybe aeruginascens, Panaeolus cyanescens, Pholiotina cyanopus, Psilocybe aztecorum, Psilocybe azurescens, Psilocybe caerulescens, Psilocybe cubensis, Psilocybe cyanescens, Psilocybe mexicana, Psilocybe semilanceata, Psilocybe semperviva, Psilocybe serbica, Psilocybe tampanensis, Psilocybe zapotecorum*, and *Stropharia cubensis*.

Without limiting this disclosure or any patent claim that matures from this disclosure, mycelium and sclerotium contain a lower concentration of structural proteins such as chitin and beta-glucans per tryptamine relative to fruiting bodies, which lower concentrations of structural proteins improve separations and thereby inhibit the loss of tryptamines during processing, and/or which lower concentrations of structural proteins result in higher concentrations of tryptamines in the tryptamine-containing compositions described herein. Without limiting this disclosure or any patent claim that matures from this disclosure, mycelium and sclerotium contain lower concentrations of laccase enzymes and other oxidoreductases per tryptamine relative to fruiting bodies, which lower concentrations of laccase enzymes and other oxidoreductases reduce the loss of tryptamines during processing. Without limiting this disclosure or any patent claim that matures from this disclosure, mycelium and sclerotium contain lower concentrations of phenolic compounds and indolic compounds other than tryptamines than fruiting bodies, which lower concentrations of phenolic compounds and indolic compounds other than tryptamines increase the purity of tryptamines in the tryptamine-containing compositions described herein. Therefore, in some embodiments, wet fungal material comprises one or both of mycelium and sclerotium, and the wet fungal material is relatively devoid of fruiting bodies.

In some embodiments, wet fungal material of this disclosure comprises at least 10 percent mycelium and/or sclerotium as a percentage of total fungal material. In some specific embodiments, wet fungal material of this disclosure comprises at least 50 percent mycelium and/or sclerotium and less than 50 percent fruiting bodies. In some very specific embodiments, wet fungal material of this disclosure comprises at least 80 percent mycelium and/or sclerotium and less than 20 percent fruiting bodies.

The compositions and methods of this disclosure are nevertheless compatible with wet fungal material that either comprises or consists of fruiting bodies, and the term "wet fungal material" shall not be construed as either (1) being limited to mycelium and/or sclerotium and/or (2) excluding fruiting bodies unless the immediate context of the term "wet fungal material" explicitly sets forth such a limitation and/or exclusion.

Without limiting this disclosure or any patent claim that matures from this disclosure, smaller fruiting bodies contain a lower concentration of structural proteins such as chitin and beta-glucans per tryptamine relative to larger fruiting bodies, which lower concentrations of structural proteins improve separations and thereby inhibit the loss of tryptamines during processing, and/or which lower concentrations of structural proteins result in higher concentrations of tryptamines in the tryptamine-containing compositions described herein. Without limiting this disclosure or any patent claim that matures from this disclosure, smaller fruiting bodies contain lower concentrations of laccase enzymes and other oxidoreductases per tryptamine relative to larger fruiting bodies, which lower concentrations of laccase enzymes and other oxidoreductases reduce the loss of tryptamines during processing. Without limiting this disclosure or any patent claim that matures from this disclosure, smaller fruiting bodies contain lower concentrations of phenolic compounds and indolic compounds other than tryptamines than larger fruiting bodies, which lower concentrations of phenolic compounds and indolic compounds other than tryptamines increase the purity of tryptamines in the tryptamine-containing compositions described herein. Therefore, in some embodiments, wet fungal material comprises fruiting bodies with a median size of no greater than ten centimeters in any direction. In some specific embodiments, the wet fungal material comprises fruiting bodies with a median size of no greater than eight centimeters in any direction. In some even more specific embodiments, the wet fungal material comprises fruiting bodies with a median size of no greater than six centimeters in any direction. In some very specific embodiments, the wet fungal material comprises fruiting bodies with a median size of no greater than four centimeters in any direction. The term "median size" refers to the median size of a number of fruiting bodies when harvested, e.g., the median size is calculated by measuring the longest distance in Cartesian space between two points on each of a number of fruiting bodies (typically a distance from the bottom of the volva of a fruiting body to the top of the pileus of the fruiting body) and dividing the sum of the longest distances by the number.

Growing fungi that comprise fruiting bodies with an average size as set forth in the foregoing paragraph may be accomplished, for example, by selecting genetics that produce smaller fruiting bodies. The inventors find, for example, that each of the length, girth, and heft of the "penis envy" strain of *Psilocybe cubensis* is tiny in every way. Growing fungi that comprise fruiting bodies with an average size as set forth in the foregoing paragraph may also be accomplished, for example, by growing fruiting bodies under growth-limiting conditions (such as on solid media with low humidity), and/or by harvesting fruiting bodies soon after rupture of their universal veils (such as less than seven days, five days, or three days after rupture).

In some embodiments, the growth media comprises liquid growth media, and a method of this disclosure comprises physically separating wet fungal material from the liquid growth media. In some specific embodiments, the method comprises decanting and/or aspirating the liquid growth media from the wet fungal material. In some specific embodiments, the method comprises physically separating the liquid growth media from the wet fungal material by centrifugation. In some very specific embodiments, the method comprises centrifugation followed by decanting and/or aspirating the liquid growth media from the wet fungal material. In some specific embodiments, the method comprises physically separating the liquid growth media from the wet fungal material by pressing liquids out of the wet fungal material. In some specific embodiments, the method comprises physically separating the liquid growth media from the wet fungal material by filtering liquids through a filter (such as a cloth filter or membrane filter) or straining the liquids through a strainer or mesh while retaining the wet fungal material. In some very specific embodiments, the method comprises pressing liquids through a filter to separate the liquid growth media from the wet fungal material.

Regardless of the separation technique, separating liquid growth media from the wet fungal material should be performed gently to inhibit the rupture of cell membranes and cell walls of the wet fungal material because such rupture may allow intracellular compartments to mix with each other and/or with the intercellular space, which might allow dephosphorylation and/or oxidation of tryptamines, and which may cause tryptamines to leak into the liquid growth media, both of which can result in the unrecoverable loss of tryptamines during extraction. Wet fungal material, for example, should not be ground or minced prior to taking measures to control for phosphatases, esterases, oxidoreductases (e.g., laccases), and reactive species (e.g., reactive oxygen species) as described herein.

In some embodiments, the fungal material comprises fruiting bodies, and the method comprises physically separating the fruiting bodies from growth media such as by cutting the fruiting bodies to physically separate the fruiting bodies from the growth media.

In some embodiments, the physical separating is performed under reduced light. For example, in some embodiments, the physical separating is performed at no greater than 300 lux such as no greater than 200 lux, no greater than 100 lux, or no greater than 50 lux.

In some embodiments, the physical separating is performed under light with a color temperature of less than 4000 K such as no greater than 3500 K, no greater than 3000 K, or no greater than 2500 K.

In some embodiments, luminous flux at greater than 500 nanometers exceeds luminous flux at less than 500 nanometers during the physical separating. In some specific embodiments, luminous flux at greater than 500 nanometers is at least 2 times greater than luminous flux at less than 500 nanometers during the physical separating. In some very specific embodiments, luminous flux at greater than 500 nanometers is at least 5 times greater than luminous flux at less than 500 nanometers during the physical separating.

In some embodiments, the method comprises drying the fungal material. The drying may comprise, for example, lyophilization, desiccation, and/or dehydration.

In some embodiments, the method comprises lyophilization, and the method comprises freezing the fungal material. The prior art teaches that lyophilization results in substantial degradation of psilocybin and other tryptamines, which the prior art generally attributes to mechanical processing prior to lyophilization. See, e.g., Klára Gotvaldová et al., *Stability of Psilocybin and its Four Analogs in the Biomass of the Psychotropic Mushroom Psilocybe cubensis*, Drug Testing and Analysis, 2021, 13:439. One of the discoveries of the inventors is that the majority of tryptamine loss observed during prior art lyophilization protocols was caused by freezing fungal material by convection. The inventors have found that freezing should instead be performed by conductive heat transfer (and not by convective heat transfer) such as by freezing in a cooling bath (instead of in a freezer). Conductive heat transfer is favored over convective heat transfer because conduction results in much more rapid cooling. Freezing the fungal material slowly, such as by convective heat transfer in a freezer, is disfavored because, while freezing inhibits reactions that degrade tryptamines, freezing nevertheless lyses membranes, which causes cellular compartments to leak thereby exposing tryptamines to enzymes and reactive species that accelerate their degradation. Without limiting this disclosure or any patent claim that matures from this disclosure, slow freezing such as by convective heat transfer in a freezer results in increased tryptamine degradation relative to rapid freezing such as by conductive heat transfer in a cooling bath, and thus, rapid freezing increases tryptamine yields and cures the defects found in prior art lyophilization protocols.

The prior art also found that, while lyophilization reduced the concentrations of phosphoryloxytryptamines including psilocybin, baeocystin, norbaeocystin, and aeruginascin, lyophilization did not affect the recovery of psilocin. See, e.g., id. The prior art provides no reason to account for such differences and overlooks the underlying chemistry. This disclosure teaches that the hydrolysis of phosphoryloxytryptamines (e.g., psilocybin) during historical extraction and analytical protocols resulted in hydroxytryptamines (e.g., psilocin), which masked the degradation of hydroxytryptamines. The prior art generally overlooks this chemistry and erroneously concludes that psilocin is stable. See, e.g., id. This disclosure instead teaches that the rate of dephosphorylation of psilocybin and other phosphoryloxytryptamines in fungal material that has not been treated to attenuate phosphatase activity is faster than the rate of oxidation of psilocin and other hydroxytryptamines, and psilocin therefore accumulated during prior art lyophilization protocols. The erroneous conclusion that psilocin was stable during prior art lyophilization protocols reflects a general unawareness of the chemistries that degrade tryptamines during both extraction and quantification protocols, which this Detailed Description addresses further below.

Fungal material may be frozen, for example, by placing the fungal material directly into a food grade liquid at a temperature of less than zero degrees Celsius (i.e., a cooling bath) such as in food grade liquid nitrogen, food grade dry ice in food grade ethanol, or food grade brine (comprising, for example, 20 to 28 percent sodium chloride by mass in water). The fungal material may be placed in such a cooling bath, for example, within a mesh cage to allow direct contact between the liquid of the cooling bath and the fungal material. Fungal material may alternatively be frozen, for example, by inserting the fungal material into a container that inhibits contact between the liquid of the cooling bath and the fungal material and inserting the container into the cooling bath, which allows for baths that comprise other than food grade solvents such as dry-ice-in-acetone cooling baths. The fungal material may be placed in a container comprising a flexible plastic barrier (such as a polyethylene barrier), and the container may optionally be vacuum-sealed to minimize the amount of insulating gas (for example, air) in the container. The fungal material may be placed, for example, between two flexible plastic sheets or within a flexible plastic pouch, vacuum sealed, and then frozen in a cooling bath.

In this disclosure, conductive heat transfer and conduction refer to cooling as a result of contact with a solid or liquid regardless of whether the liquid undergoes flow. Inserting fungal material into a container and then immersing the container in a cooling bath results in conductive heat transfer from the fungal material to the container and from the container to the liquid of the cooling bath (regardless of whether the liquid undergoes flow). Inserting fungal material directly into a cooling bath also results in conductive heat transfer from the fungal material to the liquid of the cooling bath according to this disclosure (regardless of whether the liquid undergoes flow). In this disclosure, convective heat transfer and convection refer to cooling as a result of contact with a gas. Inserting fungal material into a freezer results in both convective heat transfer between the fungal material and air (or other gas) within the freezer and conductive heat transfer between the fungal material and solids (or liquids) that the fungal material contacts within the freezer such as conductive heat transfer between the fungal material and a container that contains the fungal material and/or between such a container and a shelf on which the container is placed. Vacuum-sealing the fungal material in a container prior to placing the fungal material in a freezer does not by itself overcome the limitations posed by convective heat transfer within a freezer, for example, because conductive heat transfer from a shelf to the container, from the container to a proximal portion of the fungal material that contacts the container, and from the proximal portion to distal portions of the fungal material is inefficient at freezing the distal portions. Vacuum-sealing the fungal material in a container (such as between two polyethylene sheets) may nevertheless allow for conductive heat transfer within a freezer, for example, if the container is placed between two solid surfaces within the freezer that allow conductive heat transfer such as because a solid surface above the container exerts pressure upon the container that displaces air (or other gas) between the two solid surfaces.

In some embodiments, at least 50 percent of the outer surface area of the fungal material either directly contacts a cooling bath or contacts a container that directly contacts a cooling bath during the freezing. In some specific embodiments, at least 65 percent of the outer surface area of the fungal material either directly contacts a cooling bath or contacts a container that directly contacts a cooling bath during the freezing. In some very specific embodiments, at least 80 percent of the outer surface area of the fungal material either directly contacts a cooling bath or contacts a container that directly contacts a cooling bath during the freezing.

In some embodiments, at least 50 percent of the outer surface area of the fungal material directly contacts a liquid or surface having a temperature of less than zero degrees Celsius during the freezing. In some specific embodiments, at least 65 percent of the outer surface area of the fungal material directly contacts a liquid or surface having a temperature of less than zero degrees Celsius during the freezing. In some very specific embodiments, at least 80 percent of the outer surface area of the fungal material directly contacts a liquid or surface having a temperature of less than zero degrees Celsius during the freezing.

In some embodiments, at least 50 percent of the outer surface area of the fungal material directly contacts a container, and at least 50 percent of the container directly contacts a liquid or surface having a temperature of less than zero degrees Celsius during the freezing. In some specific embodiments, at least 65 percent of the outer surface area of the fungal material directly contacts a container, and at least 65 percent of the container directly contacts a liquid or surface having a temperature of less than zero degrees Celsius during the freezing. In some very specific embodiments, at least 80 percent of the outer surface area of the fungal material directly contacts a container, and at least 80 percent of the container directly contacts a liquid or surface having a temperature of less than zero degrees Celsius during the freezing.

Various aspects of this disclosure relate to a container that contains a liquid and fungal material, wherein the liquid has a temperature of less than 0 degrees Celsius, and the fungal material comprises tryptamines selected from one or more of psilocybin, psilocin, baeocystin, norpsilocin, norbaeocystin, 4-HT, aeruginascin, 4-hydroxy-TMT, and DMT. In some specific embodiments, the container is a dewar. In some embodiments, the liquid is selected from liquid nitrogen, ethanol, acetone, and brine. In some embodiments, the container further contains dry ice, and the liquid is in thermal communication with the dry ice. In some embodiments, the liquid is in thermal communication with the fungal material. In some specific embodiments, the liquid is a food grade liquid, and the liquid directly contacts the fungal material. In some embodiments, at least 20 percent of the fungal material is submersed in the liquid. In some specific embodiments, at least 40 percent of the fungal material is submersed in the liquid. In some very specific embodiments, at least 60 percent of the fungal material is submersed in the liquid. In some specific embodiments, the container contains a flexible-plastic container, and the flexible-plastic container contains the fungal material. In some embodiments, the flexible-plastic container comprises or consists of polyethylene. In some embodiments, the flexible-plastic container is vacuum sealed. In some embodiments, the flexible-plastic container is hermetically sealed. In some embodiments, the flexible-plastic container contains less than 10 percent gas by volume. In some specific embodiments, the flexible-plastic container contains less than 5 percent gas by volume. In some very specific embodiments, the flexible-plastic container contains less than 2 percent gas by volume. In some embodiments, at least 20 percent of the flexible-plastic container is submersed in the liquid. In some specific embodiments, at least 40 percent of the flexible-plastic container is submersed in the liquid. In some very specific embodiments, at least 60 percent of the flexible-plastic container is submersed in the liquid. In some embodiments, the fungal material comprises water, and at least 40 percent of the water of the fungal material is frozen. In some specific embodiments, at least 60 percent of the water of the fungal material is frozen. In some very specific embodiments, at least 80 percent of the water of the fungal material is frozen.

Various aspects of this disclosure relate to a flexible-plastic container that contains fungal material that comprises tryptamines selected from one or more of psilocybin, psilocin, baeocystin, norpsilocin, norbaeocystin, 4-HT, aeruginascin, 4-hydroxy-TMT, and DMT. In some embodiments, the flexible-plastic container comprises or consists of polyethylene. In some embodiments, the flexible-plastic container is vacuum sealed. In some embodiments, the flexible-plastic container is hermetically sealed. In some embodiments, the flexible-plastic container contains less than 10 percent gas by volume. In some specific embodiments, the flexible-plastic container contains less than 5 percent gas by volume. In some very specific embodiments, the flexible-plastic container contains less than 2 percent gas by volume. In some embodiments, the fungal material comprises water, and at least 40 percent of the water of the fungal material is frozen. In some specific embodiments, at least 60 percent of the water of the fungal material is frozen. In some very specific embodiments, at least 80 percent of the water of the fungal material is frozen. In some embodiments, the flexible-plastic container is opaque to blue light. In some embodiments, the flexible-plastic container transmits no greater than 20 percent of light at wavelengths less than 500 nanometers. In some specific embodiments, the flexible-plastic container transmits no greater than 10 percent of light at wavelengths less than 500 nanometers.

After freezing, the fungal material is placed within a vacuum chamber to sublime water from the fungal material (e.g., by lyophilization). The rate of sublimation should be sufficient to inhibit the melting of ice crystals, which may be achieved by one, two, or each of (1) increasing vacuum (such as to less than 10 pascals, less than 5 pascals, or less than 2.5 pascals), (2) cooling the fungal material in the vacuum chamber (such as by performing the sublimation in a cold room), and (3) insulating the fungal material within the vacuum chamber such as by minimizing contact between the fungal material and surfaces of the vacuum chamber.

In some embodiments, the frozen fungal material is inserted into a container that is opaque to blue light such as a container that transmits no greater than 20 percent of light at wavelengths less than 500 nanometers prior to the sublimation or no greater than 10 percent of light at wavelengths less than 500 nanometers.

In some embodiments, the method comprises extracting fungal material or a tryptamine-containing composition such as a manufacturing intermediate or final product with a solvent. In some specific embodiments, the method comprises extracting the fungal material or tryptamine-containing composition with a solvent selected from water, methanol, ethanol, isopropanol, acetone, and acetic acid. In some very specific embodiments, the solvent is selected from water, ethanol, and acetic acid.

The term "solvent" as used in this disclosure refers to the most abundant chemical species in a liquid phase by mole.

In some embodiments, the method comprises extracting fungal material or a tryptamine-containing composition with water, and the method produces a composition that is relatively depleted of one or more of chitin, beta-glucan, indole-3-acetic acid, and tryptophol. Chitin is insoluble in water. While cereal beta-glucan is soluble in water because plants comprise cellulose synthase that adds beta-1,4 linkages to beta-glucan, fungal beta-glucan contains only beta-1,3 linkages and also includes short beta-1,6 branching, which renders fungal beta-glucan insoluble in water. Indole-3-acetic acid and tryptophol are both insoluble in water.

Aprotic solvents inhibit the spontaneous and enzyme-catalyzed dephosphorylation of tryptamines, and they also inhibit the spontaneous and enzyme-catalyzed oxidation of tryptamines. In some embodiments, one or more tryptamines of this disclosure are dissolved in an aprotic solvent. In some specific embodiments, one or more tryptamines of this disclosure are dissolved in an aprotic solvent selected from dichloromethane, chloroform, tetrachloroethylene, ethyl acetate, acetic anhydride, acetone, cyclopentanone, acetophenone, diethyl ether, methoxyethane, dimethoxymethane, dimethoxyethane, polyethylene glycol, tetrahydrofuran, tetrahydropyran, dioxolane, 1,4-dioxane, propylene carbonate, dimethyl sulfoxide, sulfolane, ammonia, ethylenediamine, acetonitrile, pyrrolidine, piperidine, pyridine, quinoline, morpholine, 2-pyrrolidone, N-methyl-2-pyrrolidone, formamide, N-methylformamide, dimethylformamide, acetamide, dimethylacetamide, tetramethylurea, 1,3-dimethyl-2-imidazolidinone, 1,3-dimethyl-1,3-diazinan-2-one, and nitrobenzene. The foregoing solvents as well as methanol, ethanol, isopropanol, and propylene glycol are appropriate for dissolving various tryptamines, for example, for quantification thereof or for the preparation of pharmaceuticals. As described in the Summary, anionic forms of phosphoryloxytryptamines are less soluble in aprotic solvents and alcohols than zwitterionic and cationic forms, and thus, an acid or buffer may necessary to convert anionic forms of phosphoryloxytryptamines into zwitterionic or cationic forms prior to or while dissolving the phosphoryloxytryptamines in an aprotic solvent or alcohol. Suitable acids include, without limitation, acetic acid and benzoic acid. Suitable buffers are described below. Non-toxic solvents such as water, ethanol, propylene glycol, glycerol, and acetic acid may be preferable to the foregoing aprotic solvents, methanol, and isopropanol, for example, in the manufacture of dietary supplements.

In some embodiments, the method comprises extracting the fungal material or the tryptamine-containing composition with a liquid phase, wherein the liquid phase comprises a solvent according to the preceding paragraph.

In some embodiments, a composition of this disclosure comprises one or more tryptamines and an aprotic solvent. In some specific embodiments, the aprotic solvent is selected from dichloromethane, chloroform, tetrachloroethylene, ethyl acetate, acetic anhydride, acetone, cyclopentanone, acetophenone, diethyl ether, methoxyethane, dimethoxymethane, dimethoxyethane, polyethylene glycol, tetrahydrofuran, tetrahydropyran, dioxolane, 1,4-dioxane, propylene carbonate, dimethyl sulfoxide, sulfolane, ammonia, ethylenediamine, acetonitrile, pyrrolidine, piperidine, pyridine, quinoline, morpholine, 2-pyrrolidone, N-methyl-2-pyrrolidone, formamide, N-methylformamide, dimethylformamide, acetamide, dimethylacetamide, tetramethylurea, 1,3-dimethyl-2-imidazolidinone, 1,3-dimethyl-1,3-diazinan-2-one, and nitrobenzene. In some even more specific embodiments, the aprotic solvent is not chloroform, petroleum ether, or acetone. In some very specific embodiments, the aprotic solvent is selected from dichloromethane, tetrachloroethylene, ethyl acetate, diethyl ether, dimethoxyethane, tetrahydrofuran, dioxolane, 1,4-dioxane, propylene carbonate, dimethyl sulfoxide, sulfolane, acetonitrile, pyrrolidine, piperidine, pyridine, quinoline, morpholine, N-methyl-2-pyrrolidone, formamide, N-methylformamide, dimethylformamide, acetamide, dimethylacetamide, tetramethylurea, 1,3-dimethyl-2-imidazolidinone, 1,3-dimethyl-1,3-diazinan-2-one, and nitrobenzene.

The term "aprotic solvent" as used in this disclosure refers to the compounds of the preceding paragraph and like chemical species regardless of whether such a compound is the most abundant chemical species in a liquid phase by mole. Some of the "aprotic" solvents of the preceding paragraph comprise an ionizable proton (e.g., acetamide, formamide), but such solvents are nevertheless considered aprotic because any ionization is insignificant under the conditions described by this disclosure.

Hydroxytryptamines such as psilocin are generally soluble in aprotic solvents whereas phosphoryloxytryptamines such as phosphoryloxytryptamines are less soluble in aprotic solvents, but phosphoryloxytryptamines may be converted from monoanionic forms (i.e., the prevalent form at neutral pH) to zwitterionic or cationic forms with an acid or buffer as described herein to increase the solubilities of the phosphoryloxytryptamines in aprotic solvents.

In some embodiments, the method comprises dissolving one or more tryptamines of a tryptamine-containing composition in an aprotic solvent. In some specific embodiments, the method comprises injecting a composition comprising one or more tryptamines and an aprotic solvent into an HPLC column. Various aspects of this disclosure relate to an HPLC column comprising a stationary phase, a mobile phase, an aprotic solvent, and one or more tryptamines, wherein the mobile phase comprises the aprotic solvent, and the one or more tryptamines are non-covalently bound to the stationary phase. The one or more tryptamines may comprise, for example, one or more of psilocybin and psilocin.

In some embodiments, the liquid phase comprises a chaotrope that is dissolved in the solvent. Without limiting this disclosure or any patent claim that matures from this disclosure, a chaotrope can lyse cells, which liberates tryptamines from the cells, and/or denature proteins, which inhibits the activity of phosphatases, esterases, and oxidoreductases. In some specific embodiments, the liquid phase comprises a chaotrope that is dissolved in the solvent, and the chaotrope is selected from guanidinium, urea, dissolved ammonium sulfate, methanol, ethanol, isopropanol, acetone, and acetic acid. In some very specific embodiments, the liquid phase comprises a chaotrope that is dissolved in the solvent, and the chaotrope is selected from guanidinium, urea, and dissolved ammonium sulfate. In some embodiments, the solvent is water.

Most chaotropes including guanidinium, urea, and dissolved ammonium sulfate are unsuitable for use in products for human consumption and, once added, cannot be separated to make a composition suitable for human consumption, at least in the United States. The preparation of a composition comprising a chaotrope (e.g., guanidinium, urea, and/or dissolved ammonium sulfate) and one or more tryptamines (e.g., psilocybin, baeocystin, norbaeocystin, psilocin, norpsilocin, 4-HT, aeruginascin, 4-hydroxy-TMT, and/or DMT) is therefore generally performed to quantify the tryptamines in the composition, for example, by liquid chromatography (e.g., with an ultraviolet/visible light absorbance or transmittance detector (UV/Vis detector), an infrared light absorbance or transmittance detector (IR detector), a diode array detector, a refractive index detector, a charged aerosol detector (CAD), an electrochemical detector (ECD), or a mass spectrometry detector (MS detector)) or by one or more enzyme-linked immunosorbent assays (ELISAs). Gas chromatography (GS) is not generally viable for quantifying heterogenous mixtures of tryptamines because the GS requires the vaporization of analytes, which spontaneously dephosphorylates phosphoryloxytryptamines into hydroxytryptamines. GS may nevertheless be useful to quantify, for example, equivalents of psilocybin (i.e., the combined concentration of psilocybin and psilocin), equivalents of baeocystin (i.e., the combined concentration of baeocystin and norpsilocin), equivalents of norbaeocystin (i.e., the combined concentration of norbaeocystin and 4-HT), equivalents of aeruginascin (i.e., the combined concentration of aeruginascin and 4-hydroxy-TMT), and DMT in heterogenous mixtures. Appropriate GS stationary phases include, without limitation, phenyl/methyl polysiloxane (e.g., 5 percent phenyl and 95 percent methyl polysiloxane; or 35 percent phenyl and 65 percent methyl polysiloxane). Conventional flame ionization detectors (FIDs) may be used to quantify equivalents of psilocybin as well as conventional thermal conductivity detectors (TCDs). Increased sensitivity may be required to detect equivalents of baeocystin, equivalents of norbaeocystin, equivalents of aeruginascin, and DMT depending upon their concentrations in a tryptamine-containing composition. Detectors that allow for increased sensitivity may be selected from one or more of an alkali flame detector (AFD), a flame photometric detector (FPD), a photoionization detector (PID), a discharge ionization detector (DID), a pulsed discharge ionization detector (PDD), an electron capture detector (ECD), a nitrogen-phosphorous detector (NPD), a Hall electrolytic conductivity detector (ELCD), a thermionic ionization detector (TID), a helium ionization detector (HID), an IR detector, a MS detector, and a vacuum ultraviolet detector (VUV detector). The preparation of a composition comprising a chaotrope is not generally performed to prepare compositions comprising one or more tryptamines for human consumption. A composition comprising a chaotrope and one or more tryptamines may nevertheless be prepared as a manufacturing intermediate of a pharmaceutical for human consumption, for example, in which a regulatory body (e.g., the FDA) reviews the manufacturing protocols to ensure sufficient removal of the chaotrope and/or otherwise ensure an appropriate balance of safety and efficacy in the final dosage form of the pharmaceutical.

In some embodiments, the liquid phase comprises the chaotrope at a concentration of at least 1 molar. In some specific embodiments, the liquid phase comprises the chaotrope at a concentration of at least 2 molar. In some very specific embodiments, the chaotrope is guanidinium, and the liquid phase comprises the guanidinium at a concentration of at least 4 molar (such as 8 molar). In some very specific embodiments, the chaotrope is urea, and the liquid phase comprises the urea at a concentration of at least 3 molar (such as 6 molar). In some very specific embodiments, the chaotrope is dissolved ammonium sulfate, and the liquid phase comprises the dissolved ammonium sulfate at a concentration of at least 2 molar (such as 4 molar). In some embodiments, the solvent of the liquid phase is water.

Various aspects of this disclosure relate to a composition comprising a liquid phase that comprises a solvent, a chaotrope, and one or more tryptamines. In some embodiments, the solvent is water; the chaotrope is selected from guanidinium, urea, and dissolved ammonium sulfate; and the one or more tryptamines are selected from psilocybin, psilocin, baeocystin, norpsilocin, norbaeocystin, 4-HT, aeruginascin, 4-hydroxy-TMT, and DMT. In some embodiments, the liquid phase comprises a denatured laccase enzyme. In some specific embodiments, the liquid phase comprises a denatured laccase enzyme that is encoded by an amino acid sequence having at least 90 percent sequence identity with the sequence set forth in SEQ ID NO: 1, SEQ ID NO: 2, and SEQ ID NO: 3. In some very specific embodiments, the liquid phase comprises a denatured laccase enzyme that comprises the amino acid sequence set forth in SEQ ID NO: 1, SEQ ID NO: 2, or SEQ ID NO: 3. SEQ ID NO: 1, SEQ ID NO: 2, and SEQ ID NO: 3 encode three different laccase enzymes found in *Psilocybe cubensis*.

SEQ ID NO: 1

```
MTVIEADSQSVQPLTVNEITIFAGQRYSFILYANNPVGNYWIRSQPTYPDDGIQGYAGGINSAILRY

SGAPAVNPTTKKASITIPLVEADLRPLYSPAAPGLPSPGAADVNIKLDISYNSPSETFFVNNFTFPE

VPVPVLLQILSGAQSANDLLPAGSVYTLPPNKVIEISMPGGRPGSPHPMHLHGHDFSVVRSAGSNRY

NYANPVRRDVVNIGREDTDNVTIRFKTDNSGPWILHCHIFMP
```

SEQ ID NO: 2

```
MILKTLKERYMTTFPKADSTLINGKGRYPKGKPAALSVVNVEYGKRYRLRLISITCDGSYTIFIDKH

PFTVIEADGQSVVPVRAIDALTIFAGQRYSVVIVANQPIGNYWIRAQRGVVQGNVDPFEGGLNSAIL

RYKGAEEVEPVPIPYIPPNRVLRETELHALIDPEAPGKPEQDGGDVNLHFSITYDEKTKMFLINGKY
```

-continued

```
FQPPKVPVLLQLLSGTPPEELLPEGSIFTLPRNKTISISMLPGEFDTPHPFHLHGHTFSVVRSANTT

DDPAPKYNYRDPVRRDTVNLGKVDSGSNVTIRFRTDNPGPWIFHCHVDWHLERGMAIVFAEAPEEAR

KEIHPPEEWHYLCPVEDNLPESLTSISTVAIPPPTATTIEPTPFINLL

                                                            SEQ ID NO: 3
MNFLLSIATLGLGLQAYAVMIGPSATLVIGNKNIAPDGIKRSAVLAGTSLDTLSFPGPVIRATKGDT

LSLNVVNQLTDATMLMGTSIHWHGFHQKGTSWADGVVGVTQCPIAPGHSFLYQFPTANQAGTFWYHS

HYSTQYCDGLRGALIVYDPTDPYRTWYDIDDESTIITLADWYHKAAPLQTLRTAKEDSVLINGQGRV

PGDKTTDSTPLSVINIIPQKRYRFRLISISCDPAFSESIDGHSMTVIEADSQSVQPLIVNEITIFAG

QRYSFILYANNPVGNYWIRSQPTYPDDGIQGYAGGINSAILRYSGAPAVNPTTKKASITIPLVEADL

RPLYSPAAPGLPSPGAADVNIKLDISYNSPSETFFVNNSTFPEVPVPVLLQILSGAQSANDLLPAGS

VYTLPPNKVIEISMPGGRPGSPHPMHLHGHDFSVVRSAGSNRYNYANPVRRDVVNIGMEDTDNVTIR

FKTDNSGPWILHCHIDWHIEAGLAVVFTEDIPSIQFSNPPPAWDQLCPIFNAIPPQKFH
```

The phrase, "denatured laccase enzyme that is encoded by an amino acid sequence," does not mean that the laccase enzyme has such an amino acid sequence, but instead that the laccase enzyme is biosynthetically produced from such an amino acid sequence, which amino acid sequence is typically altered by one or more post-translational modifications such as cleavage of a leader peptide sequence, splicing, other proteolytic cleavage, conjunction with one or more non-catalytic protein subunits, deamidation, citrullination, phosphorylation, acylation, glycosylation, etc.

A laccase enzyme may be encoded by an amino acid sequence that has less than 100 percent sequence identity with one of SEQ ID NO: 1, SEQ ID NO: 2, and SEQ ID NO: 3, for example, due to natural intra- or inter-species variation or due to bioengineered mutations.

Other fungi that biosynthetically produce tryptamines contain homologous laccase enzymes. Highly-conserved sequences of SEQ ID NO: 3 that are important for laccase enzyme activity include VLAG (SEQ ID NO: 4), FPGP (SEQ ID NO: 5), IHWHG (SEQ ID NO: 6), WADG (SEQ ID NO: 7), QCPI (SEQ ID NO: 8), WYHSH (SEQ ID NO: 9), QYCDGLRG (SEQ ID NO: 10), ITLADWYH (SEQ ID NO: 11), LING (SEQ ID NO: 12), RYRFR (SEQ ID NO: 13), FSIDGH (SEQ ID NO: 14), QRYS (SEQ ID NO: 15), NSAILRY (SEQ ID NO: 16), AAPG (SEQ ID NO: 17), PVLLQ (SEQ ID NO: 18), GSPHP (SEQ ID NO: 19), HLHGH (SEQ ID NO: 20), RDVV (SEQ ID NO: 21), TIRF (SEQ ID NO: 22), GPWI (SEQ ID NO: 23), and HCHIDWH (SEQ ID NO: 24). At least some of the foregoing sequences are typically present in homologous laccase enzymes.

In some embodiments, the liquid phase comprises a surfactant that is dissolved in the solvent. Without limiting this disclosure or any patent claim that matures from this disclosure, a surfactant can lyse cells, which liberates tryptamines from the cells, and/or denature proteins, which inhibits the activity of phosphatases, esterases, and oxidoreductases. In some specific embodiments, the liquid phase comprises a surfactant that is dissolved in the solvent, and the surfactant is selected from 2-[(4-alkyl)phenoxypolyethoxy]ethanol (e.g., Triton X-100, Triton X-114, Nonidet P-40), tergitol, Brij-35, Brig-58, dodecyl sulfate, polysorbate 20, polysorbate 80, lauroylsarcosine, digitonin, bile salts (e.g., cholate), cetrimonium bromide, 3-{dimethyl[3-(3α,7α,12α-trihydroxy-5β-cholan-24-amido)propyl]azaniumyl}propylsulfonate (CHAPS), 3-{dimethyl[3-(3α,7α,12α-trihydroxy-5β-cholan-24-amido)propyl]azaniumyl}-2-hydroxypropylsulfonate (CHAPSO), octyl β-D-glucopyranoside (octyl glucoside), and octyl 3-D-thioglucopyranoside (octylthioglucoside). In some very specific embodiments, the surfactant is dodecyl sulfate.

Most surfactants including those set forth in the preceding paragraph are unsuitable for use in products for human consumption and, once added, cannot be separated to make a composition suitable for human consumption, at least in the United States. The preparation of a composition comprising a surfactant (e.g., those set forth in the preceding paragraph) and one or more tryptamines (e.g., psilocybin, baeocystin, norbaeocystin, psilocin, norpsilocin, 4-HT, aeruginascin, 4-hydroxy-TMT, and/or DMT) is therefore generally performed to quantify the tryptamines in the composition, for example, by liquid chromatography, by one or more ELISAs, or potentially by gas chromatography as described herein. The preparation of a composition comprising a surfactant is not generally performed to prepare compositions comprising one or more tryptamines for human consumption. A composition comprising a surfactant and one or more tryptamines may nevertheless be prepared as a manufacturing intermediate of a pharmaceutical for human consumption, for example, in which a regulatory body (e.g., the FDA) reviews the manufacturing protocols to ensure sufficient removal of the surfactant and/or otherwise ensures an appropriate balance of safety and efficacy in the final dosage form of the pharmaceutical.

In some embodiments, the liquid phase comprises the surfactant at a concentration of at least 0.5 percent by volume. In some specific embodiments, the liquid phase comprises the surfactant at a concentration of at least 1 percent by volume. In some very specific embodiments, the liquid phase comprises the surfactant at a concentration of at least 2 percent by volume.

Various aspects of this disclosure relate to a composition comprising a liquid phase that comprises a solvent, a surfactant, and one or more tryptamines. In some embodiments, the solvent is water, and the one or more tryptamines are selected from psilocybin, psilocin, baeocystin, norpsilocin, norbaeocystin, 4-HT, aeruginascin, 4-hydroxy-TMT, and DMT. In some embodiments, the liquid phase comprises a denatured laccase enzyme. In some embodiments, the liquid phase comprises a denatured laccase enzyme that is encoded by an amino acid sequence having at least 90 percent sequence identity with the sequence set forth in SEQ ID NO: 1, SEQ ID NO: 2, or SEQ ID NO: 3. In some specific embodiments, the liquid phase comprises a denatured laccase enzyme that is encoded by an amino acid sequence having at least 95 percent sequence identity with the sequence set forth in SEQ ID NO: 1, SEQ ID NO: 2, or SEQ ID NO: 3. In some even more specific embodiments, the liquid phase comprises a denatured laccase enzyme that is encoded by an amino acid sequence having at least 98 percent sequence identity with the sequence set forth in SEQ ID NO: 1, SEQ ID NO: 2, or SEQ ID NO: 3. In some very specific embodiments, the liquid phase comprises a denatured laccase enzyme that is encoded by an amino acid sequence set forth in SEQ ID NO: 1, SEQ ID NO: 2, or SEQ ID NO: 3.

Various aspects of this disclosure relate to a composition comprising a liquid phase that comprises a solvent and one or more tryptamines, wherein the solvent is selected from methanol, ethanol, isopropanol, propylene glycol, glycerol, acetone, and acetic acid, and the one or more tryptamines are selected from psilocybin, psilocin, baeocystin, norpsilocin, norbaeocystin, 4-HT, aeruginascin, 4-hydroxy-TMT, and DMT. In some embodiments, the liquid phase comprises a denatured laccase enzyme. In some embodiments, the liquid phase comprises a denatured laccase enzyme that is encoded by an amino acid sequence having at least 90 percent sequence identity with the sequence set forth in SEQ ID NO: 1, SEQ ID NO: 2, or SEQ ID NO: 3. In some specific embodiments, the liquid phase comprises a denatured laccase enzyme that is encoded by an amino acid sequence having at least 95 percent sequence identity with the sequence set forth in SEQ ID NO: 1, SEQ ID NO: 2, or SEQ ID NO: 3. In some even more specific embodiments, the liquid phase comprises a denatured laccase enzyme that is encoded by an amino acid sequence having at least 98 percent sequence identity with the sequence set forth in SEQ ID NO: 1, SEQ ID NO: 2, or SEQ ID NO: 3. In some very specific embodiments, the liquid phase comprises a denatured laccase enzyme that is encoded by an amino acid sequence set forth in SEQ ID NO: 1, SEQ ID NO: 2, or SEQ ID NO: 3. In some embodiments, the composition comprises a solid phase, and the solid phase also comprises one or more tryptamines selected from psilocybin, psilocin, baeocystin, norpsilocin, norbaeocystin, 4-HT, aeruginascin, 4-hydroxy-TMT, and DMT.

In some embodiments, the liquid phase comprises a denatured laccase enzyme that comprises the amino acid sequence(s) set forth in one, two, three, four, five, six, seven, eight, nine, ten, eleven, twelve, thirteen, fourteen, fifteen, sixteen, seventeen, eighteen, nineteen, twenty, or each of SEQ ID NO: 4 to SEQ ID NO: 24, which amino acid sequence(s) are highly conserved in the laccase enzyme encoded by the amino acid sequence set forth in SEQ ID NO: 3 and important for laccase enzyme activity.

Various aspects of this disclosure relate to a composition comprising a liquid phase that comprises a solvent and one or more tryptamines, wherein the solvent is selected from water, methanol, ethanol, isopropanol, propylene glycol, glycerol, acetic acid, dichloromethane, chloroform, tetrachloroethylene, ethyl acetate, acetic anhydride, acetone, cyclopentanone, acetophenone, diethyl ether, methoxyethane, dimethoxymethane, dimethoxyethane, polyethylene glycol, tetrahydrofuran, tetrahydropyran, dioxolane, 1,4-dioxane, propylene carbonate, dimethyl sulfoxide, sulfolane, ammonia, ethylenediamine, acetonitrile, pyrrolidine, piperidine, pyridine, quinoline, morpholine, 2-pyrrolidone, N-methyl-2-pyrrolidone, formamide, N-methylformamide, dimethylformamide, acetamide, dimethylacetamide, tetramethylurea, 1,3-dimethyl-2-imidazolidinone, 1,3-dimethyl-1,3-diazinan-2-one, and nitrobenzene. In some specific embodiments, the solvent is selected from dichloromethane, chloroform, tetrachloroethylene, ethyl acetate, acetone, diethyl ether, dimethoxyethane, polyethylene glycol, tetrahydrofuran, dioxolane, 1,4-dioxane, propylene carbonate, dimethyl sulfoxide, sulfolane, acetonitrile, pyrrolidine, piperidine, pyridine, quinoline, morpholine, N-methyl-2-pyrrolidone, formamide, N-methylformamide, dimethylformamide, acetamide, dimethylacetamide, tetramethylurea, 1,3-dimethyl-2-imidazolidinone, 1,3-dimethyl-1,3-diazinan-2-one, and nitrobenzene. In some even more specific embodiments, the solvent is selected from dichloromethane, tetrachloroethylene, ethyl acetate, diethyl ether, dimethoxyethane, tetrahydrofuran, dioxolane, 1,4-dioxane, propylene carbonate, dimethyl sulfoxide, sulfolane, acetonitrile, pyrrolidine, piperidine, pyridine, quinoline, morpholine, N-methyl-2-pyrrolidone, formamide, N-methylformamide, dimethylformamide, acetamide, dimethylacetamide, tetramethylurea, 1,3-dimethyl-2-imidazolidinone, 1,3-dimethyl-1,3-diazinan-2-one, and nitrobenzene. In some very specific embodiments, the solvent is selected from water, methanol, ethanol, and acetic acid.

In some embodiments, the liquid phase comprises an antioxidant. In some specific embodiments, the antioxidant is selected from elemental iron, iron(II), ferrous carbonate, elemental zinc, bicarbonate, ascorbate, ascorbic acid, sorbate, sorbic acid, erythorbate, erythorbic acid, a tocopherol, a tocotrienol, hydroquinone, pyrogallol, gallate, gallic acid, propyl gallate, phenolsulfonate, phenolsulfonic acid, sulfite, bisulfite, disulfite, metabisulfite, phosphite, pyrophosphite, a phosphite ester, diethylhydroxylamine, hydrazine, carbohydrazide, and methyl ethyl ketone oxime.

Various aspects of this disclosure relate to liquid chromatography. In some embodiments, the liquid chromatography is selected from thin-layer chromatography (TLC), reverse-phase HPLC, normal-phase HPLC, hydrophilic interaction liquid chromatographic (HILIC), ion-exchange, size-exclusion, and capillary electrophoresis. In some specific embodiments, the liquid chromatography is reverse-phase HPLC.

Various aspects of this disclosure relate to a liquid chromatography column. In some embodiments, the liquid chromatography column is selected from a reverse-phase HPLC column (e.g., comprising a stationary phase comprising alkyl chains), a normal-phase HPLC column (e.g., comprising a silica stationary phase), a flash chromatography column, an ion-exchange column, a size-exclusion column, and a capillary electrophoresis column. In some specific embodiments, the liquid chromatography column is a reverse-phase HPLC column. In some very specific embodiments, the liquid chromatography column is a reverse-phase HPLC column that comprises a stationary phase that comprises octadecyloxysilyl-functionalized silica gel particles (e.g., C18, type-B silica), octyloxysilyl-functionalized silica gel particles (e.g., C8, type-B silica), butyloxysilyl-functionalized silica gel particles (e.g., C4, type-B silica), propyloxysilyl-functionalized silica gel particles (e.g., C3, type-B silica), phenylpropyloxysilyl-functionalized silica gel particles (e.g., phenyl, type-B silica), cyanopropyloxysilyl-functionalized silica gel particles (e.g., cyano, type-B silica), aminopropyloxysilyl-functionalized silica gel particles (e.g., amino, type-B silica), octadecylsilyl-functionalized silica gel particles (e.g., C18, type-C silica), octylsilyl-functionalized silica gel particles (e.g., C8, type-C silica), butylsilyl-functionalized silica gel particles (e.g., C4, type-C silica), propylsilyl-functionalized silica gel particles (e.g., C3, type-C silica), phenylpropylsilyl-functionalized silica gel particles (e.g., phenyl, type-C silica), cyanopropylsilyl-functionalized silica gel particles (e.g., cyano, type-C silica), aminopropylsilyl-functionalized silica gel particles (e.g., amino, type-C silica), and 1-oxoalkylamidoalkysilyl-functionalized silica gel particles (e.g., amide, type-C silica, as in ASCENTIS® Express RP-Amide). While conventional alkyloxysilane and alkylsilane stationary phases are suitable for resolving different tryptamines, specialty and mixed-mode stationary phases can improve quantification such as stationary phases with phenyl functional groups that allow for pi-pi interactions between the phenyl functional groups and tryptamine indoles.

HPLC was historically run under acidic conditions because neutral and alkaline conditions risked hydrolyzing the silica and alkyloxysilyl functional groups of type-A silica. Type-A silica generally contains, for example, (1) metal cation impurities that can catalyze the dissolution of silica under neutral and alkaline conditions, (2) heterogeneous silanol groups that are more susceptible to nucleophilic attack under neutral and alkaline conditions, and (3) smaller pores and higher surface area that limit flow and allow localized pockets of mobile phase, which provide opportunities for hydrolysis. Type-B silica contains negligible metal cation impurities, more uniform silanol groups, less acidic silanol groups, larger pores, and less surface area, which improve the chemical stability of type-B stationary phases relative to type-A stationary phases. Type-C silica replaces alkyloxysilane chemistry with alkysilyl chemistry, which further improves chemical stability. Despite the improvements of type-B and type-C columns, most HPLC protocols continue to acidify the mobile phase, e.g., with 0.1 percent trifluoroacetic acid or formic acid, because the stationary phases remain susceptible to hydrolysis, because uniform pH is often necessary for reproducible separations, and because compelling reasons infrequently exist to adjust pH. Without limiting this disclosure or any patent claim that matures from this disclosure, acidic conditions risk hydrolyzing the phosphate groups of psilocybin, baeocystin, norbaeocystin, and aeruginascin into psilocin, norpsilocin, 4-HT, and 4-hydroxy-TMT, which impairs the accurate quantification of tryptamines.

In some embodiments, the silica of the stationary phase of the reverse-phase HPLC column is type-B silica or type-C silica. Type-A silica is more susceptible to hydrolysis at neutral pH than type-B silica and type-C silica, and type-A silica is therefore avoided in various embodiments of this disclosure. When type-C silica is used, then the attachment of the hydrocarbon portion of the stationary phase may either be standard monodentate chemistry or bidentate chemistry, in which bidentate attachment chemistry the alkyl chains (e.g., the octyl groups of a C8 column) are generally attached to two silane groups (instead of one silane group as employed in standard monodentate chemistry), which results in dual covalent attachment of each alkyl chain to two different silanes.

In some embodiments, the liquid chromatography column comprises a mobile phase, and the mobile phase has a pH that is greater than 3. In some specific embodiments, the liquid chromatography column comprises a mobile phase, and the mobile phase has a pH that is greater than 4. In some very specific embodiments, the liquid chromatography column comprises a mobile phase, and the mobile phase has a pH that is at least 5 and no greater than 8.

In some embodiments, the reverse-phase HPLC column comprises a mobile phase, and the mobile phase has a pH that is greater than 3. In some specific embodiments, the reverse-phase HPLC column comprises a mobile phase, and the mobile phase has a pH that is greater than 4. In some very specific embodiments, the reverse-phase HPLC column comprises a mobile phase, and the mobile phase has a pH that is at least 5 and no greater than 8.

In some embodiments, the liquid chromatography column comprises a mobile phase that comprises a chaotrope and one or more tryptamines. The mobile phase will comprise a chaotrope, for example, after loading the liquid chromatography column with a sample comprising the chaotrope such as a sample obtained by extracting the one or more tryptamines in a solvent comprising the chaotrope. In some specific embodiments, the liquid chromatography column comprises a mobile phase that comprises (i) a chaotrope selected from guanidinium, urea, and dissolved ammonium sulfate and (ii) one or more tryptamines selected from psilocybin, psilocin, baeocystin, norpsilocin, norbaeocystin, 4-HT, aeruginascin, 4-hydroxy-TMT, and DMT.

In some embodiments, the liquid chromatography column comprises a chaotrope and one or more tryptamines. In some specific embodiments, the liquid chromatography column comprises guanidinium and psilocybin. In some specific embodiments, the liquid chromatography column comprises guanidinium and psilocin. In some specific embodiments, the liquid chromatography column comprises urea and psilocybin. In some specific embodiments, the liquid chromatography column comprises urea and psilocin. In some specific embodiments, the liquid chromatography column comprises dissolved ammonium sulfate and psilocybin. In some specific embodiments, the liquid chromatography column comprises dissolved ammonium sulfate and psilocin.

In some embodiments, the liquid chromatography column comprises a surfactant and one or more tryptamines. In some specific embodiments, the liquid chromatography column comprises dodecyl sulfate and psilocybin. In some specific embodiments, the liquid chromatography column comprises dodecyl sulfate and psilocin.

Various aspects of this disclosure relate to compositions that comprise reduced concentrations of oxidized forms of tryptamines, e.g., relative to psychoactive tryptamines.

A first oxidation product of psilocin is a diol, which has the approximate molecular weight of 221 atomic mass units. Such diols have the chemical formulas 3-[2-(dimethylazaniumyl)ethyl]-1H-indol-2,4-diol; 3-[2-(dimethylazaniumyl)ethyl]-1H-indol-4,5-diol; and 3-[2-(dimethylazaniumyl)ethyl]-1H-indol-4,7-diol.

The term “approximate molecular weight” refers to the molecular weight of a compound calculated using the standard atomic weight of each atom in the compound; the approximate molecular weight has a precision of plus or minus 1 atomic mass unit. The actual molecular weight of a compound depends primarily upon whether the atoms of the compound are derived from atmospheric sources (e.g., the carbon sources of the growth media are derived from plants that converted carbon dioxide into carbohydrates and lipids by photosynthesis) or petrochemical sources (e.g., the compound is a reference standard that was synthesized from building blocks derived from oil). Actual molecular weight may be determined, for example, by mass spectroscopy.

Various aspects of this disclosure relate to a composition comprising psilocin and one or more oxidized diols of psilocin, wherein the one or more oxidized diols of psilocin are selected from 3-[2-(dimethylazaniumyl)ethyl]-1H-indol-2,4-diol; 3-[2-(dimethylazaniumyl)ethyl]-1H-indol-4,5-diol; and 3-[2-(dimethylazaniumyl)ethyl]-1H-indol-4,7-diol.

In some embodiments, the composition comprises psilocybin and psilocin at a combined concentration of at least 4 percent and no greater than 80 percent by dry weight, and the composition comprises the psilocin and the one or more oxidized diols of psilocin at a mole ratio of at least 1:1 (psilocin:one or more oxidized diols of psilocin). In some specific embodiments, the composition comprises the psilocin and the one or more oxidized diols of psilocin at a mole ratio of at least 5:1. In some very specific embodiments, the composition comprises the psilocin and the one or more oxidized diols of psilocin at a mole ratio of at least 10:1. Such compositions may be formulated by protecting compositions comprising psilocybin from dephosphorylation and protecting compositions comprising psilocin from oxidation as described herein.

"Percent by dry weight" refers to percent by weight of a composition after either physically removing solvents (e.g., water, alcohols, acetone, acetic acid) from the composition (e.g., by lyophilization) or by calculating the percent by weight if such solvents were removed from the composition. Naturally-occurring sources of tryptamines are unknown to result in compositions comprising much more than 1 percent tryptamines by dry weight, and thus, a composition comprising, "psilocybin and psilocin at a combined concentration of at least 4 percent . . . by dry weight" refers to a composition in which the psilocybin and psilocin are at least partially purified. Prior art attempts to partially purify psilocybin and/or psilocin result in dephosphorylation of the psilocybin into psilocin (e.g., spontaneously by hydrolysis and/or enzymatically by a fungal phosphatase or esterase) and oxidation of psilocin into oxidation products (e.g., spontaneously by oxygen and/or reactive oxygen species and/or enzymatically by fungal oxidoreductases), and thus, prior art compositions are not known to result in the relatively high ratios of tryptamines (e.g., psilocybin and psilocin) to oxidation products (e.g., the one or more oxidized diols of psilocin) disclosed herein. Purified psilocin (e.g., purified by crystallization or HPLC) nevertheless comprises the ratios disclosed herein (i.e., because the mole ratio approaches infinity), but a composition comprising "psilocybin and psilocin at a combined concentration of . . . no greater than 80 percent by dry weight" excludes purified psilocin. Other features such as solvents, chaotropes, surfactants, antioxidants, chelators, fungal molecules, and the oxidization products of a tryptamine itself (e.g., psilocin), which exist in partially-purified compositions, may further differentiate partially-purified compositions of this disclosure from compositions comprising purified tryptamines that might otherwise exhibit a relatively high ratio of tryptamines to oxidation products (e.g., a mole ratio of infinity), and the skilled person will immediately recognize the various combinations of features set forth in this disclosure that differentiate partially-purified compositions from compositions prepared from a completely-purified tryptamine.

In some embodiments, the composition comprises psilocybin and psilocin at a combined concentration of at least 4 percent and no greater than 40 percent by dry weight. In some specific embodiments, the composition comprises psilocybin and psilocin at a combined concentration of at least 6 percent and no greater than 32 percent by dry weight. In some very specific embodiments, the composition comprises psilocybin and psilocin at a combined concentration of at least 8 percent and no greater than 24 percent by dry weight.

In some embodiments, the composition comprises psilocybin, psilocin, and one or more oxidized diols of psilocin; the composition is formulated for human consumption; and the composition comprises the psilocin and the one or more oxidized diols of psilocin at a mole ratio of at least 1:1 (psilocin:one or more oxidized diols of psilocin). In some specific embodiments, the composition comprises the psilocin and the one or more oxidized diols of psilocin at a mole ratio of at least 5:1. In some very specific embodiments, the composition comprises the psilocin and the one or more oxidized diols of psilocin at a mole ratio of at least 10:1.

The term "formulated for human consumption" refers to compositions that can be orally administered such as chocolate, compositions comprising chocolate, a capsule, a pill, a tea, or a dietary supplement (such as a powder).

The mole ratio of psilocin to the one or more oxidized diols of psilocin (psilocin:one or more oxidized diols of psilocin) is indicative of the extraction methods of this disclosure (and not indicative of prior-art methods that fail to adequately control for the oxidation of psilocin and that therefore produce relatively low mole ratios of psilocin to the oxidized diols, which oxidation correlates with the blue coloration observed, for example, in prior-art manufacturing intermediates as described infra).

The oxidized diols of psilocin remain capable of binding 5-HT receptors generally (and 5HT2A specifically) and exhibiting desirable pharmacological effects. In some embodiments, a composition comprises one or more oxidized diols of psilocin. In some specific embodiments, a composition comprises 3-[2-(dimethylazaniumyl)ethyl]-1H-indol-2,4-diol. In some specific embodiments, a composition comprises 3-[2-(dimethylazaniumyl)ethyl]-1H-indol-4,5-diol. In some specific embodiments, a composition comprises 3-[2-(dimethylazaniumyl)ethyl]-1H-indol-4,7-diol.

A second oxidation product of psilocin is a dione, which has the approximate molecular weight of 219 atomic mass units. Such diones have the chemical formulas 3-[2-(dimethylazaniumyl)ethyl]-1H-indol-2,4-dione; 3-[2-(dimethylazaniumyl)ethyl]-1H-indol-4,5-dione; and 3-[2-(dimethylazaniumyl)ethyl]-1H-indol-4,7-dione and also include tautomers of the foregoing. The tautomers of the foregoing are not "diones" themselves, but the term "oxidized diones of psilocin" as used herein nevertheless includes the tautomers of the foregoing. 3-[2-(dimethylazaniumyl)ethyl]-2-hydroxyindol-4-one and 3-[2-(dimethylazaniumyl)ethyl]-4-hydroxyindol-2-one are the tautomers of 3-[2-(dimethylazaniumyl)ethyl]-1H-indol-2,4-dione. 3-[2-(dimethylazaniumyl)ethyl]-4-hydroxyindol-5-one and 3-[2-(dimethylazaniumyl)ethyl]-5-hydroxyindol-4-one are the tautomer of 3-[2-(dimethylazaniumyl)ethyl]-1H-indol-4,5-dione. 3-[2-(dimethylazaniumyl)ethyl]-4-hydroxyindol-7-one and 3-[2-(dimethylazaniumyl)ethyl]-7-hydroxyindol-4-one are the tautomers of 3-[2-(dimethylazaniumyl)ethyl]-1H-indol-4,7-dione.

Various aspects of this disclosure relate to a composition comprising psilocin and one or more oxidized diones of psilocin, wherein the one or more oxidized diones of psilocin are selected from 3-[2-(dimethylazaniumyl)ethyl]-1H-indol-2,4-dione; 3-[2-(dimethylazaniumyl)ethyl]-1H-indol-4,5-dione; 3-[2-(dimethylazaniumyl)ethyl]-1H-indol-4,7-dione; and one or more tautomers of the foregoing.

In some embodiments, the composition comprises psilocybin and psilocin at a combined concentration of at least 4 percent and no greater than 80 percent by dry weight, and the composition comprises the psilocin and the one or more oxidized diones of psilocin at a mole ratio of at least 1:1 (psilocin:one or more oxidized diones of psilocin). In some specific embodiments, the composition comprises the psilocin and the one or more oxidized diones of psilocin at a mole ratio of at least 5:1. In some very specific embodiments, the composition comprises the psilocin and the one or more oxidized diones of psilocin at a mole ratio of at least 10:1. Such compositions may be formulated by protecting compositions comprising psilocybin from dephosphorylation and protecting compositions comprising psilocin from oxidation as described herein.

In some embodiments, the composition comprises psilocybin and psilocin at a combined concentration of at least 4 percent and no greater than 40 percent by dry weight. In some specific embodiments, the composition comprises psilocybin and psilocin at a combined concentration of at least 6 percent and no greater than 32 percent by dry weight. In some very specific embodiments, the composition comprises psilocybin and psilocin at a combined concentration of at least 8 percent and no greater than 24 percent by dry weight.

In some embodiments, the composition comprises psilocybin, psilocin, and one or more oxidized diones of psilocin; the composition is formulated for human consumption; and the composition comprises the psilocin and the one or more oxidized diones of psilocin at a mole ratio of at least 1:1 (psilocin:one or more oxidized diones of psilocin). In some specific embodiments, the composition comprises the psilocin and the one or more oxidized diones of psilocin at a mole ratio of at least 5:1. In some very specific embodiments, the composition comprises the psilocin and the one or more oxidized diones of psilocin at a mole ratio of at least 10:1.

The mole ratio of psilocin to the one or more oxidized diones of psilocin (psilocin:one or more oxidized diones of psilocin) is indicative of the extraction methods of this disclosure (and not indicative of prior-art methods that fail to adequately control for the oxidation of psilocin and that therefore produce relatively low mole ratios of psilocin to the oxidized diones, which oxidation correlates with the blue coloration observed, for example, in prior-art manufacturing intermediates as described infra).

The oxidized diones of psilocin remain capable of binding 5-HT receptors generally (and 5HT2A specifically) and exhibiting desirable pharmacological effects. In some embodiments, a composition comprises one or more oxidized diones of psilocin. In some specific embodiments, the composition comprises 3-[2-(dimethylazaniumyl)ethyl]-1H-indol-2,4-dione. In some specific embodiments, the composition comprises 3-[2-(dimethylazaniumyl)ethyl]-2-hydroxyindol-4-one. In some specific embodiments, the composition comprises 3-[2-(dimethylazaniumyl)ethyl]-4-hydroxyindol-2-one. In some specific embodiments, the composition comprises 3-[2-(dimethylazaniumyl)ethyl]-1H-indol-4,5-dione. In some specific embodiments, the composition comprises 3-[2-(dimethylazaniumyl)ethyl]-4-hydroxyindol-5-one. In some specific embodiments, the composition comprises 3-[2-(dimethylazaniumyl)ethyl]-5-hydroxyindol-4-one. In some specific embodiments, the composition comprises 3-[2-(dimethylazaniumyl)ethyl]-1H-indol-4,7-dione. In some specific embodiments, the composition comprises 3-[2-(dimethylazaniumyl)ethyl]-4-hydroxyindol-7-one. In some specific embodiments, the composition comprises 3-[2-(dimethylazaniumyl)ethyl]-7-hydroxyindol-4-one.

A third oxidation product of psilocin is a diol dimer, which has the approximate molecular weight of 409 atomic mass units. Such diol dimers have the chemical formulas 3-[2-(dimethylazaniumyl)ethyl]-2-{3-[2-(dimethylazaniumyl)ethyl]-4-hydroxy-1H-indol-2-yl}-1H-indol-4-ol; 3-[2-(dimethylazaniumyl)ethyl]-2-{3-[2-(dimethylazaniumyl)ethyl]-4-hydroxy-1H-indol-5-yl}-1H-indol-4-ol; 3-[2-(dimethylazaniumyl)ethyl]-2-{3-[2-(dimethylazaniumyl)ethyl]-4-hydroxy-1H-indol-7-yl}-1H-indol-4-ol; 3-[2-(dimethylazaniumyl)ethyl]-5-{3-[2-(dimethylazaniumyl)ethyl]-4-hydroxy-1H-indol-5-yl}-1H-indol-4-ol; 3-[2-(dimethylazaniumyl)ethyl]-5-{3-[2-(dimethylazaniumyl)ethyl]-4-hydroxy-1H-indol-7-yl}-1H-indol-4-ol; and 3-[2-(dimethylazaniumyl)ethyl]-7-{3-[2-(dimethylazaniumyl)ethyl]-4-hydroxy-1H-indol-7-yl}-1H-indol-4-ol.

3-[2-(dimethylazaniumyl)ethyl]-2-{3-[2-(dimethylazaniumyl)ethyl]-4-hydroxy-1H-indol-2-yl}-1H-indol-4-ol lacks problematic sterics and are prominent species of the oxidized diol dimers.

3-[2-(dimethylazaniumyl)ethyl]-2-{3-[2-(dimethylazaniumyl)ethyl]-4-hydroxy-1H-indol-5-yl}-1H-indol-4-ol contains a steric clash between the hydroxy of the indol-5-yl and the ethyl of the indol-4-ol, and thus, may be minor or absent species of the oxidized diol dimers.

3-[2-(dimethylazaniumyl)ethyl]-2-{3-[2-(dimethylazaniumyl)ethyl]-4-hydroxy-1H-indol-7-yl}-1H-indol-4-ol contains a slight steric clash between the indole 1H protons, and thus, are less prominent species of the oxidized diol dimers.

3-[2-(dimethylazaniumyl)ethyl]-5-{3-[2-(dimethylazaniumyl)ethyl]-4-hydroxy-1H-indol-5-yl}-1H-indol-4-ol lacks problematic sterics and are prominent species of the oxidized diol dimers.

3-[2-(dimethylazaniumyl)ethyl]-5-{3-[2-(dimethylazaniumyl)ethyl]-4-hydroxy-1H-indol-7-yl}-1H-indol-4-ol contains a steric clash between the hydroxy of the indol-4-ol and the 1H proton of the indol-7-yl, and thus, may be minor or absent species of the oxidized diol dimers.

3-[2-(dimethylazaniumyl)ethyl]-7-{3-[2-(dimethylazaniumyl)ethyl]-4-hydroxy-1H-indol-7-yl}-1H-indol-4-ol contains a slight steric clash between the 1H protons of each indole and the 6H protons of the opposite indole, and thus, are less prominent species of the oxidized diol dimers.

Various aspects of this disclosure relate to a composition comprising psilocin and one or more oxidized diol dimers of psilocin, wherein the one or more oxidized diol dimers of psilocin are selected from 3-[2-(dimethylazaniumyl)ethyl]-2-{3-[2-(dimethylazaniumyl)ethyl]-4-hydroxy-1H-indol-2-yl}-1H-indol-4-ol; 3-[2-(dimethylazaniumyl)ethyl]-2-{3-[2-(dimethylazaniumyl)ethyl]-4-hydroxy-1H-indol-5-yl}-1H-indol-4-ol; 3-[2-(dimethylazaniumyl)ethyl]-2-{3-[2-(dimethylazaniumyl)ethyl]-4-hydroxy-1H-indol-7-yl}-1H-indol-4-ol; 3-[2-(dimethylazaniumyl)ethyl]-5-{3-[2-(dimethylazaniumyl)ethyl]-4-hydroxy-1H-indol-5-yl}-1H-indol-4-ol; 3-[2-(dimethylazaniumyl)ethyl]-5-{3-[2-(dimethylazaniumyl)ethyl]-4-hydroxy-1H-indol-7-yl}-1H-indol-4-ol; and 3-[2-(dimethylazaniumyl)ethyl]-7-{3-[2-(dimethylazaniumyl)ethyl]-4-hydroxy-1H-indol-7-yl}-1H-indol-4-ol.

In some embodiments, the composition comprises psilocybin and psilocin at a combined concentration of at least 4 percent and no greater than 80 percent by dry weight, and the composition comprises the psilocin and the one or more oxidized diol dimers of psilocin at a mole ratio of at least 1:1 (psilocin:one or more oxidized diol dimers of psilocin). In some specific embodiments, the composition comprises the psilocin and the one or more oxidized diol dimers of psilocin at a mole ratio of at least 5:1. In some very specific embodiments, the composition comprises the psilocin and the one or more oxidized diol dimers of psilocin at a mole ratio of at least 10:1. Such compositions may be formulated by protecting compositions comprising psilocybin from dephosphorylation and protecting compositions comprising psilocin from oxidation as described herein.

In some embodiments, the composition comprises psilocybin and psilocin at a combined concentration of at least 4 percent and no greater than 40 percent by dry weight. In some specific embodiments, the composition comprises psilocybin and psilocin at a combined concentration of at least 6 percent and no greater than 32 percent by dry weight. In some very specific embodiments, the composition comprises psilocybin and psilocin at a combined concentration of at least 8 percent and no greater than 24 percent by dry weight.

In some embodiments, the composition comprises psilocybin, psilocin, and one or more oxidized diol dimers of psilocin; the composition is formulated for human consumption; and the composition comprises the psilocin and the one or more oxidized diol dimers of psilocin at a mole ratio of at least 1:1 (psilocin:one or more oxidized diol dimers of psilocin). In some specific embodiments, the composition comprises the psilocin and the one or more oxidized diol dimers of psilocin at a mole ratio of at least 5:1. In some very specific embodiments, the composition comprises the psilocin and the one or more oxidized diol dimers of psilocin at a mole ratio of at least 10:1.

The oxidized diol dimers of psilocin lack any appreciable binding affinity to 5-HT receptors and lack any known pharmacological effects. The mole ratio of psilocin to the one or more oxidized diol dimers of psilocin (psilocin:one or more oxidized diol dimers of psilocin) is instead indicative of the extraction methods of this disclosure (and not indicative of prior-art methods that fail to adequately control for the oxidation of psilocin and that therefore produce relatively low mole ratios of psilocin to the oxidized diol dimers, which oxidation correlates with the blue coloration observed, for example, in prior-art manufacturing intermediates as described in the following paragraph).

A fourth oxidation product of psilocin is a 5-oxo-dimethyltryptamine-ylidene (5-oxo-DMT-ylidene) dimer, which has the approximate molecular weight of 407 atomic mass units. Such 5-oxo-DMT-ylidene dimers constitute the initial oxidation products of psilocin that absorb visible light to result in the characteristic blue coloration indicative of tryptamine-containing fungi. As described supra, psychedelic tryptamines absorb ultraviolet light and do not absorb appreciable amounts of visible light. Monomeric oxidation products of tryptamines similarly absorb ultraviolet light and do not absorb appreciable amounts of visible light. The diol dimers described supra absorb both ultraviolet light and visible light and display brownish coloration. Only the 5-oxo-DMT-ylidene dimers and oxidation products thereof (e.g., higher-order oligomers including trimers, tetramers, etc.) display sufficiently-conjugated pi electron systems to absorb wavelengths of visible light that allow for the characteristic blue coloration indicative of tryptamine-containing fungi. Unlike the monomeric forms of dephosphorylated tryptamines and oxidized monomers thereof, dimeric forms of tryptamines including the oxidized diols of psilocin described above as well as the 5-oxo-DMT-ylidene dimers are incapable of binding 5-HT receptors with pharmacologically-relevant affinity or otherwise exhibiting pharmacologically-relevant effects. The presence of 5-oxo-DMT-ylidene dimers and other oxidation products of psychedelic tryptamines that display a blue coloration is nevertheless desirable in contemporary psychedelic-tryptamine-containing products (such as dried fruiting bodies of the genus *Psilocybe*) because blue coloration correlates with potency. Without performing the extraction methods and quantitative analytical chemical analyses described herein, a strong blue coloration is indicative of concentrated psychedelic tryptamines—and a potent product or manufacturing intermediate—and such blue coloration may be qualitatively assessed by mere visual inspection with the naked eye. In contrast with contemporary qualitative assessments of tryptamine-containing materials to identify blue coloration, the present disclosure teaches that any blue coloration of tryptamine-containing compositions should be minimized because such blue coloration is indicative of pharmacologically-inactive oxidation products of tryptamines and a poor-understanding and/or control for the oxidative degradation of psychedelic tryptamines into pharmacologically-inactive dimers and higher-order oligomers. Additionally, contemporary manufacturers of tryptamine-containing products generally find that fruiting bodies are desirable relative to mycelium and sclerotium, for example, because fruiting bodies are readily identifiable as mushrooms whereas mycelium and sclerotium may require technical expertise and/or analysis (e.g., microscopy) to identify. This disclosure suggests that mycelium and sclerotium constitute superior natural products from which psychedelic tryptamines may be extracted, for example, because mycelium and sclerotium constitute fewer structural proteins and problematic oxidoreductases that confound the extraction of tryptamines relative to fruiting bodies.

5-oxo-DMT-ylidene dimers have the chemical formulas 3-[2-(dimethylazaniumyl)ethyl]-2-{3-[2-(dimethylazaniumyl)ethyl]-4-oxo-1H-indol-2-ylidene}-1H-indol-4-one; 3-[2-(dimethylazaniumyl)ethyl]-2-{3-[2-(dimethylazaniumyl)ethyl]-4-oxo-1H-indol-5-ylidene}-1H-indol-4-one; 3-[2-(dimethylazaniumyl)ethyl]-2-{3-[2-(dimethylazaniumyl)ethyl]-4-oxo-1H-indol-7-ylidene}-1H-indol-4-one; 3-[2-(dimethylazaniumyl)ethyl]-5-{3-[2-(dimethylazaniumyl)ethyl]-4-oxo-1H-indol-5-ylidene}-1H-indol-4-one; 3-[2-(dimethylazaniumyl)ethyl]-5-{3-[2-(dimethylazaniumyl)ethyl]-4-oxo-1H-indol-7-ylidene}-1H-indol-4-one; 3-[2-(dimethylazaniumyl)ethyl]-7-{3-[2-(dimethylazaniumyl)ethyl]-4-oxo-1H-indol-7-ylidene}-1H-indol-4-one and also include tautomers of the foregoing. The tautomers of the foregoing are not technically "5-oxo-DMT-ylidene dimers" themselves because one or both of the two oxo groups are reduced to hydroxy in the tautomers, but the term "5-oxo-DMT-ylidene dimers" as used herein nevertheless includes the tautomers of the foregoing.

3-[2-(dimethylazaniumyl)ethyl]-2-{3-[2-(dimethylazaniumyl)ethyl]-4-oxo-1H-indol-2-ylidene}-1H-indol-4-one lacks any problematic sterics and is a prominent species of the 5-oxo-DMT-ylidene dimers. The tautomers of 3-[2-(dimethylazaniumyl)ethyl]-2-{3-[2-(dimethylazaniumyl)ethyl]-4-oxo-1H-indol-2-ylidene}-1H-indol-4-one are 3-[2-(dimethylazaniumyl)ethyl]-2-{3-[2-(dimethylazaniumyl)ethyl]-4-hydroxyindol-2-ylidene}-1H-indol-4-one; 3-[2-(dimethylazaniumyl)ethyl]-2-{3-[2-(dimethylazaniumyl)ethyl]-4-hydroxy-1H-indol-2-yl}indol-4-one; and 3-[2-(dimethylazaniumyl)ethyl]-2-{3-[2-(dimethylazaniumyl)ethyl]-4-hydroxyindol-2-ylidene}indol-4-ol.

3-[2-(dimethylazaniumyl)ethyl]-2-{3-[2-(dimethylazaniumyl)ethyl]-4-oxo-1H-indol-5-ylidene}-1H-indol-4-one contains an interaction between the lone pairs of the 4-oxo group of the indol-5-ylidene and the 1-protons of the ethyl of the indol-4-one, which constrained configuration might be challenging to produce, and thus, the 3-[2-(dimethylazaniumyl)ethyl]-2-{3-[2-(dimethylazaniumyl)ethyl]-4-oxo-1H-indol-5-ylidene}-1H-indol-4-one may be less prominent than other species of the 5-oxo-DMT-ylidene dimers. The tautomers of 3-[2-(dimethylazaniumyl)ethyl]-2-{3-[2-(dimethylazaniumyl)ethyl]-4-oxo-1H-indol-5-ylidene}-1H-indol-4-one are 3-[2-(dimethylazaniumyl)ethyl]-2-{3-[2-(dimethylazaniumyl)ethyl]-4-hydroxyindol-5-ylidene}-1H-indol-4-one; 3-[2-(dimethylazaniumyl)ethyl]-5-{3-[2-(dimethylazaniumyl)ethyl]-4-hydroxyindol-2-ylidene}-1H-indol-4-one; 3-[2-(dimethylazaniumyl)ethyl]-2-{3-[2-

(dimethylazaniumyl)ethyl]-4-hydroxy-1H-indol-5-yl}indol-4-one; 3-[2-(dimethylazaniumyl)ethyl]-5-{3-[2-(dimethylazaniumyl)ethyl]-4-hydroxy-1H-indol-2-yl}indol-4-one; and 3-[2-(dimethylazaniumyl)ethyl]-2-{3-[2-(dimethylazaniumyl)ethyl]-4-hydroxyindol-5-ylidene}indol-4-ol.

3-[2-(dimethylazaniumyl)ethyl]-2-{3-[2-(dimethylazaniumyl)ethyl]-4-oxo-1H-indol-7-ylidene}-1H-indol-4-one contains a slight steric clash between its two 1H protons, and thus, 3-[2-(dimethylazaniumyl)ethyl]-2-{3-[2-(dimethylazaniumyl)ethyl]-4-oxo-1H-indol-7-ylidene}-1H-indol-4-one may favor tautomeric states that comprise a single 1H proton or no 1H protons. The tautomers of 3-[2-(dimethylazaniumyl)ethyl]-2-{3-[2-(dimethylazaniumyl)ethyl]-4-oxo-1H-indol-7-ylidene}-1H-indol-4-one are 3-[2-(dimethylazaniumyl)ethyl]-2-{3-[2-(dimethylazaniumyl)ethyl]-4-hydroxyindol-7-ylidene}-1H-indol-4-one; 3-[2-(dimethylazaniumyl)ethyl]-7-{3-[2-(dimethylazaniumyl)ethyl]-4-hydroxyindol-2-ylidene}-1H-indol-4-one; 3-[2-(dimethylazaniumyl)ethyl]-2-{3-[2-(dimethylazaniumyl)ethyl]-4-hydroxy-1H-indol-7-yl}indol-4-one; 3-[2-(dimethylazaniumyl)ethyl]-7-{3-[2-(dimethylazaniumyl)ethyl]-4-hydroxy-1H-indol-2-yl}indol-4-one; and 3-[2-(dimethylazaniumyl)ethyl]-2-{3-[2-(dimethylazaniumyl)ethyl]-4-hydroxyindol-7-ylidene}indol-4-ol.

3-[2-(dimethylazaniumyl)ethyl]-5-{3-[2-(dimethylazaniumyl)ethyl]-4-oxo-1H-indol-5-ylidene}-1H-indol-4-one lacks any problematic sterics and is a prominent species of the 5-oxo-DMT-ylidene dimers. The tautomers of 3-[2-(dimethylazaniumyl)ethyl]-5-{3-[2-(dimethylazaniumyl)ethyl]-4-oxo-1H-indol-5-ylidene}-1H-indol-4-one are 3-[2-(dimethylazaniumyl)ethyl]-5-{3-[2-(dimethylazaniumyl)ethyl]-4-hydroxyindol-5-ylidene}-1H-indol-4-one; 3-[2-(dimethylazaniumyl)ethyl]-5-{3-[2-(dimethylazaniumyl)ethyl]-4-hydroxy-1H-indol-5-yl}indol-4-one; and 3-[2-(dimethylazaniumyl)ethyl]-5-{3-[2-(dimethylazaniumyl)ethyl]-4-hydroxyindol-5-ylidene}indol-4-ol.

3-[2-(dimethylazaniumyl)ethyl]-5-{3-[2-(dimethylazaniumyl)ethyl]-4-oxo-1H-indol-7-ylidene}-1H-indol-4-one presents a problematic steric clash between the 4-oxo group of the indol-7-ylidene and the 1H proton and nitrogen of the indol-4-one, and thus, 3-[2-(dimethylazaniumyl)ethyl]-5-{3-[2-(dimethylazaniumyl)ethyl]-4-oxo-1H-indol-7-ylidene}-1H-indol-4-one and its tautomers are minor or absent species of the 5-oxo-DMT-ylidene dimers. The tautomers of 3-[2-(dimethylazaniumyl)ethyl]-5-{3-[2-(dimethylazaniumyl)ethyl]-4-oxo-1H-indol-7-ylidene}-1H-indol-4-one are 3-[2-(dimethylazaniumyl)ethyl]-5-{3-[2-(dimethylazaniumyl)ethyl]-4-hydroxyindol-7-ylidene}-1H-indol-4-one; 3-[2-(dimethylazaniumyl)ethyl]-7-{3-[2-(dimethylazaniumyl)ethyl]-4-hydroxyindol-5-ylidene}-1H-indol-4-one; 3-[2-(dimethylazaniumyl)ethyl]-5-{3-[2-(dimethylazaniumyl)ethyl]-4-hydroxy-1H-indol-7-yl}indol-4-one; 3-[2-(dimethylazaniumyl)ethyl]-7-{3-[2-(dimethylazaniumyl)ethyl]-4-hydroxy-1H-indol-5-yl}indol-4-one; and 3-[2-(dimethylazaniumyl)ethyl]-5-{3-[2-(dimethylazaniumyl)ethyl]-4-hydroxyindol-7-ylidene}indol-4-ol.

3-[2-(dimethylazaniumyl)ethyl]-7-{3-[2-(dimethylazaniumyl)ethyl]-4-oxo-1H-indol-7-ylidene}-1H-indol-4-one contains a slight steric clash between the 1H protons of each subunit and the 6H protons of the other subunit, and thus, 3-[2-(dimethylazaniumyl)ethyl]-7-{3-[2-(dimethylazaniumyl)ethyl]-4-oxo-1H-indol-7-ylidene}-1H-indol-4-one may favor tautomeric states that comprise no 1H protons. The slight steric clash is minor, however, and thus, 3-[2-(dimethylazaniumyl)ethyl]-7-{3-[2-(dimethylazaniumyl)ethyl]-4-oxo-1H-indol-7-ylidene}-1H-indol-4-one and its tautomers are prominent species of the 5-oxo-DMT-ylidene dimers. The tautomers of 3-[2-(dimethylazaniumyl)ethyl]-7-{3-[2-(dimethylazaniumyl)ethyl]-4-oxo-1H-indol-7-ylidene}-1H-indol-4-one are 3-[2-(dimethylazaniumyl)ethyl]-7-{3-[2-(dimethylazaniumyl)ethyl]-4-hydroxyindol-7-ylidene}-1H-indol-4-one; 3-[2-(dimethylazaniumyl)ethyl]-7-{3-[2-(dimethylazaniumyl)ethyl]-4-hydroxy-1H-indol-7-yl}indol-4-one; and 3-[2-(dimethylazaniumyl)ethyl]-7-{3-[2-(dimethylazaniumyl)ethyl]-4-hydroxyindol-7-ylidene}indol-4-ol.

Various aspects of this disclosure relate to a composition comprising psilocin and one or more oxidized 5-oxo-DMT-ylidene dimers of psilocin, wherein the one or more oxidized 5-oxo-DMT-ylidene dimers of psilocin are selected from 3-[2-(dimethylazaniumyl)ethyl]-2-{3-[2-(dimethylazaniumyl)ethyl]-4-oxo-1H-indol-2-ylidene}-1H-indol-4-one; 3-[2-(dimethylazaniumyl)ethyl]-2-{3-[2-(dimethylazaniumyl)ethyl]-4-oxo-1H-indol-5-ylidene}-1H-indol-4-one; 3-[2-(dimethylazaniumyl)ethyl]-2-{3-[2-(dimethylazaniumyl)ethyl]-4-oxo-1H-indol-7-ylidene}-1H-indol-4-one; 3-[2-(dimethylazaniumyl)ethyl]-5-{3-[2-(dimethylazaniumyl)ethyl]-4-oxo-1H-indol-5-ylidene}-1H-indol-4-one; 3-[2-(dimethylazaniumyl)ethyl]-5-{3-[2-(dimethylazaniumyl)ethyl]-4-oxo-1H-indol-7-ylidene}-1H-indol-4-one; 3-[2-(dimethylazaniumyl)ethyl]-7-{3-[2-(dimethylazaniumyl)ethyl]-4-oxo-1H-indol-7-ylidene}-1H-indol-4-one; and one or more tautomers of the foregoing.

In some embodiments, the composition comprises psilocybin and psilocin at a combined concentration of at least 4 percent and no greater than 80 percent by dry weight, and the composition comprises the psilocin and the one or more oxidized 5-oxo-DMT-ylidene dimers of psilocin at a mole ratio of at least 1:1 (psilocin:one or more oxidized 5-oxo-DMT-ylidene dimers of psilocin). In some specific embodiments, the composition comprises the psilocin and the one or more oxidized 5-oxo-DMT-ylidene dimers of psilocin at a mole ratio of at least 5:1. In some very specific embodiments, the composition comprises the psilocin and the one or more oxidized 5-oxo-DMT-ylidene dimers of psilocin at a mole ratio of at least 10:1. Such compositions may be formulated by protecting compositions comprising psilocybin from dephosphorylation and protecting compositions comprising psilocin from oxidation as described herein.

In some embodiments, the composition comprises psilocybin and psilocin at a combined concentration of at least 4 percent and no greater than 40 percent by dry weight. In some specific embodiments, the composition comprises psilocybin and psilocin at a combined concentration of at least 6 percent and no greater than 32 percent by dry weight. In some very specific embodiments, the composition comprises psilocybin and psilocin at a combined concentration of at least 8 percent and no greater than 24 percent by dry weight.

In some embodiments, the composition comprises psilocybin, psilocin, and one or more oxidized 5-oxo-DMT-ylidene dimers of psilocin; the composition is formulated for human consumption; and the composition comprises the psilocin and the one or more oxidized 5-oxo-DMT-ylidene dimers of psilocin at a mole ratio of at least 1:1 (psilocin:one or more oxidized 5-oxo-DMT-ylidene dimers of psilocin). In some specific embodiments, the composition comprises the psilocin and the one or more oxidized 5-oxo-DMT-ylidene dimers of psilocin at a mole ratio of at least 5:1. In some very specific embodiments, the composition comprises the psilocin and the one or more oxidized 5-oxo-DMT-ylidene dimers of psilocin at a mole ratio of at least 10:1.

The oxidized 5-oxo-DMT-ylidene dimers of psilocin lack any appreciable binding affinity to 5-HT receptors and lack any known pharmacological effects. The mole ratio of psilocin to the one or more oxidized 5-oxo-DMT-ylidene dimers of psilocin (psilocin:one or more oxidized 5-oxo-DMT-ylidene dimers of psilocin) is instead indicative of the extraction methods of this disclosure (and not indicative of prior-art methods that fail to adequately control for the oxidation of psilocin and that therefore produce relatively low mole ratios of psilocin to the oxidized 5-oxo-DMT-ylidene dimers, which oxidation correlates with the blue coloration observed, for example, in prior-art manufacturing intermediates as described supra).

A fifth oxidation product of psilocin is a triol dimer, which has the approximate molecular weight of 425 atomic mass units. Such triol dimers have the chemical formulas 3-[2-(dimethylazaniumyl)ethyl]-2-{3-[2-(dimethylazaniumyl)ethyl]-4-hydroxy-1H-indol-2-yl}-1H-indol-4,5-diol; 3-[2-(dimethylazaniumyl)ethyl]-2-{3-[2-(dimethylazaniumyl)ethyl]-4-hydroxy-1H-indol-2-yl}-1H-indol-4,7-diol; 3-[2-(dimethylazaniumyl)ethyl]-2-{3-[2-(dimethylazaniumyl)ethyl]-4-hydroxy-1H-indol-5-yl}-1H-indol-4,5-diol; 3-[2-(dimethylazaniumyl)ethyl]-2-{3-[2-(dimethylazaniumyl)ethyl]-4-hydroxy-1H-indol-5-yl}-1H-indol-4,7-diol; 3-[2-(dimethylazaniumyl)ethyl]-2-{3-[2-(dimethylazaniumyl)ethyl]-4-hydroxy-1H-indol-7-yl}-1H-indol-4,5-diol; 3-[2-(dimethylazaniumyl)ethyl]-2-{3-[2-(dimethylazaniumyl)ethyl]-4-hydroxy-1H-indol-7-yl}-1H-indol-4,7-diol; 3-[2-(dimethylazaniumyl)ethyl]-5-{3-[2-(dimethylazaniumyl)ethyl]-4-hydroxy-1H-indol-2-yl}-1H-indol-2,4-diol; 3-[2-(dimethylazaniumyl)ethyl]-5-{3-[2-(dimethylazaniumyl)ethyl]-4-hydroxy-1H-indol-2-yl}-1H-indol-4,7-diol; 3-[2-(dimethylazaniumyl)ethyl]-5-{3-[2-(dimethylazaniumyl)ethyl]-4-hydroxy-1H-indol-5-yl}-1H-indol-2,4-diol; 3-[2-(dimethylazaniumyl)ethyl]-5-{3-[2-(dimethylazaniumyl)ethyl]-4-hydroxy-1H-indol-5-yl}-1H-indol-4,7-diol; 3-[2-(dimethylazaniumyl)ethyl]-5-{3-[2-(dimethylazaniumyl)ethyl]-4-hydroxy-1H-indol-7-yl}-1H-indol-2,4-diol; 3-[2-(dimethylazaniumyl)ethyl]-5-{3-[2-(dimethylazaniumyl)ethyl]-4-hydroxy-1H-indol-7-yl}-1H-indol-4,7-diol; 3-[2-(dimethylazaniumyl)ethyl]-7-{3-[2-(dimethylazaniumyl)ethyl]-4-hydroxy-1H-indol-2-yl}-1H-indol-2,4-diol; 3-[2-(dimethylazaniumyl)ethyl]-7-{3-[2-(dimethylazaniumyl)ethyl]-4-hydroxy-1H-indol-2-yl}-1H-indol-4,5-diol; 3-[2-(dimethylazaniumyl)ethyl]-7-{3-[2-(dimethylazaniumyl)ethyl]-4-hydroxy-1H-indol-5-yl}-1H-indol-2,4-diol; 3-[2-(dimethylazaniumyl)ethyl]-7-{3-[2-(dimethylazaniumyl)ethyl]-4-hydroxy-1H-indol-5-yl}-1H-indol-4,5-diol; 3-[2-(dimethylazaniumyl)ethyl]-7-{3-[2-(dimethylazaniumyl)ethyl]-4-hydroxy-1H-indol-7-yl}-1H-indol-2,4-diol; 3-[2-(dimethylazaniumyl)ethyl]-7-{3-[2-(dimethylazaniumyl)ethyl]-4-hydroxy-1H-indol-7-yl}-1H-indol-4,5-diol; 3-[2-(dimethylazaniumyl)ethyl]-6-{3-[2-(dimethylazaniumyl)ethyl]-4-hydroxy-1H-indol-2-yl}-1H-indol-2,4-diol; 3-[2-(dimethylazaniumyl)ethyl]-6-{3-[2-(dimethylazaniumyl)ethyl]-4-hydroxy-1H-indol-2-yl}-1H-indol-4,5-diol; 3-[2-(dimethylazaniumyl)ethyl]-6-{3-[2-(dimethylazaniumyl)ethyl]-4-hydroxy-1H-indol-2-yl}-1H-indol-4,7-diol; 3-[2-(dimethylazaniumyl)ethyl]-6-{3-[2-(dimethylazaniumyl)ethyl]-4-hydroxy-1H-indol-5-yl}-1H-indol-2,4-diol; 3-[2-(dimethylazaniumyl)ethyl]-6-{3-[2-(dimethylazaniumyl)ethyl]-4-hydroxy-1H-indol-5-yl}-1H-indol-4,5-diol; 3-[2-(dimethylazaniumyl)ethyl]-6-{3-[2-(dimethylazaniumyl)ethyl]-4-hydroxy-1H-indol-5-yl}-1H-indol-4,7-diol; 3-[2-(dimethylazaniumyl)ethyl]-6-{3-[2-(dimethylazaniumyl)ethyl]-4-hydroxy-1H-indol-7-yl}-1H-indol-2,4-diol; 3-[2-(dimethylazaniumyl)ethyl]-6-{3-[2-(dimethylazaniumyl)ethyl]-4-hydroxy-1H-indol-7-yl}-1H-indol-4,5-diol; and 3-[2-(dimethylazaniumyl)ethyl]-6-{3-[2-(dimethylazaniumyl)ethyl]-4-hydroxy-1H-indol-7-yl}-1H-indol-4,7-diol. Prominent species of the triol dimers include 3-[2-(dimethylazaniumyl)ethyl]-6-{3-[2-(dimethylazaniumyl)ethyl]-4-hydroxy-1H-indol-2-yl}-1H-indol-4,5-diol; and 3-[2-(dimethylazaniumyl)ethyl]-5-{3-[2-(dimethylazaniumyl)ethyl]-4-hydroxy-1H-indol-5-yl}-1H-indol-4,7-diol.

Various aspects of this disclosure relate to a composition comprising psilocin and one or more oxidized triol dimers of psilocin, wherein the one or more oxidized triol dimers of psilocin are selected from the compounds listed in the preceding paragraph.

In some embodiments, the composition comprises psilocybin and psilocin at a combined concentration of at least 4 percent and no greater than 80 percent by dry weight, and the composition comprises the psilocin and the one or more oxidized triol dimers of psilocin at a mole ratio of at least 1:1 (psilocin:one or more oxidized triol dimers of psilocin). In some specific embodiments, the composition comprises the psilocin and the one or more oxidized triol dimers of psilocin at a mole ratio of at least 5:1. In some very specific embodiments, the composition comprises the psilocin and the one or more oxidized triol dimers of psilocin at a mole ratio of at least 10:1. Such compositions may be formulated by protecting compositions comprising psilocybin from dephosphorylation and protecting compositions comprising psilocin from oxidation as described herein.

In some embodiments, the composition comprises psilocybin and psilocin at a combined concentration of at least 4 percent and no greater than 40 percent by dry weight. In some specific embodiments, the composition comprises psilocybin and psilocin at a combined concentration of at least 6 percent and no greater than 32 percent by dry weight. In some very specific embodiments, the composition comprises psilocybin and psilocin at a combined concentration of at least 8 percent and no greater than 24 percent by dry weight.

In some embodiments, the composition comprises psilocybin, psilocin, and one or more oxidized triol dimers of psilocin; the composition is formulated for human consumption; and the composition comprises the psilocin and the one or more oxidized triol dimers of psilocin at a mole ratio of at least 1:1 (psilocin:one or more oxidized triol dimers of psilocin). In some specific embodiments, the composition comprises the psilocin and the one or more oxidized triol dimers of psilocin at a mole ratio of at least 5:1. In some very specific embodiments, the composition comprises the psilocin and the one or more oxidized triol dimers of psilocin at a mole ratio of at least 10:1.

The oxidized triol dimers of psilocin lack any appreciable binding affinity to 5-HT receptors and lack any known pharmacological effects. The mole ratio of psilocin to the one or more oxidized triol dimers of psilocin (psilocin:one or more oxidized triol dimers of psilocin) is instead indicative of the extraction methods of this disclosure (and not indicative of prior-art methods that fail to adequately control for the oxidation of psilocin and that therefore produce relatively low mole ratios of psilocin to the oxidized triol dimers, which oxidation correlates with the blue coloration observed, for example, in prior-art manufacturing intermediates as described supra).

A sixth oxidation product of psilocin is a hydroxydione dimer, which has the approximate molecular weight of 423 atomic mass units. Such hydroxydione dimers have the chemical formulas 3-[2-(dimethylazaniumyl)ethyl]-2-{3-[2-(dimethylazaniumyl)ethyl]-4-hydroxy-1H-indol-2-yl}-1H-indol-4,5-dione; 3-[2-(dimethylazaniumyl)ethyl]-2-{3-[2-(dimethylazaniumyl)ethyl]-4-hydroxy-1H-indol-2-yl}-1H-indol-4,7-dione; 3-[2-(dimethylazaniumyl)ethyl]-2-{3-[2-(dimethylazaniumyl)ethyl]-4-hydroxy-1H-indol-5-yl}-1H-indol-4,5-dione; 3-[2-(dimethylazaniumyl)ethyl]-2-{3-[2-(dimethylazaniumyl)ethyl]-4-hydroxy-1H-indol-5-yl}-1H-indol-4,7-dione; 3-[2-(dimethylazaniumyl)ethyl]-2-{3-[2-(dimethylazaniumyl)ethyl]-4-hydroxy-1H-indol-7-yl}-1H-indol-4,5-dione; 3-[2-(dimethylazaniumyl)ethyl]-2-{3-[2-(dimethylazaniumyl)ethyl]-4-hydroxy-1H-indol-7-yl}-1H-indol-4,7-dione; 3-[2-(dimethylazaniumyl)ethyl]-5-{3-[2-(dimethylazaniumyl)ethyl]-4-hydroxy-1H-indol-2-yl}-1H-indol-2,4-dione; 3-[2-(dimethylazaniumyl)ethyl]-5-{3-[2-(dimethylazaniumyl)ethyl]-4-hydroxy-1H-indol-2-yl}-1H-indol-4,7-dione; 3-[2-(dimethylazaniumyl)ethyl]-5-{3-[2-(dimethylazaniumyl)ethyl]-4-hydroxy-1H-indol-5-yl}-1H-indol-2,4-dione; 3-[2-(dimethylazaniumyl)ethyl]-5-{3-[2-(dimethylazaniumyl)ethyl]-4-hydroxy-1H-indol-5-yl}-1H-indol-4,7-dione; 3-[2-(dimethylazaniumyl)ethyl]-5-{3-[2-(dimethylazaniumyl)ethyl]-4-hydroxy-1H-indol-7-yl}-1H-indol-2,4-dione; 3-[2-(dimethylazaniumyl)ethyl]-5-{3-[2-(dimethylazaniumyl)ethyl]-4-hydroxy-1H-indol-7-yl}-1H-indol-4,7-dione; 3-[2-(dimethylazaniumyl)ethyl]-7-{3-[2-(dimethylazaniumyl)ethyl]-4-hydroxy-1H-indol-2-yl}-1H-indol-2,4-dione; 3-[2-(dimethylazaniumyl)ethyl]-7-{3-[2-(dimethylazaniumyl)ethyl]-4-hydroxy-1H-indol-2-yl}-1H-indol-4,5-dione; 3-[2-(dimethylazaniumyl)ethyl]-7-{3-[2-(dimethylazaniumyl)ethyl]-4-hydroxy-1H-indol-5-yl}-1H-indol-2,4-dione; 3-[2-(dimethylazaniumyl)ethyl]-7-{3-[2-(dimethylazaniumyl)ethyl]-4-hydroxy-1H-indol-5-yl}-1H-indol-4,5-dione; 3-[2-(dimethylazaniumyl)ethyl]-7-{3-[2-(dimethylazaniumyl)ethyl]-4-hydroxy-1H-indol-7-yl}-1H-indol-2,4-dione; 3-[2-(dimethylazaniumyl)ethyl]-7-{3-[2-(dimethylazaniumyl)ethyl]-4-hydroxy-1H-indol-7-yl}-1H-indol-4,5-dione; 3-[2-(dimethylazaniumyl)ethyl]-6-{3-[2-(dimethylazaniumyl)ethyl]-4-hydroxy-1H-indol-2-yl}-1H-indol-2,4-dione; 3-[2-(dimethylazaniumyl)ethyl]-6-{3-[2-(dimethylazaniumyl)ethyl]-4-hydroxy-1H-indol-2-yl}-1H-indol-4,5-dione; 3-[2-(dimethylazaniumyl)ethyl]-6-{3-[2-(dimethylazaniumyl)ethyl]-4-hydroxy-1H-indol-2-yl}-1H-indol-4,7-dione; 3-[2-(dimethylazaniumyl)ethyl]-6-{3-[2-(dimethylazaniumyl)ethyl]-4-hydroxy-1H-indol-5-yl}-1H-indol-2,4-dione; 3-[2-(dimethylazaniumyl)ethyl]-6-{3-[2-(dimethylazaniumyl)ethyl]-4-hydroxy-1H-indol-5-yl}-1H-indol-4,5-dione; 3-[2-(dimethylazaniumyl)ethyl]-6-{3-[2-(dimethylazaniumyl)ethyl]-4-hydroxy-1H-indol-5-yl}-1H-indol-4,7-dione; 3-[2-(dimethylazaniumyl)ethyl]-6-{3-[2-(dimethylazaniumyl)ethyl]-4-hydroxy-1H-indol-7-yl}-1H-indol-2,4-dione; 3-[2-(dimethylazaniumyl)ethyl]-6-{3-[2-(dimethylazaniumyl)ethyl]-4-hydroxy-1H-indol-7-yl}-1H-indol-4,5-dione; and 3-[2-(dimethylazaniumyl)ethyl]-6-{3-[2-(dimethylazaniumyl)ethyl]-4-hydroxy-1H-indol-7-yl}-1H-indol-4,7-dione and also include tautomers of the foregoing. The tautomers of the foregoing are not technically "hydroxydione dimers" themselves because one or both of the two oxo groups are reduced to hydroxy in the tautomers, but the term "hydroxydione dimers" as used herein nevertheless includes the tautomers of the foregoing. Prominent species of the hydroxydione dimers include 3-[2-(dimethylazaniumyl)ethyl]-5-{3-[2-(dimethylazaniumyl)ethyl]-4-hydroxy-1H-indol-5-yl}-1H-indol-4,7-dione; 3-[2-(dimethylazaniumyl)ethyl]-6-{3-[2-(dimethylazaniumyl)ethyl]-4-hydroxy-1H-indol-2-yl}-1H-indol-4,5-dione; and tautomers of the foregoing.

Various aspects of this disclosure relate to a composition comprising psilocin and one or more oxidized hydroxydione dimers of psilocin, wherein the one or more oxidized hydroxydione dimers of psilocin are selected from the compounds listed in the preceding paragraph.

In some embodiments, the composition comprises psilocybin and psilocin at a combined concentration of at least 4 percent and no greater than 80 percent by dry weight, and the composition comprises the psilocin and the one or more oxidized hydroxydione dimers of psilocin at a mole ratio of at least 1:1 (psilocin:one or more oxidized hydroxydione dimers of psilocin). In some specific embodiments, the composition comprises the psilocin and the one or more oxidized hydroxydione dimers of psilocin at a mole ratio of at least 5:1. In some very specific embodiments, the composition comprises the psilocin and the one or more oxidized hydroxydione dimers of psilocin at a mole ratio of at least 10:1. Such compositions may be formulated by protecting compositions comprising psilocybin from dephosphorylation and protecting compositions comprising psilocin from oxidation as described herein.

In some embodiments, the composition comprises psilocybin and psilocin at a combined concentration of at least 4 percent and no greater than 40 percent by dry weight. In some specific embodiments, the composition comprises psilocybin and psilocin at a combined concentration of at least 6 percent and no greater than 32 percent by dry weight. In some very specific embodiments, the composition comprises psilocybin and psilocin at a combined concentration of at least 8 percent and no greater than 24 percent by dry weight.

In some embodiments, the composition comprises psilocybin, psilocin, and one or more oxidized hydroxydione dimers of psilocin; the composition is formulated for human consumption; and the composition comprises the psilocin and the one or more oxidized hydroxydione dimers of psilocin at a mole ratio of at least 1:1 (psilocin:one or more oxidized hydroxydione dimers of psilocin). In some specific embodiments, the composition comprises the psilocin and the one or more oxidized hydroxydione dimers of psilocin at a mole ratio of at least 5:1. In some very specific embodiments, the composition comprises the psilocin and the one or more oxidized hydroxydione dimers of psilocin at a mole ratio of at least 10:1.

The oxidized hydroxydione dimers of psilocin lack any appreciable binding affinity to 5-HT receptors and lack any known pharmacological effects. The mole ratio of psilocin to the one or more oxidized hydroxydione dimers of psilocin (psilocin:one or more oxidized hydroxydione dimers of psilocin) is instead indicative of the extraction methods of this disclosure (and not indicative of prior-art methods that fail to adequately control for the oxidation of psilocin and that therefore produce relatively low mole ratios of psilocin to the oxidized hydroxydione dimers, which oxidation correlates with the blue coloration observed, for example, in prior-art manufacturing intermediates as described supra).

A seventh oxidation product of psilocin is a trione dimer, which has the approximate molecular weight of 420 atomic mass units. Such trione dimers have the chemical formulas 3-[2-(dimethylazaniumyl)ethyl]-2-{3-[2-(dimethylazaniumyl)ethyl]-4-oxo-4H-indol-2-yl}-1H-indol-4,5-dione; 3-[2-(dimethylazaniumyl)ethyl]-2-{3-[2-(dimethylazaniumyl)ethyl]-4-oxo-4H-indol-2-yl}-1H-indol-4,7-dione; 3-[2-(dimethylazaniumyl)ethyl]-2-{3-[2-(dimethylazaniumyl)ethyl]-4-oxo-4H-indol-5-yl}-1H-indol-4,5-dione; 3-[2-(dimethylazaniumyl)ethyl]-2-{3-[2-(dimethylazaniumyl)ethyl]-4-oxo-4H-indol-5-yl}-1H-indol-4,7-dione; 3-[2-(dimethylazaniumyl)ethyl]-2-{3-[2-(dimethylazaniumyl)ethyl]-4-oxo-4H-indol-7-yl}-1H-indol-4,5-dione; 3-[2-(dimethylazaniumyl)ethyl]-2-{3-[2-(dimethylazaniumyl)ethyl]-4-oxo-4H-indol-7-yl}-1H-indol-4,7-dione; 3-[2-(dimethylazaniumyl)ethyl]-5-{3-[2-(dimethylazaniumyl)ethyl]-4-oxo-4H-indol-2-yl}-1H-indol-2,4-dione; 3-[2-(dimethylazaniumyl)ethyl]-5-{3-[2-(dimethylazaniumyl)ethyl]-4-oxo-4H-indol-2-yl}-1H-indol-4,7-dione; 3-[2-(dimethylazaniumyl)ethyl]-5-{3-[2-(dimethylazaniumyl)ethyl]-4-oxo-4H-indol-5-yl}-1H-indol-2,4-dione; 3-[2-(dimethylazaniumyl)ethyl]-5-{3-[2-(dimethylazaniumyl)ethyl]-4-oxo-4H-indol-5-yl}-1H-indol-4,7-dione; 3-[2-(dimethylazaniumyl)ethyl]-5-{3-[2-(dimethylazaniumyl)ethyl]-4-oxo-4H-indol-7-yl}-1H-indol-2,4-dione; 3-[2-(dimethylazaniumyl)ethyl]-5-{3-[2-(dimethylazaniumyl)ethyl]-4-oxo-4H-indol-7-yl}-1H-indol-4,7-dione; 3-[2-(dimethylazaniumyl)ethyl]-7-{3-[2-(dimethylazaniumyl)ethyl]-4-oxo-4H-indol-2-yl}-1H-indol-2,4-dione; 3-[2-(dimethylazaniumyl)ethyl]-7-{3-[2-(dimethylazaniumyl)ethyl]-4-oxo-4H-indol-2-yl}-1H-indol-4,5-dione; 3-[2-(dimethylazaniumyl)ethyl]-7-{3-[2-(dimethylazaniumyl)ethyl]-4-oxo-4H-indol-5-yl}-1H-indol-2,4-dione; 3-[2-(dimethylazaniumyl)ethyl]-7-{3-[2-(dimethylazaniumyl)ethyl]-4-oxo-4H-indol-5-yl}-1H-indol-4,5-dione; 3-[2-(dimethylazaniumyl)ethyl]-7-{3-[2-(dimethylazaniumyl)ethyl]-4-oxo-4H-indol-7-yl}-1H-indol-2,4-dione; 3-[2-(dimethylazaniumyl)ethyl]-7-{3-[2-(dimethylazaniumyl)ethyl]-4-oxo-4H-indol-7-yl}-1H-indol-4,5-dione; 3-[2-(dimethylazaniumyl)ethyl]-6-{3-[2-(dimethylazaniumyl)ethyl]-4-oxo-4H-indol-2-yl}-1H-indol-2,4-dione; 3-[2-(dimethylazaniumyl)ethyl]-6-{3-[2-(dimethylazaniumyl)ethyl]-4-oxo-4H-indol-2-yl}-1H-indol-4,5-dione; 3-[2-(dimethylazaniumyl)ethyl]-6-{3-[2-(dimethylazaniumyl)ethyl]-4-oxo-4H-indol-2-yl}-1H-indol-4,7-dione; 3-[2-(dimethylazaniumyl)ethyl]-6-{3-[2-(dimethylazaniumyl)ethyl]-4-oxo-4H-indol-5-yl}-1H-indol-2,4-dione; 3-[2-(dimethylazaniumyl)ethyl]-6-{3-[2-(dimethylazaniumyl)ethyl]-4-oxo-4H-indol-5-yl}-1H-indol-4,5-dione; 3-[2-(dimethylazaniumyl)ethyl]-6-{3-[2-(dimethylazaniumyl)ethyl]-4-oxo-4H-indol-5-yl}-1H-indol-4,7-dione; 3-[2-(dimethylazaniumyl)ethyl]-6-{3-[2-(dimethylazaniumyl)ethyl]-4-oxo-4H-indol-7-yl}-1H-indol-2,4-dione; 3-[2-(dimethylazaniumyl)ethyl]-6-{3-[2-(dimethylazaniumyl)ethyl]-4-oxo-4H-indol-7-yl}-1H-indol-4,5-dione; and 3-[2-(dimethylazaniumyl)ethyl]-6-{3-[2-(dimethylazaniumyl)ethyl]-4-oxo-4H-indol-7-yl}-1H-indol-4,7-dione and also include tautomers of the foregoing. The tautomers of the foregoing are not technically "trione dimers" themselves because one or more of the three oxo groups are reduced to hydroxy in the tautomers, but the term "trione dimers" as used herein nevertheless includes the tautomers of the foregoing. Prominent species of the trione dimers include 3-[2-(dimethylazaniumyl)ethyl]-5-{3-[2-(dimethylazaniumyl)ethyl]-4-oxo-4H-indol-5-yl}-1H-indol-4,7-dione; 3-[2-(dimethylazaniumyl)ethyl]-6-{3-[2-(dimethylazaniumyl)ethyl]-4-oxo-4H-indol-2-yl}-1H-indol-4,5-dione; and tautomers of the foregoing.

Various aspects of this disclosure relate to a composition comprising psilocin and one or more oxidized trione dimers of psilocin, wherein the one or more oxidized trione dimers of psilocin are selected from the compounds listed in the preceding paragraph.

In some embodiments, the composition comprises psilocybin and psilocin at a combined concentration of at least 4 percent and no greater than 80 percent by dry weight, and the composition comprises the psilocin and the one or more oxidized trione dimers of psilocin at a mole ratio of at least 1:1 (psilocin:one or more oxidized trione dimers of psilocin). In some specific embodiments, the composition comprises the psilocin and the one or more oxidized trione dimers of psilocin at a mole ratio of at least 5:1. In some very specific embodiments, the composition comprises the psilocin and the one or more oxidized trione dimers of psilocin at a mole ratio of at least 10:1. Such compositions may be formulated by protecting compositions comprising psilocybin from dephosphorylation and protecting compositions comprising psilocin from oxidation as described herein.

In some embodiments, the composition comprises psilocybin and psilocin at a combined concentration of at least 4 percent and no greater than 40 percent by dry weight. In some specific embodiments, the composition comprises psilocybin and psilocin at a combined concentration of at least 6 percent and no greater than 32 percent by dry weight. In some very specific embodiments, the composition comprises psilocybin and psilocin at a combined concentration of at least 8 percent and no greater than 24 percent by dry weight.

In some embodiments, the composition comprises psilocybin, psilocin, and one or more oxidized trione dimers of psilocin; the composition is formulated for human consumption; and the composition comprises the psilocin and the one or more oxidized trione dimers of psilocin at a mole ratio of at least 1:1 (psilocin:one or more oxidized trione dimers of psilocin). In some specific embodiments, the composition comprises the psilocin and the one or more oxidized trione dimers of psilocin at a mole ratio of at least 5:1. In some very specific embodiments, the composition comprises the psilocin and the one or more oxidized trione dimers of psilocin at a mole ratio of at least 10:1.

The oxidized trione dimers of psilocin lack any appreciable binding affinity to 5-HT receptors and lack any known pharmacological effects. The mole ratio of psilocin to the one or more oxidized trione dimers of psilocin (psilocin:one or more oxidized trione dimers of psilocin) is instead indicative of the extraction methods of this disclosure (and not indicative of prior-art methods that fail to adequately control for the oxidation of psilocin and that therefore produce relatively low mole ratios of psilocin to the oxidized trione dimers, which oxidation correlates with the blue coloration observed, for example, in prior-art manufacturing intermediates as described supra).

A first oxidation product of norpsilocin is a diol, which has the approximate molecular weight of 207 atomic mass units. Such diols have the chemical formulas 3-[2-(methylazaniumyl)ethyl]-1H-indol-2,4-diol; 3-[2-(methylazaniumyl)ethyl]-1H-indol-4,5-diol; and 3-[2-(methylazaniumyl)ethyl]-1H-indol-4,7-diol.

Various aspects of this disclosure relate to a composition comprising norpsilocin and one or more oxidized diols of norpsilocin, wherein the one or more oxidized diols of norpsilocin are selected from 3-[2-(methylazaniumyl)ethyl]-1H-indol-2,4-diol; 3-[2-(methylazaniumyl)ethyl]-1H-indol-4,5-diol; and 3-[2-(methylazaniumyl)ethyl]-1H-indol-4,7-diol.

In some embodiments, the composition comprises psilocybin, psilocin, baeocystin, and norpsilocin at a combined concentration of at least 4 percent and no greater than 80 percent by dry weight, and the composition comprises the norpsilocin and the one or more oxidized diols of norpsilocin at a mole ratio of at least 1:1 (norpsilocin:one or more oxidized diols of norpsilocin). In some specific embodiments, the composition comprises the norpsilocin and the one or more oxidized diols of norpsilocin at a mole ratio of at least 5:1. In some very specific embodiments, the composition comprises the norpsilocin and the one or more oxidized diols of norpsilocin at a mole ratio of at least 10:1. Such compositions may be formulated by protecting compositions comprising psilocybin and baeocystin from dephosphorylation and protecting compositions comprising psilocin and norpsilocin from oxidation as described herein.

In some embodiments, the composition comprises psilocybin, psilocin, baeocystin, and norpsilocin at a combined concentration of at least 4 percent and no greater than 40 percent by dry weight. In some specific embodiments, the composition comprises psilocybin, psilocin, baeocystin, and norpsilocin at a combined concentration of at least 6 percent and no greater than 32 percent by dry weight. In some very specific embodiments, the composition comprises psilocybin, psilocin, baeocystin, and norpsilocin at a combined concentration of at least 8 percent and no greater than 24 percent by dry weight.

In some embodiments, the composition comprises psilocybin, psilocin, baeocystin, norpsilocin, and one or more oxidized diols of norpsilocin; the composition is formulated for human consumption; and the composition comprises the norpsilocin and the one or more oxidized diols of norpsilocin at a mole ratio of at least 1:1 (norpsilocin:one or more oxidized diols of norpsilocin). In some specific embodiments, the composition comprises the norpsilocin and the one or more oxidized diols of norpsilocin at a mole ratio of at least 5:1. In some very specific embodiments, the composition comprises the norpsilocin and the one or more oxidized diols of norpsilocin at a mole ratio of at least 10:1.

The mole ratio of norpsilocin to the one or more oxidized diols of norpsilocin (norpsilocin:one or more oxidized diols of norpsilocin) is indicative of the extraction methods of this disclosure (and not indicative of prior-art methods that fail to adequately control for the oxidation of norpsilocin and that therefore produce relatively low mole ratios of norpsilocin to the oxidized diols, which oxidation correlates with the blue coloration observed, for example, in prior-art manufacturing intermediates as described supra).

The oxidized diols of norpsilocin remain capable of binding 5-HT receptors generally (and 5HT2A specifically) and exhibiting desirable pharmacological effects. In some embodiments, a composition comprises one or more oxidized diols of norpsilocin. In some specific embodiments, a composition comprises 3-[2-(methylazaniumyl)ethyl]-1H-indol-2,4-diol. In some specific embodiments, a composition comprises 3-[2-(methylazaniumyl)ethyl]-1H-indol-4,5-diol. In some specific embodiments, a composition comprises 3-[2-(methylazaniumyl)ethyl]-1H-indol-4,7-diol.

A second oxidation product of norpsilocin is a dione, which has the approximate molecular weight of 205 atomic mass units. Such diones have the chemical formulas 3-[2-(methylazaniumyl)ethyl]-1H-indol-2,4-dione; 3-[2-(methylazaniumyl)ethyl]-1H-indol-4,5-dione; and 3-[2-(methylazaniumyl)ethyl]-1H-indol-4,7-dione and also include tautomers of the foregoing. The tautomers of the foregoing are not "diones" themselves, but the term "oxidized diones of norpsilocin" as used herein nevertheless includes the tautomers of the foregoing. 3-[2-(methylazaniumyl)ethyl]-2-hydroxyindol-4-one and 3-[2-(methylazaniumyl)ethyl]-4-hydroxyindol-2-one are the tautomers of 3-[2-(methylazaniumyl)ethyl]-1H-indol-2,4-dione. 3-[2-(methylazaniumyl) ethyl]-4-hydroxyindol-5-one and 3-[2-(methylazaniumyl) ethyl]-5-hydroxyindol-4-one are the tautomer of 3-[2-(methylazaniumyl)ethyl]-1H-indol-4,5-dione. 3-[2-(methylazaniumyl)ethyl]-4-hydroxyindol-7-one and 3-[2-(methylazaniumyl)ethyl]-7-hydroxyindol-4-one are the tautomers of 3-[2-(methylazaniumyl)ethyl]-1H-indol-4,7-dione.

Various aspects of this disclosure relate to a composition comprising norpsilocin and one or more oxidized diones of norpsilocin, wherein the one or more oxidized diones of norpsilocin are selected from 3-[2-(methylazaniumyl)ethyl]-1H-indol-2,4-dione; 3-[2-(methylazaniumyl)ethyl]-1H-indol-4,5-dione; 3-[2-(methylazaniumyl)ethyl]-1H-indol-4,7-dione; and one or more tautomers of one or more of the foregoing.

In some embodiments, the composition comprises psilocybin, psilocin, baeocystin, and norpsilocin at a combined concentration of at least 4 percent and no greater than 80 percent by dry weight, and the composition comprises the norpsilocin and the one or more oxidized diones of norpsilocin at a mole ratio of at least 1:1 (norpsilocin:one or more oxidized diones of norpsilocin). In some specific embodiments, the composition comprises the norpsilocin and the one or more oxidized diones of norpsilocin at a mole ratio of at least 5:1. In some very specific embodiments, the composition comprises the norpsilocin and the one or more oxidized diones of norpsilocin at a mole ratio of at least 10:1. Such compositions may be formulated by protecting compositions comprising psilocybin and baeocystin from dephosphorylation and protecting compositions comprising psilocin and norpsilocin from oxidation as described herein.

In some embodiments, the composition comprises psilocybin, psilocin, baeocystin, and norpsilocin at a combined concentration of at least 4 percent and no greater than 40 percent by dry weight. In some specific embodiments, the composition comprises psilocybin, psilocin, baeocystin, and norpsilocin at a combined concentration of at least 6 percent and no greater than 32 percent by dry weight. In some very specific embodiments, the composition comprises psilocybin, psilocin, baeocystin, and norpsilocin at a combined concentration of at least 8 percent and no greater than 24 percent by dry weight.

In some embodiments, the composition comprises psilocybin, psilocin, baeocystin, norpsilocin, and one or more oxidized diones of norpsilocin; the composition is formulated for human consumption; and the composition comprises the norpsilocin and the one or more oxidized diones of norpsilocin at a mole ratio of at least 1:1 (norpsilocin:one or more oxidized diones of norpsilocin). In some specific embodiments, the composition comprises the norpsilocin and the one or more oxidized diones of norpsilocin at a mole ratio of at least 5:1. In some very specific embodiments, the composition comprises the norpsilocin and the one or more oxidized diones of norpsilocin at a mole ratio of at least 10:1.

The mole ratio of norpsilocin to the one or more oxidized diones of norpsilocin (norpsilocin:one or more oxidized diones of norpsilocin) is indicative of the extraction methods of this disclosure (and not indicative of prior-art methods that fail to adequately control for the oxidation of norpsilocin and that therefore produce relatively low mole ratios of norpsilocin to the oxidized diones, which oxidation correlates with the blue coloration observed, for example, in prior-art manufacturing intermediates as described supra).

The oxidized diones of norpsilocin remain capable of binding 5-HT receptors generally (and 5HT2A specifically) and exhibiting desirable pharmacological effects. In some embodiments, a composition comprises one or more oxidized diones of norpsilocin. In some specific embodiments, the composition comprises 3-[2-(methylazaniumyl)ethyl]-1H-indol-2,4-dione. In some specific embodiments, the composition comprises 3-[2-(methylazaniumyl)ethyl]-2-hydroxyindol-4-one. In some specific embodiments, the composition comprises 3-[2-(methylazaniumyl)ethyl]-4-hydroxyindol-2-one. In some specific embodiments, the composition comprises 3-[2-(methylazaniumyl)ethyl]-1H-indol-4,5-dione. In some specific embodiments, the composition comprises 3-[2-(methylazaniumyl)ethyl]-4-hydroxy-indol-5-one. In some specific embodiments, the composition comprises 3-[2-(methylazaniumyl)ethyl]-5-hydroxyindol-4-one. In some specific embodiments, the composition comprises 3-[2-(methylazaniumyl)ethyl]-1H-indol-4,7-dione. In some specific embodiments, the composition comprises 3-[2-(methylazaniumyl)ethyl]-4-hydroxyindol-7-one. In some specific embodiments, the composition comprises 3-[2-(methylazaniumyl)ethyl]-7-hydroxyindol-4-one.

A third oxidation product of norpsilocin is a diol dimer of norpsilocin and psilocin, which has the approximate molecular weight of 395 atomic mass units. Such diol dimers have the chemical formulas 3-[2-(dimethylazaniumyl)ethyl]-2-{3-[2-(methylazaniumyl)ethyl]-4-hydroxy-1H-indol-2-yl}-1H-indol-4-ol; 3-[2-(dimethylazaniumyl)ethyl]-2-{3-[2-(methylazaniumyl)ethyl]-4-hydroxy-1H-indol-5-yl}-1H-indol-4-ol; 3-[2-(dimethylazaniumyl)ethyl]-2-{3-[2-(methylazaniumyl)ethyl]-4-hydroxy-1H-indol-7-yl}-1H-indol-4-ol; 3-[2-(dimethylazaniumyl)ethyl]-5-{3-[2-(methylazaniumyl)ethyl]-4-hydroxy-1H-indol-2-yl}-1H-indol-4-ol; 3-[2-(dimethylazaniumyl)ethyl]-5-{3-[2-(methylazaniumyl)ethyl]-4-hydroxy-1H-indol-5-yl}-1H-indol-4-ol; 3-[2-(dimethylazaniumyl)ethyl]-5-{3-[2-(methylazaniumyl)ethyl]-4-hydroxy-1H-indol-7-yl}-1H-indol-4-ol; 3-[2-(dimethylazaniumyl)ethyl]-7-{3-[2-(methylazaniumyl)ethyl]-4-hydroxy-1H-indol-2-yl}-1H-indol-4-ol; 3-[2-(dimethylazaniumyl)ethyl]-7-{3-[2-(methylazaniumyl)ethyl]-4-hydroxy-1H-indol-5-yl}-1H-indol-4-ol; and 3-[2-(dimethylazaniumyl)ethyl]-7-{3-[2-(methylazaniumyl)ethyl]-4-hydroxy-1H-indol-7-yl}-1H-indol-4-ol.

Various aspects of this disclosure relate to a composition comprising norpsilocin and one or more oxidized diol dimers of norpsilocin and psilocin, wherein the one or more oxidized diol dimers of norpsilocin and psilocin are selected from 3-[2-(dimethylazaniumyl)ethyl]-2-{3-[2-(methylazaniumyl)ethyl]-4-hydroxy-1H-indol-2-yl}-1H-indol-4-ol; 3-[2-(dimethylazaniumyl)ethyl]-2-{3-[2-(methylazaniumyl)ethyl]-4-hydroxy-1H-indol-5-yl}-1H-indol-4-ol; 3-[2-(dimethylazaniumyl)ethyl]-2-{3-[2-(methylazaniumyl)ethyl]-4-hydroxy-1H-indol-7-yl}-1H-indol-4-ol; 3-[2-(dimethylazaniumyl)ethyl]-5-{3-[2-(methylazaniumyl)ethyl]-4-hydroxy-1H-indol-2-yl}-1H-indol-4-ol; 3-[2-(dimethylazaniumyl)ethyl]-5-{3-[2-(methylazaniumyl)ethyl]-4-hydroxy-1H-indol-5-yl}-1H-indol-4-ol; 3-[2-(dimethylazaniumyl)ethyl]-5-{3-[2-(methylazaniumyl)ethyl]-4-hydroxy-1H-indol-7-yl}-1H-indol-4-ol; 3-[2-(dimethylazaniumyl)ethyl]-7-{3-[2-(methylazaniumyl)ethyl]-4-hydroxy-1H-indol-2-yl}-1H-indol-4-ol; 3-[2-(dimethylazaniumyl)ethyl]-7-{3-[2-(methylazaniumyl)ethyl]-4-hydroxy-1H-indol-5-yl}-1H-indol-4-ol; and 3-[2-(dimethylazaniumyl)ethyl]-7-{3-[2-(methylazaniumyl)ethyl]-4-hydroxy-1H-indol-7-yl}-1H-indol-4-ol.

In some embodiments, the composition comprises psilocybin, psilocin, baeocystin, and norpsilocin at a combined concentration of at least 4 percent and no greater than 80 percent by dry weight, and the composition comprises the norpsilocin and the one or more oxidized diol dimers of norpsilocin and psilocin at a mole ratio of at least 1:1 (norpsilocin:one or more oxidized diol dimers of norpsilocin and psilocin). In some specific embodiments, the composition comprises the norpsilocin and the one or more oxidized diol dimers of norpsilocin and psilocin at a mole ratio of at least 5:1. In some very specific embodiments, the composition comprises the norpsilocin and the one or more oxidized diol dimers of norpsilocin and psilocin at a mole ratio of at least 10:1. Such compositions may be formulated by protecting compositions comprising psilocybin and baeocystin from dephosphorylation and protecting compositions comprising psilocin and norpsilocin from oxidation as described herein.

In some embodiments, the composition comprises psilocybin, psilocin, baeocystin, and norpsilocin at a combined concentration of at least 4 percent and no greater than 40 percent by dry weight. In some specific embodiments, the composition comprises psilocybin, psilocin, baeocystin, and norpsilocin at a combined concentration of at least 6 percent and no greater than 32 percent by dry weight. In some very specific embodiments, the composition comprises psilocybin, psilocin, baeocystin, and norpsilocin at a combined concentration of at least 8 percent and no greater than 24 percent by dry weight.

In some embodiments, the composition comprises psilocybin, psilocin, baeocystin, norpsilocin, and one or more oxidized diol dimers of norpsilocin and psilocin; the composition is formulated for human consumption; and the composition comprises the norpsilocin and the one or more oxidized diol dimers of norpsilocin and psilocin at a mole ratio of at least 1:1 (norpsilocin:one or more oxidized diol dimers of norpsilocin and psilocin). In some specific embodiments, the composition comprises the norpsilocin and the one or more oxidized diol dimers of norpsilocin and psilocin at a mole ratio of at least 5:1. In some very specific embodiments, the composition comprises the norpsilocin and the one or more oxidized diol dimers of norpsilocin and psilocin at a mole ratio of at least 10:1.

The oxidized diol dimers of norpsilocin and psilocin lack any appreciable binding affinity to 5-HT receptors and lack any known pharmacological effects. The mole ratio of norpsilocin to the one or more oxidized diol dimers of norpsilocin and psilocin (norpsilocin:one or more oxidized diol dimers of norpsilocin and psilocin) is instead indicative of the extraction methods of this disclosure (and not indicative of prior-art methods that fail to adequately control for the oxidation of norpsilocin and that therefore produce relatively low mole ratios of norpsilocin to the oxidized diol dimers, which oxidation correlates with the blue coloration observed, for example, in prior-art manufacturing intermediates as described supra).

A fourth oxidation product of norpsilocin is a dione dimer of norpsilocin and psilocin, which has the approximate molecular weight of 392 atomic mass units. Such dione dimers have the chemical formulas 3-[2-(dimethylazaniumyl)ethyl]-2-{3-[2-(methylazaniumyl)ethyl]-4-oxo-1H-indol-2-ylidene}-1H-indol-4-one; 3-[2-(dimethylazaniumyl)ethyl]-2-{3-[2-(methylazaniumyl)ethyl]-4-oxo-1H-indol-5-ylidene}-1H-indol-4-one; 3-[2-(dimethylazaniumyl)ethyl]-2-{3-[2-(methylazaniumyl)ethyl]-4-oxo-1H-indol-7-ylidene}-1H-indol-4-one; 3-[2-(dimethylazaniumyl)ethyl]-5-{3-[2-(methylazaniumyl)ethyl]-4-oxo-1H-indol-2-ylidene}-1H-indol-4-one; 3-[2-(dimethylazaniumyl)ethyl]-5-{3-[2-(methylazaniumyl)ethyl]-4-oxo-1H-indol-5-ylidene}-1H-indol-4-one; 3-[2-(dimethylazaniumyl)ethyl]-5-{3-[2-(methylazaniumyl)ethyl]-4-oxo-1H-indol-7-ylidene}-1H-indol-4-one; 3-[2-(dimethylazaniumyl)ethyl]-7-{3-[2-(methylazaniumyl)ethyl]-4-oxo-1H-indol-2-ylidene}-1H-indol-4-one; 3-[2-(dimethylazaniumyl)ethyl]-7-{3-[2-(methylazaniumyl)ethyl]-4-oxo-1H-indol-5-ylidene}-1H-indol-4-one; and 3-[2-(dimethylazaniumyl)ethyl]-7-{3-[2-(methylazaniumyl)ethyl]-4-oxo-1H-indol-7-ylidene}-1H-indol-4-one and also include tautomers of the foregoing. The tautomers of the foregoing are not technically "dione dimers" themselves because one or both of the two oxo groups are reduced to hydroxy in the tautomers, but the term "dione dimers" as used herein nevertheless includes the tautomers of the foregoing. Prominent species of the foregoing dione dimers include 3-[2-(dimethylazaniumyl) ethyl]-5-{3-[2-(methylazaniumyl)ethyl]-4-oxo-1H-indol-5-ylidene}-1H-indol-4-one and tautomers thereof.

Various aspects of this disclosure relate to a composition comprising norpsilocin and one or more oxidized dione dimers of norpsilocin and psilocin, wherein the one or more oxidized dione dimers of norpsilocin and psilocin are selected from 3-[2-(dimethylazaniumyl)ethyl]-2-{3-[2-(methylazaniumyl)ethyl]-4-oxo-1H-indol-2-ylidene}-1H-indol-4-one; 3-[2-(dimethylazaniumyl)ethyl]-2-{3-[2-(methylazaniumyl)ethyl]-4-oxo-1H-indol-5-ylidene}-1H-indol-4-one; 3-[2-(dimethylazaniumyl)ethyl]-2-{3-[2-(methylazaniumyl)ethyl]-4-oxo-1H-indol-7-ylidene}-1H-indol-4-one; 3-[2-(dimethylazaniumyl)ethyl]-5-{3-[2-(methylazaniumyl)ethyl]-4-oxo-1H-indol-2-ylidene}-1H-indol-4-one; 3-[2-(dimethylazaniumyl)ethyl]-5-{3-[2-(methylazaniumyl)ethyl]-4-oxo-1H-indol-5-ylidene}-1H-indol-4-one; 3-[2-(dimethylazaniumyl)ethyl]-5-{3-[2-(methylazaniumyl)ethyl]-4-oxo-1H-indol-7-ylidene}-1H-indol-4-one; 3-[2-(dimethylazaniumyl)ethyl]-7-{3-[2-(methylazaniumyl)ethyl]-4-oxo-1H-indol-2-ylidene}-1H-indol-4-one; 3-[2-(dimethylazaniumyl)ethyl]-7-{3-[2-(methylazaniumyl)ethyl]-4-oxo-1H-indol-5-ylidene}-1H-indol-4-one; 3-[2-(dimethylazaniumyl)ethyl]-7-{3-[2-(methylazaniumyl)ethyl]-4-oxo-1H-indol-7-ylidene}-1H-indol-4-one; and one or more tautomers of the foregoing.

In some embodiments, the composition comprises psilocybin, psilocin, baeocystin, and norpsilocin at a combined concentration of at least 4 percent and no greater than 80 percent by dry weight, and the composition comprises the norpsilocin and the one or more oxidized dione dimers of norpsilocin and psilocin at a mole ratio of at least 1:1 (norpsilocin:one or more oxidized dione dimers of norpsilocin and psilocin). In some specific embodiments, the composition comprises the norpsilocin and the one or more oxidized dione dimers of norpsilocin and psilocin at a mole ratio of at least 5:1. In some very specific embodiments, the composition comprises the norpsilocin and the one or more oxidized dione dimers of norpsilocin and psilocin at a mole ratio of at least 10:1. Such compositions may be formulated by protecting compositions comprising psilocybin and baeocystin from dephosphorylation and protecting compositions comprising psilocin and norpsilocin from oxidation as described herein.

In some embodiments, the composition comprises psilocybin, psilocin, baeocystin, and norpsilocin at a combined concentration of at least 4 percent and no greater than 40 percent by dry weight. In some specific embodiments, the composition comprises psilocybin, psilocin, baeocystin, and norpsilocin at a combined concentration of at least 6 percent and no greater than 32 percent by dry weight. In some very specific embodiments, the composition comprises psilocybin, psilocin, baeocystin, and norpsilocin at a combined concentration of at least 8 percent and no greater than 24 percent by dry weight.

In some embodiments, the composition comprises psilocybin, psilocin, baeocystin, norpsilocin, and one or more oxidized dione dimers of norpsilocin and psilocin; the composition is formulated for human consumption; and the composition comprises the norpsilocin and the one or more oxidized dione dimers of norpsilocin and psilocin at a mole ratio of at least 1:1 (norpsilocin:one or more oxidized dione dimers of norpsilocin and psilocin). In some specific embodiments, the composition comprises the norpsilocin and the one or more oxidized dione dimers of norpsilocin and psilocin at a mole ratio of at least 5:1. In some very specific embodiments, the composition comprises the norpsilocin and the one or more oxidized dione dimers of norpsilocin and psilocin at a mole ratio of at least 10:1.

The oxidized dione dimers of norpsilocin and psilocin lack any appreciable binding affinity to 5-HT receptors and lack any known pharmacological effects. The mole ratio of norpsilocin to the one or more oxidized dione dimers of norpsilocin and psilocin (norpsilocin:one or more oxidized dione dimers of norpsilocin and psilocin) is instead indicative of the extraction methods of this disclosure (and not indicative of prior-art methods that fail to adequately control for the oxidation of norpsilocin and that therefore produce relatively low mole ratios of norpsilocin to the oxidized dione dimers, which oxidation correlates with the blue coloration observed, for example, in prior-art manufacturing intermediates as described supra).

A fifth oxidation product of norpsilocin is a triol dimer of norpsilocin and psilocin, which has the approximate molecular weight of 411 atomic mass units. Such triol dimers have the chemical formulas 3-[2-(dimethylazaniumyl)ethyl]-2-{3-[2-(methylazaniumyl)ethyl]-4-hydroxy-1H-indol-2-yl}-1H-indol-4,5-diol; 3-[2-(dimethylazaniumyl)ethyl]-2-{3-[2-(methylazaniumyl)ethyl]-4-hydroxy-1H-indol-2-yl}-1H-indol-4,7-diol; 3-[2-(dimethylazaniumyl)ethyl]-2-{3-[2-(methylazaniumyl) ethyl]-4-hydroxy-1H-indol-5-yl}-1H-indol-4,5-diol; 3-[2-(dimethylazaniumyl)ethyl]-2-{3-[2-(methylazaniumyl) ethyl]-4-hydroxy-1H-indol-5-yl}-1H-indol-4,7-diol; 3-[2-(dimethylazaniumyl)ethyl]-2-{3-[2-(methylazaniumyl) ethyl]-4-hydroxy-1H-indol-7-yl}-1H-indol-4,5-diol; 3-[2-(dimethylazaniumyl)ethyl]-2-{3-[2-(methylazaniumyl) ethyl]-4-hydroxy-1H-indol-7-yl}-1H-indol-4,7-diol; 3-[2-(dimethylazaniumyl)ethyl]-5-{3-[2-(methylazaniumyl) ethyl]-4-hydroxy-1H-indol-2-yl}-1H-indol-2,4-diol; 3-[2-(dimethylazaniumyl)ethyl]-5-{3-[2-(methylazaniumyl) ethyl]-4-hydroxy-1H-indol-2-yl}-1H-indol-4,7-diol; 3-[2-(dimethylazaniumyl)ethyl]-5-{3-[2-(methylazaniumyl) ethyl]-4-hydroxy-1H-indol-5-yl}-1H-indol-2,4-diol; 3-[2-(dimethylazaniumyl)ethyl]-5-{3-[2-(methylazaniumyl) ethyl]-4-hydroxy-1H-indol-5-yl}-1H-indol-4,7-diol; 3-[2-(dimethylazaniumyl)ethyl]-5-{3-[2-(methylazaniumyl) ethyl]-4-hydroxy-1H-indol-7-yl}-1H-indol-2,4-diol; 3-[2-(dimethylazaniumyl)ethyl]-5-{3-[2-(methylazaniumyl) ethyl]-4-hydroxy-1H-indol-7-yl}-1H-indol-4,7-diol; 3-[2-(dimethylazaniumyl)ethyl]-7-{3-[2-(methylazaniumyl) ethyl]-4-hydroxy-1H-indol-2-yl}-1H-indol-2,4-diol; 3-[2-(dimethylazaniumyl)ethyl]-7-{3-[2-(methylazaniumyl) ethyl]-4-hydroxy-1H-indol-2-yl}-1H-indol-4,5-diol; 3-[2-(dimethylazaniumyl)ethyl]-7-{3-[2-(methylazaniumyl) ethyl]-4-hydroxy-1H-indol-5-yl}-1H-indol-2,4-diol; 3-[2-(dimethylazaniumyl)ethyl]-7-{3-[2-(methylazaniumyl) ethyl]-4-hydroxy-1H-indol-5-yl}-1H-indol-4,5-diol; 3-[2-(dimethylazaniumyl)ethyl]-7-{3-[2-(methylazaniumyl) ethyl]-4-hydroxy-1H-indol-7-yl}-1H-indol-2,4-diol; 3-[2-(dimethylazaniumyl)ethyl]-7-{3-[2-(methylazaniumyl) ethyl]-4-hydroxy-1H-indol-7-yl}-1H-indol-4,5-diol; 3-[2-(dimethylazaniumyl)ethyl]-6-{3-[2-(methylazaniumyl) ethyl]-4-hydroxy-1H-indol-2-yl}-1H-indol-2,4-diol; 3-[2-(dimethylazaniumyl)ethyl]-6-{3-[2-(methylazaniumyl) ethyl]-4-hydroxy-1H-indol-2-yl}-1H-indol-4,5-diol; 3-[2-(dimethylazaniumyl)ethyl]-6-{3-[2-(methylazaniumyl) ethyl]-4-hydroxy-1H-indol-2-yl}-1H-indol-4,7-diol; 3-[2-(dimethylazaniumyl)ethyl]-6-{3-[2-(methylazaniumyl) ethyl]-4-hydroxy-1H-indol-5-yl}-1H-indol-2,4-diol; 3-[2-(dimethylazaniumyl)ethyl]-6-{3-[2-(methylazaniumyl) ethyl]-4-hydroxy-1H-indol-5-yl}-1H-indol-4,5-diol; 3-[2-

(dimethylazaniumyl)ethyl]-6-{3-[2-(methylazaniumyl) ethyl]-4-hydroxy-1H-indol-5-yl}-1H-indol-4,7-diol; 3-[2-(dimethylazaniumyl)ethyl]-6-{3-[2-(methylazaniumyl) ethyl]-4-hydroxy-1H-indol-7-yl}-1H-indol-2,4-diol; 3-[2-(dimethylazaniumyl)ethyl]-6-{3-[2-(methylazaniumyl) ethyl]-4-hydroxy-1H-indol-7-yl}-1H-indol-4,5-diol; 3-[2-(dimethylazaniumyl)ethyl]-6-{3-[2-(methylazaniumyl) ethyl]-4-hydroxy-1H-indol-7-yl}-1H-indol-4,7-diol; 3-[2-(methylazaniumyl)ethyl]-2-{3-[2-(dimethylazaniumyl) ethyl]-4-hydroxy-1H-indol-2-yl}-1H-indol-4,5-diol; 3-[2-(methylazaniumyl)ethyl]-2-{3-[2-(dimethylazaniumyl) ethyl]-4-hydroxy-1H-indol-2-yl}-1H-indol-4,7-diol; 3-[2-(methylazaniumyl)ethyl]-2-{3-[2-(dimethylazaniumyl) ethyl]-4-hydroxy-1H-indol-5-yl}-1H-indol-4,5-diol; 3-[2-(methylazaniumyl)ethyl]-2-{3-[2-(dimethylazaniumyl) ethyl]-4-hydroxy-1H-indol-5-yl}-1H-indol-4,7-diol; 3-[2-(methylazaniumyl)ethyl]-2-{3-[2-(dimethylazaniumyl) ethyl]-4-hydroxy-1H-indol-7-yl}-1H-indol-4,5-diol; 3-[2-(methylazaniumyl)ethyl]-2-{3-[2-(dimethylazaniumyl) ethyl]-4-hydroxy-1H-indol-7-yl}-1H-indol-4,7-diol; 3-[2-(methylazaniumyl)ethyl]-5-{3-[2-(dimethylazaniumyl) ethyl]-4-hydroxy-1H-indol-2-yl}-1H-indol-2,4-diol; 3-[2-(methylazaniumyl)ethyl]-5-{3-[2-(dimethylazaniumyl) ethyl]-4-hydroxy-1H-indol-2-yl}-1H-indol-4,7-diol; 3-[2-(methylazaniumyl)ethyl]-5-{3-[2-(dimethylazaniumyl) ethyl]-4-hydroxy-1H-indol-5-yl}-1H-indol-2,4-diol; 3-[2-(methylazaniumyl)ethyl]-5-{3-[2-(dimethylazaniumyl) ethyl]-4-hydroxy-1H-indol-5-yl}-1H-indol-4,7-diol; 3-[2-(methylazaniumyl)ethyl]-5-{3-[2-(dimethylazaniumyl) ethyl]-4-hydroxy-1H-indol-7-yl}-1H-indol-2,4-diol; 3-[2-(methylazaniumyl)ethyl]-5-{3-[2-(dimethylazaniumyl) ethyl]-4-hydroxy-1H-indol-7-yl}-1H-indol-4,7-diol; 3-[2-(methylazaniumyl)ethyl]-7-{3-[2-(dimethylazaniumyl) ethyl]-4-hydroxy-1H-indol-2-yl}-1H-indol-2,4-diol; 3-[2-(methylazaniumyl)ethyl]-7-{3-[2-(dimethylazaniumyl) ethyl]-4-hydroxy-1H-indol-2-yl}-1H-indol-4,5-diol; 3-[2-(methylazaniumyl)ethyl]-7-{3-[2-(dimethylazaniumyl) ethyl]-4-hydroxy-1H-indol-5-yl}-1H-indol-2,4-diol; 3-[2-(methylazaniumyl)ethyl]-7-{3-[2-(dimethylazaniumyl) ethyl]-4-hydroxy-1H-indol-5-yl}-1H-indol-4,5-diol; 3-[2-(methylazaniumyl)ethyl]-7-{3-[2-(dimethylazaniumyl) ethyl]-4-hydroxy-1H-indol-7-yl}-1H-indol-2,4-diol; 3-[2-(methylazaniumyl)ethyl]-7-{3-[2-(dimethylazaniumyl) ethyl]-4-hydroxy-1H-indol-7-yl}-1H-indol-4,5-diol; 3-[2-(methylazaniumyl)ethyl]-6-{3-[2-(dimethylazaniumyl) ethyl]-4-hydroxy-1H-indol-2-yl}-1H-indol-2,4-diol; 3-[2-(methylazaniumyl)ethyl]-6-{3-[2-(dimethylazaniumyl) ethyl]-4-hydroxy-1H-indol-2-yl}-1H-indol-4,5-diol; 3-[2-(methylazaniumyl)ethyl]-6-{3-[2-(dimethylazaniumyl) ethyl]-4-hydroxy-1H-indol-2-yl}-1H-indol-4,7-diol; 3-[2-(methylazaniumyl)ethyl]-6-{3-[2-(dimethylazaniumyl) ethyl]-4-hydroxy-1H-indol-5-yl}-1H-indol-2,4-diol; 3-[2-(methylazaniumyl)ethyl]-6-{3-[2-(dimethylazaniumyl) ethyl]-4-hydroxy-1H-indol-5-yl}-1H-indol-4,5-diol; 3-[2-(methylazaniumyl)ethyl]-6-{3-[2-(dimethylazaniumyl) ethyl]-4-hydroxy-1H-indol-5-yl}-1H-indol-4,7-diol; 3-[2-(methylazaniumyl)ethyl]-6-{3-[2-(dimethylazaniumyl) ethyl]-4-hydroxy-1H-indol-7-yl}-1H-indol-2,4-diol; 3-[2-(methylazaniumyl)ethyl]-6-{3-[2-(dimethylazaniumyl) ethyl]-4-hydroxy-1H-indol-7-yl}-1H-indol-4,5-diol; and 3-[2-(methylazaniumyl)ethyl]-6-{3-[2-(dimethylazaniumyl) ethyl]-4-hydroxy-1H-indol-7-yl}-1H-indol-4,7-diol. Prominent species of the oxidized triol dimers include 3-[2-(dimethylazaniumyl)ethyl]-6-{3-[2-(methylazaniumyl) ethyl]-4-hydroxy-1H-indol-2-yl}-1H-indol-4,5-diol; 3-[2-(dimethylazaniumyl)ethyl]-5-{3-[2-(methylazaniumyl) ethyl]-4-hydroxy-1H-indol-5-yl}-1H-indol-4,7-diol; 3-[2-(methylazaniumyl)ethyl]-6-{3-[2-(dimethylazaniumyl) ethyl]-4-hydroxy-1H-indol-2-yl}-1H-indol-4,5-diol; and 3-[2-(methylazaniumyl)ethyl]-5-{3-[2-(dimethylazaniumyl) ethyl]-4-hydroxy-1H-indol-5-yl}-1H-indol-4,7-diol.

Various aspects of this disclosure relate to a composition comprising norpsilocin and one or more oxidized triol dimers of norpsilocin and psilocin, wherein the one or more oxidized triol dimers of norpsilocin and psilocin are selected from the compounds listed in the preceding paragraph.

In some embodiments, the composition comprises psilocybin, psilocin, baeocystin, and norpsilocin at a combined concentration of at least 4 percent and no greater than 80 percent by dry weight, and the composition comprises the norpsilocin and the one or more oxidized triol dimers of norpsilocin and psilocin at a mole ratio of at least 1:1 (norpsilocin:one or more oxidized triol dimers of norpsilocin and psilocin). In some specific embodiments, the composition comprises the norpsilocin and the one or more oxidized triol dimers of norpsilocin and psilocin at a mole ratio of at least 5:1. In some very specific embodiments, the composition comprises the norpsilocin and the one or more oxidized triol dimers of norpsilocin and psilocin at a mole ratio of at least 10:1. Such compositions may be formulated by protecting compositions comprising psilocybin and baeocystin from dephosphorylation and protecting compositions comprising psilocin and norpsilocin from oxidation as described herein.

In some embodiments, the composition comprises psilocybin, psilocin, baeocystin, and norpsilocin at a combined concentration of at least 4 percent and no greater than 40 percent by dry weight. In some specific embodiments, the composition comprises psilocybin, psilocin, baeocystin, and norpsilocin at a combined concentration of at least 6 percent and no greater than 32 percent by dry weight. In some very specific embodiments, the composition comprises psilocybin, psilocin, baeocystin, and norpsilocin at a combined concentration of at least 8 percent and no greater than 24 percent by dry weight.

In some embodiments, the composition comprises psilocybin, psilocin, baeocystin, norpsilocin, and one or more oxidized triol dimers of norpsilocin and psilocin; the composition is formulated for human consumption; and the composition comprises the norpsilocin and the one or more oxidized triol dimers of norpsilocin and psilocin at a mole ratio of at least 1:1 (norpsilocin:one or more oxidized triol dimers of norpsilocin and psilocin). In some specific embodiments, the composition comprises the norpsilocin and the one or more oxidized triol dimers of norpsilocin and psilocin at a mole ratio of at least 5:1. In some very specific embodiments, the composition comprises the norpsilocin and the one or more oxidized triol dimers of norpsilocin and psilocin at a mole ratio of at least 10:1.

The oxidized triol dimers of norpsilocin and psilocin lack any appreciable binding affinity to 5-HT receptors and lack any known pharmacological effects. The mole ratio of norpsilocin to the one or more oxidized triol dimers of norpsilocin and psilocin (norpsilocin:one or more oxidized triol dimers of norpsilocin and psilocin) is instead indicative of the extraction methods of this disclosure (and not indicative of prior-art methods that fail to adequately control for the oxidation of norpsilocin and that therefore produce relatively low mole ratios of norpsilocin to the oxidized triol dimers, which oxidation correlates with the blue coloration observed, for example, in prior-art manufacturing intermediates as described supra).

A sixth oxidation product of norpsilocin is a hydroxydione dimer of norpsilocin and psilocin, which has the approximate molecular weight of 408 atomic mass units. Such hydroxydione dimers have the chemical formulas 3-[2-(dimethylazaniumyl)ethyl]-2-{3-[2-(methylazaniumyl) ethyl]-4-hydroxy-1H-indol-2-yl}-1H-indol-4,5-dione; 3-[2-(dimethylazaniumyl)ethyl]-2-{3-[2-(methylazaniumyl) ethyl]-4-hydroxy-1H-indol-2-yl}-1H-indol-4,7-dione; 3-[2-(dimethylazaniumyl)ethyl]-2-{3-[2-(methylazaniumyl) ethyl]-4-hydroxy-1H-indol-5-yl}-1H-indol-4,5-dione; 3-[2-(dimethylazaniumyl)ethyl]-2-{3-[2-(methylazaniumyl) ethyl]-4-hydroxy-1H-indol-5-yl}-1H-indol-4,7-dione; 3-[2-(dimethylazaniumyl)ethyl]-2-{3-[2-(methylazaniumyl) ethyl]-4-hydroxy-1H-indol-7-yl}-1H-indol-4,5-dione; 3-[2-(dimethylazaniumyl)ethyl]-2-{3-[2-(methylazaniumyl) ethyl]-4-hydroxy-1H-indol-7-yl}-1H-indol-4,7-dione; 3-[2-(dimethylazaniumyl)ethyl]-5-{3-[2-(methylazaniumyl) ethyl]-4-hydroxy-1H-indol-2-yl}-1H-indol-2,4-dione; 3-[2-(dimethylazaniumyl)ethyl]-5-{3-[2-(methylazaniumyl) ethyl]-4-hydroxy-1H-indol-2-yl}-1H-indol-4,7-dione; 3-[2-(dimethylazaniumyl)ethyl]-5-{3-[2-(methylazaniumyl) ethyl]-4-hydroxy-1H-indol-5-yl}-1H-indol-2,4-dione; 3-[2-(dimethylazaniumyl)ethyl]-5-{3-[2-(methylazaniumyl) ethyl]-4-hydroxy-1H-indol-5-yl}-1H-indol-4,7-dione; 3-[2-(dimethylazaniumyl)ethyl]-5-{3-[2-(methylazaniumyl) ethyl]-4-hydroxy-1H-indol-7-yl}-1H-indol-2,4-dione; 3-[2-(dimethylazaniumyl)ethyl]-5-{3-[2-(methylazaniumyl) ethyl]-4-hydroxy-1H-indol-7-yl}-1H-indol-4,7-dione; 3-[2-(dimethylazaniumyl)ethyl]-7-{3-[2-(methylazaniumyl) ethyl]-4-hydroxy-1H-indol-2-yl}-1H-indol-2,4-dione; 3-[2-(dimethylazaniumyl)ethyl]-7-{3-[2-(methylazaniumyl) ethyl]-4-hydroxy-1H-indol-2-yl}-1H-indol-4,5-dione; 3-[2-(dimethylazaniumyl)ethyl]-7-{3-[2-(methylazaniumyl) ethyl]-4-hydroxy-1H-indol-5-yl}-1H-indol-2,4-dione; 3-[2-(dimethylazaniumyl)ethyl]-7-{3-[2-(methylazaniumyl) ethyl]-4-hydroxy-1H-indol-5-yl}-1H-indol-4,5-dione; 3-[2-(dimethylazaniumyl)ethyl]-7-{3-[2-(methylazaniumyl) ethyl]-4-hydroxy-1H-indol-7-yl}-1H-indol-2,4-dione; 3-[2-(dimethylazaniumyl)ethyl]-7-{3-[2-(methylazaniumyl) ethyl]-4-hydroxy-1H-indol-7-yl}-1H-indol-4,5-dione; 3-[2-(dimethylazaniumyl)ethyl]-6-{3-[2-(methylazaniumyl) ethyl]-4-hydroxy-1H-indol-2-yl}-1H-indol-2,4-dione; 3-[2-(dimethylazaniumyl)ethyl]-6-{3-[2-(methylazaniumyl) ethyl]-4-hydroxy-1H-indol-2-yl}-1H-indol-4,5-dione; 3-[2-(dimethylazaniumyl)ethyl]-6-{3-[2-(methylazaniumyl) ethyl]-4-hydroxy-1H-indol-2-yl}-1H-indol-4,7-dione; 3-[2-(dimethylazaniumyl)ethyl]-6-{3-[2-(methylazaniumyl) ethyl]-4-hydroxy-1H-indol-5-yl}-1H-indol-2,4-dione; 3-[2-(dimethylazaniumyl)ethyl]-6-{3-[2-(methylazaniumyl) ethyl]-4-hydroxy-1H-indol-5-yl}-1H-indol-4,5-dione; 3-[2-(dimethylazaniumyl)ethyl]-6-{3-[2-(methylazaniumyl) ethyl]-4-hydroxy-1H-indol-5-yl}-1H-indol-4,7-dione; 3-[2-(dimethylazaniumyl)ethyl]-6-{3-[2-(methylazaniumyl) ethyl]-4-hydroxy-1H-indol-7-yl}-1H-indol-2,4-dione; 3-[2-(dimethylazaniumyl)ethyl]-6-{3-[2-(methylazaniumyl) ethyl]-4-hydroxy-1H-indol-7-yl}-1H-indol-4,5-dione; 3-[2-(dimethylazaniumyl)ethyl]-6-{3-[2-(methylazaniumyl) ethyl]-4-hydroxy-1H-indol-7-yl}-1H-indol-4,7-dione; 3-[2-(methylazaniumyl)ethyl]-2-{3-[2-(dimethylazaniumyl) ethyl]-4-hydroxy-1H-indol-2-yl}-1H-indol-4,5-dione; 3-[2-(methylazaniumyl)ethyl]-2-{3-[2-(dimethylazaniumyl) ethyl]-4-hydroxy-1H-indol-2-yl}-1H-indol-4,7-dione; 3-[2-(methylazaniumyl)ethyl]-2-{3-[2-(dimethylazaniumyl) ethyl]-4-hydroxy-1H-indol-5-yl}-1H-indol-4,5-dione; 3-[2-(methylazaniumyl)ethyl]-2-{3-[2-(dimethylazaniumyl) ethyl]-4-hydroxy-1H-indol-5-yl}-1H-indol-4,7-dione; 3-[2-(methylazaniumyl)ethyl]-2-{3-[2-(dimethylazaniumyl) ethyl]-4-hydroxy-1H-indol-7-yl}-1H-indol-4,5-dione; 3-[2-(methylazaniumyl)ethyl]-2-{3-[2-(dimethylazaniumyl) ethyl]-4-hydroxy-1H-indol-7-yl}-1H-indol-4,7-dione; 3-[2-(methylazaniumyl)ethyl]-5-{3-[2-(dimethylazaniumyl) ethyl]-4-hydroxy-1H-indol-2-yl}-1H-indol-2,4-dione; 3-[2-(methylazaniumyl)ethyl]-5-{3-[2-(dimethylazaniumyl) ethyl]-4-hydroxy-1H-indol-2-yl}-1H-indol-4,7-dione; 3-[2-(methylazaniumyl)ethyl]-5-{3-[2-(dimethylazaniumyl) ethyl]-4-hydroxy-1H-indol-5-yl}-1H-indol-2,4-dione; 3-[2-(methylazaniumyl)ethyl]-5-{3-[2-(dimethylazaniumyl) ethyl]-4-hydroxy-1H-indol-5-yl}-1H-indol-4,7-dione; 3-[2-(methylazaniumyl)ethyl]-5-{3-[2-(dimethylazaniumyl) ethyl]-4-hydroxy-1H-indol-7-yl}-1H-indol-2,4-dione; 3-[2-(methylazaniumyl)ethyl]-5-{3-[2-(dimethylazaniumyl) ethyl]-4-hydroxy-1H-indol-7-yl}-1H-indol-4,7-dione; 3-[2-(methylazaniumyl)ethyl]-7-{3-[2-(dimethylazaniumyl) ethyl]-4-hydroxy-1H-indol-2-yl}-1H-indol-2,4-dione; 3-[2-(methylazaniumyl)ethyl]-7-{3-[2-(dimethylazaniumyl) ethyl]-4-hydroxy-1H-indol-2-yl}-1H-indol-4,5-dione; 3-[2-(methylazaniumyl)ethyl]-7-{3-[2-(dimethylazaniumyl) ethyl]-4-hydroxy-1H-indol-5-yl}-1H-indol-2,4-dione; 3-[2-(methylazaniumyl)ethyl]-7-{3-[2-(dimethylazaniumyl) ethyl]-4-hydroxy-1H-indol-5-yl}-1H-indol-4,5-dione; 3-[2-(methylazaniumyl)ethyl]-7-{3-[2-(dimethylazaniumyl) ethyl]-4-hydroxy-1H-indol-7-yl}-1H-indol-2,4-dione; 3-[2-(methylazaniumyl)ethyl]-7-{3-[2-(dimethylazaniumyl) ethyl]-4-hydroxy-1H-indol-7-yl}-1H-indol-4,5-dione; 3-[2-(methylazaniumyl)ethyl]-6-{3-[2-(dimethylazaniumyl) ethyl]-4-hydroxy-1H-indol-2-yl}-1H-indol-2,4-dione; 3-[2-(methylazaniumyl)ethyl]-6-{3-[2-(dimethylazaniumyl) ethyl]-4-hydroxy-1H-indol-2-yl}-1H-indol-4,5-dione; 3-[2-(methylazaniumyl)ethyl]-6-{3-[2-(dimethylazaniumyl) ethyl]-4-hydroxy-1H-indol-2-yl}-1H-indol-4,7-dione; 3-[2-(methylazaniumyl)ethyl]-6-{3-[2-(dimethylazaniumyl) ethyl]-4-hydroxy-1H-indol-5-yl}-1H-indol-2,4-dione; 3-[2-(methylazaniumyl)ethyl]-6-{3-[2-(dimethylazaniumyl) ethyl]-4-hydroxy-1H-indol-5-yl}-1H-indol-4,5-dione; 3-[2-(methylazaniumyl)ethyl]-6-{3-[2-(dimethylazaniumyl) ethyl]-4-hydroxy-1H-indol-5-yl}-1H-indol-4,7-dione; 3-[2-(methylazaniumyl)ethyl]-6-{3-[2-(dimethylazaniumyl) ethyl]-4-hydroxy-1H-indol-7-yl}-1H-indol-2,4-dione; 3-[2-(methylazaniumyl)ethyl]-6-{3-[2-(dimethylazaniumyl) ethyl]-4-hydroxy-1H-indol-7-yl}-1H-indol-4,5-dione; and 3-[2-(methylazaniumyl)ethyl]-6-{3-[2-(dimethylazaniumyl) ethyl]-4-hydroxy-1H-indol-7-yl}-1H-indol-4,7-dione and also include tautomers of the foregoing. The tautomers of the foregoing are not technically "hydroxydione dimers" themselves because one or both of the two oxo groups are reduced to hydroxy in the tautomers, but the term "hydroxydione dimers" as used herein nevertheless includes the tautomers of the foregoing. Prominent species of the hydroxydione dimers include 3-[2-(dimethylazaniumyl) ethyl]-5-{3-[2-(methylazaniumyl)ethyl]-4-hydroxy-1H-indol-5-yl}-1H-indol-4,7-dione; 3-[2-(dimethylazaniumyl) ethyl]-6-{3-[2-(methylazaniumyl)ethyl]-4-hydroxy-1H-indol-2-yl}-1H-indol-4,5-dione; 3-[2-(methylazaniumyl) ethyl]-5-{3-[2-(dimethylazaniumyl)ethyl]-4-hydroxy-1H-indol-5-yl}-1H-indol-4,7-dione; 3-[2-(methylazaniumyl) ethyl]-6-{3-[2-(dimethylazaniumyl)ethyl]-4-hydroxy-1H-indol-2-yl}-1H-indol-4,5-dione; and tautomers of the foregoing.

Various aspects of this disclosure relate to a composition comprising norpsilocin and one or more oxidized hydroxydione dimers of norpsilocin and psilocin, wherein the one or more oxidized hydroxydione dimers of norpsilocin and psilocin are selected from the compounds listed in the preceding paragraph.

In some embodiments, the composition comprises psilocybin, psilocin, baeocystin, and norpsilocin at a combined concentration of at least 4 percent and no greater than 80 percent by dry weight, and the composition comprises the norpsilocin and the one or more oxidized hydroxydione dimers of norpsilocin and psilocin at a mole ratio of at least 1:1 (norpsilocin:one or more oxidized hydroxydione dimers of norpsilocin and psilocin). In some specific embodiments, the composition comprises the norpsilocin and the one or more oxidized hydroxydione dimers of norpsilocin and psilocin at a mole ratio of at least 5:1. In some very specific embodiments, the composition comprises the norpsilocin and the one or more oxidized hydroxydione dimers of norpsilocin and psilocin at a mole ratio of at least 10:1. Such compositions may be formulated by protecting compositions comprising psilocybin and baeocystin from dephosphorylation and protecting compositions comprising psilocin and norpsilocin from oxidation as described herein.

In some embodiments, the composition comprises psilocybin, psilocin, baeocystin, and norpsilocin at a combined concentration of at least 4 percent and no greater than 40 percent by dry weight. In some specific embodiments, the composition comprises psilocybin, psilocin, baeocystin, and norpsilocin at a combined concentration of at least 6 percent and no greater than 32 percent by dry weight. In some very specific embodiments, the composition comprises psilocybin, psilocin, baeocystin, and norpsilocin at a combined concentration of at least 8 percent and no greater than 24 percent by dry weight.

In some embodiments, the composition comprises psilocybin, psilocin, baeocystin, norpsilocin, and one or more oxidized hydroxydione dimers of norpsilocin and psilocin; the composition is formulated for human consumption; and the composition comprises the norpsilocin and the one or more oxidized hydroxydione dimers of norpsilocin and psilocin at a mole ratio of at least 1:1 (norpsilocin:one or more oxidized hydroxydione dimers of norpsilocin and psilocin). In some specific embodiments, the composition comprises the norpsilocin and the one or more oxidized hydroxydione dimers of norpsilocin and psilocin at a mole ratio of at least 5:1. In some very specific embodiments, the composition comprises the norpsilocin and the one or more oxidized hydroxydione dimers of norpsilocin and psilocin at a mole ratio of at least 10:1.

The oxidized hydroxydione dimers of norpsilocin and psilocin lack any appreciable binding affinity to 5-HT receptors and lack any known pharmacological effects. The mole ratio of norpsilocin to the one or more oxidized hydroxydione dimers of norpsilocin and psilocin (norpsilocin:one or more oxidized hydroxydione dimers of norpsilocin and psilocin) is instead indicative of the extraction methods of this disclosure (and not indicative of prior-art methods that fail to adequately control for the oxidation of norpsilocin and that therefore produce relatively low mole ratios of norpsilocin to the oxidized hydroxydione dimers, which oxidation correlates with the blue coloration observed, for example, in prior-art manufacturing intermediates as described supra).

A seventh oxidation product of norpsilocin is a trione dimer of norpsilocin and psilocin, which has the approximate molecular weight of 406 atomic mass units. Such trione dimers have the chemical formulas 3-[2-(dimethylazaniumyl)ethyl]-2-{3-[2-(methylazaniumyl)ethyl]-4-oxo-4H-indol-2-yl}-1H-indol-4,5-dione; 3-[2-(dimethylazaniumyl)ethyl]-2-{3-[2-(methylazaniumyl)ethyl]-4-oxo-4H-indol-2-yl}-1H-indol-4,7-dione; 3-[2-(dimethylazaniumyl)ethyl]-2-{3-[2-(methylazaniumyl)ethyl]-4-oxo-4H-indol-5-yl}-1H-indol-4,5-dione; 3-[2-(dimethylazaniumyl)ethyl]-2-{3-[2-(methylazaniumyl)ethyl]-4-oxo-4H-indol-5-yl}-1H-indol-4,7-dione; 3-[2-(dimethylazaniumyl)ethyl]-2-{3-[2-(methylazaniumyl)ethyl]-4-oxo-4H-indol-7-yl}-1H-indol-4,5-dione; 3-[2-(dimethylazaniumyl)ethyl]-2-{3-[2-(methylazaniumyl)ethyl]-4-oxo-4H-indol-7-yl}-1H-indol-4,7-dione; 3-[2-(dimethylazaniumyl)ethyl]-5-{3-[2-(methylazaniumyl)ethyl]-4-oxo-4H-indol-2-yl}-1H-indol-2,4-dione; 3-[2-(dimethylazaniumyl)ethyl]-5-{3-[2-(methylazaniumyl)ethyl]-4-oxo-4H-indol-2-yl}-1H-indol-4,7-dione; 3-[2-(dimethylazaniumyl)ethyl]-5-{3-[2-(methylazaniumyl)ethyl]-4-oxo-4H-indol-5-yl}-1H-indol-2,4-dione; 3-[2-(dimethylazaniumyl)ethyl]-5-{3-[2-(methylazaniumyl)ethyl]-4-oxo-4H-indol-5-yl}-1H-indol-4,7-dione; 3-[2-(dimethylazaniumyl)ethyl]-5-{3-[2-(methylazaniumyl)ethyl]-4-oxo-4H-indol-7-yl}-1H-indol-2,4-dione; 3-[2-(dimethylazaniumyl)ethyl]-5-{3-[2-(methylazaniumyl)ethyl]-4-oxo-4H-indol-7-yl}-1H-indol-4,7-dione; 3-[2-(dimethylazaniumyl)ethyl]-7-{3-[2-(methylazaniumyl)ethyl]-4-oxo-4H-indol-2-yl}-1H-indol-2,4-dione; 3-[2-(dimethylazaniumyl)ethyl]-7-{3-[2-(methylazaniumyl)ethyl]-4-oxo-4H-indol-2-yl}-1H-indol-4,5-dione; 3-[2-(dimethylazaniumyl)ethyl]-7-{3-[2-(methylazaniumyl)ethyl]-4-oxo-4H-indol-5-yl}-1H-indol-2,4-dione; 3-[2-(dimethylazaniumyl)ethyl]-7-{3-[2-(methylazaniumyl)ethyl]-4-oxo-4H-indol-5-yl}-1H-indol-4,5-dione; 3-[2-(dimethylazaniumyl)ethyl]-7-{3-[2-(methylazaniumyl)ethyl]-4-oxo-4H-indol-7-yl}-1H-indol-2,4-dione; 3-[2-(dimethylazaniumyl)ethyl]-7-{3-[2-(methylazaniumyl)ethyl]-4-oxo-4H-indol-7-yl}-1H-indol-4,5-dione; 3-[2-(dimethylazaniumyl)ethyl]-6-{3-[2-(methylazaniumyl)ethyl]-4-oxo-4H-indol-2-yl}-1H-indol-2,4-dione; 3-[2-(dimethylazaniumyl)ethyl]-6-{3-[2-(methylazaniumyl)ethyl]-4-oxo-4H-indol-2-yl}-1H-indol-4,5-dione; 3-[2-(dimethylazaniumyl)ethyl]-6-{3-[2-(methylazaniumyl)ethyl]-4-oxo-4H-indol-2-yl}-1H-indol-4,7-dione; 3-[2-(dimethylazaniumyl)ethyl]-6-{3-[2-(methylazaniumyl)ethyl]-4-oxo-4H-indol-5-yl}-1H-indol-2,4-dione; 3-[2-(dimethylazaniumyl)ethyl]-6-{3-[2-(methylazaniumyl)ethyl]-4-oxo-4H-indol-5-yl}-1H-indol-4,5-dione; 3-[2-(dimethylazaniumyl)ethyl]-6-{3-[2-(methylazaniumyl)ethyl]-4-oxo-4H-indol-5-yl}-1H-indol-4,7-dione; 3-[2-(dimethylazaniumyl)ethyl]-6-{3-[2-(methylazaniumyl)ethyl]-4-oxo-4H-indol-7-yl}-1H-indol-2,4-dione; 3-[2-(dimethylazaniumyl)ethyl]-6-{3-[2-(methylazaniumyl)ethyl]-4-oxo-4H-indol-7-yl}-1H-indol-4,5-dione; 3-[2-(dimethylazaniumyl)ethyl]-6-{3-[2-(methylazaniumyl)ethyl]-4-oxo-4H-indol-7-yl}-1H-indol-4,7-dione; 3-[2-(methylazaniumyl)ethyl]-2-{3-[2-(dimethylazaniumyl)ethyl]-4-oxo-4H-indol-2-yl}-1H-indol-4,5-dione; 3-[2-(methylazaniumyl)ethyl]-2-{3-[2-(dimethylazaniumyl)ethyl]-4-oxo-4H-indol-2-yl}-1H-indol-4,7-dione; 3-[2-(methylazaniumyl)ethyl]-2-{3-[2-(dimethylazaniumyl)ethyl]-4-oxo-4H-indol-5-yl}-1H-indol-4,5-dione; 3-[2-(methylazaniumyl)ethyl]-2-{3-[2-(dimethylazaniumyl)ethyl]-4-oxo-4H-indol-5-yl}-1H-indol-4,7-dione; 3-[2-(methylazaniumyl)ethyl]-2-{3-[2-(dimethylazaniumyl)ethyl]-4-oxo-4H-indol-7-yl}-1H-indol-4,5-dione; 3-[2-(methylazaniumyl)ethyl]-2-{3-[2-(dimethylazaniumyl)ethyl]-4-oxo-4H-indol-7-yl}-1H-indol-4,7-dione; 3-[2-(methylazaniumyl)ethyl]-5-{3-[2-(dimethylazaniumyl)ethyl]-4-oxo-4H-indol-2-yl}-1H-indol-2,4-dione; 3-[2-(methylazaniumyl)ethyl]-5-{3-[2-(dimethylazaniumyl)ethyl]-4-oxo-4H-indol-2-yl}-1H-indol-4,7-dione; 3-[2-(methylazaniumyl)ethyl]-5-{3-[2-(dimethylazaniumyl)ethyl]-4-oxo-4H-indol-5-yl}-1H-indol-2,4-dione; 3-[2-(methylazaniumyl)ethyl]-5-{3-[2-(dimethylazaniumyl)ethyl]-4-oxo-4H-indol-5-yl}-1H-indol-4,7-dione; 3-[2-(methylazaniumyl)ethyl]-5-{3-[2-

(dimethylazaniumyl)ethyl]-4-oxo-4H-indol-7-yl}-1H-indol-2,4-dione; 3-[2-(methylazaniumyl)ethyl]-5-{3-[2-(dimethylazaniumyl)ethyl]-4-oxo-4H-indol-7-yl}-1H-indol-4,7-dione; 3-[2-(methylazaniumyl)ethyl]-7-{3-[2-(dimethylazaniumyl)ethyl]-4-oxo-4H-indol-2-yl}-1H-indol-2,4-dione; 3-[2-(methylazaniumyl)ethyl]-7-{3-[2-(dimethylazaniumyl)ethyl]-4-oxo-4H-indol-2-yl}-1H-indol-4,5-dione; 3-[2-(methylazaniumyl)ethyl]-7-{3-[2-(dimethylazaniumyl)ethyl]-4-oxo-4H-indol-5-yl}-1H-indol-2,4-dione; 3-[2-(methylazaniumyl)ethyl]-7-{3-[2-(dimethylazaniumyl)ethyl]-4-oxo-4H-indol-5-yl}-1H-indol-4,5-dione; 3-[2-(methylazaniumyl)ethyl]-7-{3-[2-(dimethylazaniumyl)ethyl]-4-oxo-4H-indol-7-yl}-1H-indol-2,4-dione; 3-[2-(methylazaniumyl)ethyl]-7-{3-[2-(dimethylazaniumyl)ethyl]-4-oxo-4H-indol-7-yl}-1H-indol-4,5-dione; 3-[2-(methylazaniumyl)ethyl]-6-{3-[2-(dimethylazaniumyl)ethyl]-4-oxo-4H-indol-2-yl}-1H-indol-2,4-dione; 3-[2-(methylazaniumyl)ethyl]-6-{3-[2-(dimethylazaniumyl)ethyl]-4-oxo-4H-indol-2-yl}-1H-indol-4,5-dione; 3-[2-(methylazaniumyl)ethyl]-6-{3-[2-(dimethylazaniumyl)ethyl]-4-oxo-4H-indol-2-yl}-1H-indol-4,7-dione; 3-[2-(methylazaniumyl)ethyl]-6-{3-[2-(dimethylazaniumyl)ethyl]-4-oxo-4H-indol-5-yl}-1H-indol-2,4-dione; 3-[2-(methylazaniumyl)ethyl]-6-{3-[2-(dimethylazaniumyl)ethyl]-4-oxo-4H-indol-5-yl}-1H-indol-4,5-dione; 3-[2-(methylazaniumyl)ethyl]-6-{3-[2-(dimethylazaniumyl)ethyl]-4-oxo-4H-indol-5-yl}-1H-indol-4,7-dione; 3-[2-(methylazaniumyl)ethyl]-6-{3-[2-(dimethylazaniumyl)ethyl]-4-oxo-4H-indol-7-yl}-1H-indol-2,4-dione; 3-[2-(methylazaniumyl)ethyl]-6-{3-[2-(dimethylazaniumyl)ethyl]-4-oxo-4H-indol-7-yl}-1H-indol-4,5-dione; and 3-[2-(methylazaniumyl)ethyl]-6-{3-[2-(dimethylazaniumyl)ethyl]-4-oxo-4H-indol-7-yl}-1H-indol-4,7-dione and also include tautomers of the foregoing. The tautomers of the foregoing are not technically "trione dimers" themselves because one or more of the three oxo groups are reduced to hydroxy in the tautomers, but the term "trione dimers" as used herein nevertheless includes the tautomers of the foregoing. Prominent species of the trione dimers include 3-[2-(dimethylazaniumyl)ethyl]-5-{3-[2-(methylazaniumyl)ethyl]-4-oxo-4H-indol-5-yl}-1H-indol-4,7-dione; 3-[2-(dimethylazaniumyl)ethyl]-6-{3-[2-(methylazaniumyl)ethyl]-4-oxo-4H-indol-2-yl}-1H-indol-4,5-dione; 3-[2-(methylazaniumyl)ethyl]-5-{3-[2-(dimethylazaniumyl)ethyl]-4-oxo-4H-indol-5-yl}-1H-indol-4,7-dione; 3-[2-(methylazaniumyl)ethyl]-6-{3-[2-(dimethylazaniumyl)ethyl]-4-oxo-4H-indol-2-yl}-1H-indol-4,5-dione; and tautomers of the foregoing.

Various aspects of this disclosure relate to a composition comprising norpsilocin and one or more oxidized trione dimers of norpsilocin and psilocin, wherein the one or more oxidized trione dimers of norpsilocin and psilocin are selected from the compounds listed in the preceding paragraph.

In some embodiments, the composition comprises psilocybin, psilocin, baeocystin, and norpsilocin at a combined concentration of at least 4 percent and no greater than 80 percent by dry weight, and the composition comprises the norpsilocin and the one or more oxidized trione dimers of norpsilocin and psilocin at a mole ratio of at least 1:1 (norpsilocin:one or more oxidized trione dimers of norpsilocin and psilocin). In some specific embodiments, the composition comprises the norpsilocin and the one or more oxidized trione dimers of norpsilocin and psilocin at a mole ratio of at least 5:1. In some very specific embodiments, the composition comprises the norpsilocin and the one or more oxidized trione dimers of norpsilocin and psilocin at a mole ratio of at least 10:1. Such compositions may be formulated by protecting compositions comprising psilocybin and baeocystin from dephosphorylation and protecting compositions comprising psilocin and norpsilocin from oxidation as described herein.

In some embodiments, the composition comprises psilocybin, psilocin, baeocystin, and norpsilocin at a combined concentration of at least 4 percent and no greater than 40 percent by dry weight. In some specific embodiments, the composition comprises psilocybin, psilocin, baeocystin, and norpsilocin at a combined concentration of at least 6 percent and no greater than 32 percent by dry weight. In some very specific embodiments, the composition comprises psilocybin, psilocin, baeocystin, and norpsilocin at a combined concentration of at least 8 percent and no greater than 24 percent by dry weight.

In some embodiments, the composition comprises psilocybin, psilocin, baeocystin, norpsilocin, and one or more oxidized trione dimers of norpsilocin and psilocin; the composition is formulated for human consumption; and the composition comprises the norpsilocin and the one or more oxidized trione dimers of norpsilocin and psilocin at a mole ratio of at least 1:1 (norpsilocin:one or more oxidized trione dimers of norpsilocin and psilocin). In some specific embodiments, the composition comprises the norpsilocin and the one or more oxidized trione dimers of norpsilocin and psilocin at a mole ratio of at least 5:1. In some very specific embodiments, the composition comprises the norpsilocin and the one or more oxidized trione dimers of norpsilocin and psilocin at a mole ratio of at least 10:1.

The oxidized trione dimers of norpsilocin and psilocin lack any appreciable binding affinity to 5-HT receptors and lack any known pharmacological effects. The mole ratio of norpsilocin to the one or more oxidized trione dimers of norpsilocin and psilocin (norpsilocin:one or more oxidized trione dimers of norpsilocin and psilocin) is instead indicative of the extraction methods of this disclosure (and not indicative of prior-art methods that fail to adequately control for the oxidation of norpsilocin and that therefore produce relatively low mole ratios of norpsilocin to the oxidized trione dimers, which oxidation correlates with the blue coloration observed, for example, in prior-art manufacturing intermediates as described supra).

The inventors have discovered (as should be readily apparent to those of ordinary skill in the relevant arts) that the heterogeneity of both psychedelic tryptamines and pharmacologically-inactive oxidation products thereof impaired the ability of prior art methods to determine whether any given extraction was performed quantitatively. Specifically, the myriad oxidation products of tryptamines means that many oxidation products are present at relatively low concentrations relative to prevalent tryptamines such as psilocybin and psilocin. The aggregate amount of such oxidation products may be both significant and challenging to directly quantify. This contrasts, for example, with the degradation of tetrahydrocannabinol (THC) during manufacturing processes that produce THC-containing products, which displays a prominent oxidation product, namely cannabinol (CBN). One may therefore approximate loss caused by oxidation by measuring CBN. Such calculations are unnecessary for THC because methods exist to quantitatively extract cannabinoids (e.g., THC and its naturally-occurring form tetrahydrocannabinolic acid) from most compositions without oxidizing any cannabinoids, which allows direct methods to quantify yields. The lack of analogous quantitative extraction methods in the prior art for tryptamines, however, means that no direct methods previously existed to quantify yields. Further, the lack of a single, prominent oxidation product analogous to CBN means that tryptamine loss to oxidation cannot be indirectly calculated by measuring such a single, prominent oxidation product following an extraction-even when implementing the improved extraction techniques described herein.

Various aspects of this disclosure relate to a process to inactivate enzymes of a tryptamine-containing fungal material. Various aspects of this disclosure relate to a product manufactured by a process to inactivate enzymes of a tryptamine-containing fungal material.

The terms "process" and "method" are synonyms as used in this disclosure.

In some embodiments, the process comprises heating tryptamine-containing fungal material. In some specific embodiments, the process comprises heating a starting fungal material to a temperature range of at least 40 degrees Celsius and no greater than 150 degrees Celsius and holding the starting fungal material within the temperature range for a period of time to produce a heat-inactivated fungal material. Without limiting this disclosure or any patent claim that matures from this disclosure, fungal enzymes (e.g., phosphatases, esterases, oxidoreductases, laccases) remain active at temperatures lower than about 40 degrees Celsius, and temperatures lower than about 40 degrees Celsius are inefficient at denaturing such fungal enzymes. Without limiting this disclosure or any patent claim that matures from this disclosure, temperatures greater than about 150 degrees Celsius significantly increase the thermal decomposition rate of phosphoryloxytryptamines (e.g., psilocybin, baeocystin, norbaeocystin, aeruginascin) and hydroxytryptamines (e.g., psilocin, norpsilocin, 4-HT, 4-hydroxy-TMT, bufotenin). Without limiting this disclosure or any patent claim that matures from this disclosure, heating tryptamines at temperatures greater than 125 degrees Celsius for greater than 90 minutes results in significant thermal decomposition of phosphoryloxytryptamines and hydroxytryptamines. In some embodiments, the period of time is no greater than 90 minutes.

Unlike culinary mushrooms such as *Agaricus bisporus*, which produces button and portobello mushrooms, mushrooms that contain psychedelic tryptamines generally have not been bred to select against the production of proteins, polysaccharides, phenolic compounds, indoles other than tryptamines, and other compounds that can cause gastrointestinal distress and other undesirable symptoms. *A. bisporus*, for example, contains relatively low amounts of beta-glucans and chitin compared to undomesticated mushrooms. Individuals who consume mushrooms that contain psychedelic tryptamines may therefore experience one or more of bloating, gas, cramping, nausea, vomiting, diarrhea, headaches, fever, and other side effects that are unrelated to psychedelic tryptamines. Additionally, many individuals are allergic to fungi. Without limiting this disclosure or any patent claim that matures from this disclosure, heating fungal material as described herein can denature proteins and/or degrade other compounds that cause gastrointestinal distress, allergies, and other undesirable side effects.

In some embodiments, the process comprises heating a starting fungal material to a temperature range of at least 40 degrees Celsius and no greater than 140 degrees Celsius and holding the starting fungal material within the temperature range for the period of time. In some specific embodiments, the process comprises heating a starting fungal material to a temperature range of at least 40 degrees Celsius and no greater than 120 degrees Celsius and holding the starting fungal material within the temperature range for the period of time. In some even more specific embodiments, the process comprises heating a starting fungal material to a temperature range of at least 40 degrees Celsius and no greater than 100 degrees Celsius and holding the starting fungal material within the temperature range for the period of time. In some very specific embodiments, the process comprises heating a starting fungal material to a temperature range of at least 44 degrees Celsius and no greater than 91 degrees Celsius and holding the starting fungal material within the temperature range for the period of time.

In some embodiments, the period of time is at least 1 second. In some specific embodiments, the period of time is at least 10 seconds. In some even more specific embodiments, the period of time is at least 1 minute. In some very specific embodiments, the period of time is at least 5 minutes.

In some embodiments, the period of time is at least 2 minutes and no greater than 90 minutes. In some specific embodiments, the period of time is at least 5 minutes and no greater than 60 minutes. In some even more specific embodiments, the period of time is at least 5 minutes and no greater than 45 minutes. In some very specific embodiments, the period of time is at least 5 minutes and no greater than 30 minutes.

In some embodiments, the starting fungal material comprises one or more of mycelium, sclerotium, and fruiting bodies.

In some embodiments, at least 10 percent of the starting fungal material consists of mycelium and sclerotium, and no greater than 90 percent of the starting fungal material consists of fruiting bodies. In some specific embodiments, at least 50 percent of the starting fungal material consists of mycelium and sclerotium, and no greater than 50 percent of the starting fungal material consists of fruiting bodies. In some even more specific embodiments, at least 80 percent of the starting fungal material consists of mycelium and sclerotium, and no greater than 20 percent of the starting fungal material consists of fruiting bodies. In some very specific embodiments, at least 90 percent of the starting fungal material consists of mycelium and sclerotium, and no greater than 10 percent of the starting fungal material consists of fruiting bodies.

In some embodiments, the starting fungal material comprises wet fungal material as described herein.

In some embodiments, the process comprises growing the starting fungal material in a container comprising liquid growth media. In some specific embodiments, the process comprises growing the starting fungal material in a container comprising liquid growth media and draining, decanting, and/or aspirating the liquid growth media from the container.

In some embodiments, the process comprises growing the starting fungal material in a container, wherein heating the starting fungal material and holding the starting fungal material within the temperature range for the period of time is performed while the starting fungal material is contained within the container.

In some embodiments, the heating is performed in an autoclave. The term "autoclave" as used in this disclosure refers to an apparatus comprising a chamber configured to convectively heat contents within the chamber with steam. An autoclave of this disclosure is typically configured to purge air and other gases within the chamber (optionally with a vacuum) because heating with steam is generally more efficient than heating with hot air; heating with steam allows the denaturation of enzymes on the order of minutes whereas heating with hot air may require one or more hours to achieve comparable denaturation. Other methods of convective heating may nevertheless be employed for heating the starting fungal material and holding the starting fungal material within the temperature range for the period of time such as by heating the starting fungal material within a dehydrator or commercial convection oven. Such other methods may nevertheless require heating for a longer period of time (e.g., greater than 60 minutes) to denature enzymes, however, which may also increase the undesirable thermal decomposition of phosphoryloxytryptamines and hydroxytryptamines.

In some embodiments, the process comprises inserting the starting fungal material into an autoclave, wherein heating the starting fungal material and holding the starting fungal material within the temperature range for the period of time is performed in the autoclave. In some specific embodiments, the process comprises inserting the container that contains the starting fungal material into an autoclave.

In some embodiments, the process comprises inserting the starting fungal material into a dehydrator or convection oven, wherein heating the starting fungal material and holding the starting fungal material within the temperature range for the period of time is performed in the dehydrator or convection oven. In some specific embodiments, the process comprises inserting the container that contains the starting fungal material into a dehydrator or convection oven.

In some embodiments, the heating is performed by convection by contacting the starting fungal material with a heated gas. In some specific embodiments, the heated gas is steam. In some specific embodiments, the heated gas is air.

In some embodiments, the heating is performed with a high-temperature short-time (HTST) pasteurizer, which allows for periods of time that range from about 10 seconds to about 1 minute. HTST pasteurizers are known in the art and generally comprise (A) a heating section that comprises a heat exchanger (for example, in which steam is injected directly into the starting fungal material or in which the heat exchanger circulates a heated liquid that jackets the staring fungal material within the heating section), (B) a holding section that holds the starting fungal material within the temperature range for the period of time, and (C) a cooling section that comprises a second heat exchanger that cools the heat-inactivated fungal material (for example, a plate cooler).

In some embodiments, the heating is performed with a ultra high temperature (UHT) pasteurizer, which allows for periods of time that range from about 1 second to about 10 seconds. UHT pasteurizers are generally similar to HTST pasteurizers and may also comprise a pre-heating section (for example, comprising a plate heat exchange or a shell-and-tube heat exchanger). UHT pasteurization is generally performed at higher temperatures than HTST pasteurization, but UHT pasteurization is performed for shorter periods of time than HTST pasteurization such that the magnitude of heat transfer is comparable during both processes.

In some embodiments, the heating is performed with a HTST pasteurizer or a UHT pasteurizer, the temperature range is at least 60 degrees Celsius and no greater than 150 degrees Celsius, and the period of time is at least 1 second and no greater than 2 minutes.

HTST and UHT pasteurizers are generally configured to pasteurize liquids. The starting fungal material may therefore be processed such that it can flow such as by mechanically processing the starting fungal material into a solids-in-liquid suspension before introducing it into a HTST or UHT pasteurizer. Additionally, an apparatus that is conceptually analogous to a HTST or UHT pasteurizer may be configured with larger lumens through which the starting fungal material flows to inhibit the fungal material from clogging the lumens of the apparatus. Larger lumens reduce the efficiency of heat transfer, however, and may therefore require a longer period of time for holding the starting fungal material within the temperature range to effectively denature the enzymes of the starting fungal material (e.g., on the order of minutes).

In some embodiments, the heating is performed in a heated bath. A heated bath contains a liquid. Denaturation of enzymes can generally be performed at or below the boiling point of water, and thus, in some embodiments, the liquid of the heated bath is water. Alternate liquids are not particularly limiting as long as the boiling point of an alternate liquid is greater than the temperature range; alternate liquids include, for example, mineral oil and glycerol. Heating performed in a heated bath is a form of conductive heating as the term "conductive heating" is used herein regardless of whether the liquid of the heated bath underdoes flow. Heated baths generally allow for increased energy transfer relative to convective heating with a gas, which allows for the denaturation of enzymes on the order of minutes.

In some embodiments, inserting the starting fungal material into the heated bath comprises inserting a container comprising the starting fungal material into the heated bath.

In some embodiments, the container comprises a flexible plastic barrier such as a polyethylene barrier.

Flexible plastic barriers allow the displacement of gases (e.g., air) from a container, which gases may otherwise insulate starting fungal material within the container and inhibit heat transfer and thereby increase the period of time required to denature enzymes at any given temperature; displacing or removing gases (for example via vacuum) therefore improves heat transfer, reduces the period of time required to denature enzymes, and concomitantly reduces the thermal decomposition of phosphoryloxytryptamines and hydroxytryptamines. In some specific embodiments, the container comprises a flexible plastic barrier, and the process comprises vacuum-sealing the container. The fungal material may be placed, for example, between two flexible plastic sheets or within a flexible plastic pouch, vacuum sealed, and then inserted into a heating bath.

Flexible plastic barriers allow for relatively large surface-area-to-volume ratios, which improve heat transfer from a heating bath to the starting fungal material, for example, when the flexible plastic barrier comprises flexible plastic sheets between which the starting fungal material is sealed or when the flexible plastic barrier is a flexible plastic pouch. Vacuum sealing a flexible plastic barrier can further increase the surface-area-to-volume ratio of a container. In some embodiments, the container has a surface-area-to-volume ratio of at least 20 per meter. In some specific embodiments, the container has a surface-area-to-volume ratio of at least 40 per meter. In some even more specific embodiments, the container has a surface-area-to-volume ratio of at least 60 per meter. In some very specific embodiments, the container has a surface-area-to-volume ratio of at least 80 per meter.

A container in which starting fungal material is grown generally does not comprise a flexible plastic barrier, and thus, any container in which a starting fungal material is heated may be different from the container in which the starting fungal material is grown, but this distinction shall not limit this specification or any patent claim that matures from this disclosure.

In some embodiments, the heating comprises irradiating the starting fungal material with infrared or microwave radiation. Heating by radiation allows for both rapid energy transfer (which advantageously reduces the period of time required to denature enzymes) and precise control of heat transfer, which allows precise control of the balance between the denaturation of enzymes and thermal degradation of phosphoryloxytryptamines and hydroxytryptamines.

Regardless of the method of heating (i.e., by convection, conduction, or irradiation), processes may advantageously be optimized by adjusting energy transfer during heating (e.g., by adjusting the temperature range and period of time) to arrive at processes that maximize the denaturation of enzymes and minimize thermal degradation of phosphoryloxytryptamines and hydroxytryptamines. Depending upon the type of starting fungal material (e.g., mycelium, sclerotium, fruiting bodies), amount of the starting fungal material (e.g., 500 grams, 5 kilograms, 20 kilograms), surface area of the starting fungal material during the heating, and the heating method, optimization may result in different temperature ranges and periods of time for heating as described supra. The temperature ranges and periods of time of this disclosure nevertheless encompass a majority of the working ranges within which those of ordinary skill in the art may optimize a process to strike an appropriate balance between denaturing enzymes and minimizing thermal degradation.

In some embodiments, the enzymes are selected from phosphatase enzymes, oxidoreductase enzymes, and laccase enzymes, i.e., the starting fungal material comprises one or more phosphatase enzymes, oxidoreductase enzymes, and laccase enzymes.

In some embodiments, heating the starting fungal material and holding the starting fungal material within the temperature range for the period of time denatures the phosphatase enzymes, the oxidoreductase enzymes, and/or the laccase enzymes. The term "denature" refers to a measurable loss of enzymatic activity as the term is used in this disclosure in relation to an enzyme; enzymatic activity may be assessed, for example, with an assay such as those described infra.

In some embodiments, the phosphatase enzyme is encoded by an amino acid sequence having at least 90 percent sequence identity with the sequence set forth in SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, or SEQ ID NO: 89, which encode phosphatase enzymes of *Psilocybe cubensis*, or SEQ ID NO: 90, which encodes a phosphatase enzyme of *Panaeolus cyanescens*. In some specific embodiments, the phosphatase enzyme is encoded by an amino acid sequence having at least 95 percent sequence identity with the sequence set forth in any one of SEQ ID NO: 25 to SEQ ID NO: 90. In some even more specific embodiments, the phosphatase enzyme is encoded by an amino acid sequence having at least 98 percent sequence identity with the sequence set forth in any one of SEQ ID NO: 25 to SEQ ID NO: 90. In some very specific embodiments, the phosphatase enzyme is encoded by an amino acid sequence having the sequence set forth in any one of SEQ ID NO: 25 to SEQ ID NO: 90.

SEQ ID NO: 25

```
MTVGQTIVPIFDLPEDLQIHVVQYQHTERPIEDRYSVNLSDDGRRLLIGVYDGHGGPETADHISQIL

PSRLLAHPSSQHAEQFELLDNSMISNFKKDHSIFRRRSSNWVHNAQLMKSGSAALVLDVDLSNLSAS

YANLGDCRLVLCDSNSSQKAVSFCTTDLNMNTPSERERLIQEHPKEDYLNVGGRLFGRLMCTRGFGD

GYYKLPKGIFGSSLHRKYIDTISSIERKGKIPMNAQYASLFYAYKTPPYITAWPDTGNLQLKKGDVV

ILATDGLWDLVSTEDATRIVLQGMAEQENNLAKFLLEMVKATISIGDDVTILVYRA
```

SEQ ID NO: 26

```
MPFSPPFPPHDPTDKNGYETVIKRWPIILTGVVDTVHNACHRLTVQLSEIGDEDAEKKKVLQEKTTE

GTAIIEKLSKLKYEMARDRVLVEIPQDGEASADLYNTELEALKQDNRNTWFTAPWLFAEYRLLRSFF

VQTQHWKTYDPFEDQKLKTFKHSGKAIFQIAKTIHELGSDVEGVKSDPEKLKILFNEMIQMCLWGNA

TDLSLLTQMTEADIQNLQTVGKDARIARQQFILKDDEEAVWSYIETLKDAQVDFVLDNSGFELFTDL

VFADFLVSYTPYVSKVVFHPKLIPWFVSDVTPPDFKATLSILSDVTFFPEEVVNSPDVNTDYLKEMV

GRWKKYVDEGVFALSVPLDTPLGGDAGSEVGEFWTTPRPYWDMKTEAPVTFSQLAESGLVIFKGDLN

YRKLTGDIKWPAWTPFEEAIGPLAGSFPILSLRTNKADVVVGVEREVADRLDARGEKWRVDGRYALV

SFLPKA
```

SEQ ID NO: 27

```
MSGKTPAKASSPAPTHSRETSYQNGVTHDLDVQSLKQRFLTNDVTPGLQGKDVYDSTLSWWRAGIRR

KLVATVQWESWIIAAMQEKIRTPWLDAYFVYSSILGTHTFFMILLPALFFFGYDETGRALLAILGLG

IYGSSVIKDLFCSPRPFAPPVTRLTIGSHHLEYGFPSTHSTNSVSIALIFFAHVHRLASTPIPSSQT
```

-continued

IISTITNGTSTIINSSDTTEYMISPRLYYFINFILFIYAFSVVFGRLYTAMHSFTDCITGILLGAGI

WWAHTDWAGAPYLLEPSNPLNALCAFLGFGTLQPSGALLVEMGQGLAAGKWIEKWIQYGGWEVPLIL

IPLCLFAVHVHPQPVDDCPCFEDAIAILSVVLGSLVSRWAVCYSQAGMDLVKNVIMPGSGWILEAGQ

WVQVEREWNDVLVWWTFAAIKMSFGILVIFVWRLLAKSALHIILPPTFRLLARAFQLPHRRFYTPAT

EYKSVPSEFHSSADGGGFELHPIPSVIDLPSAGNVGIEIGGIGSGVEGHSGSRTVMAKDLKMRSGNG

HRNANGAANGNAHPSNEKAFNGKAGVGAHRTDKESTGKDGQPDDVRHYDADVLTKVIVYAGIAVIAC

EVLPLAFDLFGWGVGSHVTIL

SEQ ID NO: 28

MAPNCEPLCVFGDRLYFTTFPHPPPPPHALNKQDSEHGNQPRIRSRPKGSSSASTSDHYASYYYFTI

DDQLLYLSFFQDWGPLNLAMVYKACILIHELLEDKDLASHRLVLYSSDDPKRKANAALLMALYVMIV

QRRAPWEAFHPIAELEFMPFRDAGRGPSDENLSIQDCLWGLWKAMQHGLCDMNEFSVEDYEYYEKVE

NGDWNWLTPNFIAFASPVDTNWIKREKEAKESTNSSNPGSISRTPSSSGSNLALQRKLPTPYLNCLD

YFEKRNIKLVVRLNTELYDRNTFLDRGIDHMELYFDDGTNPTDEIVRTFLDVADRIVESGGVVAVHC

KAGLGRTGTLIGAYLIWKYGFTANEAIAFMRIVRPGTVVGPQQQYMYLKQLEWAKWAAVDEIKKAQA

QAQAATSPVPIPIVTPATPPAEADDDAVMQTTPKSQKIALPPVTPSRHVAAAAAQAKAIAPPGQPRK

TPNAKRVAQDSDDEDEDESSDVLPALGIAPPTRKVKTVPSRGVTASDQRPSRVTRSTANASVIQKAG

TGAAAPDSPIKASRQGPNKIPRLATTKTTSAARALAAANVQQIQPRTLRNNANAVPPTPSRLPTLAG

KRAHTQNSSSLTDVAAIKPSADKKANAEGWVPNNVASVVVPASKSERPGLRSVRRRRSSFSAADVVA

SEQ ID NO: 29

MSLSRPTSSSISSLLKCYTPALARHISRKARPTPALRNRFFARLNAAVNTNSPSSSSSSASSSSSAT

STDDSNILFARGNGRGTVPVRPYTFHIGASWAGKPEDPRGMKKVPFPPDTLIGAWRDNTLMRSRGGQ

TLDAGEDFFFVQEVLVPIYPALPLLSPLKAHVLTRIFLILQMRNRSGVSFGVADGVGGWIDSGVDPA

LFSQALMYHAHRYSRNAWAGEPEIDPTMDYEEREQVEGWEMTPYECLDLAYGGVLREKFVLAGSSTA

CIISLNASSGVLRSANLGDSGYSILRNTQIVYRQRSQTHFFNCPKQLTKLPTNNGRKFSRACVDSPN

EADTYETKLRDGDIVVAYTDGFSDNVFPSEMVTICSLVARAGGTEEEQVQAMADRLVEYSRQCMKSK

LRVSPFEREASRVGQYFRGGKPDDVTVIVALIRETS

SEQ ID NO: 30

MDAKLKALKVVDLRNILATARVQVPAKATKNDLIAKILASNAALDTYAALYPPDDLLAPPEEVDWNE

DQIDTPPPQQQQQQQQQKVAPAPAPAPEPAPQSAPTPAPAPVAPSDTTQSSAEDIELEKRKQRAARF

GIPLVEPHQKKTRPAAKSAAVAASIDPKVLEQRAARFGLNTQAPDAKANSNGKKRSAPTTQDVDPEE

LERRRKRAERFGTGIPRIQPNMTPELVKKTTDMGWSQTDALWVYTSLPEPLLSSELERLSFAHTKCD

TDVVGFQPCPNPEETSQDRFVINDWPLPNGTWIFRAIFDGHAGHETADYASSALPDIIKGALTAVVE

KDAHPSSSAVSEALSNAISSFDKGIGQAIVDLFPDEQALAEMPIEDIQRIINDNGPNSATILKGMRG

TTALVSLADPAKANIWVASLGDCAAVLGLKEISGEWNAQVLSKAHNGENDVEEERVRQEHPGEEECM

MDNRVLGAIAVTRAIGDESFKLPAIYTERVELNSNPGFLVPDKVRGYIGRSKTPPYMTGVPEVEHIN

LKALNATSTFLIMCSDGLTDLYDDRLKLNEVLASRWVGIVGEQYGLKDRKNLALTLLRDGLGADEEN

KGEKISRMITVEMAFKWMDDTTILVVPL

SEQ ID NO: 31

MAYRCLLKLPSHSATKPRSIARYHDYIRAATPGRTERPYITFTTHVQPAGSIRVPLSSPKVIGVVNS

RGNRRQILNQVHQEDFYGFATLSLPPEELRLSLKRDHGVDWDPSQVGDVLARQVLFVGIYDGHGGSA

VAQYLRQELHGLFESVDKSLIPELFGWIKEIGGYFKRFKGGAIAPWIDGTNKEEMTLEARATLTFFE

VDKNLSADNAAQACGATASVAVLQSLDAPATPFFSAEKLALTVAHCGDTRVLLCSTINGQVFPMTEN

HYPDARIESIRLRRMMGSSLITDSYGESRWMGSLANTRWYVLNTILQNLGDLNYKKEGITPEPEVRS

-continued

KLLNGREWAFLVLVSDGISSILSDAEIVDLARGCNDPKTAAERILAFSEELGGEDNATAIVVPLAGW

GKITGPDATKDLRAYRQKQAVGSERQRLSCEIPSSKYTSLLISPAAPVSLLSTSGVPAEIQKRGESS

AVWGVKPRMNTLPQIRR

SEQ ID NO: 32

MAAPTQNGNGVQHSSGAAPSRVTLHLGHLPSKKDIKAPWPRTPTRVDPNNPPWPAYRGYHEYSFAHA

TMQSRLPTILGKAIEDATRTLNSQSSEERVVDLVQCIDRMGDLMIDLSGNAKLRPIIDDDEADVALW

NKEIAKYFQGKDEMNAPWLFAEAYKYRRLHEAFSISKFWRDYDVFYRQKCDTFSRSSDAVFELSLRF

AEPFKINESLSPKEKLEAERLMFLELTQVCLWGNSTDLSLLINMTEDQIKSLQSTGGDSLAATEKNI

LGNDMHRLWDRVRQLREKTGGRIDFVLDNAGFELYCDCVYADFLIQSGLANQIRFHGKRYPWFVSDV

TKKDWEWLLNTMVYGQLFPKASDAERESLRRLGLRWKQYEKEGKWVYEQHPFWCTGYTFWDLHSEAP

DLFLHLSRSDLVIFKGDLNHRKLTYDCAAPASTQFEDAIGPMASSAGAPVIASLRTIKSDVVVGLGP

QGDEISDELTKNEPGWKISGKYAVVLLSEGRPGEPVRFA

SEQ ID NO: 33

MAYRCLLKLPSHSATKPRSIARYHDYIRAATPGRTERPYITFTTHVQPAGSIRVPLSSPKVIGVVNS

RGNRRQILNQVHQEDFYGFATLSLPPEELRLSLKRDHGVDWDPSQVGDVLARQVLFVGIYDGHGGSA

VAQYLRQELHGLFESVDKSLIPELFGWIKEIGGYFKRFKGGAIAPWIDGTNKEEMTLEARATLTFFE

VDKNLSADNAAQACGATASVAVLQSLDAPATPFFSAEKLALTVAHCGDTRVLLCSTLNGQVFPMTEN

HYPDARIESIRLRRMMGSSLITDSYGESRWMGSLANTRWYVLNTILQNLGDLNYKKEGITPEPEVRS

KLLNGREWAFLVLVSDGISSILSDAEIVDLARGCNDPKTAAERILAFSEELGGEDNATAIVVPLAGW

GKITGPDATKDLRAYRQKQAVGSERQRLSCEIPSSKYTSLLISPAAPVSLLSTSGVPAEIQKRGESS

AVWGVKPRMNTLPQIRR

SEQ ID NO: 34

MHLAKICFSAALLSTTVHGLPTAPQGRGILDEVGILDDILVEDSPAYPDPANAGNTLIDLQTFVSLR

QIDLGGLAAALSAALTTLGVNVGDKLGNLQERVKLIGAIGLPGKSTTVSIAGCSAKAKTGETSGSDL

GMSLKTGVSLGACNAGREFEATATLGGLENSRTVKASVESSPDSGFGVISDIDDTVKISNTLDKLAL

LRSTLLDDPKPVPGMPELYSSLSQSLDDPQFVYITASPFQLYPFLNDFELDTTYSSAKGPIFTSNLTI

ADPSEIIQFVTSSNTEAFKLASIDRLNGMYPNKKWLAIGDSTQKDPEVYAQSIRKHGDWIACAWIRR

VEGANNTDARFAAAFADIPASRFRIYTDADIPGLADIDVAGGEC

SEQ ID NO: 35

MLLSTLLSATVILGVVAAPPPDHDHQPPKHNKIVPGIVEDRFISIWLENTDSTDAQADPNFAALTQQ

SLRLTNYFAVTHPSEPNYVASVGGEYFGMQNDNLNRIPANISTIVDLLEEKGISWAEYQEDMPETGF

QGFQQLAPSGANDYVRKHNPLIIYDSVANSTTRSANIKNFTLFEQDLASNNIPQWLFITPNMINDGH

DTNITFASSWARGFLEPLLKNPHENGPKTLILLTFDESGSDGIQNRVDSILLGNAVPKHLIGTEDSS

FYTHYSGIATIEANWNLHTLGRYDVGANVFSFVAEKTGDKLRTLENPPLSETFLNASYPGVENTGPK

APLPIPNTRLVVNGRFVHPKVVEIWGSPALQSCTTYTDSVQVPSLANPPVLPAGCL

SEQ ID NO: 36

MSGSTNRHHHSGSFSGHTAGPTQQQPSASHHALESHEGKDFSKRPVPQVPPPATHKPSDHDFYVYDG

GERKVNHEYLKKHFYREGRLTEAQALYIIEHVTNIFSREPNMVPLKSPVTICGDIHGQYYDLMKMFE

VGGNLQDSLYLFLGDYVDRGDFGIECLLYLYALKISSPSRIVLLRGNHECRHLTEYFTFKRECLHKY

SEKVYEACLRSFCALPISALVDGKFFCVHGGISPELIKLSDLDHINRFTEPGSHGLLCDLLWSDPIV

NFGHENEPAPTGQGVTPGTTFMHNNTRGCSYFYTYEAVCQFLERNNLLTVIRGHEAQDAGYTMHRKT

PKRNFPSVITIFSAPNYLDVYHNRGAILKYANKNITIRQYNSTAHPFWLPNEMDAFTWSLPFVGQKI

TEMLLAILSICSNDELAESDSDGEEAQAAPADLAARRQLIKNKILAVGRMQKVFQLLREEAENATEL

-continued

DGVTATSTAVSKPGADALSVQGARLNKSIRTFADARRSDMANERLPEFNEQQKPTIFPVPSMRNTSR

RSSAEGLDMEDLIKRALEDDSVVDDGGVVEMLAEKIARGRSVTGRPGALKRHETT

SEQ ID NO: 37

MRNTVTCFFVCFAISTAAGTVIHYPPIASNINNLTFALNGFGSPGIFTTSKTPDSQYGVYNWCNMPH

VRQREYIMPGKNYTLQYVEIIQRHHKRTPYASNTFFKEDVPWSCDGAGATFGSISPNGPGSSVSPVQ

WRGYIDQQNPWTTSVGPGFAGSSCQFPQITSQGLEDSITHGSDLRAVYASRLGLGPTFEPTKAIIRV

TNNVITSQVASGLVAGLFPLSKSHDVAVLIQSSTIDSLEPTYSCNAASKLLSDYTTGSSGELWKDHL

AQAAPLYSRLDNISGIATLDTAGWHSSLDHYYDNLSAKQCHGKTLPCNLNDTSECVTQKDANTVYRL

GNWEYSYRFRDAPASAEYSSLRYGAWVLELKSHLQNNINGTSNVAHDGSVSALLGFLQIDQMVWPGM

GSEIVFELYSSADQPNEHFIRVLWGGQPMKTSTPLGLLDMIPVTIFFDYIDSMIGTSKDLFTNCNQ

SEQ ID NO: 38

METPLAEAATQETASLSDSLHDNPASSSASTQAQELQPPTESVYSEPKGPRVHTPQVRLPPAFNKFI

LYENRLRFFIIASNASDSRHRIIKIDRTTQDEELNIIEDEVEYTGKQMTAMLKMLDDGNRASGGLGK

AKMFFGIAGFIRFTAGWYMILITKRSVVALLGGHYLYHCENSDIVPVPFNHKIEKPAEEQRLMNIFK

QVDMSKNFYFSYTYDLTSTLQHNLTGEVRSGENDWPINDRFAWNFHMLTAPFSKQATPPLNHYWLLP

LVHGHVDQAKLTVLGRVIFVTLIARRSRHFAGARYLKRGANDEGNVANEVETEQIVCEALTTPFYYP

DRGKGDAHRHRRPSPNYTSYVQYRGSIPIYWTQETTSMSPKPPIEISVVDPFYTAASRHFDDLFKRY

GAPITILNLIKRREPVPRESKLLDEYTQCVRYLNQFLPRGKKMVYRAWDMSRAYKEKTQDVISYLED

IAEESIQMTKFFHSGPEPYSHYLNSEGEEAKASWRGTISLQNGICRTNCVDCLDRTNAAQFVFGKRA

LGHQLYALGVVDSPNLAFDSDAVNMLTEMYHDHGDTIALQYTGSALVNRVETYRRMPHWNSHSRDII

ENIRRFYTNSLLDADKQTAINLFLGVQNERAITHPPVRSGYRKWFHEEYLGPSRDVNDFQESLRRFV

QQRGDYWVEYYRPLLFTSLGKHFAYSMNSTLKLPGKTAKDMNVSPFQPHGYRPAQGDPSSRVVQGVR

RWIGSHHPSREILRAGKPIVRQEAKRPPPKPQVQDNKSTEALALASLDPAVPEKEEKEYTKYIVQIE

DTPGMIPYNGLSDLKHYVEVVQIARGQLDYYPDDETCDHYSKYVERNSTRYPGGKGREAFHVSFNYG

RWLDGWQEM

SEQ ID NO: 39

MLHHQRPPVHNDTSTTSEDDDDDDDNDVFEDTLQLSDSDSSNPSSPTGRAGPSIKLDEPLPDDITKD

LEALQQLRQSVKKNLRLRPIRSRTDLRKLDLDLDSIISRSASFTAAASPAAPPLTALSPTSSIASSY

FTPSSDTPQSALFSAIQAPRPSPMSPPVSLAAQTLASRLIQPKRPLLIDTRPLAAHQSYHLRHSINI

AIPSLILKRCRRPGGGLQSLDALRQFTTTELGKIQWDALMCPGGPWDGDVVVYDDEMDPKDKDNLGI

TAWAIIPVISPLLTYGSVAYLEGGLSIAGHHPELQALVTTADELDSISDMHNNSIPPPLSTTSSRGG

MKRSAGLLQLDTQAATRLKKLPEIELASTTSSKPPSPLPISPLPIMSSMMTSSSSSSSSQSISTADA

QPMDVVDASPSPPPSSIGERRPAPPRRPNLRRIDTKSAERLGPPKLSVRTKQMRSATLAVPPTLSLS

IQAPPQSPSHLNLLYSTHSPPPSARYPMTPSTDPANYLTPYYTPPHTPGTPKPVLPPSPITARPDLD

PPTTEDAFPVFTISTILPNFLFLGPELTAPEHVAELQALGVKRILNIAAECDDDHGLRLREVEDKYY

KIPMRDTVEEDNISRGVREVCDILDDARLHSAATYVHCKAGKSRSVTAVMAYLIHANHWTLSSAYAF

VLERRKGISPNIGFVSELMNFEEQELGGKSVGVQPTLSNPSHHGHGHGANGAGTGGEGGGGGGGIGL

PESYVLASGASRRSGAHVRESLPPMDTHSGQLNGLGGGVGGAGGGGPMSAGGIMDRVLGDSGQEMEI

KDSYGRYRHARRAPVDETTLQPMRRVSKAGLESASWS

SEQ ID NO: 40

MSLLIGCYADTNIVLINDDGWAVAQLRSEYSALKSAGYNVILSAPAINKSGTGSSTTTPKQLEVPCQ

FETCPVGSPAYGYESFDRNINYVNGYPVDAVKYGIKTLAPSIFGSIPTLVISGTNIGTNLGSISGSG

-continued

TVGAAAAAALEGIPSIAFSGSSGSTVSYTTLTSNPSSSSSKSAKIYTDLVLKFSAALLNNSGTLLPK

GVSLNVNFASTSSCSSASNYKFVLTRVKSSSSATDVTTCGTNKLTDESTAIKKGCIATVSVFNATTK

ADVGSSTQSIVLGKLKPILECL

SEQ ID NO: 41

MRLTPSLLALSLISTCAAQKKVVLTNDDGWATAQIRAEYAALQAAGENVILSAPAINKSGTGSSTTT

PTTLTTACEFNTCPSGSPATGANSTDPRINYVNAFPVDAVRFGIQTLAPKFFGSKPDFVISGSNIGT

NLGSIGGSGTVGAASEAALEGIPSIAFSGSSGSQVSYTTLSDTTTTSTMAANIYTSLILKLTNQLLN

NTSPILPAGISLNVNFASISSCPSASSFKFVLTRLESSSATDVTTCGTNKLTPESTAIKEGCIATVS

VFNASTKADVNSATQGVVLNKLQPILGCL

SEQ ID NO: 42

MSTSASSPSSPSSSSISDPDRWIAQLKTCTHLSEPDMKKLCAMVRNILLEESNIQPVSSPVTICGDI

HGQFWDLLELLRKGGDVPGTSYIFMGDFVDRGHYSLETVSLLFALKARYPDRVTLLRGNHESRQITQ

IIDGHTLCVHGGLSPDIRTLDSIRTLSRAQEIPHEGAFCDLMWSDPDDIENWAVSPRGAGWLFGGSV

VKEFNHVNALSLIARAHQLVQEGYKYMFDKQLVTVWSAPNYCYRCGNMAGIMTVRDDGGQTFEVFEA

AAENERDAMGAGGLGGMGGGMGMGGGFGARRGGVSVFVFTIRSLFREFLLCEFSLT

SEQ ID NO: 43

MAESTYPTTQYLAGDFVLSAGSVLFRRRPRLGTSTSTSTSTSNPTNTLEPELEICILHYLTHDEWLL

PKGRKDRGEPIERTAVRETYEETGYVCALWPQRMPTLATVPVPAPGQGAGQQSHGLEVPMEDGYGLI

EPIAVTVREIARGRVKIIYWYITVVEEGVEKVEGSQMENENFESMFVDVREAEERLTERGDRDVVRV

AIDIVCGRGVVQGADTHSGTLSAV

SEQ ID NO: 44

MAAPRHPTTQYLAGSFVLSAGSVLFRRRASTNTLEICILHQLTRDEWLLPKGRKDRGETIEQAAVRE

TYEETGYVCALWPQRMPTRATVPGVSNVHVVEIAGGLVEPIAVTVRDLGSSNSKIIFWYITVVEEGV

EKVEGSQMENENFESVFVDVEDAVERLTFQVDREVVNLAIDIVVGGRIVESTSSGTLNAV

SEQ ID NO: 45

MQAQPGSRSPRFHLLLSFLIVLSLPHLIGAESILGDNNTCDNAHILERNADCDPQRAAMTWNTTKET

TANTGAKMYGYRYPQVPLEVDNYPVGPEGLQLEQVHVYVRHGERTPVGVRLTDPPASIPEYWMMCKT

ARRFRAAVSSALGPSPNQAPHLSVRNDELEETLQTQKVVERKDGTLVEGECLLGELTDLGRQSTYSF

GQNLRRLYVERLGFIPDTLPSSDIVYFRSINMPRTIESLQQVVHGLYPTNKCLDGAQPPLRIRNGKD

ENLIGNTYACKRLEILQAGFANAAAQAYNRSLERLDKKVSKYLNGNPIRVDGKPRASGIMDTIRASI

AHGIKVPPEFEDKTIVDVIDVCSTLFLPYGHPLRTIYALDKTEEVRRLAMGRLLDDMSRKMQTKIQQ

READPLKILVHSTHDTAIAGLCSTEDVEDDKWPAFTASITFELFKTREPESDQTRSQSILTRMGSPS

SSSQYYVRMRHQNKDMTLPICAQSGNHLEGHPEFCTFSAFKARVKELTPTEWDDECLPAGKP

SEQ ID NO: 46

MWALVSLLSLLALYARGIVIPSLQSHDVSVPPDSINPYPGKPRLLFKKDGTFKITVFSDLHFGENPW

DDWGPEQDVNSTILMNAVLADEKPDYVVLNGDLITGENTFRENSTSLIDEIMKPLNAAKIPFSSTHG

NHDNQANITHEEEIQRELKVAPLSYTRMAPKGVGGTEGPGNYWVPIYRDAKDLAPILVLWFFDSRGG

FSPNPDSVPVPDWVDESVAGWIESESQAMEKAWGPAELRGALAFVHIPPHAIQVLQTNLDSDKNPGL

NDDILGDGSVQDSSAQGEDIPFWDALNSNVKNLHAIISGHDHGNEWCAREFTKDVIFCFDKHSGYGG

YSSAGWGHGVRNLVFHTPDPKAGVETWIRLQEGDTRARITLDDNYGR

SEQ ID NO: 47

MPLVAREMDAWLSGSPDRVAVLHCKAGKGRSGTMACTYLLSLGDVPQPPQLERNQTSKERAKRRIED

ALDVLPPDEENQPPVASRPTSPPFVTPAIGISDTAGIFDAESGGRPSIPTAGAEKSFTDSLKGVLDL

HTARRMKPPSEQDGKAKQGVSIPSQRRFLYYWALILAHEAPSHLWGLGSLKSTNINLQSSCLDKNAI

-continued

QRPKVLLTQLNIRMRETSNMKMNFVKAANMVIERTNMAKAPENTSTQLWASMARYDDKMVNLLEEWE

AYTRDSSGNMGKRRPGSDHLPRGESTEDEVLSHIFKTGKWDKGKMVRSFARLGVTDSKKNEGSVVID

EKHGKIRVYALRPLSDKRWEGLKHDLHKHSAQNNDEHQTIEANATTLGVSRSEANSINEVVPKDAKV

DHKIENGIILDAAREVRIKLYMGQVEMGWFWFIPTFHMSQPPPSSTSTEKVDPTILKANMTLSRKDI

DFPLGVGSAIIDIDIQMEWAMPSPPSPSAVDISNLEPPLRTRTEDSKIGTDPEPEQSGLAAALQAIV

GSDGMEGMGNVGVRETVEAKQGADE

SEQ ID NO: 48

MDEIIPGLWIGDLASALDVEELKSHSIFSILSAMRGRVTIHETFIRHQIKLDDTEDEDILTHELPSI

NFIQEELDKGRGVLVHCQAGISRSSTIVAAYLMYSQKIDPNAALALIKQKRPNVEPNQGFLYQLELF

HTARYKISRREKSVRRFYMERTVGEVMNGDGSLPETGMFARYPSDSVPATPSETSAPAFPIPRRRIR

CKKCRQELATREHMLDHGQLGPATPAIGTPASVSPAVSRRPSGSSGQGSLRPLIRPSISSGLTDSLA

MSSIQEHPSTEQKLDLSSSQQESNSTSASTFALETEEDADEPTAVGSPLSLKVNADGTAAADISIHK

SEILGRQLSDAVISTIDDRNAHLSRRNSHHKVPSDAAVVESPMELPDTTIEQPSRLISPSDLSAQLF

SNPKLAGLRSPTLPSQSTLSNNSVKGSTPVSAPILVNPQCSGYFVEPMGWMEHFLEGGQLAGKITCP

NKKCGAKLGNYDWAGVCCGCKEWVTPGFCINRSKVDEVL

SEQ ID NO: 49

MADTATEIDLDSVIDRLLEGELAWSYLCSGKTEAVGRVGCEEGLGRCCLSTVGVAGQWDISASLQYP

IVWLFQTHVARDDSPPTKTFPAKSNVHPQTLHGLLISVPIAKIARLLLARKALHHRRHHQTVIMRGN

RPGKPVQLAEYEIKYLCTKAREIFINQPILLELEAPIKICGDIHGQYYDLLRLFEYGGFPPEANYLE

LGDYVDRGKQSLETICLLLAYKIKYPENFFILRGNHECASINRIYGFYDECKRRYNIKLWKTFTDCF

NCLPIAAIIDEKIFTMHGGLSPDLQSMEQIRRVMRPTDVPDTGLLCDLLWSDPDKDITGWSENDRGV

SFTFGPDVVSRFLQKHDMDLICRAHQVVEDGYEFFAKRHLVTLFSAPNYCGEFDNAGAMMSVDETLL

CSFQILKPAEKKAKYPYGGINMGGRGPVTPPRKPKKSNKMG

SEQ ID NO: 50

MSEDMPSSWRYLTSAGNRISSFKGYLSGREPGAGWRSGRTTPNASQAPRDEPRQSWRAWAGQKIRVR

RRGQYDATESNELINIFPGWAARRYASQQDEYGRGPRPFELEVFVSGYAISYRSPENASRSQRAFIR

LAKGFASLPKIVDSAADVRPNSSSFAQLTPSTEALLAQVKLPPRPTDIADDYDIDALERQLRLAKTT

DDPLKDDSASLSSSSSASSSTNDLPSTGRETADSVVNSVAENTADVIKRLHANLERRLQPFWSSTLP

NRVVRLHLFSAPHNDSSSTSVGPGNTDDVDELATDAQNGPLASQDVMTGVDGSFQVKENIPWEDLCH

HPRALHIAFGEAEVEHELLIVAQLLPLNPSSSSLSVDSSPISTPLTSLTRIPVTYSPIRVISDIDDT

VKFSGVLSGARAVFHNVFVKDLRDNVIPGMGEWYAAMWSRGVRFHYVSNGPFEILPVLNEFFEVSQL

PPGSIKLKSYAGRSLFTGLLSAPAARKRAGIVDILDSFPDSRFFLIGDSGEQDLELYADIARERPDR

ILAVFVRDADANTFGGPPALEDPTGWKAMGAAGTRPIERPLVSRSESGMTNGSFSPSISSYSKYSSF

FSSNSGSSTPNVRTGDANETPRPNTFGFDSGRQPSTSASVDDKALAKARDQSYLGVGALTAEPESMR

SGDAVTPPRLSAVTGPAIYVNSPNNSSREPQDVMQSPGKFVDQPPKATPPPSIRSSMSSLGPASAAA

SFRSQRTGSSTSSGSSNTTGKRISSISEAEKKRNDLQMRVYRARTQMPSHIPLRIFRDPSECVEAQE

ILDQER

SEQ ID NO: 51

MLSFPAANWQKALGSTSALGKNLKYGRVASPIIPGRLYLSDLYTATDEEKIRELGITHIITVMEYKP

ALPDFIEEGKRMHIPIADSSQSDILQYLDATTNFIKRALEENEMNKVLVHCFQGISRSATVVCAYLV

ATTSMTAESSITHVQSLRGIVSPNDGFRRQLNQYGDQYVKLKAKPKPNQAITEDVLKFGGGIAARIR

RLKGIDTAEKSP

-continued

SEQ ID NO: 52
MGWQSWDVVTITDQSTPSEVPTKPSIGGDLETSVDWWNVTKPEEKVDFSSLPLDTWSPTLPHDTGLS
EIAVTRCVINPEVGGDLCAPDTTSEQDAIKGKWVRVPRNLNLEAGYLSGWLNIYYRRTRRQDINLIT
EIRLYPQNEQPPTLDGWHKAQTSLRAGIRGLPPLFLWYKTGKTSGDMSPEEKMNIITELDVLYGEDT
PWYGFEKLDPPTIAQQSKVEATWITYRRGVKIPPRAPPLHESHSGKFKVLQVADLHFSVSQGFCRDT
ILSPCEHSDNLTNTLISHVIDQEKPDLIVETGDQLNGQGSSWDPKSVLAKFSKAVTAKGVPWAAVFG
NHDEEDGMAKEQQVTLMKSLPYSLVERGPKDVHGVGNYVLKVFSPDPSKTHTLTLYFLDSGSYSKGV
LDWFGFFKPTEYDWIHVSKASIRQIERPFTPDTGKDLGSVWGRQDDQVIPGTRRLAKPNALMFFHMP
LPETYLKADINPNTGKALDVGVSGQEPPGNAKSNDGFFEKGILKAMESNHVSNRNALEVKAIGNGHC
HITENCRRVKGVWFCFGGGGSYSGYGKIGFDRRFRIYDVSDFGETIKTYKRTEKDEIIDEMILTGKG
APPLPS

SEQ ID NO: 53
MLRSKQYCGEDALEWANRPFFVDWAVTGVIWLLSYFVSASPVYQRDFTLSDPDISHPHRKDQIESWL
NNLISLFCPLLVFVGVGCIKRSMLVIHHSAIGLFTARGVARLITEAFKHSVGRLRPDFLARCRWDEA
LKKCTGERDKILAGRKSFPSGHSSTAFAGMLFLSLWIAGQTAAWCFAVPKSGHNERSSRMLSFALSL
LPIFWAAHVAVTRIQDYRHHTEDVIIGSLLGCISALLSYLLEWPNPLSQDSYEPSVYGEPRLLYTYT
GRNHQRTRTTEFELGRFEAEDVDSTYV

SEQ ID NO: 54
MVKRHKAATSLRHPSDTVSVVLSSALYLGPCSAASSESFLSTKSITQVLSVGSTPSPKVEGVVYHRL
SLSDSTTSSISNTIDAATEIIKAALQSNKGRGRILVHCSAGVSRSPTIVCGYLMKEHNMSLKNALGL
IVRARPQVSPNPGFLNQLKDLEVALFGSSSLDIDELPRREIDRLALENDDGDNVQLSHTVNN

SEQ ID NO: 55
MYSPPSKTFVADAVLFDMDGTLTDSIAAVEAAWAKVASEIGQDPEHVIAATHGKRAVDNLSQFKPHL
AEEEMEREVERFENTILYYADAHHLHGPNSGSVTPPSDVSYASSAHDTPDLTPGPSAPASRRSSVSA
FESRRPSFGSRLLNMLSQAARLRAHNEDVVVVDEDGSEKDNLIQPGYPAVEKKNALNATLEAWQMEA
ASVDRSIRILPGVRKMIDSLPEGRYAVATSGAKTYAYGCMKRVGIVPPPVTITADDKRLKAGKPAPD
PFLLAAECLGYDPKRCVVFEDSPSGIKAGVASGATVVAVCTSHERSKIENCGAHYIIEDMESISCHV
GDDDRLVFTITSSG

SEQ ID NO: 56
MGTNTISHIKASLFSAPAGTILVHACNTHGAWGSGIALAFRDIYPAAYGVYRAHCQAHGESLVGTCL
LIPGDDAHDIACLFTSRAYGRRKDAPAQILAATRAAVMDLLEKNVSNKPLHACRENSGKFGVPWQET
EAVLKDLKVTMTVYSTD

SEQ ID NO: 57
MAQTLRYMNGDELADIMKSGKVPQKDFVVVDVRDDDYAGGNIKGSVNYPSAEFLGNVDQLVKVTKEV
PLVIFHCTLSQVRGPKAARIYSETRKNILSNDIPHEVAILRDGFSQFQVKYKDDADLVEKWDKNVWA
SDWS

SEQ ID NO: 58
MIRFDNLPPEVMQAMCTPMHNILPPTNQSPGSLYLGSLSAIQDTSLLRQHNITHLVQVLDVPWLPVS
EKDGFECYKIPIQDEGSVDLRPYLEAVCAWIARALAQGRSVLVHCQQGISRSPAIIIAYLMRVHHMS
YSNAHSFVLKKRACIKPNSGFVRALQDWESSLGTAVRPGMTRRFTS

SEQ ID NO: 59
MDFMDKSSKDWGILNGVKLQKPKLSFPELSSYKPLRTLSPNEFPIDDPTKRVLIVGDIHGQMTYLEK
LMQKVKYSPSQDVLLHVGDIVSKGPLEGSLAVLQFMVSNNVTGVRGNHDQLVVEWRNWYDWVTDSLG
GKEWLDGLQARWEKAVSKDPDTELEAWLKREKKASTRREKAWWKLIPKGWVILDDHYYVAKEMSDQH
FQYLLDLPLRLYIPSAHTFIVHAGLLPCDPRYPVEDEARQPLARIPTLTRRPSGNQTGVNTTLLHDV

-continued

DANSTSTSLMSNKSIDALRNLQETGILTQIPQNSDPWVVLNMRNVLPDGRISKQFGEGMPWSKLWKQ

HMQSCLGYTREPRIASRDADDDIDASGNETTVDDSDDDEQGVKKYNLLCYPSTTVYGHAAGRGLDAK

RWSFGLDTGCIYRRRLSALMIKGQSKDLKDVDSTENGTMPRYEDDEEDEDEDEGEDDDRDEGDGNDE

DEDEDEDEDEDDEDHSDLAAKNKHKNKAKTPWLPFGDNHRATVASVRCKPRS

SEQ ID NO: 60

MEHEIDGWIEQLSQCKQLSEADVKKLCDKTREILMEESNVQPVRCPVTVCGDIHGQFHDLSELFRIG

GNSPDTNYLFMGDYVDRGYYSVETVILLVAMKLRYRDRVTILRGNHESRQITQVYGFYDECLRKYGN

ASVWRYFTDLFDFLPLTALIDNQIFCLHGGLSPSIDTLDHVRSIDRVQEVPHEGPMCDLLWSDPDDR

CGWGISPRGAGYTFGQDISEAFNHNNGLTLVARAHQLVMEGYSWGQDRNVVTIFSAPNYCYRCGNQA

AIMEIDEKLSYSFLQFDPAPRAGEPLVSRRVPDYFL

SEQ ID NO: 61

MPPRTSILFLALAGAGIVSAQTFQRLGTCPTLGCVFPPDQTDFLAGQLFDIRLEVHAPVNGSEAYNG

GIVNEKFSFCIQSGKGSCQDVTTFFKLRDPALEKWSFSYFEDLFARDAGEITVVNVASKAYRAPGTY

KAKLTYNGGSTTVATWTVREPATQRKAKNVLLFIGDGMTQPMITAARLIAHKSINGKYQSLMQMDQM

DNLGHQMTHSVDSFITDSANSATALYTGKKSSVNALNVYADSSKNSFDDPKIETIAELFRRRIGGAL

GIVSTAFIADATPAALCAHTRDRGQYAAVVTEYLYGASAVNASYAWPTSCDAPDVIFGGGAEQFIAG

KGSPNGTDFYKAFETKGYNVIYSNTELKSAPVKEKTLGIFSTGNMAKWIDRNVLTENLNGLKNSPTG

DGSDATDQPGLKDMTLKAIDILQARTKRNSGWEMMSEAASIDKMMHALDYDRALGELLELDDTIRAS

IAHLKKIGEYENTLIVVTADHGHGFDVFGGADTKYIAAQRDDRSKRGGVGTYGESGLSGYTVSEGSL

PNNNTIVYGSQGPNFPVQWNPRYTYAAGFGANPDHRESYVLNTEGPRVATVSSPEGIVVNPTDNVDG

FNVGGTIGTTESQGVHSLQDVSVFANGPGSEAFRGVYSAVDIFFKMADALALGRANN

SEQ ID NO: 62

MDVDHPHGLVYPNGLLAALPVLHPPPDNDPHTLNTNTPHHHHNHPRPRPRTRSPRHTASPPIRALSA

PQFADLHLQHTLAHPPDNTLFPFLHGLEGDNHAQNTFFASSFANNTTTNSNGNQRHHYQHQHQHGAE

PPPRITPRVPHYRGLVWVVCEDDLERARDWASLRVLRRKPVGPTSTATATANANANVSTNAAGGIAG

EDDTDHNPHAPSSSDSSSSASSSSSDSSSLYDDEDEDLDLDLDLDPAHAHAHSQPERGVDTDAQDIL

LMLEATNEAAVAAKAAAVAVAAKDLDTDKGALEDKEKERERMGYRDRPLDAELDLDTDPDEEDADAD

EDEDGSHTSASAAQVRLPSTQTQTQPQVISLEEVFTVDTGNAKGTQNYEGAHMHPVAHRPALVLAPP

VAVPGVGVGVGGGKGLGIDINTIANGHAVSSIANGNVVSSYANGHANANSNSNSNGKGGTTTTTTNA

TANAQITTSTTTHATHTSLSPLTFATISPSSSLSATSASASTSTSSSPSSSVSSSSSFVDSPPHSVS

VSPSASVSASPSLTGSPSMSMSGDTEGEGEGEWSPATSISHIAGSPLSKEVDVDVDANAELGVEGEG

GQGRPMSLLEIELDAKRVGRLQSRQESGHPHEHEQQSQSQSQHEHQELIPTTSPASASPLPLPLPLP

LPLSSPSSSSLPLPLPTTLLQPDSNPKPKPKPKERRATDPTKPPLLTSTFRPKELLRRVKGQGRKHS

HGHGLGHGRHREKGRLRVDVGGNGNGVVGGGEGEGEGEQDEDVDVDEDEEDGRWEFVPARVPDGISL

RNFGIQVLESRWRVVGSYTWRSAAGLVCALQALSDGSGAKVGKERNGWWDRQAPYPIYATLSDIVIY

SPHGATPAALALARRFRAAIKAKRAERLRAAGLDDESIRGAERALKAREAVQNKLDMMEREGSGDSG

SSGSNFGPVYEDDNTAQQQQHQMPELQTEKDSAMHPHIAALHRRRAEFLEYNVFVLDADEDEMRRAM

PHMMMRVCGAGVPGGLGLGVSVEASAVGSAATATATATATVFGADTALMDGGAHTDRSDGHVIELKR

EEELAAAEARRVRMEAEAEGMGMVVDTVEAGVDVDAMDVDEVVDIVAAAASRVAAEQAQAEKTEEKD

TKKEEEEEDILPNTVDFALREREEMRDLTKASEIISLPPITSASSRGQTKTPVEYSDLGPSPVWDPR

VGQVYLGNSGDVPLTPDVPTQFRHAASVARAAAAATTTTDANAEENAKWNWKTLTRHLRGVDGLMKE

YNGELGLEYQHGFEEEDAEGTLPADDPFNYAATNDPAHGFGYDICVECHDLAPFPSAAHLRAAEEHL

-continued

GMLDVMWRERWERAWTARLVRLCAGKSAEEQARIRNMHAPPTPPRPPPHANAVIHLPFPSSPPNSQG

TMVALMPVVRFLEKWIQPVPVPVIVPPPPPPPVAPVQESQKGESPPATTGGAGSRRWSSVTALMPSF

PVFPGSGSSNNNTTKAAPTPPPSSPLPPAPARMRSMTSPSSSMSHHPPTPVQARSRPLKILLYSSDG

YTESSVPALCLLMAIKSLMLPEAYLELQVEKRRSFFVYQTDLGLLRRVENRLREEREREKEKERERE

RERERLATGVYLSSSSSSTGGGSINANGKRTAGGPVVVPARGGYWSGSSSSAGNANSNQNPGTTSNP

TPSAFTGRPAAKSVSFAHAPGYMQQQSSSHQVATSSISGASSASSPSMAQLVPHARVVSSQQSTSAS

QFSQKPQFEFGSLPATPPAGMTTTQQPQPQPPMMGVVKGRPRASTSPWLPSLFGGDHQSWENDPRED

GSFPSRVLPFLYLGNLNHASNVYMLHALGITHVVSVGECALVPPPHHMSMHGGAGDACARPGPGAHF

VPGKGPGGHGSLWIEEREGRIKVLDIKGVCDDGIDTLEPQLEPICDWIDKARQEGGQVLVHCRVGVS

RSATVTIAYVMKHLNLPLVDAYLIVRSRRLSVLIQPNMRLLYNLCGWEIKLAKERAGGDERKLKKEL

ARTLTWPYLSKEVHALNEKYLH

SEQ ID NO: 63

MNTLGYVARQFDVLASPTSEKKSDDKPRLPRVSTWSTKSFLLPPPTVPTTRTTPKRSHSSPSFRPQP

QQPLPPDVTMAPSCKPHIDSVIDRIFVIRVELLVWDHLKSAWSSLVRIVQDRQSVRLIQDSKPLQAL

KDKTEEVALTVVDSVSSSSSSLSPTPPPQVASVLENVSASRAATPPIPPRKTPFHLPKTLVLDLDET

LIHSTSRPIPFETSTGSGILSLGSFGRSNKGAGHMVEVVLGGRSTIYHVYKRPFVDFFLRTVSSWYT

LVIFTASMQEYADPVIDWLDAGRGILEHRFFRDSCTQLPNGSYTKDLSLIEADLSRVCLVDNSPISY

TVNEANGIPIEGWTHDPSDEALLDLLPVLDSLRFTSDVRRVLGLRSAGVMHRHHDS

SEQ ID NO: 64

MVWKNINAVENRLFLGNIMAARSTRSLAENRITHILSVCPDPIPAELPEAGIVHQRINIEDVDYADL

LIHLPAACRFIEQALASGGVVLVHCVQGISRSAAVVAAYLMYSRRINSTQALNIVRTARDHIWPNPG

FQEQLVLFELCQYAPSRSNGIYVNWRTQLERRLRAAGLPY

SEQ ID NO: 65

MPHTTLHVDAILFDMDGTLVDSTAGVVGAWELFRQTYPTIDVHNILSSAHGVRTVDNLRKYCGIEDP

EILEAESARFEQAIVISSTQGGRQGIVLLPGVKPIMEEIAPGRYGPKPCWAICTSATRDYATSALNT

AGIPIPDVFVASEDVSQGKPFPDPYLLGAKLSGVKPENCIVFEDAPNGVRSGRDAGCKTVALLTTHS

REQLEAAKPDYIVKDLSSVSITRTATGVSVTLQTL

SEQ ID NO: 66

MRDLDPLDPDYVQDVLSKPPFVTIPGVINVRDLGNYPSTTEKGLITRPGYLFRSAELSGITEDGKVK

LRELGVTKAFDLRSDTEIRKYNTPLPQIDGVEVVHTPVFQTADYSPEMMAKRYQLYASGKTEAFLEL

YSQILDNGGRAFGAILRHVRDRPNEGCVFHCTAGKDRTGIMAAIFLKLAGVDNELISRDYALTRVGR

EPAREMIMARLSKEPLFASNNEAALNMFTCRHETMQAFLQHFDEKYGGAVTYLKEYVGESDEDIVTI

RRNILTPGLPRL

SEQ ID NO: 67

MTRNAPASLSEVLKDQLYVGNLSAALSVEQRKKHGITHILSVCPEYPTTGATQDHLNISIEDSEYAD

LLIHLPETCRFIDDALRKGGRVLVHCVMGISRSPAVVAAYLMKTRGYLAPEAITFVRQRRPQVHLNY

GFAVQLDTFRKCGFAPSLANPIYRSWKRRNEQDVTAFLNHLVDTVSIIPDKLFLSSEFPSDPQQTWS

LLMDLGITHLLSISPTEIATTTTAGAVTHHHHVNVDSRAPDALLSTLPDICAYVDGAIKRGGRVLVH

SMVESRACAAVCAYLMSIRQYTATEAFGVINEALPLFNPTRNFIRTLEVFEECGYAPGPNLSSSARS

SAKSENFSCELESSKESGMIYDDTRRDFGLGFSENFGNVGANVNMNKRSSKIAPSQHAPISVR

SEQ ID NO: 68

MPSDLDKQIEQLTRCEPISEEQVKRLCLKAREILIEEGNVQVVDSPVTICGDIHGQFFDLMELFKVG

GFCPETNYLFMGDFVDRGFYSVETFLLLLALKVRYPERITLIRGNHESRQITQVYGFYDECQRKYGS

-continued

SNVWRWCCEVFDYLALGAIVDGRVFCVHGGLSPNLNSIDQIRAIDRKQEVPHDGPMCDLLWSDPDDI

QGWGLSPRGAGFLFGADTTKIFAHNNAIDLIARAHQLAMEGFKLMFDQTIVTVWSAPNYCYRCGNVA

SILELDEHLAQEYKVENHAPVDVKSIPAKRPPADYFL

SEQ ID NO: 69

MSFHRGGSGHNTHHSQYPQPWTLAPTNPTVSPPSASPESPSYHARPARNVSEIIPRLYISDLAFAEN

PALLTSYRITHILSTLSDTIFRPPPTLLPVQPIRMQVRIEDLPFAELAGHLPSTTAFIRDALNSSPN

AHVLVHCAEGVSRSVSVVAAYLMAAYGWTPTEAVHFIKSKRRVANPNFGFIQQLHEYSRDSLGRMIP

NPTPPFSTPH

SEQ ID NO: 70

MKRFFERASKPFSLPNASKANDAAETASAPAPAPATAATSASTGPSAKLPSSNHANLPGTTGTTGLH

PRYTLPAVAHPCPHSHLALLATKDGLLIRPHVKGQATIAQSAYIKISWGKTIRIEEIETVVGDGAEE

TVDWKDGVVVYGIVGILELYSCSYLLVITSRTEVGHIIDPRHEVYGVKGVTDIPLVEDRAKMALNTL

AARNVALTRPSLIPRRQGTDVSVDVDDDQNSKPDPESSTKPSPRVQFLSNPAIKFLTPKALSSTNLD

AGNSIARPSSAQSTVSDISTPSSEASVATSPVIKTLASRLSFWSRLSKRINSPIDANFPPIEPMSLT

EEQEVLDNLMQDGKEEPAAVIESILSSTAPPPVTTEERHSELETKVIRETIREFTKGDMYFAYTFDL

TRSLQHKQEQFLKAQKQHDLLAGLGALPSPENQSHVPLSPMDGKFLALVEPYPSLPLWRRVDKQFWW

NEWMSKPFIDAGLHTYVLPIMQGYCQVTKFNIPSSPVTVEEDVDVDYILVSRRSRYRPGLRYQRRGI

DEGAHVANFVETETIMRVDTVVNLAEQAGKEGAITQAYRNYMHELNLKEATYCEYDFHTETKGMKYE

NISTLIESMERTFESQGYFWVSDNVVFSQQKGVFRVNCIDCLDRTNVVQSAFARYMLNKQLGAVALL

NPSNSGRTDADLAFNDVWANNGDAISRAYAGTSALKGDFTRTGKRDLTGMLNDGVNSLARMYTSTES

DWFSQAVIDEMLGNRTTSVESEFLLQLKSTDPRDLIRLSKIRAEAIATSVSRVLPEGERLLSGWTLF

SPEELNTKVGMKFEEKVLLLSVKALYIVSYDYTLEKVKLYTRVPLGDIISITKGAYILSPLEESSCD

PEQNAGFVVTWLSSNQESRVTSYSVRNSLDFSNRNGPPSPLGPPSPSSPGFPLGNKPARGRSNTMPT

ASLSNILTGNVSFSTAGASGTVNFGAFKVLPIDPGRVRRHSSYGSEASDGGGGMSDEMRGAATCREA

VDLIVERIERACGDVGGAQGKNFIVLEDVVSLAEAQRMTSVYAKMEYGVKRLLWLGG

SEQ ID NO: 71

MRLLAFAHIICLSVNLISANHNVYERNLAYKSPFVDHPQLAHNTRNLHDTNIQRRQTIDAASFKDEH

YITFYGSDFSNGDPFDTSVLLWTRAVPISSTGALPDQSVPVCLSFKIATTSDLSGKIIDSGEAFTSY

DVDWTVKVEASGLKPDTKYFYQFSDCASKTSSPIGSTRTIASANNLMFPEQGWFNAYGFAAHNTTAD

IFIHLGDYIYESLGSGAKIGRQTLGRELATIHDYRQRLNQYRTDQSLVTAHQNAPWITVWYVADNSW

KAGTADSNDTTIGCAFSPSGACFTDRKLAAVRAYHEWMPIRQVDPQDKLRIWRNFQIGKLLDLTMLD

TRQYDRDLTDVYYNTVDLDAWDGYRANRARVLDHLYNNKISNTIILSGDSHANWVSDLAHPNDTVTY

NPTTGAGAIGVEFAGTAVTSGSAFGSGITPEKADVISRTLVDVNADLQWSEGSYRGFFTLSIDSDHL

NATYYAMRNVSFANLDGFASAQFTVKAGQNRLSRPVAGGSVNAGVLKSQL

SEQ ID NO: 72

MTTSAMSTPFLDRLIESSTRRSYKRQKRSHSPPQKSSMAFLASPSGQFLSAPLAPSRKKSQRFLATN

NEIDEFLSSDLEVSFASNVSLNSPPREHQSLAASDCEPMDISPAPAKHSSRLSASGHRPRAFTSGAR

LFGNDLSNSNSQLLSSPQLAIGQATKSSSGTQGTKKTQRSALPFEWLATSRVPEPPTPEGFRQPSSP

MDDAMDVDTSYIADSAIEPADFDPVPESAAPTITDENQLFHDTMSPRRSFESPAGPELRKRRSFSPE

SARAPKYQSSSPIPPSSPSESKLERMAAGAAASRLGKPGLQGLGAPSASFLRRPRRPVLSAMVQPYD

QHAQSAYPTLESPPSISRDSEEDPSPRGSAPVRRAFSAFLPPSVYTELEEDETSFEGQDMSSPAQAY

SKRQQVKTIRRCDGTEDFRPLTGVTALVQNESPSAKFMAAGLPGFGDNEAHGKLLPCHRVTEDGLMR

-continued

ITCDTLNDLLDGKYDEDIIAYHIIDCRFDYEYNGGHIPGAVNINTTAAVEELLLGPSLTKPKASVSG

DKARKTILVFHCEFSAKRGPTFAKHLRAKDRAMNNHVYPKIHYPEVYILEGGYCQYFKDSAHRCEPC

GYVTMDDPNHATSRREDLDQFRKAKFGRHKSYAYGDANGKSLSFGQQQQQQPKRNTAPSAPPSLFAA

ATAARSRRGGNGTGSGLMTLAEDGNVTADADDTDTDLGDSPCPPPIKATTLKAKKGVRTSIVRSETY

GPIRMPY

SEQ ID NO: 73

MPKAAPMTPIRRRKLIYSYAPDWALTIVLAAFFFSLDKVDGYRRVFSLEDSSIRHPYAVHERVPNVA

LYFICFVAPFLIMPIVNFITVRSWWDFHNSSLGLILGLSMTGSLTQIVKITVGRPRPDLLDRCKPPP

GLTDPPYGSTDWTVCTQTDNGILRDGFRSFFSGHSSMSFAGLGFLAYYLAGKVHLEDNRGHASKAWL

ALSPFMAASLVAISRTMDYRHHWQDVLVGSLVGTFFAFFTYRQYYPPLSSELSHRPYSPRIKREDND

RAVLPTHIDQFNGQTNIGNRHQYSDSTDDHFELAGTVPRPPGPGRLENVWKQGAGSPDLSQEDVVAG

GSANIQSTSGGAFVPLRNPGTTMT

SEQ ID NO: 74

MELGENGTIKSPEISHELAEEHWTKLQFTWISKSYKVEIADSDRLYDLKAAIYSLTKVPNERQKILG

LVKGKLPPDEVRISELTILPTKKFTLIGTPEGDEIKDPSQLESLPDVVNDLDVDFTENMVASNRYQH

DTRNIRKVQEAIRNLNINIIHPLRQGKKLLVLDIDYTILDTKPLTSGSLPPAECARPGLHEFLEAIY

PYYDILDKTSMFTVFTERDSKPWTHSVKALQIIWSHFPQFNATNTIHVDDLSRNFALNPKEGLKISA

FKNAHTPQAWEDRELYKLARYMVYIANIDDFTTLSHKNWKNVVKRLPGPS

SEQ ID NO: 75

MPLNIPALLVPFQLSIFPRLVIPALVVHDIRQVDFQALRRAGYRGAIFDKDNCLTLPHKDTLIPELQ

EAWKSCKETFGERNVLIVSNSAGTHLDAGGIQAESVSHHLGVPVLSHKAMKPAYSCITAIRGYFKSL

PDPVEDNELIVVGDRVFTDLVLANRMRMQYQRRSSKTRPLPDASNENQESCPVPQGPLSIWTKGVWE

RESMLMRKMEYGLISLMEGLTVPPKEEFVNVGAFVKPFPVRKDAKPTGLLAFLKFMYKREI

SEQ ID NO: 76

MSDQSTPSPSLAASSPPTSLPPSPELQKLNLSSEVSEQDKQEALRLKAAANKAFTSHEFNDAARLYS

ESIQKNPNEPTVWCNRAYARMKLEEYGYALTDASQAITLDPKYAKAYYRRATCYMQVMKYQAAVADE

KKVLALEPNNDTVRGQLVSTQKLIRKIEFEKAIEVEGEKDPVVRCREIIQEGGCEVDSNYTGPKLPQ

SEDGKFYMTQEFLQEMIEWFKQGKTLPKRYAWEIVMGAHEQFIKEESLVSVDIPDGVTCDVIGDVHG

QFYDVLHLFSLTGPPSEKHYLLMNGDLVDRGSWSIEVILLAFSYKWLYPKYMYINRGNHEAKDMNRT

YGFEGEAKHKHGEQAYKLFAHVFTTLPLSTLVNATKPPPSKDNAILSPEGFKRFFVVHGGLFSKDGV

TLEDIRKIDRVGRQPGQEGIMCELLWTDPQEAPGRGPSKRGVGIAFGPDVTKRWCTLNGVTGVIRSH

EVRQNGYEIEHEGLCTTVESAPNYVDQSGNKGAFIRIDSAGNRKYTQFEASPHPPMKPMAYIQGGLG

SLMM

SEQ ID NO: 77

MASPKRQLVVFDFDWSMSDQDTDRWIFEVLAPDLRRKMKTLKDQVQWTDLVGQSLREAFARGITKEQ

IIHTLQIMPFHPAMVRAVTELKNRGETTFLCLSNANSVFIKTILESKGLSNLFHEIITNPAEWDPSG

LLKVSRRVDPSGPQHSCKVGCSPNMCKGEELEAFLSRQGIEYDHIAYVGDGTNDFCPILRLRSQDTI

FCRTGRGLQKRIEKEGEQEGLKCNIQYWGGAWEIEEKFSKL

SEQ ID NO: 78

MAPFDLDACIQQLLRKQLLHEVLLREICEKTKEVLMRESNVVHVSAPVTVVGDIHGQFYDLIEIFRI

GGYAPNTNYLFLGDYVDRGLFSVETISLLTCLKLRYPDRVQLIRGNHESRAVTQTYGFYTECVRKYG

SSHVWTYFTDMEDELTLSVVIDDRIFCVHGGLSPSIHSIDQIKVVDRFREIPHEGPMADLVWSDPDP

EKEDFAISPRGAGYTFGSGVVYKFLDQNNMSHILRAHQLCMEGYSSLFDKHLSTVWSAPNYCYRCGN

SASILEVGPGGSMYFNVFDAAPENDRDGPNQQAAQNAAGKLPEYFL

-continued

SEQ ID NO: 79
MTSNYRLGPGSSSPQTTTCPTASTSTAAASDHPDDLQHSQRKLQALFIEDIPRPLTAVCARPIPNSY
WATPLLLACEYPWTPKNPNKPKLDALLRAGVRTFIDLTECGELLPYSSILSQRSALLGIDPATIEYH
RFAIRDRCLPESINHMYRVLDTLRDNQERGRISAVHCRGGIGRTGMVIGCWLVESGIARDGKEALAI
IAREWKTVEKCKRYPHSPETGAQFDFVAKFHPSPKQLHATLELESEDA

SEQ ID NO: 80
MMGVVLVELGGIKSTAAIYKTLSPVTSSSELKLAPTLLSVFTSRLSKSRPQSPQPPGASMGQQPSKK
SKKAGKDKDRESPADGATSEAHHDPNDDNTPQSSISRATAPSTAHSSDSSSLPNGNPSINVSDPAGS
TVPSSATSARAHGSPYPPQATIPSIETAQLSESLPSPLPSPMTASLPLDIPVTQTILSNGNALSPSS
MTSNGNAPTSESVGNGGAKDRLKQFDVDDMIQRLLDVGYTGKVSKSLCLKNTEITAICLAARDVELS
QPTLVELSPPVKIVGDVHGQYSDLIRLFEMCGFPPAANYLFLGDYVDRGKQSLETILLLLCYKIKYP
ENFFLLRGNHECANVTRVYGFYDECKRRCNIKTWKTFIDVENCLPIAAIVASKIFCVHGGLSPSLHS
MEDIKRIQRPTDVPDYGLLNDLLWSDPSDTALDWEDNERGVSYCFGKAIINEFLVRYDMDLICRAHM
VVEDGYEFWNDRTLVTVFSAPNYCGEFDNYGACMSVSEDLLCAFELLKPLDGAALRKEMTKAKRKSV
MTTA

SEQ ID NO: 81
MAAPHRRRRAPASLRIDAPSLALPLAIALADEDSSTTLSSADSDYPPFHAQPEDRSSRKNMKKLSLT
LRSSPAPLDPPLPVSPVPADTRRRPSVISLPAPTPTPASLIHRKDEDGPSDAAPYANGPIQIIPGIW
IGSEDNARDWKCLVERGIRSILNVAKEVLLPEDTPIPATPLRLAASTPNERNRPPKDDPTYYPAHLP
SGRPAMHYLKLQWSHGQQNLVDDGFKAGMAFADAALSRGEGCLIHCQCGISRSATMVIALVMRAAAE
RHTSVPPEVWSLQGMQGAYTFVKEKSPHVGPNMSLIYQLLEYEKKLRGDKASPSDSDGSSDDEEEWG
RRRQMLDDASDNEADERESHIVMQEAKALDKAMEDRIVARKSSASSMSSTGSGIGMGPAWRSRYGSR
KRTGSVASNQTNQSFWSEDLVEEDEEQELLGTGGAFDSESRLDRASLTATSSPEDEQHDSTPRNESL
MALHGPATARPPPSAPVWKSSFNIPPPPKTAVRSTFDIPPRPKPRGKPRPMGLSLLPVVPSSPVTLV
IETESSDENDHQPGPPPTQQPPPAKPTLPLPPVRQRAESRKLVPPPLHLRSSVLRRASSSSTSTTGS
ADVAGLSTPSQTLFVFPPSPTLTTRTPSTMTLTSNFAGPVPFPSLSTPRVSTFHSKGRTRSFIGLGA
PPTPTVAFSKVDVRGYVGLE

SEQ ID NO: 82
MDSFAQAIADRFKQSAILSVPPPPDPARPNVFPAIDPASLDDWLTDPTALILDIRPHAAFSAARIPH
AISLSVPSTLLKRPLFSLQRLSAMLPSSAARNRFSAWAAASRILVYDADSSSVPDSSNIAGLLRKFK
ADGFQRDLVWLKGGFHALWRDRRDLIDTSPPTPDNEHDDDDDESASSDPKSSLLKTRHLPMAAFSLS
STTVHSSPRFNTSAAGAPSAPKFVQPSSGLLPAAISAPTNSHPAFNPFEDTIRQNTELSHGITDRIP
LRLPKRVRRRIHELPFPWLQDIARRAANAPHHHGSYSDSTSSESEDDEGATQADIEEGKEALAMQFF
KIELSEQRRMMGIMEHHSRESGQVSQMASSSHTSNPFPYSITAGVEKGAKNRYRHIWPFEHARVRLH
QKKETDDDYINASYIQPLGTTKRYIATQGPLPATFTDFWTLCWEQNVHVIVMLTREVEGAMVKCGAY
WSDTVFGPLRLRLVSTEGLPSVDERPTTAGFFSQHSSLSVQPPSRVTSQRRFPHSAGSQRRYRHHHY
HNKSSETVKRIFELTHTGYPEAKPRRIVHLQYLEWPDMNVPEDPRGVLGLVKQVEEAVRETQMDDQP
SEPKKRRKGSNQVSLTDIDEKTGVAMHTLGGNNPVLLHCSAGVGRTGGFIAVDAILDAIRREVRNAR
TGDAMDVAPDSHKATTISEKTATLDLTNRQGSGEPTTEESRTIHVRMATPMQVDHPDQFENEAADAT
MSSSGTMQWAENVRDETGIVGSSNGPSQTTEECRFPSSSNLSESTPESSNLAGASETPHKHGSYYYN
PSSSLGTSVSGSSSYFKAHPQHQFTSDLLQASFNHQKPSASEQRHRTISAPPVHSTSATLGRYHRDI
VRSLVSSPSPLHLKKGSSDLPDLSNSRVETVVKPFALSLDLMSSPSKSLSSLHPPMSSDAESPPSRS

-continued

QSPSADEASFKFKSSKKASSPVNGSTSTCKVTPPDGQPKTFDYKEPRPLHEDYTPPPLTTEDDPIWE

VVQDMREQRMSLCQSLRQYVFVHAAIIEGSLMVLDEEKEAAEGLIPPSRKTSKPATPTATSSSADVP

QTPRSSTSASRSPKSSPSRRQNSHPYSHELASIASSSSISIGKRGASPTELPKENKEGDLMLSKRPS

VKRKQRSGDDLNVVDDARYHPVPVRVTSSVLHMGGVSAPSARAMPP

SEQ ID NO: 83

MDGTLIDSTPGVLRAWRIFSDDYKLGDSESVAHETHGRRLYDTLKEYCGITDEERLLQEIDRFEEEV

IEGGPMALPGAIDLLRKLNSDPSTSSKWTIVTSASNKYAPRALERSGVPLPSVGIITSNDVSEGKPH

PAPYLAGSLRCSINPENCLVVEDAISGLKSGRAAGCRTLAVCTSTLRSKILDSGVQPDFIVSDLTKV

SVAVVDNKLQVTVDQS

SEQ ID NO: 84

MAEHRPAPRLFVVRHGQTEWSQNGQTGRSDIPLTDVGVEQVKKMAPLLVGEGRLLDPKNICTAQVSP

RQRAATTFHLLFDHTVEPDYVLTEEVREWDYGEYEGLKPAEIQKINPGWKIWNDGCPGGESVEDMQA

RVDGVIKKVRQYHKEYKEEGKHTRDVLIVAHGHFSRVLISRWINFPLCLGTHENVEPGSVSILSYNH

NSLDEPALNGLNLVASGA

SEQ ID NO: 85

MGEAVLKEVARKRGIEIVVDSCGTAGYHVGESPDERTVAICQKHNVPIDSYARQVATSDEVRETHIL

ASDESNLQNLNRIKPSNTTADVRLWGSYLDNKPIPDPYYGGMSDFEKVYQQCVRLSNAFLDEVTTKD

SKS

SEQ ID NO: 86

MDDSEPTPLHLPQNLPYPLKITSLNAAQNATVDRKSRLLEYSFVYSPPGPEQLPETRFGTWDSTLDG

VVKAWNLKVGDVVTRKKAAESPAIFVVEPCKHEIQISGLCALCAKDMTIADYLDVSDTSRANIQMTH

SAHGPTVSLEYAKRLERESADHLLKSRKLSLIVDLDQTIVHATVDPTVGEWINEGLAWEARQAKKAS

TTPPDDGAPTANDADDDDECNPNWEALKDVKSFRLGPESFGPLAVRSAHRGKGKNKMVETEGCMYYI

KPRPGWKEFLRETATKYEMHVYTMGTRAYAEEVCAAIDPDGNIFGGRLLSRDESGNDFFVGIGDINS

SFLPKIEPLTPVLNVPQATPTASINGSSTSPIPNNNANPVTPDVPTTVAADGEISELENAMFTQNNA

ALDAQLEERPLAKKEKELQEHEIQEQQAAEKTPTPPETPASVEKLPTPTPSPKPEKMHKKALLKNDD

YELERIGKLLNEVHTRFFTAYDTRRANENAKAKAAAAKAYDVTRIIPRIRSEVFEGVHILFSSVIPL

DTKPETTEIWRMAHMFGAQCSTELTSNITHVVAAKRGTVKVDMARRRGGIKIVWLAWFTDSIALWRR

QDEKPYLLDDPPVVIPASSPTTEYHQLSSDLDIDSDDWDQEPPEMKETGPLHLEAINWDDINDEVEA

AMNESDDEYDEYYAAFKSGNVSEDDTTDGGANNTSQTMTTRKRFRSATPSDGGGGNDEYLGTGSRKR

MRSKTPSDAGSDYGSPLARRKKAAAGRTGYSKLKEGITADDIEGGDAVINDVNESGNGTALPDAQGS

SPAAYDEEEDGEDDDEEEEEEEDDFLARELEEEWG

SEQ ID NO: 87

MPSFLKSKQTTAKTTTIPPWLILANTDKHIYKVERLLSSREATRYAARDASHQIALKASESTQHDKS

PVFKRSSQRKEGSAVDFVEYYGITAGLHEDNRDLNRYTDIIPYDRTRIIVHDGSPPAVGDESEGKRH

ERYLNANWVLEKFGHKWWIATQAPLRHTAHAFLSVMLQPSVRPPHVDLPLKDSKTRRVRTVVQLARN

VENGRKKADAYFPSEVGRSVVVLAEHGWRAPPLKVTLLAKKAIDEAHCIQSTVSVAPIKNATSHLAE

GRHGTGVQDEDNHGQAIVFNHLLYLSWPDHGVPSPEDRLSLVHFIQLVDRINRDTSQCPIHSAATTN

HICEELDPDPPIIVGCSAGIGRTGAFVALSSLLRKYGFLLPAAHPTIAPHVYTSPLGPIPSDPDLQD

DLVLQEVDSLREQRPGMVERKVQMSLIYEVLASVLASESN

SEQ ID NO: 88

MATIKLENFRGCLALAGQAVDNEVNTDPSFANLIRSGALKPSQKLYHITVITKDELRMISSEQIQKI

TSTEVDPKSLESLGIGGKEQAGIYWVVIIWAAGQKLRKQAGLPPKHFHITLSSNDIHDVDKGINSLI

-continued

SRDLPEVSGVEALDHTIFTLQQFAQYNEATEYSSRLILTDPNSHKGFLRMGDACFANGSHKIAMLSY

ACAYQRSGDQKVQSYCMKKLTECSKETEWGLVFQEHEKEQIENLSEISSLLLKPWSQDLQERLSDQG

NTPSLLLEPRQPLYIPSTKNMGAKLHFYRLPRFFRWLIPYHLAIMSTPKNEDDITALASAPLGIRHV

LTLTEEEPLRPAWFQGKSISNTFLPVPNYYPPSIEQMDLVMRLFDDQDKLPLLVHCGGGKGRAGTVA

ACYLAAFGENKPRHDQDHPELAATEAISSLRALRPGSLETSRQEEFVSRWCSTIWKRQSVYPDIPSE

PSPSPMEVEGKLSADNDLFVLVGLPGSGKSWFSKSLISRDPSKWTHISQDDSRSKEACETEIGRSPK

GKHVLLDRCNTSAADRKIWLDLASNWCVSPVCILEDYSQELCTSRAQMRAGHPTLPPGSRVRNAVDQ

MQKIFMKPTLKEGFKAVITVRSFAAAEEAVLRFSSPVSILKFPRTPHLINTGAASADDVHTDLAVET

NTAAGHTVITEKIDGANMGFSLSSDRSRIIVQNRSHYVNSSTHEQFRKLGLWVERHDQELRRVLDRD

PYFPERYILYGEWVYATHSIPYTSLPDYFIAYDLFDRSTKTWADTATLRHLLGETSIATAPIVHEGT

MPTESQLLRMVQQPSMFYDGRVEGVYVKLEVNKCVKLRGKVVRSDFISGNEHWTRGGVRVNGLRLDQ

TGVE

SEQ ID NO: 89

MHSLGLFALISLLPYLVVAQRASTFAGATTTAVFPPPNAGIAATDTNFPDGSKVGFPGPTRTGDEAA

AIETAPVAAKVDSFFPLINGGAEDSTPMDPFDVLVHLGNLSPFQSVPSSAFGLPGASPLIPEGCDIV

QAHLLHRHGARYPTADSGPPGFAAKVNAAANSGSGFSAKGDLSFLNTWTYKLGGDILTPFGRSQLEN

LGVGFRVKYGQLLKGFKNLPVFRTTSEARMLDSALHFATGFFGVQKYQDSYHQLITIEHGGKQNNTL

APYESCTNGLNAVAAFGDIQSQKWAQIYLAPAVKRLNANLRGLQLNVTDLFAMQQLCAFETVALGYS

SFCDLFTEEEWRGFEYQSDLQFWYSFGPGNPASSAMGIGYVQELVSRLTKTRITTFDTTVNASIVTS

DILFPLDQPIYVDATHDTILTAIFAAMNLTTLAANGPLPTDHIPKGQTFFANQLAPFAANVVGQVLS

CPASSKPTHIRWIINDGVVPLTGIKGCKPDKNGMCEINTFIAGMKQRMQEIDENFDCFANYTVPVPD

NIVNGQYPQNLKPKKK

SEQ ID NO: 90

MEPAEIDQWIEQLSQCKQLSEADVKKLCDKTREILMEESNVQIVKCPVTVCGDIHGQFHDLSELFRI

GGNSPDTNYLFMGDYVDRGYYSVETVILLVALKLRYRHRVTILRGNHESRQITQVYGFYDECLRKYG

NASVWRFFTDLEDELPLTALIDNQIFCLHGGLSPSIDTLDHVRSIDRVQEVPHEGPMCDLLWSDPDD

RCGWGISPRGAGYTFGQDISEAFNHNNGLTLVARAHQLVMEGYSWGQDRNVVTIFSAPNYCYRCGNQ

AAIMEIDEKLSYSFLQFDPAPRAGEPLVSRRVPDYFLRDLGGSGLLRLNEWTTMIFLYGVPAGFALL

GTAFLWSRLKQYRRTRCLGYIPGPPSESFLIGVLNRFYHPIDGWKFHDKLMKTYGGVVRLKGVLGAN

ELYVYDPKALHHILVKDLDIYGETDAFYAGNKVIFGEGILSSEGEQHRRHKKMLNPVFSAAHFRGMV

PLFHEITHKARQSLEKKVANGPVEIDMLSWMTRVALELIAQSGLGYSEDTLEDDSIPHPYSRASKDL

VPLSSGSMLLRNIIMPPLVKIGYKWKRFSRFFLEVFPWRTLSKIKGLVDVLHSTSVEIFQAKKKALE

AGDEAMLEQLGQGKDIISILMKANTRASAEDRMSDTELIGQVTSLTFAATDTTSGALASTLQQLARH

PEVQDKLREEIRTAREVHGDLDYDQLFALPYLDAVCRETLRLYPPVLNAQRTQVVPNALYDLRIDEF

SSVLQDVVLPLHAPLKGYKGEDIREIFIPQGTAVHVSILSANRNPALWGPDYAEWKPERWLNPLPNE

LVNAKMPGIYSHILSFLGGGRACLGVKFAQLELKTVLTVIVDSLRFEPAKRDAVWQMNMLLTPNVDP

EGKFPNLPLKVSLAK

The phrase, "the phosphatase enzyme is encoded by an amino acid sequence," does not mean that the phosphatase enzyme has such an amino acid sequence, but instead that the phosphatase enzyme is biosynthetically produced from such an amino acid sequence, which amino acid sequence is typically altered by one or more post-translational modifications such as cleavage of a leader peptide sequence, splicing, other proteolytic cleavage, conjunction with one or more non-catalytic protein subunits, deamidation, citrullination, phosphorylation, acylation, glycosylation, etc.

A phosphatase enzyme may be encoded by an amino acid sequence that has less than 100 percent sequence identity with one of SEQ ID NO: 25 to SEQ ID NO: 90, for example, due to natural intra- or inter-species variation or due to bioengineered mutations.

The denaturation of relevant phosphatase enzymes may be assessed, for example, by performing a colorimetric assay with a para-nitrophenyl phosphate substrate. Para-nitrophenyl phosphate comprises a phosphorylated aromatic, which is chemically similar to the phosphorylated indole of a phosphoryloxytryptamine. Colorimetric assays performed with a para-nitrophenyl phosphate substrate therefore provide suitable methods to assess phosphorylase activity that are relevant to this disclosure.

In some embodiments, the starting fungal material has native phosphatase activity, which is measurable using a colorimetric assay with a para-nitrophenyl phosphate substrate; the heat-inactivated fungal material has attenuated phosphatase activity, which is measurable using the colorimetric assay with the para-nitrophenyl phosphate substrate; and the native phosphatase activity is greater than the attenuated phosphatase activity as measurable using the colorimetric assay with the para-nitrophenyl phosphate substrate.

In some embodiments, the native phosphatase activity is at least 100 percent greater than the attenuated phosphatase activity. In some specific embodiments, the native phosphatase activity is at least 250 percent greater than the attenuated phosphatase activity. In some even more specific embodiments, the native phosphatase activity is at least 500 percent greater than the attenuated phosphatase activity. In some very specific embodiments, the native phosphatase activity is at least 1,000 percent greater than the attenuated phosphatase activity.

The denaturation of relevant oxidoreductase enzymes may be assessed, for example, by performing a fluorogenic assay with a 10-acetyl-3,7-dihydroxyphenoxazine (ADHP, e.g., AMPLEX® Red) substrate. ADHP comprises an aromatic ring system with pendant hydroxyl groups, which is chemically similar to the indole of a hydroxytryptamine. Fluorogenic assays performed with an ADHP substrate therefore provide suitable methods to assess oxidoreductase activity that are relevant to this disclosure.

In some embodiments, the starting fungal material has native oxidoreductase activity, which is measurable using a fluorogenic assay with an ADHP substrate; the heat-inactivated fungal material has attenuated oxidoreductase activity, which is measurable using the fluorogenic assay with the ADHP substrate; and the native oxidoreductase activity is greater than the attenuated oxidoreductase activity as measurable using the fluorogenic assay with the ADHP substrate.

In some embodiments, the native oxidoreductase activity is at least 100 percent greater than the attenuated oxidoreductase activity. In some specific embodiments, the native oxidoreductase activity is at least 250 percent greater than the attenuated oxidoreductase activity. In some even more specific embodiments, the native oxidoreductase activity is at least 500 percent greater than the attenuated oxidoreductase activity. In some very specific embodiments, the native oxidoreductase activity is at least 1,000 percent greater than the attenuated oxidoreductase activity.

The denaturation of relevant laccase enzymes may be assessed, for example, by performing a colorimetric assay with a laccase enzyme substrate such as syringaldazine or 2,2'-azino-bis(3-ethylbenzothiazoline-6-sulfonate) (ABTS). Syringaldazine comprises an aromatic structure with pendant hydroxyl groups, which is chemically similar to the indole of a hydroxytryptamine, and ABTS comprises a benzothiazoline, which is chemically similar to the indole of tryptamines generally. Colorimetric assays performed with a syringaldazine or ABTS substrate therefore provide suitable methods to assess laccase activity that are relevant to this disclosure.

In some embodiments, the starting fungal material has native laccase activity, which is measurable using a colorimetric assay with a syringaldazine or ABTS substrate; the heat-inactivated fungal material has attenuated laccase activity, which is measurable using the colorimetric assay with the syringaldazine or ABTS substrate; and the native laccase activity is greater than the attenuated laccase activity as measurable using the colorimetric assay with the syringaldazine or ABTS substrate.

In some embodiments, the native laccase activity is at least 100 percent greater than the attenuated laccase activity. In some specific embodiments, the native laccase activity is at least 250 percent greater than the attenuated laccase activity. In some even more specific embodiments, the native laccase activity is at least 500 percent greater than the attenuated laccase activity. In some very specific embodiments, the native laccase activity is at least 1,000 percent greater than the attenuated laccase activity.

In some embodiments, the starting fungal material comprises psilocybin, and denaturing the phosphatase enzymes inhibits dephosphorylation of the psilocybin into psilocin.

In some embodiments, the process is performed such that the heat-inactivated fungal material comprises the psilocybin and the psilocin at a mole ratio of at least 3:2 (psilocybin: psilocin). In some specific embodiments, the process is performed such that the heat-inactivated fungal material comprises the psilocybin and the psilocin at a mole ratio of at least 2:1. In some very specific embodiments, the process is performed such that the heat-inactivated fungal material comprises the psilocybin and the psilocin at a mole ratio of at least 3:1.

In some embodiments, the starting fungal material comprises baeocystin, and denaturing the phosphatase enzymes inhibits dephosphorylation of the baeocystin into norpsilocin.

In some embodiments, the process is performed such that the heat-inactivated fungal material comprises the baeocystin and the norpsilocin at a mole ratio of at least 3:2 (baeocystin:norpsilocin). In some specific embodiments, the process is performed such that the heat-inactivated fungal material comprises the baeocystin and the norpsilocin at a mole ratio of at least 2:1. In some very specific embodiments, the process is performed such that the heat-inactivated fungal material comprises the baeocystin and the norpsilocin at a mole ratio of at least 3:1.

In some embodiments, the starting fungal material comprises norbaeocystin, and denaturing the phosphatase enzymes inhibits dephosphorylation of the norbaeocystin into 4-HT.

In some embodiments, the process is performed such that the heat-inactivated fungal material comprises the norbaeocystin and the 4-HT at a mole ratio of at least 3:2 (norbaeocystin:4-HT). In some specific embodiments, the process is performed such that the heat-inactivated fungal material comprises the norbaeocystin and the 4-HT at a mole ratio of at least 2:1. In some very specific embodiments, the process is performed such that the heat-inactivated fungal material comprises the norbaeocystin and the 4-HT at a mole ratio of at least 3:1.

In some embodiments, the starting fungal material comprises aeruginascin, and denaturing the phosphatase enzymes inhibits dephosphorylation of the aeruginascin into 4-hydroxy-TMT.

In some embodiments, the process is performed such that the heat-inactivated fungal material comprises the aeruginascin and the 4-hydroxy-TMT at a mole ratio of at least 3:2 (aeruginascin:4-hydroxy-TMT). In some specific embodiments, the process is performed such that the heat-inactivated fungal material comprises the aeruginascin and the 4-hydroxy-TMT at a mole ratio of at least 2:1. In some very specific embodiments, the process is performed such that the heat-inactivated fungal material comprises the aeruginascin and the 4-hydroxy-TMT at a mole ratio of at least 3:1.

In some embodiments, denaturing the oxidoreductase enzymes inhibits oxidation of psilocin into oxidized diols and diones of psilocin selected from 3-[2-(dimethylazaniumyl)ethyl]-1H-indol-2,4-diol; 3-[2-(dimethylazaniumyl)ethyl]-1H-indol-4,5-diol; 3-[2-(dimethylazaniumyl)ethyl]-1H-indol-4,7-diol; 3-[2-(dimethylazaniumyl)ethyl]-1H-indol-2,4-dione; 3-[2-(dimethylazaniumyl)ethyl]-1H-indol-4,5-dione; 3-[2-(dimethylazaniumyl)ethyl]-1H-indol-4,7-dione; and tautomers of the diones.

In some embodiments, the process is performed such that the heat-inactivated fungal material comprises the psilocin and the oxidized diols and diones of psilocin at a mole ratio of at least 2:1 (psilocin:oxidized diols and diones of psilocin). In some specific embodiments, the process is performed such that the heat-inactivated fungal material comprises the psilocin and the oxidized diols and diones of psilocin at a mole ratio of at least 5:1. In some very specific embodiments, the process is performed such that the heat-inactivated fungal material comprises the psilocin and the oxidized diols and diones of psilocin at a mole ratio of at least 10:1.

In some embodiments, denaturing the oxidoreductase enzymes inhibits oxidation of norpsilocin into oxidized diols and diones of norpsilocin selected from 3-[2-(methylazaniumyl)ethyl]-1H-indol-2,4-diol; 3-[2-(methylazaniumyl)ethyl]-1H-indol-4,5-diol; 3-[2-(methylazaniumyl)ethyl]-1H-indol-4,7-diol; 3-[2-(methylazaniumyl)ethyl]-1H-indol-2,4-dione; 3-[2-(methylazaniumyl)ethyl]-1H-indol-4,5-dione; 3-[2-(methylazaniumyl)ethyl]-1H-indol-4,7-dione; and tautomers of the diones.

In some embodiments, the process is performed such that the heat-inactivated fungal material comprises the norpsilocin and the oxidized diols and diones of norpsilocin at a mole ratio of at least 2:1 (norpsilocin:oxidized diols and diones of norpsilocin). In some specific embodiments, the process is performed such that the heat-inactivated fungal material comprises the norpsilocin and the oxidized diols and diones of norpsilocin at a mole ratio of at least 5:1. In some very specific embodiments, the process is performed such that the heat-inactivated fungal material comprises the norpsilocin and the oxidized diols and diones of norpsilocin at a mole ratio of at least 10:1.

In some embodiments, denaturing the oxidoreductase enzymes inhibits oxidation of 4-HT into oxidized diols and diones of 4-HT selected from 3-(2-azaniumylethyl)-1H-indol-2,4-diol; 3-(2-azaniumylethyl)-1H-indol-4,5-diol; 3-(2-azaniumylethyl)-1H-indol-4,7-diol; 3-(2-azaniumylethyl)-1H-indol-2,4-dione; 3-(2-azaniumylethyl)-1H-indol-4,5-dione; 3-(2-azaniumylethyl)-1H-indol-4,7-dione; and tautomers of the diones.

In some embodiments, the process is performed such that the heat-inactivated fungal material comprises the 4-HT and the oxidized diols and diones of 4-HT at a mole ratio of at least 2:1 (4-HT:oxidized diols and diones of 4-HT). In some specific embodiments, the process is performed such that the heat-inactivated fungal material comprises the 4-HT and the oxidized diols and diones of 4-HT at a mole ratio of at least 5:1. In some very specific embodiments, the process is performed such that the heat-inactivated fungal material comprises the 4-HT and the oxidized diols and diones of 4-HT at a mole ratio of at least 10:1.

In some embodiments, denaturing the oxidoreductase enzymes inhibits oxidation of 4-hydroxy-TMT into oxidized diols and diones of 4-hydroxy-TMT selected from 2-(2,4-dihydroxy-1H-indol-3-yl)ethyl-trimethylazanium; 2-(4,5-dihydroxy-1H-indol-3-yl)ethyl-trimethylazanium; 2-(4,7-dihydroxy-1H-indol-3-yl)ethyl-trimethylazanium; 2-(2,4-dioxo-1H-indol-3-yl)ethyl-trimethylazanium; 2-(4,5-dioxo-1H-indol-3-yl)ethyl-trimethylazanium; 2-(4,7-dioxo-1H-indol-3-yl)ethyl-trimethylazanium; and tautomers of the diones.

In some embodiments, the process is performed such that the heat-inactivated fungal material comprises the 4-hydroxy-TMT and the oxidized diols and diones of 4-hydroxy-TMT at a mole ratio of at least 2:1 (4-hydroxy-TMT: oxidized diols and diones of 4-hydroxy-TMT). In some specific embodiments, the process is performed such that the heat-inactivated fungal material comprises the 4-hydroxy-TMT and the oxidized diols and diones of 4-hydroxy-TMT at a mole ratio of at least 5:1. In some very specific embodiments, the process is performed such that the heat-inactivated fungal material comprises the 4-hydroxy-TMT and the oxidized diols and diones of 4-hydroxy-TMT at a mole ratio of at least 10:1.

In some embodiments, denaturing the laccase enzymes inhibits the dimerization of psilocin into 5-oxo-dimethyl-tryptamine-ylidene dimers (5-oxo-DMT-ylidene dimers) selected from 3-[2-(dimethylazaniumyl)ethyl]-2-{3-[2-(dimethylazaniumyl)ethyl]-4-oxo-1H-indol-2-ylidene}-1H-indol-4-one; 3-[2-(dimethylazaniumyl)ethyl]-2-{3-[2-(dimethylazaniumyl)ethyl]-4-oxo-1H-indol-5-ylidene}-1H-indol-4-one; 3-[2-(dimethylazaniumyl)ethyl]-2-{3-[2-(dimethylazaniumyl)ethyl]-4-oxo-1H-indol-7-ylidene}-1H-indol-4-one; 3-[2-(dimethylazaniumyl)ethyl]-5-{3-[2-(dimethylazaniumyl)ethyl]-4-oxo-1H-indol-5-ylidene}-1H-indol-4-one; 3-[2-(dimethylazaniumyl)ethyl]-5-{3-[2-(dimethylazaniumyl)ethyl]-4-oxo-1H-indol-7-ylidene}-1H-indol-4-one; 3-[2-(dimethylazaniumyl)ethyl]-7-{3-[2-(dimethylazaniumyl)ethyl]-4-oxo-1H-indol-7-ylidene}-1H-indol-4-one; and tautomers of the foregoing.

In some embodiments, the process is performed such that the heat-inactivated fungal material comprises the psilocin and the 5-oxo-DMT-ylidene dimers at a mole ratio of at least 2:1 (psilocin: 5-oxo-DMT-ylidene dimers). In some specific embodiments, the process is performed such that the heat-inactivated fungal material comprises the psilocin and the 5-oxo-DMT-ylidene dimers at a mole ratio of at least 5:1. In some very specific embodiments, the process is performed such that the heat-inactivated fungal material comprises the psilocin and the 5-oxo-DMT-ylidene dimers at a mole ratio of at least 10:1.

In some embodiments, denaturing the laccase enzymes inhibits the dimerization of norpsilocin and psilocin into oxidized dione dimers of norpsilocin and psilocin selected from 3-[2-(dimethylazaniumyl)ethyl]-2-{3-[2-(methylazaniumyl)ethyl]-4-oxo-1H-indol-2-ylidene}-1H-indol-4-one; 3-[2-(dimethylazaniumyl)ethyl]-2-{3-[2-(methylazaniumyl)ethyl]-4-oxo-1H-indol-5-ylidene}-1H-indol-4-one; 3-[2-(dimethylazaniumyl)ethyl]-2-{3-[2-(methylazaniumyl)ethyl]-4-oxo-1H-indol-7-ylidene}-1H-indol-4-one; 3-[2-(dimethylazaniumyl)ethyl]-5-{3-[2-(methylazaniumyl)ethyl]-4-oxo-1H-indol-2-ylidene}-1H-indol-4-one; 3-[2-(dimethylazaniumyl)ethyl]-5-{3-[2-(methylazaniumyl)ethyl]-4-oxo-1H-indol-5-ylidene}-1H-indol-4-one; 3-[2-(dimethylazaniumyl)ethyl]-5-{3-[2-(methylazaniumyl)ethyl]-4-oxo-1H-indol-7-ylidene}-1H-indol-4-one; 3-[2-(dimethylazaniumyl)ethyl]-7-{3-[2-(methylazaniumyl)ethyl]-4-oxo-1H-indol-2-ylidene}-1H-indol-4-one; 3-[2-(dimethylazaniumyl)ethyl]-7-{3-[2-(methylazaniumyl)ethyl]-4-oxo-1H-indol-5-ylidene}-1H-indol-4-one; 3-[2-(dimethylazaniumyl)ethyl]-7-{3-[2-(methylazaniumyl)ethyl]-4-oxo-1H-indol-7-ylidene}-1H-indol-4-one; and tautomers of the foregoing.

In some embodiments, the process is performed such that the heat-inactivated fungal material comprises the norpsilocin and the oxidized dione dimers of norpsilocin and psilocin at a mole ratio of at least 2:1 (norpsilocin:oxidized dione dimers of norpsilocin and psilocin). In some specific embodiments, the process is performed such that the heat-inactivated fungal material comprises the norpsilocin and the oxidized dione dimers of norpsilocin and psilocin at a mole ratio of at least 5:1. In some very specific embodiments, the process is performed such that the heat-inactivated fungal material comprises the norpsilocin and the oxidized dione dimers of norpsilocin and psilocin at a mole ratio of at least 10:1.

In some embodiments, denaturing the laccase enzymes inhibits the dimerization of 4-HT and psilocin into oxidized dione dimers of 4-HT and psilocin selected from 3-[2-(dimethylazaniumyl)ethyl]-2-{3-(2-azaniumylethyl)-4-oxo-1H-indol-2-ylidene}-1H-indol-4-one; 3-[2-(dimethylazaniumyl)ethyl]-2-{3-(2-azaniumylethyl)-4-oxo-1H-indol-5-ylidene}-1H-indol-4-one; 3-[2-(dimethylazaniumyl)ethyl]-2-{3-(2-azaniumylethyl)-4-oxo-1H-indol-7-ylidene}-1H-indol-4-one; 3-[2-(dimethylazaniumyl)ethyl]-5-{3-(2-azaniumylethyl)-4-oxo-1H-indol-2-ylidene}-1H-indol-4-one; 3-[2-(dimethylazaniumyl)ethyl]-5-{3-(2-azaniumylethyl)-4-oxo-1H-indol-5-ylidene}-1H-indol-4-one; 3-[2-(dimethylazaniumyl)ethyl]-5-{3-(2-azaniumylethyl)-4-oxo-1H-indol-7-ylidene}-1H-indol-4-one; 3-[2-(dimethylazaniumyl)ethyl]-7-{3-(2-azaniumylethyl)-4-oxo-1H-indol-2-ylidene}-1H-indol-4-one; 3-[2-(dimethylazaniumyl)ethyl]-7-{3-(2-azaniumylethyl)-4-oxo-1H-indol-5-ylidene}-1H-indol-4-one; 3-[2-(dimethylazaniumyl)ethyl]-7-{3-(2-azaniumylethyl)-4-oxo-1H-indol-7-ylidene}-1H-indol-4-one; and tautomers of the foregoing.

In some embodiments, the process is performed such that the heat-inactivated fungal material comprises the 4-HT and the oxidized dione dimers of 4-HT and psilocin at a mole ratio of at least 2:1 (4-HT:oxidized dione dimers of 4-HT and psilocin). In some specific embodiments, the process is performed such that the heat-inactivated fungal material comprises the 4-HT and the oxidized dione dimers of 4-HT and psilocin at a mole ratio of at least 5:1. In some very specific embodiments, the process is performed such that the heat-inactivated fungal material comprises the 4-HT and the oxidized dione dimers of 4-HT and psilocin at a mole ratio of at least 10:1.

In some embodiments, the process comprises rapidly cooling the heat-inactivated fungal material to a temperature no greater than 10 degrees Celsius following the heating. In some specific embodiments, the process comprises inserting the heat-inactivated fungal material into a cold environment having a temperature of no greater than 10 degrees Celsius following the heating. The cold environment may be, for example, a refrigerator, freezer, cold room, cooling bath, container containing ice, or container containing dry ice.

Various aspects of this disclosure relate to a composition comprising a polypeptide and one or more tryptamines selected from psilocybin, baeocystin, norbaeocystin, aeruginascin, psilocin, norpsilocin, 4-HT, 4-hydroxy-TMT, and DMT. In some embodiments, the composition comprises trimethylglycine.

In some embodiments, the composition comprises the psilocybin and the psilocin at a combined concentration of at least 2 percent by dry weight. In some specific embodiments, the composition comprises the psilocybin and the psilocin at a combined concentration of at least 4 percent and no greater than 80 percent by dry weight.

In some embodiments, the polypeptide encodes a phosphatase enzyme, and the phosphatase enzyme lacks phosphatase enzyme activity.

In some embodiments, the composition comprises the psilocybin and the psilocin at a mole ratio of at least 1:1 (psilocybin:psilocin). In some specific embodiments, the composition comprises the psilocybin and the psilocin at a mole ratio of at least 3:2. In some even more specific embodiments, the composition comprises the psilocybin and the psilocin at a mole ratio of at least 2:1. In some very specific embodiments, the composition comprises the psilocybin and the psilocin at a mole ratio of at least 3:1. The precise mole ratio of psilocybin to psilocin depends, for example, upon the mole ratio in starting fungal material as well as fidelity to the methodology described in this disclosure.

In some embodiments, the composition comprises baeocystin and norpsilocin at a mole ratio of at least 1:1 (baeocystin:norpsilocin). In some specific embodiments, the composition comprises the baeocystin and the norpsilocin at a mole ratio of at least 3:2. In some even more specific embodiments, the composition comprises the baeocystin and the norpsilocin at a mole ratio of at least 2:1. In some very specific embodiments, the composition comprises the baeocystin and the psilocin at a mole ratio of at least 3:1. The precise mole ratio of baeocystin to norpsilocin depends, for example, upon the mole ratio in starting fungal material as well as fidelity to the methodology described in this disclosure.

In some embodiments, the composition comprises norbaeocystin and 4-HT at a mole ratio of at least 1:1 (norbaeocystin:4-HT). In some specific embodiments, the composition comprises the norbaeocystin and the 4-HT at a mole ratio of at least 3:2. In some even more specific embodiments, the composition comprises the norbaeocystin and the 4-HT at a mole ratio of at least 2:1. In some very specific embodiments, the composition comprises the norbaeocystin and the 4-HT at a mole ratio of at least 3:1. The precise mole ratio of norbaeocystin to 4-HT depends, for example, upon the mole ratio in starting fungal material as well as fidelity to the methodology described in this disclosure.

In some embodiments, the composition comprises aeruginascin and 4-hydroxy-TMT at a mole ratio of at least 1:1 (aeruginascin:4-hydroxy-TMT). In some specific embodiments, the composition comprises the aeruginascin and the 4-hydroxy-TMT at a mole ratio of at least 3:2. In some even more specific embodiments, the composition comprises the aeruginascin and the 4-hydroxy-TMT at a mole ratio of at least 2:1. In some very specific embodiments, the composition comprises the aeruginascin and the 4-hydroxy-TMT at a mole ratio of at least 3:1. The precise mole ratio of aeruginascin to 4-hydroxy-TMT depends, for example, upon the mole ratio in starting fungal material as well as fidelity to the methodology described in this disclosure.

In some embodiments, the polypeptide encodes a laccase enzyme, and the laccase enzyme lacks laccase enzyme activity. In some specific embodiments, the polypeptide has at least 90 percent sequence identity with at least 100 consecutive amino acids set forth in SEQ ID NO: 1, SEQ ID NO: 2, or SEQ ID NO: 3. In some very specific embodiments, the polypeptide comprises at least 100 consecutive amino acids set forth in SEQ ID NO: 1, SEQ ID NO: 2, or SEQ ID NO: 3.

In some embodiments, the polypeptide comprises the amino acid sequence(s) set forth in one, two, three, four, five, six, seven, eight, nine, ten, eleven, twelve, thirteen, fourteen, fifteen, sixteen, seventeen, eighteen, nineteen, twenty, or each of SEQ ID NO: 4 to SEQ ID NO: 24, which amino acid sequence(s) are highly conserved in the laccase enzyme encoded by the amino acid sequence set forth in SEQ ID NO: 3 and important for laccase enzyme activity.

In some embodiments, the composition comprises psilocin and one or more 5-oxo-DMT-ylidene dimers at a mole ratio of at least 1:1 (psilocin:one or more 5-oxo-DMT-ylidene dimers), wherein the one or more 5-oxo-DMT-ylidene dimers include each such 5-oxo-DMT-ylidene dimer that is present in the composition (including tautomers of 5-oxo-DMT-ylidene dimers). In some specific embodiments, the composition comprises the psilocin and the one or more 5-oxo-DMT-ylidene dimers at a mole ratio of at least 2:1. In some even more specific embodiments, the composition comprises the psilocin and the one or more 5-oxo-DMT-ylidene dimers at a mole ratio of at least 5:1. In some very specific embodiments, the composition comprises the psilocin and the one or more 5-oxo-DMT-ylidene dimers at a mole ratio of at least 10:1.

In some embodiments, the composition comprises norpsilocin and one or more oxidized dione dimers of norpsilocin and psilocin at a mole ratio of at least 1:1 (norpsilocin:one or more oxidized dione dimers of norpsilocin and psilocin), wherein the one or more oxidized dione dimers of norpsilocin and psilocin include each such oxidized dione dimer that is present in the composition (including tautomers of oxidized dione dimers). In some specific embodiments, the composition comprises the norpsilocin and the one or more oxidized dione dimers of norpsilocin and psilocin at a mole ratio of at least 2:1. In some even more specific embodiments, the composition comprises the norpsilocin and the one or more oxidized dione dimers of norpsilocin and psilocin at a mole ratio of at least 5:1. In some very specific embodiments, the composition comprises the norpsilocin and the one or more oxidized dione dimers of norpsilocin and psilocin at a mole ratio of at least 10:1.

In some embodiments, the composition comprises 4-HT and one or more oxidized dione dimers of 4-HT and psilocin at a mole ratio of at least 1:1 (4-HT:one or more oxidized dione dimers of 4-HT and psilocin), wherein the one or more oxidized dione dimers of 4-HT and psilocin include each such oxidized dione dimer that is present in the composition (including tautomers of oxidized dione dimers). In some specific embodiments, the composition comprises the 4-HT and the one or more oxidized dione dimers of 4-HT and psilocin at a mole ratio of at least 2:1. In some even more specific embodiments, the composition comprises the 4-HT and the one or more oxidized dione dimers of 4-HT and psilocin at a mole ratio of at least 5:1. In some very specific embodiments, the composition comprises the 4-HT and the one or more oxidized dione dimers of 4-HT and psilocin at a mole ratio of at least 10:1.

In some embodiments, the composition comprises a chaotrope. In some specific embodiments, the composition comprises a chaotrope selected from guanidinium, urea, and ammonium sulfate.

In some embodiments, the composition comprises the chaotrope, and the phosphatase enzyme lacks phosphatase enzyme activity because the phosphatase enzyme is denatured. In some specific embodiments, the phosphatase enzyme is denatured by the chaotrope.

In some embodiments, the composition comprises the chaotrope, and the laccase enzyme lacks laccase enzyme activity because the laccase enzyme is denatured. In some specific embodiments, the laccase enzyme is denatured by the chaotrope.

In some embodiments, the composition comprises a chaotrope selected from guanidinium, urea, and ammonium sulfate, and the composition comprises the chaotrope and psilocybin at a mole ratio of at least 100:1 (chaotrope: psilocybin).

In some embodiments, the composition comprises a chaotrope selected from guanidinium, urea, and ammonium sulfate, and the composition comprises the chaotrope and psilocin at a mole ratio of at least 100:1 (chaotrope:psilocin).

In some embodiments, the composition comprises a surfactant. In some specific embodiments, the composition comprises a surfactant selected from a 2-[(4-alkyl)phenoxy-polyethoxy]ethanol, tergitol, Brij-35, Brig-58, dodecyl sulfate, polysorbate 20, polysorbate 80, lauroylsarcosine, digitonin, bile salts, cetrimonium bromide, CHAPS, CHAPSO, octyl glucoside, and octylthioglucoside.

In some embodiments, the composition comprises the surfactant, and the phosphatase enzyme lacks phosphatase enzyme activity because the phosphatase enzyme is denatured. In some specific embodiments, the phosphatase enzyme is denatured by the surfactant.

In some embodiments, the composition comprises the surfactant, and the laccase enzyme lacks laccase enzyme activity because the laccase enzyme is denatured. In some specific embodiments, the laccase enzyme is denatured by the surfactant.

In some embodiments, the composition comprises a surfactant selected from a 2-[(4-alkyl)phenoxypolyethoxy] ethanol, tergitol, Brij-35, Brig-58, dodecyl sulfate, polysorbate 20, polysorbate 80, lauroylsarcosine, digitonin, bile salts, cetrimonium bromide, CHAPS, CHAPSO, octyl glucoside, and octylthioglucoside, wherein the composition comprises the surfactant and the psilocybin at a mole ratio of at least 1:1 (surfactant:psilocybin).

In some embodiments, the composition comprises a surfactant selected from a 2-[(4-alkyl)phenoxypolyethoxy] ethanol, tergitol, Brij-35, Brig-58, dodecyl sulfate, polysorbate 20, polysorbate 80, lauroylsarcosine, digitonin, bile salts, cetrimonium bromide, CHAPS, CHAPSO, octyl glucoside, and octylthioglucoside, wherein the composition comprises the surfactant and the psilocin at a mole ratio of at least 1:1 (surfactant:psilocin).

In some embodiments, the composition comprises a chelator. In some specific embodiments, the composition comprises a chelator selected from EDTA, EGTA, DTPA, triethylenetetramine (TETA), deferoxamine, nitrilotriacetic acid, tris(2-carboxyethyl)phosphine (TCEP), 1,10-phenanthroline, 2,2'-bipyridyl, bathocuproine, 4,5-dihydroxy-1,3-benzenedisulfonate, penicillamine, dimercaprol, and tetrathiomolybdate. In some very specific embodiments, the composition comprises a chelator, and the chelator is bound to a metal cation.

In some embodiments, the composition comprises a chelator, the chelator is bound to a metal cation, the phosphatase enzyme requires the metal cation as a cofactor, and the phosphatase enzyme lacks phosphatase enzyme activity because it lacks its metal cation cofactor. In some specific embodiments, the phosphatase enzyme requires a metal cation selected from divalent magnesium cation ($Mg^{2+}$), divalent manganese cation ($Mn^{2+}$), iron(II), and iron(III) as a cofactor, and the phosphatase enzyme lacks phosphatase enzyme activity because it lacks its metal cation cofactor.

In some embodiments, the composition comprises a chelator, the chelator is bound to a metal cation, the laccase enzyme requires the metal cation as a cofactor, and the laccase enzyme lacks laccase enzyme activity because it lacks its metal cation cofactor. In some specific embodiments, the laccase enzyme requires a metal cation selected from copper(I) and copper(II) as a cofactor, and the laccase enzyme lacks laccase enzyme activity because it lacks its metal cation cofactor.

In some embodiments, the psilocybin comprises (A) a cationic species of psilocybin, which has a net charge of +1, (B) a zwitterionic species of psilocybin, which has a net charge of 0, and (C) an anionic species of psilocybin, which has a net charge of −1. Without limiting this disclosure or any patent claim that matures from this disclosure, the zwitterionic species of psilocybin is less susceptible to spontaneous dephosphorylation than the anionic species of psilocybin, and the zwitterionic species of psilocybin is less susceptible to spontaneous dephosphorylation than the cationic species of psilocybin. The relative abundance of the cationic, zwitterionic, and anionic species of psilocybin may be adjusted, for example, by adjusting the pH and/or nature of a solvent. Higher pH increases the anionic species of psilocybin relative to the zwitterionic and cationic species, and higher pH also increases the zwitterionic species of psilocybin relative to the cationic species. Lower pH increases the cationic species of psilocybin relative to the zwitterionic and cationic species, and higher pH also increases the zwitterionic species of psilocybin relative to the anionic species. Hydrophobic solvents have varying effects that tend to favor the zwitterionic species.

Various aspects of this disclosure relate to a liquid chromatography column comprising a composition as described herein, wherein the composition is a liquid (e.g., in which solutes of the liquid partition into and out of the stationary phase of the liquid chromatography column). Various compositions of this disclosure comprise both liquids and solids; liquids and solids of such compositions may be separated (for example, by centrifugation, decanting, aspirating, and/or filtering) to load a liquid of such a composition onto a liquid chromatography column, in which case, the liquid chromatography column comprises a liquid portion of a composition as described herein.

A liquid chromatography column generally comprises a stationary phase, analytes that are bound to the stationary phase, a mobile phase, and solutes that are dissolved in the mobile phase. When a liquid chromatography column comprises a composition of this disclosure, then the composition typically comprises the analytes that are bound to the stationary phase, the mobile phase, and the solutes that are dissolved in the mobile phase. In some specific embodiments, the liquid chromatography column is a reverse-phase HPLC column as described herein supra.

Various aspects of this disclosure relate to a method to quantify the amount of a tryptamine in a composition, comprising (A) providing a composition as described anywhere in this disclosure; (B) providing a liquid chromatography column; (C) introducing the composition (or a liquid portion of the composition) into the liquid chromatography column; and (D) measuring an amount of the tryptamine that elutes from the column, wherein the tryptamine that is measured is selected from psilocybin, baeocystin, norbaeocystin, aeruginascin, psilocin, norpsilocin, 4-HT, 4-hydroxy-TMT, DMT, and bufotenin. In some embodiments, (E) the liquid chromatography column has a mobile phase; (F) the tryptamine is a phosphoryloxytryptamine (e.g., psilocybin, baeocystin, norbaeocystin, aeruginascin), which comprises a cationic species that has a net charge of +1, a zwitterionic species that has a net charge of 0, and an anionic species that has a net charge of −1; and (G) the method comprises buffering the mobile phase such that (i) a mole ratio of the zwitterionic species to the cationic species (zwitterionic species:cationic species) does not fall below 50:1 on the column and (ii) a mole ratio of the zwitterionic species to the anionic species (zwitterionic species:anionic species) does not exceed 5000:1 on the column. In some specific embodiments, the method comprises buffering the mobile phase such that (i) the mole ratio of the zwitterionic species to the cationic species does not fall below 500:1 on the column, and (ii) the mole ratio of the zwitterionic species to the anionic species does not exceed 500:1 on the column. In some even more specific embodiments, the method comprises buffering the mobile phase such that (i) the mole ratio of the zwitterionic species to the cationic species does not fall below 5000:1 on the column, and (ii) the mole ratio of the zwitterionic species to the anionic species does not exceed 50:1 on the column. In some very specific embodiments, the method comprises buffering the mobile phase such that (i) the mole ratio of the zwitterionic species to the cationic species does not fall below 50,000:1 on the column, and (ii) the mole ratio of the zwitterionic species to the anionic species does not exceed 5:1 on the column.

In some embodiments, the mobile phase is buffered with formate/formic acid (formate buffer); acetate/acetic acid (acetate buffer); propionate/propionic acid (propionate buffer); citrate/hydrogen citrate or hydrogen citrate/citric acid (citrate buffer); bicarbonate/carbonic acid (bicarbonate buffer); hydrogen phosphate/dihydrogen phosphate (phosphate buffer); orthoboric acid/monoanionic orthoborate (borate buffer); ammonia/ammonium (ammonia buffer); cholamine/2-azaniumylethyl(trimethyl)azanium (cholamine buffer); zwitterionic glycine/anionic glycine (glycine buffer); 2-aminoacetamide/2-azaniumylacetamide (glycinamide buffer); (2-aminoacetamido)acetate/(2-azaniumylacetamido)acetate (glycylglycine buffer); 2-[bis(2-hydroxyethyl)]azaniumylacetate/2-[bis(2-hydroxyethyl)]aminoacetate (bicine buffer); 2-[tris(hydroxymethyl)methyl]azaniumylacetate/2-[tris(hydroxymethyl)methyl]aminoacetate (tricine buffer); [tris(hydroxymethyl)methyl]azanium/[tris(hydroxymethyl)methyl]amine (TRIS buffer); 2,2'-[(2-amino-2-oxoethyl)azaniumdiyl]diacetate/2,2'-[(2-amino-2-oxoethyl)azanediyl]diacetate (ADA buffer); 2-[(2-amino-2-oxoethyl)azaniumyl]ethylsulfonate/2-[(2-amino-2-oxoethyl)amino]ethylsulfonate (ACES buffer); 2-[bis(2-hydroxyethyl)

azaniumyl]ethylsulfonate/2-[bis(2-hydroxyethyl)amino]ethylsulfonate (BES buffer); 3-[bis(2-hydroxyethyl)azaniumyl]-2-hydroxypropanesulfonate/3-[bis(2-hydroxyethyl)amino]-2-hydroxypropanesulfonate (DIPSO buffer); 2-{[tris(hydroxymethyl)methyl]azaniumyl}ethylsulfonate/2-{[tris(hydroxymethyl)methyl]amino}ethylsulfonate (TES buffer); 3-{[tris(hydroxymethyl)methyl]azaniumyl}propylsulfonate/3-{[tris(hydroxymethyl)methyl]amino}propylsulfonate (TAPS buffer); 3-{[tris(hydroxymethyl)methyl]azaniumyl}-2-hydroxypropylsulfonate/3-{[tris(hydroxymethyl)methyl]amino}-2-hydroxypropylsulfonate (TAPSO buffer); 2-(morpholinium-4-yl)ethylsulfonate/2-(morpholin-4-yl)ethylsulfonate (MES buffer); 3-(morpholinium-4-yl)propylsulfonate/3-(morpholin-4-yl)propylsulfonate (MOPS buffer); 2-hydroxy-3-(morpholinium-4-yl)propylsulfonate/2-hydroxy-3-(morpholin-4-yl)propylsulfonate (MOPSO buffer); 2-[4-(2-hydroxyethyl)piperazinium-1-yl]ethylsulfonate/2-[4-(2-hydroxyethyl)piperazin-1-yl]ethylsulfonate (HEPES buffer); 3-[4-(2-hydroxyethyl)piperazinium-1-yl]propylsulfonate/3-[4-(2-hydroxyethyl)piperazin-1-yl]propylsulfonate (HEPPS buffer); 3-[4-(2-hydroxyethyl)piperazinium-1-yl]-2-hydroxypropylsulfonate/3-[4-(2-hydroxyethyl)piperazin-1-yl]-2-hydroxypropylsulfonate (HEPPSO buffer); 1,4-bis(2-sulfonatoethyl)piperazinium/1,4-bis(2-sulfonatoethyl)piperazine (PIPES buffer); or 1,4-bis(2-hydroxy-3-sulfonatopropyl)piperazinium/1,4-bis(2-hydroxy-3-sulfonatopropyl)piperazine (POPSO buffer). In some specific embodiments, the mobile phase is buffered with acetate buffer, propionate buffer, citrate buffer, bicarbonate buffer, phosphate buffer, borate buffer, TRIS buffer, ADA buffer, ACES buffer, BES buffer, DIPSO buffer, TES buffer, TAPS buffer, or TAPSO buffer. In some very specific embodiments, the mobile phase is buffered with acetate buffer, propionate buffer, citrate buffer, bicarbonate buffer, phosphate buffer, or TRIS buffer.

In some embodiments, the mobile phase comprises a molar concentration of formate and a molar concentration of formic acid, and the molar concentration of the formate is greater than the molar concentration of the formic acid.

In some embodiments, the mobile phase comprises a molar concentration of acetate and a molar concentration of acetic acid, and the molar concentration of the acetate is greater than the molar concentration of the acetic acid.

In some embodiments, the mobile phase comprises a molar concentration of propionate and a molar concentration of propionic acid, and the molar concentration of the propionate is greater than the molar concentration of the propionic acid.

In some embodiments, the mobile phase comprises a molar concentration of citrate and a molar concentration of hydrogen citrate, and the molar concentration of the citrate is greater than the molar concentration of the hydrogen citrate.

In some embodiments, the mobile phase comprises a molar concentration of bicarbonate and a molar concentration of carbonic acid, and the molar concentration of the bicarbonate is greater than the molar concentration of the carbonic acid.

In some embodiments, the mobile phase comprises a molar concentration of dihydrogen phosphate and a molar concentration of phosphoric acid, and the molar concentration of the dihydrogen phosphate is greater than the molar concentration of the phosphoric acid.

Various aspects of this disclosure relate to a method of loading a sample onto an HPLC column, wherein the sample is a composition that comprises one or more tryptamines and a buffer selected from formate buffer, acetate buffer, propionate buffer, citrate buffer, bicarbonate buffer, phosphate buffer, borate buffer, ammonia buffer, cholamine buffer, glycine buffer, glycinamide buffer, glycylglycine buffer, bicine buffer, tricine buffer, TRIS buffer, ADA buffer, ACES buffer, BES buffer, DIPSO buffer, TES buffer, TAPS buffer, TAPSO buffer, MES buffer, MOPS buffer, MOPSO buffer, HEPES buffer, HEPPS buffer, HEPPSO buffer, PIPES buffer, and POPSO buffer. In some specific embodiments, the one or more tryptamines comprise one or more phosphoryloxytryptamines. In some even more specific embodiments, the one or more tryptamines comprise psilocybin. In some very specific embodiments, the one or more tryptamines comprise psilocybin and psilocin. In some specific embodiments, the buffer is acetate buffer, propionate buffer, citrate buffer, bicarbonate buffer, phosphate buffer, borate buffer, TRIS buffer, ADA buffer, ACES buffer, BES buffer, DIPSO buffer, TES buffer, TAPS buffer, or TAPSO buffer. In some very specific embodiments, the buffer is acetate buffer, propionate buffer, citrate buffer, bicarbonate buffer, phosphate buffer, or TRIS buffer.

Various aspects of this disclosure relate to a method to protect a phosphoryloxytryptamine from dephosphorylation, wherein the phosphoryloxytryptamine comprises a cationic species that has a net charge of +1, a zwitterionic species that has a net charge of 0, and an anionic species that has a net charge of −1; and the method comprises buffering a composition comprising the phosphoryloxytryptamine such that a mole ratio of the zwitterionic species to the cationic species (zwitterionic species:cationic species) in the buffered composition is at least 50:1, and a mole ratio of the zwitterionic species to the anionic species (zwitterionic species:anionic species) in the buffered composition is no greater than 5000:1. In some specific embodiments, the mole ratio of the zwitterionic species to the cationic species is at least 500:1, and the mole ratio of the zwitterionic species to the anionic species is no greater than 500:1. In some even more specific embodiments, the mole ratio of the zwitterionic species to the cationic species is at least 5000:1, and the mole ratio of the zwitterionic species to the anionic species is no greater than 50:1. In some very specific embodiments, the mole ratio of the zwitterionic species to the cationic species is at least 50,000:1, and the mole ratio of the zwitterionic species to the anionic species is no greater than 5:1. In some embodiments, the phosphoryloxytryptamine is selected from psilocybin, baeocystin, norbaeocystin, and aeruginascin. In some specific embodiments, the phosphoryloxytryptamine is psilocybin. In some embodiments, the composition is buffered with a buffer selected from formate buffer, acetate buffer, propionate buffer, citrate buffer, bicarbonate buffer, phosphate buffer, borate buffer, ammonia buffer, cholamine buffer, glycine buffer, glycinamide buffer, glycylglycine buffer, bicine buffer, tricine buffer, TRIS buffer, ADA buffer, ACES buffer, BES buffer, DIPSO buffer, TES buffer, TAPS buffer, TAPSO buffer, MES buffer, MOPS buffer, MOPSO buffer, HEPES buffer, HEPPS buffer, HEPPSO buffer, PIPES buffer, and POPSO buffer. In some specific embodiments, the buffer is acetate buffer, propionate buffer, citrate buffer, bicarbonate buffer, phosphate buffer, borate buffer, TRIS buffer, ADA buffer, ACES buffer, BES buffer, DIPSO buffer, TES buffer, TAPS buffer, or TAPSO buffer. In some very specific embodiments, the buffer is acetate buffer, propionate buffer, citrate buffer, bicarbonate buffer, phosphate buffer, or TRIS buffer.

Various aspects of this disclosure relate to a composition comprising a phosphoryloxytryptamine and a buffer, wherein the phosphoryloxytryptamine comprises a cationic species that has a net charge of +1, a zwitterionic species that has a net charge of 0, and an anionic species that has a net charge of −1. In some embodiments, the composition comprises a mole ratio of the zwitterionic species to the cationic species (zwitterionic species:cationic species) of at least 50:1, and the composition comprises a mole ratio of the zwitterionic species to the anionic species (zwitterionic species:anionic species) of no greater than 5000:1. In some specific embodiments, the mole ratio of the zwitterionic species to the cationic species is at least 500:1, and the mole ratio of the zwitterionic species to the anionic species is no greater than 500:1. In some even more specific embodiments, the mole ratio of the zwitterionic species to the cationic species is at least 5000:1, and the mole ratio of the zwitterionic species to the anionic species is no greater than 50:1. In some very specific embodiments, the mole ratio of the zwitterionic species to the cationic species is at least 50,000:1, and the mole ratio of the zwitterionic species to the anionic species is no greater than 5:1. In some embodiments, the phosphoryloxytryptamine is selected from psilocybin, baeocystin, norbaeocystin, and aeruginascin. In some specific embodiments, the phosphoryloxytryptamine is psilocybin. In some embodiments, the buffer is selected from formate buffer, acetate buffer, propionate buffer, citrate buffer, bicarbonate buffer, phosphate buffer, borate buffer, ammonia buffer, cholamine buffer, glycine buffer, glycinamide buffer, glycylglycine buffer, bicine buffer, tricine buffer, TRIS buffer, ADA buffer, ACES buffer, BES buffer, DIPSO buffer, TES buffer, TAPS buffer, TAPSO buffer, MES buffer, MOPS buffer, MOPSO buffer, HEPES buffer, HEPPS buffer, HEPPSO buffer, PIPES buffer, and POPSO buffer. In some specific embodiments, the buffer is acetate buffer, propionate buffer, citrate buffer, bicarbonate buffer, phosphate buffer, borate buffer, TRIS buffer, ADA buffer, ACES buffer, BES buffer, DIPSO buffer, TES buffer, TAPS buffer, or TAPSO buffer. In some very specific embodiments, the buffer is acetate buffer, propionate buffer, citrate buffer, bicarbonate buffer, phosphate buffer, or TRIS buffer.

Various aspects of this disclosure relate to a composition comprising one or more tryptamines and a buffer selected from formate buffer, acetate buffer, propionate buffer, citrate buffer, bicarbonate buffer, phosphate buffer, borate buffer, ammonia buffer, cholamine buffer, glycine buffer, glycinamide buffer, glycylglycine buffer, bicine buffer, tricine buffer, TRIS buffer, ADA buffer, ACES buffer, BES buffer, DIPSO buffer, TES buffer, TAPS buffer, TAPSO buffer, MES buffer, MOPS buffer, MOPSO buffer, HEPES buffer, HEPPS buffer, HEPPSO buffer, PIPES buffer, and POPSO buffer. In some specific embodiments, the one or more tryptamines comprise one or more phosphoryloxytryptamines. In some even more specific embodiments, the one or more tryptamines comprise psilocybin. In some very specific embodiments, the one or more tryptamines comprise psilocybin and psilocin. In some specific embodiments, the buffer is acetate buffer, propionate buffer, citrate buffer, bicarbonate buffer, phosphate buffer, borate buffer, TRIS buffer, ADA buffer, ACES buffer, BES buffer, DIPSO buffer, TES buffer, TAPS buffer, or TAPSO buffer. In some very specific embodiments, the buffer is acetate buffer, propionate buffer, citrate buffer, bicarbonate buffer, phosphate buffer, or TRIS buffer.

Various aspects of this disclosure relate to a composition comprising one or more tryptamines, formate, and formic acid, wherein the composition comprises a molar concentration of formate and a molar concentration of formic acid, and the molar concentration of the formate is greater than the molar concentration of the formic acid.

Various aspects of this disclosure relate to a composition comprising a salt that comprises zwitterionic psilocybin and formate. In some embodiments, the composition further comprises a salt that comprises cationic psilocybin and formate. In some embodiments, the composition further comprises a salt that comprises anionic psilocybin and formate.

Various aspects of this disclosure relate to a composition comprising one or more tryptamines, acetate, and acetic acid, wherein the composition comprises a molar concentration of acetate and a molar concentration of acetic acid, and the molar concentration of the acetate is greater than the molar concentration of the acetic acid.

Various aspects of this disclosure relate to a composition comprising a salt that comprises zwitterionic psilocybin and acetate. In some embodiments, the composition further comprises a salt that comprises cationic psilocybin and acetate. In some embodiments, the composition further comprises a salt that comprises anionic psilocybin and acetate.

Various aspects of this disclosure relate to a composition comprising one or more tryptamines, propionate, and propionic acid, wherein the composition comprises a molar concentration of propionate and a molar concentration of propionic acid, and the molar concentration of the propionate is greater than the molar concentration of the propionic acid.

Various aspects of this disclosure relate to a composition comprising a salt that comprises zwitterionic psilocybin and propionate. In some embodiments, the composition further comprises a salt that comprises cationic psilocybin and propionate. In some embodiments, the composition further comprises a salt that comprises anionic psilocybin and propionate.

Various aspects of this disclosure relate to a composition comprising one or more tryptamines, citrate, and hydrogen citrate, wherein the composition comprises a molar concentration of citrate and a molar concentration of hydrogen citrate, and the molar concentration of the citrate is greater than the molar concentration of the hydrogen citrate.

Various aspects of this disclosure relate to a composition comprising a salt that comprises zwitterionic psilocybin and citrate. In some embodiments, the composition further comprises a salt that comprises anionic psilocybin and citrate.

Various aspects of this disclosure relate to a composition comprising a salt that comprises zwitterionic psilocybin and hydrogen citrate. In some embodiments, the composition further comprises a salt that comprises anionic psilocybin and hydrogen citrate.

Various aspects of this disclosure relate to a composition comprising one or more tryptamines, bicarbonate, and carbonic acid, wherein the composition comprises a molar concentration of bicarbonate and a molar concentration of carbonic acid, and the molar concentration of the bicarbonate is greater than the molar concentration of the carbonic acid.

Various aspects of this disclosure relate to a composition comprising a salt that comprises zwitterionic psilocybin and bicarbonate. In some embodiments, the composition further comprises a salt that comprises anionic psilocybin and bicarbonate.

Various aspects of this disclosure relate to a composition comprising one or more tryptamines, dihydrogen phosphate, and phosphoric acid, wherein the composition comprises a molar concentration of dihydrogen phosphate and a molar concentration of phosphoric acid, and the molar concentration of the dihydrogen phosphate is greater than the molar concentration of the phosphoric acid.

Various aspects of this disclosure relate to a composition comprising a salt that comprises zwitterionic psilocybin and dihydrogen phosphate. In some embodiments, the composition further comprises a salt that comprises cationic psilocybin and dihydrogen phosphate. In some embodiments, the composition further comprises a salt that comprises anionic psilocybin and dihydrogen phosphate.

Various aspects of this disclosure relate to an orally-available product, comprising an outer layer and an inner core, wherein the inner core comprises one or more tryptamines selected from psilocybin, psilocin, baeocystin, norpsilocin, norbaeocystin, 4-HT, aeruginascin, 4-hydroxy-TMT, DMT, and bufotenin.

In some embodiments, the outer layer is opaque and inhibits the transmittance of light to the inner core.

In some embodiments, the outer layer inhibits the diffusion of molecular oxygen and/or water vapor into the inner core.

In some embodiments, the outer layer has a surface-area-to-volume ratio of less than 10 per meter. In some specific embodiments, the outer layer has a surface-area-to-volume ratio of less than 8 per meter. In some very specific embodiments, the outer layer has a surface-area-to-volume ratio of less than 6 per meter. Smaller surface-area-to-volume ratios minimize the diffusion of gases (e.g., oxygen and water vapor) into the inner core.

In some embodiments, the orally-available product lacks an outer layer (e.g., the orally-available product consists of the inner core) and has a surface-area-to-volume ratio of less than 10 per meter. In some specific embodiments, the orally-available product lacks an outer layer and has a surface-area-to-volume ratio of less than 8 per meter. In some very specific embodiments, the orally-available product lacks an outer layer and has a surface-area-to-volume ratio of less than 6 per meter. The inner core may nevertheless be wrapped with a barrier layer (e.g., comprising one or more of aluminum foil and plastic), which barrier layer inhibits the transmittance of light to the inner core and/or inhibits the diffusion of gasses into the inner core.

In some embodiments, the outer layer has a thickness of at least 200 microns. In some specific embodiments, the outer layer has a thickness of at least 1 millimeter. In some very specific embodiments, the outer layer has a thickness of at least 2 millimeters. Increasing the thickness of the outer layer reduces the diffusion of gases into the inner core and may also inhibit the transmission of light into the inner core.

In some embodiments, the inner core comprises chocolate; the inner core is a product obtained by a process of separating water from a composition comprising ingredients of the inner core; the ingredients comprise the chocolate, the one or more tryptamines, and the water; and the composition has a pH of at least 5 and no greater than 9 prior to the separating, which inhibits the spontaneous dephosphorylation of phosphoryloxytryptamines (e.g., psilocybin) into hydroxytryptamines (e.g., psilocin).

In some embodiments, separating water from the composition comprising the ingredients comprises producing one or more salts as described herein, wherein the one or more salts comprises one or more of zwitterionic psilocybin and anionic psilocybin. In some specific embodiments, the inner core comprises the one or more salts.

In some embodiments, the inner core comprises a solid binder in which the one or more tryptamines are disposed; the inner core is a product obtained by a process of separating water from a composition comprising one or more ingredients of the inner core; the composition comprises the water, the one or more tryptamines, and a solid binder, wherein the solid binder is partially or completely dissolved in the water; and the composition has a pH of at least 5 and no greater than 9 prior to the separating, which inhibits the spontaneous dephosphorylation of phosphoryloxytryptamines into hydroxytryptamines. In some embodiments, the solid binder is selected from arabinogalactan, starch, modified food starch, cellulose, microcrystalline cellulose, methylcellulose, methyl ethyl cellulose, HPC, HPMC, and NaCMC.

In some embodiments, the inner core comprises a lipid-based filling; the inner core is a product obtained by a process of dispersing the one or more tryptamines in the lipid-based filling; the lipid-based filling inhibits the spontaneous dephosphorylation of phosphoryloxytryptamines into hydroxytryptamines; and the lipid-based filling inhibits oxidation of the one or more tryptamines. In some embodiments, the lipid-based filling is selected from cocoa butter and coconut oil.

In some embodiments, the inner core comprises the psilocybin and the psilocin at a mole ratio of at least 1:1 (psilocybin:psilocin). In some specific embodiments, the inner core comprises the psilocybin and the psilocin at a mole ratio of at least 3:2. In some even more specific embodiments, the inner core comprises the psilocybin and the psilocin at a mole ratio of at least 2:1. In some very specific embodiments, the inner core comprises the psilocybin and the psilocin at a mole ratio of at least 3:1. The precise mole ratio of psilocybin to psilocin depends, for example, upon the mole ratio in starting fungal material as well as fidelity to the methodology described in this disclosure.

In some embodiments, the orally-available product comprises a polypeptide, wherein the polypeptide encodes a phosphorylase enzyme, and the polypeptide is denatured as described herein such that the phosphorylase enzyme lacks phosphorylase activity.

In some embodiments, the orally-available product comprises a polypeptide, wherein the polypeptide encodes a laccase enzyme, and the polypeptide is denatured as described herein such that the laccase enzyme lacks laccase activity.

In some embodiments, the laccase enzyme has at least 90 percent sequence identity with at least 100 consecutive amino acids set forth in SEQ ID NO: 1, SEQ ID NO: 2, or SEQ ID NO: 3. In some specific embodiments, the polypeptide comprises at least 100 consecutive amino acids set forth in SEQ ID NO: 1, SEQ ID NO: 2, or SEQ ID NO: 3.

In some embodiments, the laccase enzyme comprises the amino acid sequence(s) set forth in one, two, three, four, five, six, seven, eight, nine, ten, eleven, twelve, thirteen, fourteen, fifteen, sixteen, seventeen, eighteen, nineteen, twenty, or each of SEQ ID NO: 4 to SEQ ID NO: 24, which amino acid sequence(s) are highly conserved in the laccase enzyme encoded by the amino acid sequence set forth in SEQ ID NO: 3 and important for laccase enzyme activity.

In some embodiments, the inner core comprises psilocin and one or more 5-oxo-DMT-ylidene dimers at a mole ratio of at least 1:1 (psilocin:one or more 5-oxo-DMT-ylidene dimers), wherein the one or more 5-oxo-DMT-ylidene dimers include each such 5-oxo-DMT-ylidene dimer (including tautomers of 5-oxo-DMT-ylidene dimers) that is present in the inner core. In some specific embodiments, the inner core comprises psilocin and the one or more 5-oxo-DMT-ylidene dimers at a mole ratio of at least 2:1. In some even more specific embodiments, the inner core comprises psilocin and the one or more 5-oxo-DMT-ylidene dimers at a mole ratio of at least 5:1. In some very specific embodiments, the inner core comprises psilocin and the one or more 5-oxo-DMT-ylidene dimers at a mole ratio of at least 10:1.

In some embodiments, the inner core comprises norpsilocin and one or more oxidized dione dimers of norpsilocin and psilocin at a mole ratio of at least 1:1 (norpsilocin:one or more oxidized dione dimers of norpsilocin and psilocin), wherein the one or more oxidized dione dimers of norpsilocin and psilocin include each such oxidized dione dimer (including tautomers of oxidized dione dimers) that is present in the inner core. In some specific embodiments, the inner core comprises norpsilocin and the one or more oxidized dione dimers of norpsilocin and psilocin at a mole ratio of at least 2:1. In some even more specific embodiments, the inner core comprises norpsilocin and the one or more oxidized dione dimers of norpsilocin and psilocin at a mole ratio of at least 5:1. In some very specific embodiments, the inner core comprises norpsilocin and the one or more oxidized dione dimers of norpsilocin and psilocin at a mole ratio of at least 10:1.

In some embodiments, the inner core comprises 4-HT and one or more oxidized dione dimers of 4-HT and psilocin at a mole ratio of at least 1:1 (4-HT:one or more oxidized dione dimers of 4-HT and psilocin), wherein the one or more oxidized dione dimers of 4-HT and psilocin include each such oxidized dione dimer (including tautomers of oxidized dione dimers) that is present in the inner core. In some specific embodiments, the inner core comprises 4-HT and the one or more oxidized dione dimers of 4-HT and psilocin at a mole ratio of at least 2:1. In some even more specific embodiments, the inner core comprises 4-HT and the one or more oxidized dione dimers of 4-HT and psilocin at a mole ratio of at least 5:1. In some very specific embodiments, the inner core comprises 4-HT and the one or more oxidized dione dimers of 4-HT and psilocin at a mole ratio of at least 10:1.

In some embodiments, the orally-available product comprises an antioxidant. In some specific embodiments, the inner core of the orally-available product comprises the antioxidant. In some very specific embodiments, the antioxidant is selected from one or more of a sulfite salt, a bisulfite salt, a metabisulfite salt, a sorbate salt, sorbic acid, an ascorbate salt, ascorbic acid, a tocopherol, and a tocotrienol. Antioxidants can help inhibit the oxidation of tryptamines within the product.

In some embodiments, the orally-available product comprises a sequestrant. In some specific embodiments, the inner core of the orally-available product comprises the sequestrant. In some very specific embodiments, the sequestrant is selected from one or more of an EDTA salt, a phosphate salt, a pyrophosphate salt, a tripolyphosphate salt, a metaphosphate salt, a hexametaphosphate salt, a diacetate salt, and a gluconate salt. Sequestrants can help inhibit the oxidation of tryptamines within the product.

Various aspects of this disclosure relate to an orally-available product comprising an outer layer and an inner core, wherein the orally-available product has a length of no greater than 6 millimeters, and the inner core comprises one or more tryptamines selected from psilocybin, psilocin, baeocystin, norpsilocin, norbaeocystin, 4-HT, aeruginascin, 4-hydroxy-TMT, and bufotenin.

The term "length" as used in this disclosure refers to the longest dimension of an orally-available product in Cartesian space. In some embodiments, the length of the orally-available product is at least 10 microns and no greater than 2 millimeters. In some specific embodiments, the length of the orally-available product is at least 20 microns and no greater than 1 millimeters. In some very specific embodiments, the length of the orally-available product is at least 50 microns and no greater than 800 microns.

In some embodiments, the outer layer is opaque and inhibits the transmittance of light to the inner core.

In some embodiments, the outer layer inhibits the diffusion of molecular oxygen and water vapor into the inner core.

In some embodiments, the inner core comprises one or more binders selected from arabinogalactan, starch, modified food starch, cellulose, microcrystalline cellulose, methylcellulose, methyl ethyl cellulose, HPC, HPMC, and NaCMC.

In some embodiments, the inner core comprises psilocybin and psilocin; the inner core is a product obtained by a process of separating water from a composition comprising ingredients of the inner core; the ingredients comprise a binder, the psilocybin, the psilocin, and the water; and the composition has a pH of at least 5 and no greater than 9 prior to the separating, which inhibits the spontaneous dephosphorylation of psilocybin into psilocin.

In some embodiments, separating water from the composition comprising the ingredients comprises producing one or more salts as described herein, wherein the one or more salts comprises one or more of zwitterionic psilocybin and anionic psilocybin. In some specific embodiments, the inner core comprises the one or more salts.

In some embodiments, the inner core comprises the psilocybin and the psilocin at a mole ratio of at least 1:1 (psilocybin:psilocin). In some specific embodiments, the inner core comprises the psilocybin and the psilocin at a mole ratio of at least 3:2. In some even more specific embodiments, the inner core comprises the psilocybin and the psilocin at a mole ratio of at least 2:1. In some very specific embodiments, the inner core comprises the psilocybin and the psilocin at a mole ratio of at least 3:1. The precise mole ratio of psilocybin to psilocin depends, for example, upon the mole ratio in starting fungal material as well as fidelity to the methodology described in this disclosure.

Various aspects of this disclosure relate to a container that contains an orally-available product as described herein. In some specific embodiments, the container is hermetically sealed. In some specific embodiments, the container contains one or more dosage units of the orally-available product, and the container is labeled for sale to a consumer.

In some embodiments, the container contains an oxygen-absorbing agent. In some specific embodiments, the container contains an oxygen-absorbing agent, and the oxygen-absorbing agent is in fluid communication with the orally-available product. The oxygen-absorbing agent, for example, may be contained within a packet within the container. Suitable oxygen-absorbing agents include iron powder.

In some embodiments, the container contains a desiccant. In some specific embodiments, the container contains a desiccant, and the desiccant is in fluid communication with the orally-available product. The desiccant may be contained, for example, within a packet within the container. Suitable oxygen-absorbing agents include silica, bentonite, activated carbon, and calcium oxide.

Various aspects of this disclosure relate to an extended-release formulation, comprising one or more extended-release excipients and a neuroplastic agent or a prodrug thereof.

In some embodiments, (A) the neuroplastic agent causes psychedelic side effects; (B) the psychedelic side effects display tachyphylaxis in human patients; (C) extended release of the neuroplastic agent results in tachyphylaxis that attenuates the psychedelic side effects; (D) the extended-release formulation comprises the neuroplastic agent and one or more extended-release excipients; (E) the extended-release excipients delay the Tmax of the neuroplastic agent relative to formulations that lack the one or more extended-release excipients; and (F) the extended-release excipients reduce the peak serum concentration (Cmax) of the neuroplastic agent relative to formulations that lack the one or more extended-release excipients.

Various aspects of this disclosure relate to a method to minimize psychedelic side effects following administration of a neuroplastic agent or a prodrug thereof, comprising administering an extended-release formulation of the neuroplastic agent and/or the prodrug to a patient in need thereof (e.g., as described in the preceding paragraph).

In some embodiments, the extended-release formulation is administered in an amount sufficient for the neuroplastic agent and/or the prodrug to cause desirable pharmacological effects in the patient. In some specific embodiments, the desirable pharmacological effects are neuroplastic effects.

In some embodiments, the neuroplastic agent or the prodrug thereof is selected from psilocybin, psilocin, baeocystin, norpsilocin, norbaeocystin, 4-HT, aeruginascin, 4-hydroxy-TMT, DMT, 5-MeO-DMT, and bufotenin.

In some embodiments, the neuroplastic agent is a tryptamine. In some specific embodiments, the neuroplastic agent is a hydroxytryptamine. In some very specific embodiments, the neuroplastic agent is a hydroxytryptamine, and the prodrug thereof is a phosphoryloxytryptamine.

In some embodiments, the neuroplastic agent is psilocin, and the prodrug thereof is psilocybin.

In some embodiments, the neuroplastic agent is norpsilocin, and the prodrug thereof is baeocystin.

In some embodiments, the neuroplastic agent is 4-HT, and the prodrug thereof is norbaeocystin.

In some embodiments, the neuroplastic agent is 4-hydroxy-TMT, and the prodrug thereof is aeruginascin.

In some embodiments, the neuroplastic agent is DMT, and the extended-release formulation lacks a prodrug.

In some embodiments, the administering is oral administering, transdermal administering, or implantation. In some specific embodiments, the administering is oral administering.

In preferred embodiments, the patient has a gastrointestinal tract. In specific preferred embodiments, the patient has a gastrointestinal tract that has a temperature.

In some embodiments, the one or more extended-release excipients comprise a hydrophilic polymer that displays a low permeability to the neuroplastic agent and/or the prodrug thereof, which low permeability inhibits release of the neuroplastic agent and/or the prodrug thereof.

In some embodiments, oral administering results in hydration of the hydrophilic polymer in the gastrointestinal tract of the patient, and the hydration of the hydrophilic polymer causes the hydrophilic polymer to swell and thereby increase its permeability to the neuroplastic agent and/or the prodrug thereof.

In some embodiments, the hydrophilic polymer swells over a period of time in the gastrointestinal tract of the patient following the oral administering.

In some embodiments, the hydrophilic polymer releases the neuroplastic agent and/or the prodrug thereof as the hydrophilic polymer swells.

In some embodiments, the hydrophilic polymer is selected from HPC, HPMC, methylcellulose, carboxymethyl cellulose (e.g., NaCMC), polyacrylic acid, polyethylene oxide (PEO), guar gum, and xanthan gum.

In some embodiments, the hydrophilic polymer delays the Tmax of the neuroplastic agent in the extended-release formulation.

In some embodiments, the hydrophilic polymer reduces the Cmax of the neuroplastic agent in the extended-release formulation.

In some embodiments, the one or more extended-release excipients comprise a hydrophobic polymer that displays a low permeability to the neuroplastic agent and/or the prodrug thereof, which low permeability inhibits release of the neuroplastic agent and/or the prodrug thereof.

In some embodiments, oral administering results in hydration of the hydrophobic polymer in the gastrointestinal tract of the patient, and the hydration of the hydrophobic polymer causes the hydrophobic polymer to swell and thereby increase its permeability to the neuroplastic agent and/or the prodrug thereof.

In some embodiments, the hydrophobic polymer swells over a period of time in the gastrointestinal tract of the patient following the oral administering.

In some embodiments, the hydrophobic polymer releases the neuroplastic agent and/or the prodrug thereof as the hydrophobic polymer swells.

In some embodiments, the hydrophobic polymer is selected from ethylcellulose, cellulose acetate, cellulose acetate phthalate, PVP, PVA, poly(methyl methacrylate), poly(methacrylic acid, methyl methacrylate), poly(methacrylic acid, methyl ethacrylate), poly(ethyl acrylate, methyl methacrylate), poly(methyl acrylate, methyl methacrylate, methacrylic acid), poly(ethylacrylate, methyl-methacrylate, and chloro trimethyl-ammonioethyl methacrylate), and poly [butyl methacrylate, (2-dimethylaminoethyl)methacrylate, methyl methacrylate].

In some embodiments, the hydrophobic polymer delays the Tmax of the neuroplastic agent in the extended-release formulation.

In some embodiments, the hydrophobic polymer reduces the Cmax of the neuroplastic agent in the extended-release formulation.

In some embodiments, the one or more extended-release excipients comprise a hydrophilic polymer and a hydrophobic polymer that display low permeabilities to the neuroplastic agent and/or the prodrug thereof, which low permeabilities inhibit release of the neuroplastic agent and/or the prodrug thereof.

In some embodiments, oral administering results in hydration of the hydrophilic polymer and the hydrophobic polymer in the gastrointestinal tract of the patient, and the hydration of the hydrophilic polymer and the hydrophobic polymer causes the hydrophilic polymer and the hydrophobic polymer to swell and to thereby increase their permeabilities to the neuroplastic agent and/or the prodrug thereof.

In some embodiments, the hydrophilic polymer and the hydrophobic polymer swell over a period of time in the gastrointestinal tract of the patient following the oral administering.

In some embodiments, the hydrophilic polymer and the hydrophobic polymer release the neuroplastic agent and/or the prodrug thereof as the hydrophilic polymer and the hydrophobic polymer swell.

In some embodiments, the one or more extended-release excipients comprise a solid-phase lipid that inhibits release of the neuroplastic agent and/or the prodrug thereof.

In some embodiments, oral administering results in melting, dissolution, and/or dispersion of the solid-phase lipid at the temperature of the gastrointestinal tract of the patient.

In some embodiments, the solid-phase lipid melts, dissolves, and/or disperses over a period of time in the gastrointestinal tract of the patient following the oral administering.

In some embodiments, the solid-phase lipid releases the neuroplastic agent and/or the prodrug thereof as the solid-phase lipid melts, dissolves, and/or disperses.

In some embodiments, solid-phase lipid is selected from a C10-C24 fatty acid that has a melting point of at least 27 degrees Celsius (e.g., stearic acid), a salt of a C10-C24 fatty acid (e.g., magnesium stearate), and a wax (e.g., beeswax or carnauba wax).

In some embodiments, the solid-phase lipid delays the Tmax of the neuroplastic agent in the extended-release formulation.

In some embodiments, the solid-phase lipid reduces the Cmax of the neuroplastic agent in the extended-release formulation.

In some embodiments, the one or more extended-release excipients comprise a soluble binder or filler that inhibits release of the neuroplastic agent and/or the prodrug thereof.

In some embodiments, oral administering results in dissolution of the soluble binder or filler in the gastrointestinal tract of the patient.

In some embodiments, the soluble binder or filler dissolves over a period of time in the gastrointestinal tract of the patient following the oral administering.

In some embodiments, the soluble binder or filler releases the neuroplastic agent and/or the prodrug thereof as the soluble binder or filler dissolves.

In some embodiments, the soluble binder or filler is selected from sodium chloride, potassium chloride, calcium sulfate, magnesium silicate, sucrose, lactose, mannitol, sorbitol, sodium bicarbonate, potassium bicarbonate, sodium carbonate, and potassium carbonate.

In some embodiments, the soluble binder or filler delays the Tmax of the neuroplastic agent in the extended-release formulation.

In some embodiments, the soluble binder or filler reduces the Cmax of the neuroplastic agent in the extended-release formulation.

In some embodiments, Tmax is greater than 4 hours in the patient. In some specific embodiments, Tmax is at least 6 hours in the patient. In some even more specific embodiments, Tmax is at least 8 hours in the patient. In some very specific embodiments, Tmax is at least 10 hours in the patient.

In some embodiments, the extended-release formulation releases the neuroplastic agent into the gastrointestinal tract of the patient over a period of at least 8 hours. In some specific embodiments, the extended-release formulation releases the neuroplastic agent into the gastrointestinal tract of the patient over a period of at least 12 hours. In some very specific embodiments, the extended-release formulation releases the neuroplastic agent into the gastrointestinal tract of the patient over a period of at least 16 hours.

In some embodiments, the neuroplastic agent and/or the prodrug thereof have a baseline potential for abuse; the extended-release formulation has an attenuated potential for abuse; and the delay in Tmax and/or reduction of Cmax reduce the baseline potential for abuse to attenuate the potential for abuse.

Various aspects of this disclosure relate to a composition that comprises tryptamines.

In some embodiments, the tryptamines comprise phosphoryloxytryptamines and hydroxytryptamines.

In some embodiments, the phosphoryloxytryptamines comprise psilocybin. In some specific embodiments, the phosphoryloxytryptamines comprise psilocybin and baeocystin. In some specific embodiments, the phosphoryloxytryptamines comprise psilocybin and norbaeocystin. In some very specific embodiments, the phosphoryloxytryptamines comprise psilocybin, baeocystin, and norbaeocystin.

In some embodiments, the phosphoryloxytryptamines are selected from psilocybin, baeocystin, norbaeocystin, and aeruginascin.

In some embodiments, the psilocybin comprises zwitterionic psilocybin. In some specific embodiments, the psilocybin comprises zwitterionic psilocybin and anionic psilocybin. In some specific embodiments, the psilocybin comprises zwitterionic psilocybin and cationic psilocybin. In some very specific embodiments, the psilocybin comprises zwitterionic psilocybin, anionic psilocybin, and cationic psilocybin.

In some embodiments, the psilocybin is selected from zwitterionic psilocybin, anionic psilocybin, cationic psilocybin, and dianionic psilocybin.

Zwitterionic psilocybin comprises a monoanionic phosphonate ester and a cationic azanium and has the chemical formula [2-(4-phosphonooxy-1H-indol-3-yl)ethyl]-dimethylazanium, in which phosphonooxy is the monoanionic phosphonate ester.

In some embodiments, the composition comprises zwitterionic psilocybin, and the zwitterionic psilocybin is a solute that is dissolved in a solvent.

In some embodiments, the composition comprises a solid phase, the solid phase comprises a salt, and the salt comprises the zwitterionic psilocybin. In some specific embodiments, the salt comprises the zwitterionic psilocybin and an anion. In some specific embodiments, the salt comprises the zwitterionic psilocybin and a cation. In some very specific embodiments, the salt comprises the zwitterionic psilocybin, an anion, and a cation.

Anionic psilocybin comprises a dianionic phosphonate ester and a cationic azanium and has the chemical formula [2-(4-phosphonatooxy-1H-indol-3-yl)ethyl]-dimethylazanium, in which phosphonatooxy is the dianionic phosphonate ester.

In some embodiments, the composition comprises anionic psilocybin, and the anionic psilocybin is a solute that is dissolved in a solvent.

In some embodiments, the composition comprises a solid phase, the solid phase comprises a salt, and the salt comprises the anionic psilocybin. In some specific embodiments, the salt comprises the anionic psilocybin and an anion. In some specific embodiments, the salt comprises the anionic psilocybin and a cation. In some very specific embodiments, the salt comprises the anionic psilocybin, an anion, and a cation.

Cationic psilocybin comprises an uncharged phosphonate ester and a cationic azanium and has the chemical formula [2-(4-phosphonooxy-1H-indol-3-yl)ethyl]-dimethylazanium, in which phosphonooxy is the uncharged phosphonate ester.

In some embodiments, the composition comprises cationic psilocybin, and the cationic psilocybin is a solute that is dissolved in a solvent.

In some embodiments, the composition comprises a solid phase, the solid phase comprises a salt, and the salt comprises the cationic psilocybin. In some specific embodiments, the salt comprises the cationic psilocybin and an anion.

Dianionic psilocybin comprises a dianionic phosphonate ester and an uncharged amine and has the chemical formula [2-(4-phosphonatooxy-1H-indol-3-yl)ethyl]-dimethylamine, in which phosphonatooxy is the dianionic phosphonate ester.

In some embodiments, the composition comprises dianionic psilocybin, and the dianionic psilocybin is a solute that is dissolved in a solvent.

In some embodiments, the composition comprises a solid phase, the solid phase comprises a salt, and the salt comprises the dianionic psilocybin. In some specific embodiments, the salt comprises the dianionic psilocybin and a cation.

In some embodiments, the baeocystin comprises zwitterionic baeocystin. In some specific embodiments, the baeocystin comprises zwitterionic baeocystin and anionic baeocystin. In some specific embodiments, the baeocystin comprises zwitterionic baeocystin and cationic baeocystin. In some very specific embodiments, the baeocystin comprises zwitterionic baeocystin, anionic baeocystin, and cationic baeocystin.

In some embodiments, the baeocystin is selected from zwitterionic baeocystin, anionic baeocystin, cationic baeocystin, and dianionic baeocystin.

Zwitterionic baeocystin comprises a monoanionic phosphonate ester and a cationic azanium and has the chemical formula [2-(4-phosphonooxy-1H-indol-3-yl)ethyl]-methylazanium, in which phosphonooxy is the monoanionic phosphonate ester.

In some embodiments, the composition comprises zwitterionic baeocystin, and the zwitterionic baeocystin is a solute that is dissolved in a solvent.

In some embodiments, the composition comprises a solid phase, the solid phase comprises a salt, and the salt comprises the zwitterionic baeocystin. In some specific embodiments, the salt comprises the zwitterionic baeocystin and an anion. In some specific embodiments, the salt comprises the zwitterionic baeocystin and a cation. In some very specific embodiments, the salt comprises the zwitterionic baeocystin, an anion, and a cation.

Anionic baeocystin comprises a dianionic phosphonate ester and a cationic azanium and has the chemical formula [2-(4-phosphonatooxy-1H-indol-3-yl)ethyl]-methylazanium, in which phosphonatooxy is the dianionic phosphonate ester.

In some embodiments, the composition comprises anionic baeocystin, and the anionic baeocystin is a solute that is dissolved in a solvent.

In some embodiments, the composition comprises a solid phase, the solid phase comprises a salt, and the salt comprises the anionic baeocystin. In some specific embodiments, the salt comprises the anionic baeocystin and an anion. In some specific embodiments, the salt comprises the anionic baeocystin and a cation. In some very specific embodiments, the salt comprises the anionic baeocystin, an anion, and a cation.

Cationic baeocystin comprises an uncharged phosphonate ester and a cationic azanium and has the chemical formula [2-(4-phosphonooxy-1H-indol-3-yl)ethyl]-methylazanium, in which phosphonooxy is the uncharged phosphonate ester.

In some embodiments, the composition comprises cationic baeocystin, and the cationic baeocystin is a solute that is dissolved in a solvent.

In some embodiments, the composition comprises a solid phase, the solid phase comprises a salt, and the salt comprises the cationic baeocystin. In some specific embodiments, the salt comprises the cationic baeocystin and an anion.

Dianionic baeocystin comprises a dianionic phosphonate ester and an uncharged amine and has the chemical formula [2-(4-phosphonatooxy-1H-indol-3-yl)ethyl]-methylamine, in which phosphonatooxy is the dianionic phosphonate ester.

In some embodiments, the composition comprises dianionic baeocystin, and the dianionic baeocystin is a solute that is dissolved in a solvent.

In some embodiments, the composition comprises a solid phase, the solid phase comprises a salt, and the salt comprises the dianionic baeocystin. In some specific embodiments, the salt comprises the dianionic baeocystin and a cation.

In some embodiments, the norbaeocystin comprises zwitterionic norbaeocystin. In some specific embodiments, the norbaeocystin comprises zwitterionic norbaeocystin and anionic norbaeocystin. In some specific embodiments, the norbaeocystin comprises zwitterionic norbaeocystin and cationic norbaeocystin. In some very specific embodiments, the norbaeocystin comprises zwitterionic norbaeocystin, anionic norbaeocystin, and cationic norbaeocystin.

In some embodiments, the norbaeocystin is selected from zwitterionic norbaeocystin, anionic norbaeocystin, cationic norbaeocystin, and dianionic norbaeocystin.

Zwitterionic norbaeocystin comprises a monoanionic phosphonate ester and a cationic azanium and has the chemical formula 2-(4-phosphonooxy-1H-indol-3-yl)ethylazanium, in which phosphonooxy is the monoanionic phosphonate ester.

In some embodiments, the composition comprises zwitterionic norbaeocystin, and the zwitterionic norbaeocystin is a solute that is dissolved in a solvent.

In some embodiments, the composition comprises a solid phase, the solid phase comprises a salt, and the salt comprises the zwitterionic norbaeocystin. In some specific embodiments, the salt comprises the zwitterionic norbaeocystin and an anion. In some specific embodiments, the salt comprises the zwitterionic norbaeocystin and a cation. In some very specific embodiments, the salt comprises the zwitterionic norbaeocystin, an anion, and a cation.

Anionic norbaeocystin comprises a dianionic phosphonate ester and a cationic azanium and has the chemical formula 2-(4-phosphonatooxy-1H-indol-3-yl)ethylazanium, in which phosphonatooxy is the dianionic phosphonate ester.

In some embodiments, the composition comprises anionic norbaeocystin, and the anionic norbaeocystin is a solute that is dissolved in a solvent.

In some embodiments, the composition comprises a solid phase, the solid phase comprises a salt, and the salt comprises the anionic norbaeocystin. In some specific embodiments, the salt comprises the anionic norbaeocystin and an anion. In some specific embodiments, the salt comprises the anionic norbaeocystin and a cation. In some very specific embodiments, the salt comprises the anionic norbaeocystin, an anion, and a cation.

Cationic norbaeocystin comprises an uncharged phosphonate ester and a cationic azanium and has the chemical formula 2-(4-phosphonooxy-1H-indol-3-yl)ethylazanium, in which phosphonooxy is the uncharged phosphonate ester.

In some embodiments, the composition comprises cationic norbaeocystin, and the cationic norbaeocystin is a solute that is dissolved in a solvent.

In some embodiments, the composition comprises a solid phase, the solid phase comprises a salt, and the salt comprises the cationic norbaeocystin. In some specific embodiments, the salt comprises the cationic norbaeocystin and an anion.

Dianionic norbaeocystin comprises a dianionic phosphonate ester and an uncharged amine and has the chemical formula 2-(4-phosphonatooxy-1H-indol-3-yl)ethylamine, in which phosphonatooxy is the dianionic phosphonate ester.

In some embodiments, the composition comprises dianionic norbaeocystin, and the dianionic norbaeocystin is a solute that is dissolved in a solvent.

In some embodiments, the composition comprises a solid phase, the solid phase comprises a salt, and the salt comprises the dianionic norbaeocystin. In some specific embodiments, the salt comprises the dianionic norbaeocystin and a cation.

In some embodiments, the aeruginascin comprises zwitterionic aeruginascin. In some specific embodiments, the aeruginascin comprises zwitterionic aeruginascin and anionic aeruginascin. In some specific embodiments, the aeruginascin comprises zwitterionic aeruginascin and cationic aeruginascin. In some very specific embodiments, the aeruginascin comprises zwitterionic aeruginascin, anionic aeruginascin, and cationic aeruginascin.

In some embodiments, the aeruginascin is selected from zwitterionic aeruginascin, anionic aeruginascin, and cationic aeruginascin.

Zwitterionic aeruginascin comprises a monoanionic phosphonate ester and a cationic azanium and has the chemical formula [2-(4-phosphonooxy-1H-indol-3-yl)ethyl]-trimethylazanium, in which phosphonooxy is the monoanionic phosphonate ester.

In some embodiments, the composition comprises zwitterionic aeruginascin, and the zwitterionic aeruginascin is a solute that is dissolved in a solvent.

In some embodiments, the composition comprises a solid phase, the solid phase comprises a salt, and the salt comprises the zwitterionic aeruginascin. In some specific embodiments, the salt comprises the zwitterionic aeruginascin and an anion. In some specific embodiments, the salt comprises the zwitterionic aeruginascin and a cation. In some very specific embodiments, the salt comprises the zwitterionic aeruginascin, an anion, and a cation.

Anionic aeruginascin comprises a dianionic phosphonate ester and a cationic azanium and has the chemical formula [2-(4-phosphonatooxy-1H-indol-3-yl)ethyl]-trimethylazanium, in which phosphonatooxy is the dianionic phosphonate ester.

In some embodiments, the composition comprises anionic aeruginascin, and the anionic aeruginascin is a solute that is dissolved in a solvent.

In some embodiments, the composition comprises a solid phase, the solid phase comprises a salt, and the salt comprises the anionic aeruginascin. In some specific embodiments, the salt comprises the anionic aeruginascin and an anion. In some specific embodiments, the salt comprises the anionic aeruginascin and a cation. In some very specific embodiments, the salt comprises the anionic aeruginascin, an anion, and a cation.

Cationic aeruginascin comprises an uncharged phosphonate ester and a cationic azanium and has the chemical formula [2-(4-phosphonooxy-1H-indol-3-yl)ethyl]-trimethylazanium, in which phosphonooxy is the uncharged phosphonate ester.

In some embodiments, the composition comprises cationic aeruginascin, and the cationic aeruginascin is a solute that is dissolved in a solvent.

In some embodiments, the composition comprises a solid phase, the solid phase comprises a salt, and the salt comprises the cationic aeruginascin. In some specific embodiments, the salt comprises the cationic aeruginascin and an anion.

In some embodiments, the hydroxytryptamines comprise psilocin. In some specific embodiments, the hydroxytryptamines comprise psilocin and norpsilocin. In some specific embodiments, the hydroxytryptamines comprise psilocin and 4-HT. In some very specific embodiments, the hydroxytryptamines comprise psilocin, norpsilocin, and 4-HT.

In some embodiments, the hydroxytryptamines are selected from psilocin, norpsilocin, 4-HT, and 4-hydroxy-TMT.

In some embodiments, the psilocin comprises cationic psilocin. Cationic psilocin lacks a phosphonate ester, comprises a cationic azanium, and has the chemical formula [2-(4-hydroxy-1H-indol-3-yl)ethyl]-dimethylazanium.

In some embodiments, the composition comprises cationic psilocin, and the cationic psilocin is a solute that is dissolved in a solvent.

In some embodiments, the composition comprises a solid phase, the solid phase comprises a salt, and the salt comprises the cationic psilocin. In some specific embodiments, the salt comprises the cationic psilocin and an anion.

In some embodiments, the psilocin comprises molecular psilocin.

Molecular psilocin lacks a phosphonate ester, comprises an uncharged amine, and has the chemical formula 3-[2-(dimethylamino)ethyl]-1H-indol-4-ol.

In some embodiments, the norpsilocin comprises cationic norpsilocin. Cationic norpsilocin lacks a phosphonate ester, comprises a cationic azanium, and has the chemical formula [2-(4-hydroxy-1H-indol-3-yl)ethyl]-methylazanium.

In some embodiments, the composition comprises cationic norpsilocin, and the cationic norpsilocin is a solute that is dissolved in a solvent.

In some embodiments, the composition comprises a solid phase, the solid phase comprises a salt, and the salt comprises the cationic norpsilocin. In some specific embodiments, the salt comprises the cationic norpsilocin and an anion. In some embodiments, the norpsilocin comprises molecular A norpsilocin.

Molecular norpsilocin lacks a phosphonate ester, comprises an uncharged amine, and has the chemical formula 3-[2-(methylamino)ethyl]-1H-indol-4-ol.

In some embodiments, the 4-HT comprises cationic 4-HT. Cationic 4-HT lacks a phosphonate ester, comprises a cationic azanium, and has the chemical formula 2-(4-hydroxy-1H-indol-3-yl)ethylazanium.

In some embodiments, the composition comprises cationic 4-HT, and the cationic 4-HT is a solute that is dissolved in a solvent.

In some embodiments, the composition comprises a solid phase, the solid phase comprises a salt, and the salt comprises the cationic 4-HT. In some specific embodiments, the salt comprises the cationic 4-HT and an anion.

In some embodiments, the 4-HT comprises molecular 4-HT.

Molecular 4-HT lacks a phosphonate ester, comprises an uncharged amine, and has the chemical formula 3-(2-aminoethyl)-1H-indol-4-ol.

In some embodiments, the 4-hydroxy-TMT comprises cationic 4-hydroxy-TMT. Cationic 4-hydroxy-TMT lacks a phosphonate ester, comprises a cationic azanium, and has the chemical formula [2-(4-hydroxy-1H-indol-3-yl)ethyl]-trimethylazanium.

In some embodiments, the composition comprises cationic 4-hydroxy-TMT, and the cationic 4-hydroxy-TMT is a solute that is dissolved in a solvent.

In some embodiments, the composition comprises a solid phase, the solid phase comprises a salt, and the salt comprises the cationic 4-hydroxy-TMT. In some specific embodiments, the salt comprises the cationic 4-hydroxy-TMT and an anion.

In some embodiments, a cation of a salt of this disclosure is selected from one or more of sodium cation, potassium cation, calcium cation, magnesium cation, arginine, lysine, choline, cationic psilocybin, and cationic psilocin. In some specific embodiments, the cation is selected from one, two, or each of sodium cation, potassium cation, cationic psilocybin, and cationic psilocin. In some very specific embodiments, the cation is sodium cation. In some very specific embodiments, the cation is potassium cation. In some very specific embodiments, the cation is cationic psilocybin. In some very specific embodiments, the cation is cationic psilocin.

In some embodiments an anion of a salt of this disclosure is selected from chloride, phosphate, hydrogen phosphate, dihydrogen phosphate, carbonate, bicarbonate, sulfate, formate, acetate, propionate, and anionic psilocybin. In some specific embodiments the anion is selected from one or more of chloride, dihydrogen phosphate, bicarbonate, acetate, and anionic psilocybin. In some very specific embodiments, the anion is chloride. In some very specific embodiments, the anion is dihydrogen phosphate. In some very specific embodiments, the anion is bicarbonate. In some very specific embodiments, the anion is acetate. In some very specific embodiments, the anion is anionic psilocybin.

Various aspects of this disclosure relate to a salt that comprise a zwitterionic phosphoryloxytryptamine and an anion, wherein the anion is a conjugate base of a weak acid. Without limiting this disclosure or any patent claim that matures from this disclosure, an anion that is a conjugate base of a weak acid can buffer pH when the salt is dissolved in a solvent such as water, which buffering can inhibit the conversion of the zwitterionic phosphoryloxytryptamine into a cationic form of the phosphoryloxytryptamine and thereby inhibit spontaneous dephosphorylation of the phosphoryloxytryptamine. Suitable anions include, without limitation, formate, acetate, propionate, butyrate, valerate, caproate, caprylate, sorbate, ascorbate, erythorbate, lactate, pyruvate, malonate, monohydrogen malonate, succinate, monohydrogen succinate, adipate, monohydrogen adipate, fumarate, monohydrogen fumarate, malate, monohydrogen malate, tartrate, monohydrogen tartrate, citrate, hydrogen citrate, dihydrogen citrate, aconitate, monohydrogen aconitate, dihydrogen aconitate, thiodipropionate, monohydrogen thiodipropionate, cinnamate, hydrocinnamate, aspartate, glutamate, carbonate, bicarbonate, phosphate, monohydrogen phosphate, dihydrogen phosphate, monohydrogen diphosphate, sulfate, borate, and an anionic form of the phosphoryloxytryptamine. In some embodiments, the anion is selected from acetate, aspartate, glutamate, bicarbonate, and dihydrogen phosphate. In some specific embodiments, the anion is selected from acetate and dihydrogen phosphate. In some very specific embodiments, the anion is acetate. In some very specific embodiments, the anion is dihydrogen phosphate. In some very specific embodiments, the anion is the anionic form of the phosphoryloxytryptamine. In some embodiments, the zwitterionic phosphoryloxytryptamine is selected from zwitterionic psilocybin, zwitterionic baeocystin, zwitterionic norbaeocystin, and zwitterionic aeruginascin. In some specific embodiments, the zwitterionic phosphoryloxytryptamine is zwitterionic psilocybin. In some very specific embodiments, the zwitterionic phosphoryloxytryptamine is zwitterionic psilocybin and the anion is anionic psilocybin. In some very specific embodiments, the zwitterionic phosphoryloxytryptamine is zwitterionic baeocystin and the anion is anionic psilocybin. In some very specific embodiments, the zwitterionic phosphoryloxytryptamine is zwitterionic norbaeocystin and the anion is anionic psilocybin. In some very specific embodiments, the zwitterionic phosphoryloxytryptamine is zwitterionic aeruginascin and the anion is anionic psilocybin.

[2] In some embodiments, the salt comprises a zwitterionic phosphoryloxytryptamine, an anion, and a cation, wherein the anion is a conjugate base of a weak acid. In some embodiments, the cation is selected from sodium cation, potassium cation, calcium cation, magnesium cation, arginine, lysine, choline, cationic psilocybin, and cationic psilocin. In some specific embodiments, the cation is selected from sodium cation and potassium cation. In some specific embodiments, the cation is selected from cationic psilocybin, cationic baeocystin, cationic norbaeocystin, cationic aeruginascin, cationic psilocin, cationic norpsilocin, cationic 4-HT, and cationic 4-hydroxy-TMT. In some very specific embodiments, the zwitterionic phosphoryloxytryptamine is zwitterionic psilocybin, and the cation is cationic psilocybin. In some very specific embodiments, the zwitterionic phosphoryloxytryptamine is zwitterionic psilocybin, and the cation is cationic psilocin. In some very specific embodiments, the zwitterionic phosphoryloxytryptamine is zwitterionic baeocystin, and the cation is cationic psilocybin or cationic baeocystin. In some very specific embodiments, the zwitterionic phosphoryloxytryptamine is zwitterionic baeocystin, and the cation is cationic psilocin or cationic norpsilocin. In some very specific embodiments, the zwitterionic phosphoryloxytryptamine is zwitterionic norbaeocystin, and the cation is cationic psilocybin or cationic norbaeocystin. In some very specific embodiments, the zwitterionic phosphoryloxytryptamine is zwitterionic norbaeocystin, and the cation is cationic psilocin or cationic 4-HT. In some very specific embodiments, the zwitterionic phosphoryloxytryptamine is zwitterionic aeruginascin, and the cation is cationic psilocybin or cationic aeruginascin. In some very specific embodiments, the zwitterionic phosphoryloxytryptamine is zwitterionic aeruginascin, and the cation is cationic psilocin or cationic 4-hydroxy-TMT.

Various aspects of this disclosure relate to a salt that comprise a cationic hydroxytryptamine and an anion, wherein the anion is a conjugate base of a weak acid. Without limiting this disclosure or any patent claim that matures from this disclosure, an anion that is a conjugate base of a weak acid can buffer pH when the salt is dissolved in a solvent such as water, which buffering can inhibit acid-based oxidation of the cationic hydroxytryptamine. Suitable anions include, without limitation, formate, acetate, propionate, butyrate, valerate, caproate, caprylate, sorbate, ascorbate, erythorbate, lactate, pyruvate, malonate, monohydrogen malonate, succinate, monohydrogen succinate, adipate, monohydrogen adipate, fumarate, monohydrogen fumarate, malate, monohydrogen malate, tartrate, monohydrogen tartrate, citrate, hydrogen citrate, dihydrogen citrate, aconitate, monohydrogen aconitate, dihydrogen aconitate, thiodipropionate, monohydrogen thiodipropionate, cinnamate, hydrocinnamate, aspartate, glutamate, carbonate, bicarbonate, phosphate, monohydrogen phosphate, dihydrogen phosphate, monohydrogen diphosphate, sulfate, borate, and anionic psilocybin. In some embodiments, the anion is selected from acetate, aspartate, glutamate, bicarbonate, and dihydrogen phosphate. In some specific embodiments, the anion is selected from acetate and dihydrogen phosphate. In some very specific embodiments, the anion is acetate. In some very specific embodiments, the anion is dihydrogen phosphate. In some very specific embodiments, the anion is anionic psilocybin. In some embodiments, the hydroxytryptamine is selected from cationic psilocin, cationic norpsilocin, cationic 4-HT and cationic 4-hydroxy-TMT. In some specific embodiments, the hydroxytryptamine is selected from cationic psilocin, cationic norpsilocin, cationic 4-HT and cationic 4-hydroxy-TMT, and the anion is selected from acetate, aspartate, glutamate, bicarbonate, and dihydrogen phosphate. In some very specific embodiments, the hydroxytryptamine is selected from cationic psilocin, cationic norpsilocin, cationic 4-HT and cationic 4-hydroxy-TMT, and the anion is selected from acetate, bicarbonate, and dihydrogen phosphate. In some specific embodiments, hydroxytryptamine is cationic psilocin. In some very specific embodiments, the hydroxytryptamine is cationic psilocin and the anion is anionic psilocybin. In some specific embodiments, hydroxytryptamine is cationic norpsilocin. In some very specific embodiments, the hydroxytryptamine is cationic norpsilocin and the anion is anionic psilocybin or anionic baeocystin. In some specific embodiments, hydroxytryptamine is cationic 4-HT. In some very specific embodiments, the hydroxytryptamine is cationic 4-HT and the anion is anionic psilocybin or anionic norbaeocystin. In some specific embodiments, hydroxytryptamine is cationic 4-hydroxy-TMT. In some very specific embodiments, the hydroxytryptamine is cationic 4-hydroxy-TMT and the anion is anionic psilocybin or anionic aeruginascin.

In some embodiments, the zwitterionic psilocybin has a rate of spontaneous dephosphorylation per mole in the composition, which converts the psilocybin into additional psilocin.

In some embodiments, the anionic psilocybin has a rate of spontaneous dephosphorylation per mole in the composition, which converts the psilocybin into additional psilocin.

In some embodiments, the cationic psilocybin has a rate of spontaneous dephosphorylation per mole in the composition, which converts the psilocybin into additional psilocin.

In some embodiments, the dianionic psilocybin has a rate of spontaneous dephosphorylation per mole in the composition, which converts the psilocybin into additional psilocin.

In some embodiments, the rate of spontaneous dephosphorylation for the zwitterionic psilocybin per mole of the zwitterionic psilocybin is less than the rate of spontaneous dephosphorylation for the anionic psilocybin per mole of the anionic psilocybin in the composition.

In some embodiments, the composition comprises the zwitterionic psilocybin and the anionic psilocybin at a mole ratio of at least 1:2 (zwitterionic psilocybin:anionic psilocybin). In some specific embodiments, the composition comprises the zwitterionic psilocybin and the anionic psilocybin at a mole ratio of at least 1:1. In some even more specific embodiments, the composition comprises the zwitterionic psilocybin and the anionic psilocybin at a mole ratio of at least 3:1. In some very specific embodiments, the composition comprises the zwitterionic psilocybin and the anionic psilocybin at a mole ratio of at least 16:1.

In some embodiments, the mole ratio for the zwitterionic psilocybin and the anionic psilocybin in the composition results in a lower rate of spontaneous dephosphorylation for the psilocybin of the composition per mole of the psilocybin relative to a lower mole ratio. In some specific embodiments, the mole ratio of at least 1:2 results in a lower rate of spontaneous dephosphorylation relative to a lower mole ratio of less than 1:2. In some specific embodiments, the mole ratio of at least 1:1 results in a lower rate of spontaneous dephosphorylation relative to a lower mole ratio of less than 1:1. In some specific embodiments, the mole ratio of at least 3:1 results in a lower rate of spontaneous dephosphorylation relative to a lower mole ratio of less than 3:1. In some specific embodiments, the mole ratio of at least 16:1 results in a lower rate of spontaneous dephosphorylation relative to a lower mole ratio of less than 16:1.

In some embodiments, the composition comprises the zwitterionic psilocybin and the anionic psilocybin at a mole ratio of no greater than 25,000:1. In some specific embodiments, the composition comprises the zwitterionic psilocybin and the anionic psilocybin at a mole ratio of no greater than 5000:1. In some very specific embodiments, the composition comprises the zwitterionic psilocybin and the anionic psilocybin at a mole ratio of no greater than 500:1.

In some embodiments, the rate of spontaneous dephosphorylation for the zwitterionic psilocybin per mole of the zwitterionic psilocybin is less than the rate of spontaneous dephosphorylation for the cationic psilocybin per mole of the cationic psilocybin in the composition.

In some embodiments, the composition comprises the zwitterionic psilocybin and the cationic psilocybin at a mole ratio of at least 15:1 (zwitterionic psilocybin:cationic psilocybin). In some specific embodiments, the composition comprises the zwitterionic psilocybin and the cationic psilocybin at a mole ratio of at least 240:1. In some even more specific embodiments, the composition comprises the zwitterionic psilocybin and the cationic psilocybin at a mole ratio of at least 3200:1. In some very specific embodiments, the composition comprises the zwitterionic psilocybin and the cationic psilocybin at a mole ratio of at least 38,000:1.

In some embodiments, the mole ratio for the zwitterionic psilocybin and the cationic psilocybin in the composition results in a lower rate of spontaneous dephosphorylation for the psilocybin of the composition per mole of the psilocybin relative to a lower mole ratio. In some specific embodiments, the mole ratio of at least 15:1 results in a lower rate of spontaneous dephosphorylation relative to a lower mole ratio of less than 15:1. In some specific embodiments, the mole ratio of at least 240:1 results in a lower rate of spontaneous dephosphorylation relative to a lower mole ratio of less than 240:1. In some specific embodiments, the mole ratio of at least 3200:1 results in a lower rate of spontaneous dephosphorylation relative to a lower mole ratio of less than 3200:1. In some specific embodiments, the mole ratio of at least 38,000:1 results in a lower rate of spontaneous dephosphorylation relative to a lower mole ratio of less than 38,000:1.

In some embodiments, the composition comprises the zwitterionic psilocybin and the cationic psilocybin at a mole ratio of no greater than 150,000:1. In some specific embodiments, the composition comprises the zwitterionic psilocybin and the cationic psilocybin at a mole ratio of no greater than 100,000:1. In some very specific embodiments, the composition comprises the zwitterionic psilocybin and the cationic psilocybin at a mole ratio of no greater than 50,000:1.

In some embodiments, the rate of spontaneous dephosphorylation for the zwitterionic psilocybin per mole of the zwitterionic psilocybin is less than the rate of spontaneous dephosphorylation for the dianionic psilocybin per mole of the dianionic psilocybin in the composition.

In some embodiments, the composition comprises the zwitterionic psilocybin and the dianionic psilocybin at a mole ratio of at least 400:1 (zwitterionic psilocybin:dianionic psilocybin). In some specific embodiments, the composition comprises the zwitterionic psilocybin and the dianionic psilocybin at a mole ratio of at least 4,000:1. In some even more specific embodiments, the composition comprises the zwitterionic psilocybin and the dianionic psilocybin at a mole ratio of at least 10,000:1. In some very specific embodiments, the composition comprises the zwitterionic psilocybin and the dianionic psilocybin at a mole ratio of at least 20,000:1.

In some embodiments, the mole ratio for the zwitterionic psilocybin and the dianionic psilocybin in the composition results in a lower rate of spontaneous dephosphorylation for the psilocybin of the composition per mole of the psilocybin relative to a lower mole ratio. In some specific embodiments, the mole ratio of at least 400:1 results in a lower rate of spontaneous dephosphorylation relative to a lower mole ratio of less than 400:1. In some specific embodiments, the mole ratio of at least 4000:1 results in a lower rate of spontaneous dephosphorylation relative to a lower mole ratio of less than 4000:1. In some specific embodiments, the mole ratio of at least 10,000:1 results in a lower rate of spontaneous dephosphorylation relative to a lower mole ratio of less than 10,000:1. In some specific embodiments, the mole ratio of at least 20,000:1 results in a lower rate of spontaneous dephosphorylation relative to a lower mole ratio of less than 20,000:1.

In some embodiments, the zwitterionic baeocystin has a rate of spontaneous dephosphorylation per mole in the composition, which converts the baeocystin into additional norpsilocin.

In some embodiments, the anionic baeocystin has a rate of spontaneous dephosphorylation per mole in the composition, which converts the baeocystin into additional norpsilocin.

In some embodiments, the cationic baeocystin has a rate of spontaneous dephosphorylation per mole in the composition, which converts the baeocystin into additional norpsilocin.

In some embodiments, the dianionic baeocystin has a rate of spontaneous dephosphorylation per mole in the composition, which converts the baeocystin into additional norpsilocin.

In some embodiments, the rate of spontaneous dephosphorylation for the zwitterionic baeocystin per mole of the zwitterionic baeocystin is less than the rate of spontaneous dephosphorylation for the anionic baeocystin per mole of the anionic baeocystin in the composition.

In some embodiments, the composition comprises the zwitterionic baeocystin and the anionic baeocystin at a mole ratio of at least 1:2 (zwitterionic baeocystin:anionic baeocystin). In some specific embodiments, the composition comprises the zwitterionic baeocystin and the anionic baeocystin at a mole ratio of at least 1:1. In some even more specific embodiments, the composition comprises the zwitterionic baeocystin and the anionic baeocystin at a mole ratio of at least 3:1. In some very specific embodiments, the composition comprises the zwitterionic baeocystin and the anionic baeocystin at a mole ratio of at least 16:1.

In some embodiments, the mole ratio for the zwitterionic baeocystin and the anionic baeocystin in the composition results in a lower rate of spontaneous dephosphorylation for the baeocystin of the composition per mole of the baeocystin relative to a lower mole ratio. In some specific embodiments, the mole ratio of at least 1:2 results in a lower rate of spontaneous dephosphorylation relative to a lower mole ratio of less than 1:2. In some specific embodiments, the mole ratio of at least 1:1 results in a lower rate of spontaneous dephosphorylation relative to a lower mole ratio of less than 1:1. In some specific embodiments, the mole ratio of at least 3:1 results in a lower rate of spontaneous dephosphorylation relative to a lower mole ratio of less than 3:1. In some specific embodiments, the mole ratio of at least 16:1 results in a lower rate of spontaneous dephosphorylation relative to a lower mole ratio of less than 16:1.

In some embodiments, the composition comprises the zwitterionic baeocystin and the anionic baeocystin at a mole ratio of no greater than 25,000:1. In some specific embodiments, the composition comprises the zwitterionic baeocystin and the anionic baeocystin at a mole ratio of no greater than 5000:1. In some very specific embodiments, the composition comprises the zwitterionic baeocystin and the anionic baeocystin at a mole ratio of no greater than 500:1.

In some embodiments, the rate of spontaneous dephosphorylation for the zwitterionic baeocystin per mole of the zwitterionic baeocystin is less than the rate of spontaneous dephosphorylation for the cationic baeocystin per mole of the cationic baeocystin in the composition.

In some embodiments, the composition comprises the zwitterionic baeocystin and the cationic baeocystin at a mole ratio of at least 15:1 (zwitterionic baeocystin:cationic baeocystin). In some specific embodiments, the composition comprises the zwitterionic baeocystin and the cationic baeocystin at a mole ratio of at least 240:1. In some even more specific embodiments, the composition comprises the zwitterionic baeocystin and the cationic baeocystin at a mole ratio of at least 3200:1. In some very specific embodiments, the composition comprises the zwitterionic baeocystin and the cationic baeocystin at a mole ratio of at least 38,000:1.

In some embodiments, the mole ratio for the zwitterionic baeocystin and the cationic baeocystin in the composition results in a lower rate of spontaneous dephosphorylation for the baeocystin of the composition per mole of the baeocystin relative to a lower mole ratio. In some specific embodiments, the mole ratio of at least 15:1 results in a lower rate of spontaneous dephosphorylation relative to a lower mole ratio of less than 15:1. In some specific embodiments, the mole ratio of at least 240:1 results in a lower rate of spontaneous dephosphorylation relative to a lower mole ratio of less than 240:1. In some specific embodiments, the mole ratio of at least 3200:1 results in a lower rate of spontaneous dephosphorylation relative to a lower mole ratio of less than 3200:1. In some specific embodiments, the mole ratio of at least 38,000:1 results in a lower rate of spontaneous dephosphorylation relative to a lower mole ratio of less than 38,000:1.

In some embodiments, the composition comprises the zwitterionic baeocystin and the cationic baeocystin at a mole ratio of no greater than 150,000:1. In some specific embodiments, the composition comprises the zwitterionic baeocystin and the cationic baeocystin at a mole ratio of no greater than 100,000:1. In some very specific embodiments, the composition comprises the zwitterionic baeocystin and the cationic baeocystin at a mole ratio of no greater than 50,000:1.

In some embodiments, the rate of spontaneous dephosphorylation for the zwitterionic baeocystin per mole of the zwitterionic baeocystin is less than the rate of spontaneous dephosphorylation for the dianionic baeocystin per mole of the dianionic baeocystin in the composition.

In some embodiments, the composition comprises the zwitterionic baeocystin and the dianionic baeocystin at a mole ratio of at least 400:1 (zwitterionic baeocystin:dianionic baeocystin). In some specific embodiments, the composition comprises the zwitterionic baeocystin and the dianionic baeocystin at a mole ratio of at least 4,000:1. In some even more specific embodiments, the composition comprises the zwitterionic baeocystin and the dianionic baeocystin at a mole ratio of at least 10,000:1. In some very specific embodiments, the composition comprises the zwitterionic baeocystin and the dianionic baeocystin at a mole ratio of at least 20,000:1.

In some embodiments, the mole ratio for the zwitterionic baeocystin and the dianionic baeocystin in the composition results in a lower rate of spontaneous dephosphorylation for the baeocystin of the composition per mole of the baeocystin relative to a lower mole ratio. In some specific embodiments, the mole ratio of at least 400:1 results in a lower rate of spontaneous dephosphorylation relative to a lower mole ratio of less than 400:1. In some specific embodiments, the mole ratio of at least 4,000:1 results in a lower rate of spontaneous dephosphorylation relative to a lower mole ratio of less than 4,000:1. In some specific embodiments, the mole ratio of at least 10,000:1 results in a lower rate of spontaneous dephosphorylation relative to a lower mole ratio of less than 10,000:1. In some specific embodiments, the mole ratio of at least 20,000:1 results in a lower rate of spontaneous dephosphorylation relative to a lower mole ratio of less than 20,000:1.

In some embodiments, the zwitterionic norbaeocystin has a rate of spontaneous dephosphorylation per mole in the composition, which converts the norbaeocystin into additional 4-HT.

In some embodiments, the anionic norbaeocystin has a rate of spontaneous dephosphorylation per mole in the composition, which converts the norbaeocystin into additional 4-HT.

In some embodiments, the cationic norbaeocystin has a rate of spontaneous dephosphorylation per mole in the composition, which converts the norbaeocystin into additional 4-HT.

In some embodiments, the dianionic norbaeocystin has a rate of spontaneous dephosphorylation per mole in the composition, which converts the norbaeocystin into additional 4-HT.

In some embodiments, the rate of spontaneous dephosphorylation for the zwitterionic norbaeocystin per mole of the zwitterionic norbaeocystin is less than the rate of spontaneous dephosphorylation for the anionic norbaeocystin per mole of the anionic norbaeocystin in the composition.

In some embodiments, the composition comprises the zwitterionic norbaeocystin and the anionic norbaeocystin at a mole ratio of at least 1:2 (zwitterionic norbaeocystin: anionic norbaeocystin). In some specific embodiments, the composition comprises the zwitterionic norbaeocystin and the anionic norbaeocystin at a mole ratio of at least 1:1. In some even more specific embodiments, the composition comprises the zwitterionic norbaeocystin and the anionic norbaeocystin at a mole ratio of at least 3:1. In some very specific embodiments, the composition comprises the zwitterionic norbaeocystin and the anionic norbaeocystin at a mole ratio of at least 16:1.

In some embodiments, the mole ratio for the zwitterionic norbaeocystin and the anionic norbaeocystin in the composition results in a lower rate of spontaneous dephosphorylation for the norbaeocystin of the composition per mole of the norbaeocystin relative to a lower mole ratio. In some specific embodiments, the mole ratio of at least 1:2 results in a lower rate of spontaneous dephosphorylation relative to a lower mole ratio of less than 1:2. In some specific embodiments, the mole ratio of at least 1:1 results in a lower rate of spontaneous dephosphorylation relative to a lower mole ratio of less than 1:1. In some specific embodiments, the mole ratio of at least 3:1 results in a lower rate of spontaneous dephosphorylation relative to a lower mole ratio of less than 3:1. In some specific embodiments, the mole ratio of at least 16:1 results in a lower rate of spontaneous dephosphorylation relative to a lower mole ratio of less than 16:1.

In some embodiments, the composition comprises the zwitterionic norbaeocystin and the anionic norbaeocystin at a mole ratio of no greater than 25,000:1. In some specific embodiments, the composition comprises the zwitterionic norbaeocystin and the anionic norbaeocystin at a mole ratio of no greater than 5000:1. In some very specific embodiments, the composition comprises the zwitterionic norbaeocystin and the anionic norbaeocystin at a mole ratio of no greater than 500:1.

In some embodiments, the rate of spontaneous dephosphorylation for the zwitterionic norbaeocystin per mole of the zwitterionic norbaeocystin is less than the rate of spontaneous dephosphorylation for the cationic norbaeocystin per mole of the cationic norbaeocystin in the composition.

In some embodiments, the composition comprises the zwitterionic norbaeocystin and the cationic norbaeocystin at a mole ratio of at least 15:1 (zwitterionic norbaeocystin: cationic norbaeocystin). In some specific embodiments, the composition comprises the zwitterionic norbaeocystin and the cationic norbaeocystin at a mole ratio of at least 240:1. In some even more specific embodiments, the composition comprises the zwitterionic norbaeocystin and the cationic norbaeocystin at a mole ratio of at least 3200:1. In some very specific embodiments, the composition comprises the zwitterionic norbaeocystin and the cationic norbaeocystin at a mole ratio of at least 38,000:1.

In some embodiments, the mole ratio for the zwitterionic norbaeocystin and the cationic norbaeocystin in the composition results in a lower rate of spontaneous dephosphorylation for the norbaeocystin of the composition per mole of the norbaeocystin relative to a lower mole ratio. In some specific embodiments, the mole ratio of at least 15:1 results in a lower rate of spontaneous dephosphorylation relative to a lower mole ratio of less than 15:1. In some specific embodiments, the mole ratio of at least 240:1 results in a lower rate of spontaneous dephosphorylation relative to a lower mole ratio of less than 240:1. In some specific embodiments, the mole ratio of at least 3200:1 results in a lower rate of spontaneous dephosphorylation relative to a lower mole ratio of less than 3200:1. In some specific embodiments, the mole ratio of at least 38,000:1 results in a lower rate of spontaneous dephosphorylation relative to a lower mole ratio of less than 38,000:1.

In some embodiments, the composition comprises the zwitterionic norbaeocystin and the cationic norbaeocystin at a mole ratio of no greater than 150,000:1. In some specific embodiments, the composition comprises the zwitterionic norbaeocystin and the cationic norbaeocystin at a mole ratio of no greater than 100,000:1. In some very specific embodiments, the composition comprises the zwitterionic norbaeocystin and the cationic norbaeocystin at a mole ratio of no greater than 50,000:1.

In some embodiments, the rate of spontaneous dephosphorylation for the zwitterionic norbaeocystin per mole of the zwitterionic norbaeocystin is less than the rate of spontaneous dephosphorylation for the dianionic norbaeocystin per mole of the dianionic norbaeocystin in the composition.

In some embodiments, the composition comprises the zwitterionic norbaeocystin and the dianionic norbaeocystin at a mole ratio of at least 400:1 (zwitterionic norbaeocystin: dianionic norbaeocystin). In some specific embodiments, the composition comprises the zwitterionic norbaeocystin and the dianionic norbaeocystin at a mole ratio of at least 4,000:1. In some even more specific embodiments, the composition comprises the zwitterionic norbaeocystin and the dianionic norbaeocystin at a mole ratio of at least 10,000:1. In some very specific embodiments, the composition comprises the zwitterionic norbaeocystin and the dianionic norbaeocystin at a mole ratio of at least 20,000:1.

In some embodiments, the mole ratio for the zwitterionic norbaeocystin and the dianionic norbaeocystin in the composition results in a lower rate of spontaneous dephosphorylation for the norbaeocystin of the composition per mole of the norbaeocystin relative to a lower mole ratio. In some specific embodiments, the mole ratio of at least 400:1 results in a lower rate of spontaneous dephosphorylation relative to a lower mole ratio of less than 400:1. In some specific embodiments, the mole ratio of at least 4,000:1 results in a lower rate of spontaneous dephosphorylation relative to a lower mole ratio of less than 4,000:1. In some specific embodiments, the mole ratio of at least 10,000:1 results in a lower rate of spontaneous dephosphorylation relative to a lower mole ratio of less than 10,000:1. In some specific embodiments, the mole ratio of at least 20,000:1 results in a lower rate of spontaneous dephosphorylation relative to a lower mole ratio of less than 20,000:1.

In some embodiments, the zwitterionic aeruginascin has a rate of spontaneous dephosphorylation per mole in the composition, which converts the aeruginascin into additional 4-hydroxy-TMT.

In some embodiments, the anionic aeruginascin has a rate of spontaneous dephosphorylation per mole in the composition, which converts the aeruginascin into additional 4-hydroxy-TMT.

In some embodiments, the rate of spontaneous dephosphorylation for the zwitterionic aeruginascin per mole of the zwitterionic aeruginascin is less than the rate of spontaneous dephosphorylation for the anionic aeruginascin per mole of the anionic aeruginascin in the composition.

In some embodiments, the composition comprises the zwitterionic aeruginascin and the anionic aeruginascin at a mole ratio of at least 1:2 (zwitterionic aeruginascin:anionic aeruginascin). In some specific embodiments, the composition comprises the zwitterionic aeruginascin and the anionic aeruginascin at a mole ratio of at least 1:1. In some even more specific embodiments, the composition comprises the zwitterionic aeruginascin and the anionic aeruginascin at a mole ratio of at least 3:1. In some very specific embodiments, the composition comprises the zwitterionic aeruginascin and the anionic aeruginascin at a mole ratio of at least 16:1.a In some embodiments, the mole ratio for the zwitterionic aeruginascin and the anionic aeruginascin in the composition results in a lower rate of spontaneous dephosphorylation for the aeruginascin of the composition per mole of the aeruginascin relative to a lower mole ratio. In some specific embodiments, the mole ratio of at least 1:2 results in a lower rate of spontaneous dephosphorylation relative to a lower mole ratio of less than 1:2. In some specific embodiments, the mole ratio of at least 1:1 results in a lower rate of spontaneous dephosphorylation relative to a lower mole ratio of less than 1:1. In some specific embodiments, the mole ratio of at least 3:1 results in a lower rate of spontaneous dephosphorylation relative to a lower mole ratio of less than 3:1. In some specific embodiments, the mole ratio of at least 16:1 results in a lower rate of spontaneous dephosphorylation relative to a lower mole ratio of less than 16:1.

In some embodiments, the composition comprises the zwitterionic aeruginascin and the anionic aeruginascin at a mole ratio of no greater than 25,000:1. In some specific embodiments, the composition comprises the zwitterionic norbaeocystin and the anionic norbaeocystin at a mole ratio of no greater than 5000:1. In some very specific embodiments, the composition comprises the zwitterionic norbaeocystin and the anionic norbaeocystin at a mole ratio of no greater than 500:1.

In some embodiments, the cationic aeruginascin has a rate of spontaneous dephosphorylation per mole in the composition, which converts the aeruginascin into additional 4-hydroxy-TMT.

In some embodiments, the rate of spontaneous dephosphorylation for the zwitterionic aeruginascin per mole of the zwitterionic aeruginascin is less than the rate of spontaneous dephosphorylation for the cationic aeruginascin per mole of the cationic aeruginascin in the composition.

In some embodiments, the composition comprises the zwitterionic aeruginascin and the cationic aeruginascin at a mole ratio of at least 15:1 (zwitterionic aeruginascin:cationic aeruginascin). In some specific embodiments, the composition comprises the zwitterionic aeruginascin and the cationic aeruginascin at a mole ratio of at least 240:1. In some even more specific embodiments, the composition comprises the zwitterionic aeruginascin and the cationic aeruginascin at a mole ratio of at least 3200:1. In some very specific embodiments, the composition comprises the zwitterionic aeruginascin and the cationic aeruginascin at a mole ratio of at least 38,000:1.

In some embodiments, the mole ratio for the zwitterionic aeruginascin and the cationic aeruginascin in the composition results in a lower rate of spontaneous dephosphorylation for the aeruginascin of the composition per mole of the aeruginascin relative to a lower mole ratio. In some specific embodiments, the mole ratio of at least 15:1 results in a lower rate of spontaneous dephosphorylation relative to a lower mole ratio of less than 15:1. In some specific embodiments, the mole ratio of at least 240:1 results in a lower rate of spontaneous dephosphorylation relative to a lower mole ratio of less than 240:1. In some specific embodiments, the mole ratio of at least 3200:1 results in a lower rate of spontaneous dephosphorylation relative to a lower mole ratio of less than 3200:1. In some specific embodiments, the mole ratio of at least 38,000:1 results in a lower rate of spontaneous dephosphorylation relative to a lower mole ratio of less than 38,000:1.

In some embodiments, the composition comprises the zwitterionic aeruginascin and the cationic aeruginascin at a mole ratio of no greater than 150,000:1. In some specific embodiments, the composition comprises the zwitterionic aeruginascin and the cationic aeruginascin at a mole ratio of no greater than 100,000:1. In some very specific embodiments, the composition comprises the zwitterionic aeruginascin and the cationic aeruginascin at a mole ratio of no greater than 50,000:1.

In some embodiments, the composition comprises a polypeptide.

In some embodiments, the polypeptide encodes either a phosphatase enzyme or a portion thereof.

In some embodiments, the phosphatase enzyme is encoded by an amino acid sequence having at least 90 percent sequence identity with the sequence set forth in SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, or SEQ ID NO: 90 (hereinafter one of SEQ ID NO: 25-90). In some specific embodiments, the phosphatase enzyme is encoded by an amino acid sequence having at least 95 percent sequence identity with the sequence set forth in one of SEQ ID NO: 25-90. In some even more specific embodiments, the phosphatase enzyme is encoded by an amino acid sequence having at least 98 percent sequence identity with the sequence set forth in one of SEQ ID NO: 25-90. In some very specific embodiments, the phosphatase enzyme is encoded by the amino acid sequence set forth in one of SEQ ID NO: 25-90.

In some embodiments, the polypeptide is denatured in the composition such that the polypeptide lacks phosphatase enzyme activity.

In some embodiments, the phosphatase enzyme is capable of dephosphorylating the psilocybin into additional psilocin.

In some embodiments, the composition comprises the psilocybin and the psilocin at a mole ratio of at least 1:1 (psilocybin:psilocin). In some specific embodiments, the composition comprises the psilocybin and the psilocin at a mole ratio of at least 3:2. In some even more specific embodiments, the composition comprises the psilocybin and the psilocin at a mole ratio of at least 3:1. In some very specific embodiments, the composition comprises the psilocybin and the psilocin at a mole ratio of at least 9:1.

In some embodiments, the mole ratio for the psilocybin and the psilocin in the composition is indicative of effective denaturation of the polypeptide to inhibit phosphatase enzyme activity. In some specific embodiments, the mole ratio of at least 1:1 for the psilocybin and the psilocin is indicative of effective denaturation of the polypeptide to inhibit phosphatase enzyme activity relative to a lower mole ratio of less than 1:1. In some specific embodiments, the mole ratio of at least 3:2 for the psilocybin and the psilocin is indicative of effective denaturation of the polypeptide to inhibit phosphatase enzyme activity relative to a lower mole ratio of less than 3:2. In some specific embodiments, the mole ratio of at least 3:1 for the psilocybin and the psilocin is indicative of effective denaturation of the polypeptide to inhibit phosphatase enzyme activity relative to a lower mole ratio of less than 3:1. In some specific embodiments, the mole ratio of at least 9:1 for the psilocybin and the psilocin is indicative of effective denaturation of the polypeptide to inhibit phosphatase enzyme activity relative to a lower mole ratio of less than 9:1.

In some embodiments, the psilocybin and the psilocin each have a different rate of spontaneous oxidation per mole in the composition.

In some embodiments, the rate of spontaneous oxidation for the psilocybin per mole of the psilocybin is less than the rate of spontaneous oxidation for the psilocin per mole of the psilocin in the composition.

In some embodiments, the mole ratio for the psilocybin and the psilocin in the composition results in a lower rate of spontaneous oxidation for the tryptamines per mole of the tryptamines of the composition relative to a lower mole ratio. In some specific embodiments, the mole ratio of at least 1:1 for the psilocybin and the psilocin in the composition results in a lower rate of spontaneous oxidation relative to a lower mole ratio of less than 1:1. In some specific embodiments, the mole ratio of at least 3:2 for the psilocybin and the psilocin in the composition results in a lower rate of spontaneous oxidation relative to a lower mole ratio of less than 3:2. In some specific embodiments, the mole ratio of at least 3:1 for the psilocybin and the psilocin in the composition results in a lower rate of spontaneous oxidation relative to a lower mole ratio of less than 3:1. In some specific embodiments, the mole ratio of at least 9:1 for the psilocybin and the psilocin in the composition results in a lower rate of spontaneous oxidation relative to a lower mole ratio of less than 9:1.

In some embodiments, the composition comprises the psilocybin and the psilocin at a mole ratio of no greater than 400:1. In some specific embodiments, the composition comprises the psilocybin and the psilocin at a mole ratio of no greater than 120:1. In some very specific embodiments, the composition comprises the psilocybin and the psilocin at a mole ratio of no greater than 80:1.

In some embodiments, the composition comprises the baeocystin and the norpsilocin at a mole ratio of at least 1:1 (baeocystin:norpsilocin). In some specific embodiments, the composition comprises the baeocystin and the norpsilocin at a mole ratio of at least 3:2. In some even more specific embodiments, the composition comprises the baeocystin and the norpsilocin at a mole ratio of at least 3:1. In some very specific embodiments, the composition comprises the baeocystin and the norpsilocin at a mole ratio of at least 9:1.

In some embodiments, the phosphatase enzyme is capable of dephosphorylating the baeocystin into additional norpsilocin.

In some embodiments, the mole ratio for the baeocystin and the norpsilocin in the composition is indicative of effective denaturation of the polypeptide to inhibit phosphatase enzyme activity. In some specific embodiments, the mole ratio of at least 1:1 for the baeocystin and the norpsilocin is indicative of effective denaturation of the polypeptide to inhibit phosphatase enzyme activity relative to a lower mole ratio of less than 1:1. In some specific embodiments, the mole ratio of at least 3:2 for the baeocystin and the norpsilocin is indicative of effective denaturation of the polypeptide to inhibit phosphatase enzyme activity relative to a lower mole ratio of less than 3:2. In some specific embodiments, the mole ratio of at least 3:1 for the baeocystin and the norpsilocin is indicative of effective denaturation of the polypeptide to inhibit phosphatase enzyme activity relative to a lower mole ratio of less than 3:1. In some specific embodiments, the mole ratio of at least 9:1 for the baeocystin and the norpsilocin is indicative of effective denaturation of the polypeptide to inhibit phosphatase enzyme activity relative to a lower mole ratio of less than 9:1.

In some embodiments, the baeocystin and the norpsilocin each have a different rate of spontaneous oxidation per mole in the composition.

In some embodiments, the rate of spontaneous oxidation for the baeocystin per mole of the baeocystin is less than the rate of spontaneous oxidation for the norpsilocin per mole of the norpsilocin in the composition.

In some embodiments, the mole ratio for the baeocystin and the norpsilocin in the composition correlates with a lower rate of spontaneous oxidation for the tryptamines per mole of the tryptamines of the composition relative to a lower mole ratio. In some specific embodiments, the mole ratio of at least 1:1 for the baeocystin and the norpsilocin in the composition correlates with a lower rate of spontaneous oxidation relative to a lower mole ratio of less than 1:1. In some specific embodiments, the mole ratio of at least 3:2 for the baeocystin and the norpsilocin in the composition correlates with a lower rate of spontaneous oxidation relative to a lower mole ratio of less than 3:2. In some specific embodiments, the mole ratio of at least 3:1 for the baeocystin and the norpsilocin in the composition correlates with a lower rate of spontaneous oxidation relative to a lower mole ratio of less than 3:1. In some specific embodiments, the mole ratio of at least 9:1 for the baeocystin and the norpsilocin in the composition correlates with a lower rate of spontaneous oxidation relative to a lower mole ratio of less than 9:1.

In some embodiments, the composition comprises the baeocystin and the norpsilocin at a mole ratio of no greater than 400:1. In some specific embodiments, the composition comprises the baeocystin and the norpsilocin at a mole ratio of no greater than 120:1. In some very specific embodiments, the composition comprises the baeocystin and the norpsilocin at a mole ratio of no greater than 80:1.

In some embodiments, the composition comprises the norbaeocystin and the 4-HT at a mole ratio of at least 1:1 (norbaeocystin:4-HT). In some specific embodiments, the composition comprises the norbaeocystin and the 4-HT at a mole ratio of at least 3:2. In some even more specific embodiments, the composition comprises the norbaeocystin and the 4-HT at a mole ratio of at least 3:1. In some very specific embodiments, the composition comprises the norbaeocystin and the 4-HT at a mole ratio of at least 9:1.

In some embodiments, the phosphatase enzyme is capable of dephosphorylating the norbaeocystin into additional 4-HT.

In some embodiments, the mole ratio for the norbaeocystin and the 4-HT in the composition is indicative of effective denaturation of the polypeptide to inhibit phosphatase enzyme activity. In some specific embodiments, the mole ratio of at least 1:1 for the norbaeocystin and the 4-HT is indicative of effective denaturation of the polypeptide to inhibit phosphatase enzyme activity relative to a lower mole ratio of less than 1:1. In some specific embodiments, the mole ratio of at least 3:2 for the norbaeocystin and the 4-HT is indicative of effective denaturation of the polypeptide to inhibit phosphatase enzyme activity relative to a lower mole ratio of less than 3:2. In some specific embodiments, the mole ratio of at least 3:1 for the norbaeocystin and the 4-HT is indicative of effective denaturation of the polypeptide to inhibit phosphatase enzyme activity relative to a lower mole ratio of less than 3:1. In some specific embodiments, the mole ratio of at least 9:1 for the norbaeocystin and the 4-HT is indicative of effective denaturation of the polypeptide to inhibit phosphatase enzyme activity relative to a lower mole ratio of less than 9:1.

In some embodiments, the norbaeocystin and the 4-HT each have a different rate of spontaneous oxidation per mole in the composition.

In some embodiments, the rate of spontaneous oxidation for the norbaeocystin per mole of the norbaeocystin is less than the rate of spontaneous oxidation for the 4-HT per mole of the 4-HT in the composition.

In some embodiments, the mole ratio for the norbaeocystin and the 4-HT in the composition correlates with a lower rate of spontaneous oxidation for the tryptamines per mole of the tryptamines of the composition relative to a lower mole ratio. In some specific embodiments, the mole ratio of at least 1:1 for the norbaeocystin and the 4-HT in the composition correlates with a lower rate of spontaneous oxidation relative to a lower mole ratio of less than 1:1. In some specific embodiments, the mole ratio of at least 3:2 for the norbaeocystin and the 4-HT in the composition correlates with a lower rate of spontaneous oxidation relative to a lower mole ratio of less than 3:2. In some specific embodiments, the mole ratio of at least 3:1 for the norbaeocystin and the 4-HT in the composition correlates with a lower rate of spontaneous oxidation relative to a lower mole ratio of less than 3:1. In some specific embodiments, the mole ratio of at least 9:1 for the norbaeocystin and the 4-HT in the composition correlates with a lower rate of spontaneous oxidation relative to a lower mole ratio of less than 9:1.

In some embodiments, the composition comprises the norbaeocystin and the 4-HT at a mole ratio of no greater than 400:1. In some specific embodiments, the composition comprises the norbaeocystin and the 4-HT at a mole ratio of no greater than 120:1. In some very specific embodiments, the composition comprises the norbaeocystin and the 4-HT at a mole ratio of no greater than 80:1.

In some embodiments, the composition comprises the aeruginascin and the 4-hydroxy-TMT at a mole ratio of at least 1:1 (aeruginascin:4-hydroxy-TMT). In some specific embodiments, the composition comprises the aeruginascin and the 4-hydroxy-TMT at a mole ratio of at least 3:2. In some even more specific embodiments, the composition comprises the aeruginascin and the 4-hydroxy-TMT at a mole ratio of at least 3:1. In some very specific embodiments, the composition comprises the aeruginascin and the 4-hydroxy-TMT at a mole ratio of at least 9:1.

In some embodiments, the phosphatase enzyme is capable of dephosphorylating the aeruginascin into additional 4-hydroxy-TMT.

In some embodiments, the mole ratio for the aeruginascin and the 4-hydroxy-TMT in the composition is indicative of effective denaturation of the polypeptide to inhibit phosphatase enzyme activity. In some specific embodiments, the mole ratio of at least 1:1 for the aeruginascin and the 4-hydroxy-TMT is indicative of effective denaturation of the polypeptide to inhibit phosphatase enzyme activity relative to a lower mole ratio of less than 1:1. In some specific embodiments, the mole ratio of at least 3:2 for the aeruginascin and the 4-hydroxy-TMT is indicative of effective denaturation of the polypeptide to inhibit phosphatase enzyme activity relative to a lower mole ratio of less than 3:2. In some specific embodiments, the mole ratio of at least 3:1 for the aeruginascin and the 4-hydroxy-TMT is indicative of effective denaturation of the polypeptide to inhibit phosphatase enzyme activity relative to a lower mole ratio of less than 3:1. In some specific embodiments, the mole ratio of at least 9:1 for the aeruginascin and the 4-hydroxy-TMT is indicative of effective denaturation of the polypeptide to inhibit phosphatase enzyme activity relative to a lower mole ratio of less than 9:1.

In some embodiments, the aeruginascin and the 4-hydroxy-TMT each have a different rate of spontaneous oxidation per mole in the composition.

In some embodiments, the rate of spontaneous oxidation for the aeruginascin per mole of the aeruginascin is less than the rate of spontaneous oxidation for the 4-hydroxy-TMT per mole of the 4-hydroxy-TMT in the composition.

In some embodiments, the mole ratio for the aeruginascin and the 4-hydroxy-TMT in the composition correlates with a lower rate of spontaneous oxidation for the tryptamines per mole of the tryptamines of the composition relative to a lower mole ratio. In some specific embodiments, the mole ratio of at least 1:1 for the aeruginascin and the 4-hydroxy-TMT in the composition correlates with a lower rate of spontaneous oxidation relative to a lower mole ratio of less than 1:1. In some specific embodiments, the mole ratio of at least 3:2 for the aeruginascin and the 4-hydroxy-TMT in the composition correlates with a lower rate of spontaneous oxidation relative to a lower mole ratio of less than 3:2. In some specific embodiments, the mole ratio of at least 3:1 for the aeruginascin and the 4-hydroxy-TMT in the composition correlates with a lower rate of spontaneous oxidation relative to a lower mole ratio of less than 3:1. In some specific embodiments, the mole ratio of at least 9:1 for the aeruginascin and the 4-hydroxy-TMT in the composition correlates with a lower rate of spontaneous oxidation relative to a lower mole ratio of less than 9:1.

In some embodiments, the composition comprises the aeruginascin and the 4-hydroxy-TMT at a mole ratio of no greater than 400:1. In some specific embodiments, the composition comprises the aeruginascin and the 4-hydroxy-TMT at a mole ratio of no greater than 120:1. In some very specific embodiments, the composition comprises the aeruginascin and the 4-hydroxy-TMT at a mole ratio of no greater than 80:1.

In some embodiments, the composition comprises the psilocin and one or more oxidized diones of psilocin at a mole ratio of at least 5:1 (psilocin:oxidized diones). In some specific embodiments, the composition comprises the psilocin and one or more oxidized diones of psilocin at a mole ratio of at least 10:1. In some even more specific embodiments, the composition comprises the psilocin and one or more oxidized diones of psilocin at a mole ratio of at least 84:1. In some very specific embodiments, the composition comprises the psilocin and one or more oxidized diones of psilocin at a mole ratio of at least 756:1.

In some embodiments, the composition is a product that is produced by a process, and the mole ratio for the psilocin and the oxidized diones of psilocin in the composition is indicative of effective control for acidity (such as by optimizing a mole ratio of zwitterionic phosphoryloxytryptamines to cationic phosphoryloxytryptamines as described herein), alkalinity (such as by optimizing a mole ratio of zwitterionic phosphoryloxytryptamines to anionic phosphoryloxytryptamines as described herein), light (such as by optimizing illuminance, color temperature, wavelengths of light, and/or the surface-area-to-volume ratio of the composition as described herein), temperature (such as by freezing or otherwise cooling the composition as described herein), water (such as by dehydrating or lyophilizing the composition as described herein), oxygen (such as by optimizing the surface-area-to-volume ratio of the composition and/or storing the composition under vacuum as described herein), transition metals (e.g., such as by chelating iron(III), copper (II), and/or other transition metals as described herein), and/or reactive oxygen species (such as by introducing one or more antioxidants into a composition as described herein) in the process relative to a lower mole ratio. In some specific embodiments, the mole ratio of at least 5:1 for the psilocin and the oxidized diones of psilocin is indicative of effective control for acidity, alkalinity, light, temperature, water, oxygen, transition metals, and/or reactive oxygen species in the process relative to a lower mole ratio of less than 5:1. In some specific embodiments, the mole ratio of at least 10:1 for the psilocin and the oxidized diones of psilocin is indicative of effective control for acidity, alkalinity, light, temperature, water, oxygen, transition metals, and/or reactive oxygen species in the process relative to a lower mole ratio of less than 10:1. In some specific embodiments, the mole ratio of at least 84:1 for the psilocin and the oxidized diones of psilocin is indicative of effective control for acidity, alkalinity, light, temperature, water, oxygen, transition metals, and/or reactive oxygen species in the process relative to a lower mole ratio of less than 84:1. In some specific embodiments, the mole ratio of at least 756:1 for the psilocin and the oxidized diones of psilocin is indicative of effective control for acidity, alkalinity, light, temperature, water, oxygen, transition metals, and/or reactive oxygen species in the process relative to a lower mole ratio of less than 756:1.

In some embodiments, each of the one or more oxidized diones of psilocin is a cation that comprises a cationic azaniumyl group such that each of the one or more oxidized diones of psilocin has an approximate molecular weight of 219 atomic mass units.

In some embodiments, the one or more oxidized diones of psilocin are selected from 3-[2-(dimethylazaniumyl)ethyl]-1H-indol-2,4-dione; 3-[2-(dimethylazaniumyl)ethyl]-1H-indol-4,5-dione; 3-[2-(dimethylazaniumyl)ethyl]-1H-indol-4,7-dione; and tautomers of the foregoing; and the tautomers consist of 3-[2-(dimethylazaniumyl)ethyl]-2-hydroxyindol-4-one; 3-[2-(dimethylazaniumyl)ethyl]-4-hydroxyindol-2-one; 3-[2-(dimethylazaniumyl)ethyl]-4-hydroxyindol-5-one; 3-[2-(dimethylazaniumyl)ethyl]-5-hydroxyindol-4-one; 3-[2-(dimethylazaniumyl)ethyl]-4-hydroxyindol-7-one; and 3-[2-(dimethylazaniumyl)ethyl]-7-hydroxyindol-4-one.

In some embodiments, the one or more oxidized diones of psilocin comprise 3-[2-(dimethylazaniumyl)ethyl]-7-hydroxyindol-4-one or a tautomer thereof.

In some embodiments, the composition comprises the norpsilocin and one or more oxidized diones of norpsilocin at a mole ratio of at least 5:1 (norpsilocin:oxidized diones). In some specific embodiments, the composition comprises the norpsilocin and one or more oxidized diones of norpsilocin at a mole ratio of at least 10:1. In some even more specific embodiments, the composition comprises the norpsilocin and one or more oxidized diones of norpsilocin at a mole ratio of at least 84:1. In some very specific embodiments, the composition comprises the norpsilocin and one or more oxidized diones of norpsilocin at a mole ratio of at least 756:1.

In some embodiments, the composition is a product that is produced by a process, and the mole ratio for the norpsilocin and the oxidized diones of norpsilocin in the composition is indicative of effective control for acidity (such as by optimizing a mole ratio of zwitterionic phosphoryloxytryptamines to cationic phosphoryloxytryptamines as described herein), alkalinity (such as by optimizing a mole ratio of zwitterionic phosphoryloxytryptamines to anionic phosphoryloxytryptamines as described herein), light (such as by optimizing illuminance, color temperature, wavelengths of light, and/or the surface-area-to-volume ratio of the composition as described herein), temperature (such as by freezing or otherwise cooling the composition as described herein), water (such as by dehydrating or lyophilizing the composition as described herein), oxygen (such as by optimizing the surface-area-to-volume ratio of the composition and/or storing the composition under vacuum as described herein), transition metals (e.g., such as by chelating iron(III), copper(II), and/or other transition metals as described herein), and/or reactive oxygen species (such as by introducing one or more antioxidants into a composition as described herein) in the process relative to a lower mole ratio. In some specific embodiments, the mole ratio of at least 5:1 for the norpsilocin and the oxidized diones of norpsilocin is indicative of effective control for acidity, alkalinity, light, temperature, water, oxygen, transition metals, and/or reactive oxygen species in the process relative to a lower mole ratio of less than 5:1. In some specific embodiments, the mole ratio of at least 10:1 for the norpsilocin and the oxidized diones of norpsilocin is indicative of effective control for acidity, alkalinity, light, temperature, water, oxygen, transition metals, and/or reactive oxygen species in the process relative to a lower mole ratio of less than 10:1. In some specific embodiments, the mole ratio of at least 84:1 for the norpsilocin and the oxidized diones of norpsilocin is indicative of effective control for acidity, alkalinity, light, temperature, water, oxygen, transition metals, and/or reactive oxygen species in the process relative to a lower mole ratio of less than 84:1. In some specific embodiments, the mole ratio of at least 756:1 for the norpsilocin and the oxidized diones of norpsilocin is indicative of effective control for acidity, alkalinity, light, temperature, water, oxygen, transition metals, and/or reactive oxygen species in the process relative to a lower mole ratio of less than 756:1.

In some embodiments, each of the one or more oxidized diones of norpsilocin is a cation that comprises a cationic azaniumyl group such that each of the one or more oxidized diones of norpsilocin has an approximate molecular weight of 205 atomic mass units.

In some embodiments, the one or more oxidized diones of norpsilocin are selected from 3-[2-(methylazaniumyl)ethyl]-1H-indol-2,4-dione; 3-[2-(methylazaniumyl)ethyl]-1H-indol-4,5-dione; 3-[2-(methylazaniumyl)ethyl]-1H-indol-4,7-dione; and tautomers of the foregoing; and the tautomers consist of 3-[2-(methylazaniumyl)ethyl]-2-hydroxyindol-4-one; 3-[2-(methylazaniumyl)ethyl]-4-hydroxyindol-2-one; 3-[2-(methylazaniumyl)ethyl]-4-hydroxyindol-5-one; 3-[2-(methylazaniumyl)ethyl]-5-hydroxyindol-4-one; 3-[2-(methylazaniumyl)ethyl]-4-hydroxyindol-7-one; and 3-[2-(methylazaniumyl)ethyl]-7-hydroxyindol-4-one.

In some embodiments, the one or more oxidized diones of norpsilocin comprise 3-[2-(methylazaniumyl)ethyl]-7-hydroxyindol-4-one or a tautomer thereof.

In some embodiments, the composition comprises the 4-HT and one or more oxidized diones of 4-HT at a mole ratio of at least 5:1 (4-HT:oxidized diones). In some specific embodiments, the composition comprises the 4-HT and one or more oxidized diones of 4-HT at a mole ratio of at least 10:1. In some even more specific embodiments, the composition comprises the 4-HT and one or more oxidized diones of 4-HT at a mole ratio of at least 84:1. In some very specific embodiments, the composition comprises the 4-HT and one or more oxidized diones of 4-HT at a mole ratio of at least 756:1.

In some embodiments, the composition is a product that is produced by a process, and the mole ratio for the 4-HT and the oxidized diones of 4-HT in the composition is indicative of effective control for acidity (such as by optimizing a mole ratio of zwitterionic phosphoryloxytryptamines to cationic phosphoryloxytryptamines as described herein), alkalinity (such as by optimizing a mole ratio of zwitterionic phosphoryloxytryptamines to anionic phosphoryloxytryptamines as described herein), light (such as by optimizing illuminance, color temperature, wavelengths of light, and/or the surface-area-to-volume ratio of the composition as described herein), temperature (such as by freezing or otherwise cooling the composition as described herein), water (such as by dehydrating or lyophilizing the composition as described herein), oxygen (such as by optimizing the surface-area-to-volume ratio of the composition and/or storing the composition under vacuum as described herein), transition metals (e.g., such as by chelating iron(III), copper(II), and/or other transition metals as described herein), and/or reactive oxygen species (such as by introducing one or more antioxidants into a composition as described herein) in the process relative to a lower mole ratio. In some specific embodiments, the mole ratio of at least 5:1 for the 4-HT and the oxidized diones of 4-HT is indicative of effective control for acidity, alkalinity, light, temperature, water, oxygen, transition metals, and/or reactive oxygen species in the process relative to a lower mole ratio of less than 5:1. In some specific embodiments, the mole ratio of at least 10:1 for the 4-HT and the oxidized diones of 4-HT is indicative of effective control for acidity, alkalinity, light, temperature, water, oxygen, transition metals, and/or reactive oxygen species in the process relative to a lower mole ratio of less than 10:1. In some specific embodiments, the mole ratio of at least 84:1 for the 4-HT and the oxidized diones of 4-HT is indicative of effective control for acidity, alkalinity, light, temperature, water, oxygen, transition metals, and/or reactive oxygen species in the process relative to a lower mole ratio of less than 84:1. In some specific embodiments, the mole ratio of at least 756:1 for the 4-HT and the oxidized diones of 4-HT is indicative of effective control for acidity, alkalinity, light, temperature, water, oxygen, transition metals, and/or reactive oxygen species in the process relative to a lower mole ratio of less than 756:1.

In some embodiments, each of the one or more oxidized diones of 4-HT is a cation that comprises a cationic azaniumyl group such that each of the one or more oxidized diones of 4-HT has an approximate molecular weight of 191 atomic mass units.

In some embodiments, the one or more oxidized diones of 4-HT are selected from 3-(2-azaniumylethyl)-1H-indol-2,4-dione; 3-(2-azaniumylethyl)-1H-indol-4,5-dione; 3-(2-azaniumylethyl)-1H-indol-4,7-dione; and tautomers of the foregoing; and the tautomers consist of 3-(2-azaniumylethyl)-2-hydroxyindol-4-one; 3-(2-azaniumylethyl)-4-hydroxyindol-2-one; 3-(2-azaniumylethyl)-4-hydroxyindol-5-one; 3-(2-azaniumylethyl)-5-hydroxyindol-4-one; 3-(2-azaniumylethyl)-4-hydroxyindol-7-one; and 3-(2-azaniumylethyl)-7-hydroxyindol-4-one.

In some embodiments, the one or more oxidized diones of 4-HT comprise 3-(2-azaniumylethyl)-7-hydroxyindol-4-one or a tautomer thereof.

In some embodiments, the composition comprises the aeruginascin and one or more oxidized diones of aeruginascin at a mole ratio of at least 5:1 (aeruginascin:oxidized diones). In some specific embodiments, the composition comprises the aeruginascin and one or more oxidized diones of aeruginascin at a mole ratio of at least 10:1. In some even more specific embodiments, the composition comprises the aeruginascin and one or more oxidized diones of aeruginascin at a mole ratio of at least 84:1. In some very specific embodiments, the composition comprises the aeruginascin and one or more oxidized diones of aeruginascin at a mole ratio of at least 756:1.

In some embodiments, the composition is a product that is produced by a process, and the mole ratio for the aeruginascin and the oxidized diones of aeruginascin in the composition is indicative of effective control for acidity (such as by optimizing a mole ratio of zwitterionic phosphoryloxytryptamines to cationic phosphoryloxytryptamines as described herein), alkalinity (such as by optimizing a mole ratio of zwitterionic phosphoryloxytryptamines to anionic phosphoryloxytryptamines as described herein), light (such as by optimizing illuminance, color temperature, wavelengths of light, and/or the surface-area-to-volume ratio of the composition as described herein), temperature (such as by freezing or otherwise cooling the composition as described herein), water (such as by dehydrating or lyophilizing the composition as described herein), oxygen (such as by optimizing the surface-area-to-volume ratio of the composition and/or storing the composition under vacuum as described herein), transition metals (e.g., such as by chelating iron(III), copper(II), and/or other transition metals as described herein), and/or reactive oxygen species (such as by introducing one or more antioxidants into a composition as described herein) in the process relative to a lower mole ratio. In some specific embodiments, the mole ratio of at least 5:1 for the aeruginascin and the oxidized diones of aeruginascin is indicative of effective control for acidity, alkalinity, light, temperature, water, oxygen, transition metals, and/or reactive oxygen species in the process relative to a lower mole ratio of less than 5:1. In some specific embodiments, the mole ratio of at least 10:1 for the aeruginascin and the oxidized diones of aeruginascin is indicative of effective control for acidity, alkalinity, light, temperature, water, oxygen, transition metals, and/or reactive oxygen species in the process relative to a lower mole ratio of less than 10:1. In some specific embodiments, the mole ratio of at least 84:1 for the aeruginascin and the oxidized diones of aeruginascin is indicative of effective control for acidity, alkalinity, light, temperature, water, oxygen, transition metals, and/or reactive oxygen species in the process relative to a lower mole ratio of less than 84:1. In some specific embodiments, the mole ratio of at least 756:1 for the aeruginascin and the oxidized diones of aeruginascin is indicative of effective control for acidity, alkalinity, light, temperature, water, oxygen, transition metals, and/or reactive oxygen species in the process relative to a lower mole ratio of less than 756:1.

In some embodiments, each of the one or more oxidized diones of aeruginascin is a cation that comprises a cationic azaniumyl group such that each of the one or more oxidized diones of aeruginascin has an approximate molecular weight of 233 atomic mass units.

In some embodiments, the one or more oxidized diones of aeruginascin are selected from 3-[2-(trimethylazaniumyl)ethyl]-1H-indol-2,4-dione; 3-[2-(trimethylazaniumyl)ethyl]-1H-indol-4,5-dione; 3-[2-(trimethylazaniumyl)ethyl]-1H-indol-4,7-dione; and tautomers of the foregoing; and the tautomers consist of 3-[2-(trimethylazaniumyl)ethyl]-2-hydroxyindol-4-one; 3-[2-(trimethylazaniumyl)ethyl]-4-hydroxyindol-2-one; 3-[2-(trimethylazaniumyl)ethyl]-4-hydroxyindol-5-one; 3-[2-(trimethylazaniumyl)ethyl]-5-hydroxyindol-4-one; 3-[2-(trimethylazaniumyl)ethyl]-4-hydroxyindol-7-one; and 3-[2-(trimethylazaniumyl)ethyl]-7-hydroxyindol-4-one.

In some embodiments, the one or more oxidized diones of aeruginascin comprise 3-[2-(trimethylazaniumyl)ethyl]-7-hydroxyindol-4-one or a tautomer thereof.

In some embodiments, the polypeptide encodes either a laccase enzyme or a portion thereof.

In some embodiments, the laccase enzyme is encoded by an amino acid sequence having at least 90 percent sequence identity with the sequence set forth in SEQ ID NO: 1, SEQ ID NO: 2, or SEQ ID NO: 3. In some specific embodiments, the laccase enzyme is encoded by an amino acid sequence having at least 95 percent sequence identity with the sequence set forth in SEQ ID NO: 1, SEQ ID NO: 2, or SEQ ID NO: 3. In some even more specific embodiments, the laccase enzyme is encoded by an amino acid sequence having at least 98 percent sequence identity with the sequence set forth in SEQ ID NO: 1, SEQ ID NO: 2, or SEQ ID NO: 3. In some very specific embodiments, the laccase enzyme is encoded by the amino acid sequence set forth in SEQ ID NO: 1, SEQ ID NO: 2, or SEQ ID NO: 3.

In some embodiments, the polypeptide comprises one or more amino acid sequences set forth in one or more of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, and SEQ ID NO: 24.

In some embodiments, the laccase enzyme is capable of oxidizing psilocin. In some specific embodiments, the laccase enzyme is capable of oxidizing psilocin into one or more oxidized dimers of psilocin. In some very specific embodiments, the laccase enzyme is capable of oxidizing the psilocin into one or more oxidized diol dimers of psilocin.

In some embodiments, the laccase enzyme is capable of oxidizing norpsilocin. In some specific embodiments, the laccase enzyme is capable of oxidizing norpsilocin into one or more oxidized dimers of norpsilocin and psilocin. In some very specific embodiments, the laccase enzyme is capable of oxidizing the norpsilocin into one or more oxidized diol dimers of norpsilocin and psilocin.

In some embodiments, the laccase enzyme is capable of oxidizing 4-HT. In some specific embodiments, the laccase enzyme is capable of oxidizing 4-HT into one or more oxidized dimers of 4-HT and psilocin. In some specific embodiments, the laccase enzyme is capable of oxidizing the 4-HT into one or more oxidized diol dimers of 4-HT and psilocin.

In some embodiments, the laccase enzyme is capable of oxidizing 4-hydroxy-TMT. In some specific embodiments, the laccase enzyme is capable of oxidizing 4-hydroxy-TMT into one or more oxidized dimers of 4-hydroxy-TMT and psilocin. In some very specific embodiments, the laccase enzyme is capable of oxidizing the 4-hydroxy-TMT into one or more oxidized diol dimers of 4-hydroxy-TMT and psilocin.

In some embodiments, the polypeptide is denatured in the composition such that the polypeptide lacks laccase enzyme activity.

In some embodiments, the composition comprises the psilocin and the one or more oxidized diol dimers of psilocin at a mole ratio of at least 5:1 (psilocin:oxidized diol dimers). In some specific embodiments, the composition comprises the psilocin and the one or more oxidized diol dimers of psilocin at a mole ratio of at least 10:1. In some even more specific embodiments, the composition comprises the psilocin and the one or more oxidized diol dimers of psilocin at a mole ratio of at least 84:1. In some very specific embodiments, the composition comprises the psilocin and the one or more oxidized diol dimers of psilocin at a mole ratio of at least 756:1.

In some embodiments, the mole ratio for the psilocin and the oxidized diol dimers of psilocin in the composition is indicative of effective denaturation of the polypeptide to inhibit laccase enzyme activity relative to a lower mole ratio. In some specific embodiments, the mole ratio of at least 5:1 for the psilocin and the oxidized diol dimers of psilocin is indicative of effective denaturation of the polypeptide to inhibit laccase enzyme activity relative to a lower mole ratio of less than 5:1. In some specific embodiments, the mole ratio of at least 10:1 for the psilocin and the oxidized diol dimers of psilocin is indicative of effective denaturation of the polypeptide to inhibit laccase enzyme activity relative to a lower mole ratio of less than 10:1. In some specific embodiments, the mole ratio of at least 84:1 for the psilocin and the oxidized diol dimers of psilocin is indicative of effective denaturation of the polypeptide to inhibit laccase enzyme activity relative to a lower mole ratio of less than 84:1. In some specific embodiments, the mole ratio of at least 756:1 for the psilocin and the oxidized diol dimers of psilocin is indicative of effective denaturation of the polypeptide to inhibit laccase enzyme activity relative to a lower mole ratio of less than 756:1.

In some embodiments, each of the one or more oxidized diol dimers of psilocin is a dication that comprises two monocationic azaniumyl groups such that each of the one or more oxidized diol dimers of psilocin has an approximate molecular weight of 409 atomic mass units.

In some embodiments, the one or more oxidized diol dimers of psilocin are selected from 3-[2-(dimethylazaniumyl)ethyl]-2-{3-[2-(dimethylazaniumyl)ethyl]-4-hydroxy-1H-indol-2-yl}-1H-indol-4-ol; 3-[2-(dimethylazaniumyl)ethyl]-2-{3-[2-(dimethylazaniumyl)ethyl]-4-hydroxy-1H-indol-5-yl}-1H-indol-4-ol; 3-[2-(dimethylazaniumyl)ethyl]-2-{3-[2-(dimethylazaniumyl)ethyl]-4-hydroxy-1H-indol-7-yl}-1H-indol-4-ol; 3-[2-(dimethylazaniumyl)ethyl]-5-{3-[2-(dimethylazaniumyl)ethyl]-4-hydroxy-1H-indol-5-yl}-1H-indol-4-ol; 3-[2-(dimethylazaniumyl)ethyl]-5-{3-[2-(dimethylazaniumyl)ethyl]-4-hydroxy-1H-indol-7-yl}-1H-indol-4-ol; and 3-[2-(dimethylazaniumyl)ethyl]-7-{3-[2-(dimethylazaniumyl)ethyl]-4-hydroxy-1H-indol-7-yl}-1H-indol-4-ol.

In some embodiments, the oxidized diol dimers of psilocin comprise 3-[2-(dimethylazaniumyl)ethyl]-2-{3-[2-(dimethylazaniumyl)ethyl]-4-hydroxy-1H-indol-2-yl}-1H-indol-4-ol.

In some embodiments, the oxidized diol dimers of psilocin comprise 3-[2-(dimethylazaniumyl)ethyl]-5-{3-[2-(dimethylazaniumyl)ethyl]-4-hydroxy-1H-indol-5-yl}-1H-indol-4-ol.

In some embodiments, the oxidized diol dimers of psilocin comprise 3-[2-(dimethylazaniumyl)ethyl]-7-{3-[2-(dimethylazaniumyl)ethyl]-4-hydroxy-1H-indol-7-yl}-1H-indol-4-ol.

In some embodiments, the composition comprises the norpsilocin and the one or more oxidized diol dimers of norpsilocin and psilocin at a mole ratio of at least 5:1 (norpsilocin:oxidized diol dimers of norpsilocin and psilocin). In some specific embodiments, the composition comprises the norpsilocin and the one or more oxidized diol dimers of norpsilocin and psilocin at a mole ratio of at least 10:1. In some even more specific embodiments, the composition comprises the norpsilocin and the one or more oxidized diol dimers of norpsilocin and psilocin at a mole ratio of at least 84:1. In some very specific embodiments, the composition comprises the norpsilocin and the one or more oxidized diol dimers of norpsilocin and psilocin at a mole ratio of at least 756:1.

In some embodiments, the mole ratio for the norpsilocin and the oxidized diol dimers of norpsilocin and psilocin in the composition is indicative of effective denaturation of the polypeptide to inhibit laccase enzyme activity relative to a lower mole ratio. In some specific embodiments, the mole ratio of at least 5:1 for the norpsilocin and the oxidized diol dimers of norpsilocin and psilocin is indicative of effective denaturation of the polypeptide to inhibit laccase enzyme activity relative to a lower mole ratio of less than 5:1. In some specific embodiments, the mole ratio of at least 10:1 for the norpsilocin and the oxidized diol dimers of norpsilocin and psilocin is indicative of effective denaturation of the polypeptide to inhibit laccase enzyme activity relative to a lower mole ratio of less than 10:1. In some specific embodiments, the mole ratio of at least 84:1 for the norpsilocin and the oxidized diol dimers of norpsilocin and psilocin is indicative of effective denaturation of the polypeptide to inhibit laccase enzyme activity relative to a lower mole ratio of less than 84:1. In some specific embodiments, the mole ratio of at least 756:1 for the norpsilocin and the oxidized diol dimers of norpsilocin and psilocin is indicative of effective denaturation of the polypeptide to inhibit laccase enzyme activity relative to a lower mole ratio of less than 756:1.

In some embodiments, each of the one or more oxidized diol dimers of norpsilocin and psilocin is a dication that comprises two monocationic azaniumyl groups such that each of the one or more oxidized diol dimers of norpsilocin and psilocin has an approximate molecular weight of 395 atomic mass units.

In some embodiments, the one or more oxidized diol dimers of norpsilocin and psilocin are selected from 3-[2-(dimethylazaniumyl)ethyl]-2-{3-[2-(methylazaniumyl)ethyl]-4-hydroxy-1H-indol-2-yl}-1H-indol-4-ol; 3-[2-(dimethylazaniumyl)ethyl]-2-{3-[2-(methylazaniumyl)ethyl]-4-hydroxy-1H-indol-5-yl}-1H-indol-4-ol; 3-[2-(methylazaniumyl)ethyl]-2-{3-[2-(dimethylazaniumyl)ethyl]-4-hydroxy-1H-indol-5-yl}-1H-indol-4-ol; 3-[2-(dimethylazaniumyl)ethyl]-2-{3-[2-(methylazaniumyl)ethyl]-4-hydroxy-1H-indol-7-yl}-1H-indol-4-ol; 3-[2-(methylazaniumyl)ethyl]-2-{3-[2-(dimethylazaniumyl)ethyl]-4-hydroxy-1H-indol-7-yl}-1H-indol-4-ol; 3-[2-(dimethylazaniumyl)ethyl]-5-{3-[2-(methylazaniumyl)ethyl]-4-hydroxy-1H-indol-5-yl}-1H-indol-4-ol; 3-[2-(dimethylazaniumyl)ethyl]-5-{3-[2-(methylazaniumyl)ethyl]-4-hydroxy-1H-indol-7-yl}-1H-indol-4-ol; 3-[2-(methylazaniumyl)ethyl]-5-{3-[2-(dimethylazaniumyl)ethyl]-4-hydroxy-1H-indol-7-yl}-1H-indol-4-ol; and 3-[2-(dimethylazaniumyl)ethyl]-7-{3-[2-(methylazaniumyl)ethyl]-4-hydroxy-1H-indol-7-yl}-1H-indol-4-ol.

In some embodiments, the oxidized diol dimers of norpsilocin and psilocin comprise 3-[2-(dimethylazaniumyl)ethyl]-2-{3-[2-(methylazaniumyl)ethyl]-4-hydroxy-1H-indol-2-yl}-1H-indol-4-ol.

In some embodiments, the oxidized diol dimers of norpsilocin and psilocin comprise 3-[2-(dimethylazaniumyl)ethyl]-5-{3-[2-(methylazaniumyl)ethyl]-4-hydroxy-1H-indol-5-yl}-1H-indol-4-ol.

In some embodiments, the oxidized diol dimers of norpsilocin and psilocin comprise 3-[2-(dimethylazaniumyl)ethyl]-7-{3-[2-(methylazaniumyl)ethyl]-4-hydroxy-1H-indol-7-yl}-1H-indol-4-ol.

In some embodiments, the composition comprises the 4-HT and the one or more oxidized diol dimers of 4-HT and psilocin at a mole ratio of at least 5:1 (4-HT:oxidized diol dimers of 4-HT and psilocin). In some specific embodiments, the composition comprises the 4-HT and the one or more oxidized diol dimers of 4-HT and psilocin at a mole ratio of at least 10:1. In some even more specific embodiments, the composition comprises the 4-HT and the one or more oxidized diol dimers of 4-HT and psilocin at a mole ratio of at least 84:1. In some very specific embodiments, the composition comprises the 4-HT and the one or more oxidized diol dimers of 4-HT and psilocin at a mole ratio of at least 756:1.

In some embodiments, the mole ratio for the 4-HT and the oxidized diol dimers of 4-HT and psilocin in the composition is indicative of effective denaturation of the polypeptide to inhibit laccase enzyme activity relative to a lower mole ratio. In some specific embodiments, the mole ratio of at least 5:1 for the 4-HT and the oxidized diol dimers of 4-HT and psilocin is indicative of effective denaturation of the polypeptide to inhibit laccase enzyme activity relative to a lower mole ratio of less than 5:1. In some specific embodiments, the mole ratio of at least 10:1 for the 4-HT and the oxidized diol dimers of 4-HT and psilocin is indicative of effective denaturation of the polypeptide to inhibit laccase enzyme activity relative to a lower mole ratio of less than 10:1. In some specific embodiments, the mole ratio of at least 84:1 for the 4-HT and the oxidized diol dimers of 4-HT and psilocin is indicative of effective denaturation of the polypeptide to inhibit laccase enzyme activity relative to a lower mole ratio of less than 84:1. In some specific embodiments, the mole ratio of at least 756:1 for the 4-HT and the oxidized diol dimers of 4-HT and psilocin is indicative of effective denaturation of the polypeptide to inhibit laccase enzyme activity relative to a lower mole ratio of less than 756:1.

In some embodiments, each of the one or more oxidized diol dimers of 4-HT and psilocin is a dication that comprises two monocationic azaniumyl groups such that each of the one or more oxidized diol dimers of 4-HT and psilocin has an approximate molecular weight of 380 atomic mass units.

In some embodiments, the one or more oxidized diol dimers of 4-HT and psilocin are selected from 3-[2-(dimethylazaniumyl)ethyl]-2-[3-(2-azaniumylethyl)-4-hydroxy-1H-indol-2-yl]-1H-indol-4-ol; 3-[2-(dimethylazaniumyl)ethyl]-2-[3-(2-azaniumylethyl)-4-hydroxy-1H-indol-5-yl]-1H-indol-4-ol; 3-(2-azaniumylethyl)-2-{3-[2-(dimethylazaniumyl)ethyl]-4-hydroxy-1H-indol-5-yl}-1H-indol-4-ol; 3-[2-(dimethylazaniumyl)ethyl]-2-[3-(2-azaniumylethyl)-4-hydroxy-1H-indol-7-yl]-1H-indol-4-ol; 3-(2-azaniumylethyl)-2-{3-[2-(dimethylazaniumyl)ethyl]-4-hydroxy-1H-indol-7-yl}-1H-indol-4-ol; 3-[2-(dimethylazaniumyl)ethyl]-5-[3-(2-azaniumylethyl)-4-hydroxy-1H-indol-5-yl]-1H-indol-4-ol; 3-[2-(dimethylazaniumyl)ethyl]-5-[3-(2-azaniumylethyl)-4-hydroxy-1H-indol-7-yl]-1H-indol-4-ol; 3-(2-azaniumylethyl)-5-{3-[2-(dimethylazaniumyl)ethyl]-4-hydroxy-1H-indol-7-yl}-1H-indol-4-ol; and 3-[2-(dimethylazaniumyl)ethyl]-7-[3-(2-azaniumylethyl)-4-hydroxy-1H-indol-7-yl]-1H-indol-4-ol.

In some embodiments, the oxidized diol dimers of 4-HT and psilocin comprise 3-[2-(dimethylazaniumyl)ethyl]-2-[3-(2-azaniumylethyl)-4-hydroxy-1H-indol-2-yl]-1H-indol-4-ol.

In some embodiments, the oxidized diol dimers of 4-HT and psilocin comprise 3-[2-(dimethylazaniumyl)ethyl]-5-[3-(2-azaniumylethyl)-4-hydroxy-1H-indol-5-yl]-1H-indol-4-ol.

In some embodiments, the oxidized diol dimers of 4-HT and psilocin comprise 3-[2-(dimethylazaniumyl)ethyl]-7-[3-(2-azaniumylethyl)-4-hydroxy-1H-indol-7-yl]-1H-indol-4-ol.

In some embodiments, the composition comprises the 4-hydroxy-TMT and the one or more oxidized diol dimers of 4-hydroxy-TMT and psilocin at a mole ratio of at least 5:1 (4-hydroxy-TMT:oxidized diol dimers of 4-hydroxy-TMT and psilocin). In some specific embodiments, the composition comprises the 4-hydroxy-TMT and the one or more oxidized diol dimers of 4-hydroxy-TMT and psilocin at a mole ratio of at least 10:1. In some even more specific embodiments, the composition comprises the 4-hydroxy-TMT and the one or more oxidized diol dimers of 4-hydroxy-TMT and psilocin at a mole ratio of at least 84:1. In some very specific embodiments, the composition comprises the 4-hydroxy-TMT and the one or more oxidized diol dimers of 4-hydroxy-TMT and psilocin at a mole ratio of at least 756:1.

In some embodiments, the mole ratio for the 4-hydroxy-TMT and the oxidized diol dimers of 4-hydroxy-TMT and psilocin in the composition is indicative of effective denaturation of the polypeptide to inhibit laccase enzyme activity relative to a lower mole ratio. In some specific embodiments, the mole ratio of at least 5:1 for the 4-hydroxy-TMT and the oxidized diol dimers of 4-hydroxy-TMT and psilocin is indicative of effective denaturation of the polypeptide to inhibit laccase enzyme activity relative to a lower mole ratio of less than 5:1. In some specific embodiments, the mole ratio of at least 10:1 for the 4-hydroxy-TMT and the oxidized diol dimers of 4-hydroxy-TMT and psilocin is indicative of effective denaturation of the polypeptide to inhibit laccase enzyme activity relative to a lower mole ratio of less than 10:1. In some specific embodiments, the mole ratio of at least 84:1 for the 4-hydroxy-TMT and the oxidized diol dimers of 4-hydroxy-TMT and psilocin is indicative of effective denaturation of the polypeptide to inhibit laccase enzyme activity relative to a lower mole ratio of less than 84:1. In some specific embodiments, the mole ratio of at least 756:1 for the 4-hydroxy-TMT and the oxidized diol dimers of 4-hydroxy-TMT and psilocin is indicative of effective denaturation of the polypeptide to inhibit laccase enzyme activity relative to a lower mole ratio of less than 756:1.

In some embodiments, each of the one or more oxidized diol dimers of 4-hydroxy-TMT and psilocin is a dication that comprises two monocationic azaniumyl groups such that each of the one or more oxidized diol dimers of 4-hydroxy-TMT and psilocin has an approximate molecular weight of 423 atomic mass units.

In some embodiments, the one or more oxidized diol dimers of 4-hydroxy-TMT and psilocin are selected from 3-[2-(dimethylazaniumyl)ethyl]-2-{3-[2-(trimethylazaniumyl)ethyl]-4-hydroxy-1H-indol-2-yl}-1H-indol-4-ol; 3-[2-(dimethylazaniumyl)ethyl]-2-{3-[2-(trimethylazaniumyl)ethyl]-4-hydroxy-1H-indol-5-yl}-1H-indol-4-ol; 3-[2-(trimethylazaniumyl)ethyl]-2-{3-[2-(dimethylazaniumyl)ethyl]-4-hydroxy-1H-indol-5-yl}-1H-indol-4-ol; 3-[2-(dimethylazaniumyl)ethyl]-2-{3-[2-(trimethylazaniumyl)ethyl]-4-hydroxy-1H-indol-7-yl}-1H-indol-4-ol; 3-[2-(trimethylazaniumyl)ethyl]-2-{3-[2-(dimethylazaniumyl)ethyl]-4-hydroxy-1H-indol-7-yl}-1H-indol-4-ol; 3-[2-(dimethylazaniumyl)ethyl]-5-{3-[2-(trimethylazaniumyl)

ethyl]-4-hydroxy-1H-indol-5-yl}-1H-indol-4-ol; 3-[2-(dimethylazaniumyl)ethyl]-5-{3-[2-(trimethylazaniumyl)ethyl]-4-hydroxy-1H-indol-7-yl}-1H-indol-4-ol; 3-[2-(trimethylazaniumyl)ethyl]-5-{3-[2-(dimethylazaniumyl)ethyl]-4-hydroxy-1H-indol-7-yl}-1H-indol-4-ol; and 3-[2-(dimethylazaniumyl)ethyl]-7-{3-[2-(trimethylazaniumyl)ethyl]-4-hydroxy-1H-indol-7-yl}-1H-indol-4-ol.

In some embodiments, the oxidized diol dimers of 4-hydroxy-TMT and psilocin comprise 3-[2-(dimethylazaniumyl)ethyl]-2-{3-[2-(trimethylazaniumyl)ethyl]-4-hydroxy-1H-indol-2-yl}-1H-indol-4-ol.

In some embodiments, the oxidized diol dimers of 4-hydroxy-TMT and psilocin comprise 3-[2-(dimethylazaniumyl)ethyl]-5-{3-[2-(trimethylazaniumyl)ethyl]-4-hydroxy-1H-indol-5-yl}-1H-indol-4-ol.

In some embodiments, the oxidized diol dimers of 4-hydroxy-TMT and psilocin comprise 3-[2-(dimethylazaniumyl)ethyl]-7-{3-[2-(trimethylazaniumyl)ethyl]-4-hydroxy-1H-indol-7-yl}-1H-indol-4-ol.

Either (i) the laccase enzyme is capable of oxidizing the one or more oxidized diol dimers of psilocin into one or more oxidized ylidene dimers of psilocin, (ii) the one or more oxidized diol dimers of psilocin can undergo spontaneous oxidation into one or more oxidized ylidene dimers of psilocin, or (iii) both (i) and (ii).

In some embodiments, the laccase enzyme is capable of catalyzing at least one reaction that oxidizes the psilocin into the one or more oxidized ylidene dimers of psilocin. For example, the laccase enzyme may be capable of oxidizing the psilocin into the one or more oxidized diol dimers of psilocin, which can then undergo further enzymatic or spontaneous oxidation into the one or more oxidized ylidene dimers of psilocin.

In some embodiments, the composition comprises the psilocin and the one or more oxidized ylidene dimers of psilocin at a mole ratio of at least 5:1 (psilocin:oxidized ylidene dimers). In some specific embodiments, the composition comprises the psilocin and the one or more oxidized ylidene dimers of psilocin at a mole ratio of at least 10:1. In some even more specific embodiments, the composition comprises the psilocin and the one or more oxidized ylidene dimers of psilocin at a mole ratio of at least 84:1. In some very specific embodiments, the composition comprises the psilocin and the one or more oxidized ylidene dimers of psilocin at a mole ratio of at least 756:1.

In some embodiments, the mole ratio for the psilocin and the oxidized ylidene dimers of psilocin in the composition is indicative of effective denaturation of the polypeptide to inhibit laccase enzyme activity relative to a lower mole ratio. In some specific embodiments, the mole ratio of at least 5:1 for the psilocin and the oxidized ylidene dimers of psilocin is indicative of effective denaturation of the polypeptide to inhibit laccase enzyme activity relative to a lower mole ratio of less than 5:1. In some specific embodiments, the mole ratio of at least 10:1 for the psilocin and the oxidized ylidene dimers of psilocin is indicative of effective denaturation of the polypeptide to inhibit laccase enzyme activity relative to a lower mole ratio of less than 10:1. In some specific embodiments, the mole ratio of at least 84:1 for the psilocin and the oxidized ylidene dimers of psilocin is indicative of effective denaturation of the polypeptide to inhibit laccase enzyme activity relative to a lower mole ratio of less than 84:1. In some specific embodiments, the mole ratio of at least 756:1 for the psilocin and the oxidized ylidene dimers of psilocin is indicative of effective denaturation of the polypeptide to inhibit laccase enzyme activity relative to a lower mole ratio of less than 756:1.

In some embodiments, each of the one or more oxidized ylidene dimers of psilocin is a dication that comprises two monocationic azaniumyl groups such that each of the one or more oxidized ylidene dimers of psilocin has an approximate molecular weight of 407 atomic mass units.

In some embodiments, the one or more oxidized ylidene dimers of psilocin are selected from 3-[2-(dimethylazaniumyl)ethyl]-2-{3-[2-(dimethylazaniumyl)ethyl]-4-oxo-1H-indol-2-ylidene}-1H-indol-4-one; 3-[2-(dimethylazaniumyl)ethyl]-2-{3-[2-(dimethylazaniumyl)ethyl]-4-oxo-1H-indol-5-ylidene}-1H-indol-4-one; 3-[2-(dimethylazaniumyl)ethyl]-2-{3-[2-(dimethylazaniumyl)ethyl]-4-oxo-1H-indol-7-ylidene}-1H-indol-4-one; 3-[2-(dimethylazaniumyl)ethyl]-5-{3-[2-(dimethylazaniumyl)ethyl]-4-oxo-1H-indol-5-ylidene}-1H-indol-4-one; 3-[2-(dimethylazaniumyl)ethyl]-5-{3-[2-(dimethylazaniumyl)ethyl]-4-oxo-1H-indol-7-ylidene}-1H-indol-4-one; 3-[2-(dimethylazaniumyl)ethyl]-7-{3-[2-(dimethylazaniumyl)ethyl]-4-oxo-1H-indol-7-ylidene}-1H-indol-4-one; and tautomers of the foregoing; and the tautomers consist of 3-[2-(dimethylazaniumyl)ethyl]-2-{3-[2-(dimethylazaniumyl)ethyl]-4-hydroxyindol-2-ylidene}-1H-indol-4-one; 3-[2-(dimethylazaniumyl)ethyl]-2-{3-[2-(dimethylazaniumyl)ethyl]-4-hydroxy-1H-indol-2-yl}indol-4-one; 3-[2-(dimethylazaniumyl)ethyl]-2-{3-[2-(dimethylazaniumyl)ethyl]-4-hydroxyindol-2-ylidene}indol-4-ol; 3-[2-(dimethylazaniumyl)ethyl]-2-{3-[2-(dimethylazaniumyl)ethyl]-4-hydroxyindol-5-ylidene}-1H-indol-4-one; 3-[2-(dimethylazaniumyl)ethyl]-5-{3-[2-(dimethylazaniumyl)ethyl]-4-hydroxyindol-2-ylidene}-1H-indol-4-one; 3-[2-(dimethylazaniumyl)ethyl]-2-{3-[2-(dimethylazaniumyl)ethyl]-4-hydroxy-1H-indol-5-yl}indol-4-one; 3-[2-(dimethylazaniumyl)ethyl]-5-{3-[2-(dimethylazaniumyl)ethyl]-4-hydroxy-1H-indol-2-yl}indol-4-one; 3-[2-(dimethylazaniumyl)ethyl]-2-{3-[2-(dimethylazaniumyl)ethyl]-4-hydroxyindol-5-ylidene}indol-4-ol; 3-[2-(dimethylazaniumyl)ethyl]-2-{3-[2-(dimethylazaniumyl)ethyl]-4-hydroxyindol-7-ylidene}-1H-indol-4-one; 3-[2-(dimethylazaniumyl)ethyl]-7-{3-[2-(dimethylazaniumyl)ethyl]-4-hydroxyindol-2-ylidene}-1H-indol-4-one; 3-[2-(dimethylazaniumyl)ethyl]-2-{3-[2-(dimethylazaniumyl)ethyl]-4-hydroxy-1H-indol-7-yl}indol-4-one; 3-[2-(dimethylazaniumyl)ethyl]-7-{3-[2-(dimethylazaniumyl)ethyl]-4-hydroxy-1H-indol-2-yl}indol-4-one; 3-[2-(dimethylazaniumyl)ethyl]-2-{3-[2-(dimethylazaniumyl)ethyl]-4-hydroxyindol-7-ylidene}indol-4-ol; 3-[2-(dimethylazaniumyl)ethyl]-5-{3-[2-(dimethylazaniumyl)ethyl]-4-hydroxyindol-5-ylidene}-1H-indol-4-one; 3-[2-(dimethylazaniumyl)ethyl]-5-{3-[2-(dimethylazaniumyl)ethyl]-4-hydroxy-1H-indol-5-yl}indol-4-one; 3-[2-(dimethylazaniumyl)ethyl]-5-{3-[2-(dimethylazaniumyl)ethyl]-4-hydroxyindol-5-ylidene}indol-4-ol; 3-[2-(dimethylazaniumyl)ethyl]-5-{3-[2-(dimethylazaniumyl)ethyl]-4-hydroxyindol-7-ylidene}-1H-indol-4-one; 3-[2-(dimethylazaniumyl)ethyl]-7-{3-[2-(dimethylazaniumyl)ethyl]-4-hydroxyindol-5-ylidene}-1H-indol-4-one; 3-[2-(dimethylazaniumyl)ethyl]-5-{3-[2-(dimethylazaniumyl)ethyl]-4-hydroxy-1H-indol-7-yl}indol-4-one; 3-[2-(dimethylazaniumyl)ethyl]-7-{3-[2-(dimethylazaniumyl)ethyl]-4-hydroxy-1H-indol-5-yl}indol-4-one; 3-[2-(dimethylazaniumyl)ethyl]-5-{3-[2-(dimethylazaniumyl)ethyl]-4-hydroxyindol-7-ylidene}indol-4-ol; 3-[2-(dimethylazaniumyl)ethyl]-7-{3-[2-(dimethylazaniumyl)ethyl]-4-hydroxyindol-7-ylidene}-1H-indol-4-one; 3-[2-(dimethylazaniumyl)ethyl]-7-{3-[2-(dimethylazaniumyl)ethyl]-4-hydroxy-1H-indol-7-yl}indol-4-one; and 3-[2-

(dimethylazaniumyl)ethyl]-7-{3-[2-(dimethylazaniumyl) ethyl]-4-hydroxyindol-7-ylidene}indol-4-ol.

In some embodiments, the oxidized ylidene dimers of psilocin comprise 3-[2-(dimethylazaniumyl)ethyl]-2-{3-[2-(dimethylazaniumyl)ethyl]-4-hydroxyindol-2-ylidene}indol-4-ol or a tautomer thereof.

In some embodiments, the oxidized ylidene dimers of psilocin comprise 3-[2-(dimethylazaniumyl)ethyl]-5-{3-[2-(dimethylazaniumyl)ethyl]-4-hydroxyindol-5-ylidene}indol-4-ol or a tautomer thereof.

In some embodiments, the oxidized ylidene dimers of psilocin comprise 3-[2-(dimethylazaniumyl)ethyl]-7-{3-[2-(dimethylazaniumyl)ethyl]-4-hydroxyindol-7-ylidene}indol-4-ol or a tautomer thereof.

Either (i) the laccase enzyme is capable of oxidizing the one or more oxidized diol dimers of norpsilocin and psilocin into one or more oxidized ylidene dimers of norpsilocin and psilocin, (ii) the one or more oxidized diol dimers of norpsilocin and psilocin can undergo spontaneous oxidation into one or more oxidized ylidene dimers of norpsilocin and psilocin, or (iii) both (i) and (ii).

In some embodiments, the laccase enzyme is capable of catalyzing at least one reaction that oxidizes the norpsilocin into the one or more oxidized ylidene dimers of norpsilocin and psilocin. For example, the laccase enzyme may be capable of oxidizing the norpsilocin into the one or more oxidized diol dimers of norpsilocin and psilocin, which can then undergo further enzymatic or spontaneous oxidation into the one or more oxidized ylidene dimers of norpsilocin and psilocin.

In some embodiments, the composition comprises the norpsilocin and the one or more oxidized ylidene dimers of norpsilocin and psilocin at a mole ratio of at least 5:1 (norpsilocin:oxidized ylidene dimers of norpsilocin and psilocin). In some specific embodiments, the composition comprises the norpsilocin and the one or more oxidized ylidene dimers of norpsilocin and psilocin at a mole ratio of at least 10:1. In some even more specific embodiments, the composition comprises the norpsilocin and the one or more oxidized ylidene dimers of norpsilocin and psilocin at a mole ratio of at least 84:1. In some very specific embodiments, the composition comprises the norpsilocin and the one or more oxidized ylidene dimers of norpsilocin and psilocin at a mole ratio of at least 756:1.

In some embodiments, the mole ratio for the norpsilocin and the oxidized ylidene dimers of norpsilocin and psilocin in the composition is indicative of effective denaturation of the polypeptide to inhibit laccase enzyme activity relative to a lower mole ratio. In some specific embodiments, the mole ratio of at least 5:1 for the norpsilocin and the oxidized ylidene dimers of norpsilocin and psilocin is indicative of effective denaturation of the polypeptide to inhibit laccase enzyme activity relative to a lower mole ratio of less than 5:1. In some specific embodiments, the mole ratio of at least 10:1 for the norpsilocin and the oxidized ylidene dimers of norpsilocin and psilocin is indicative of effective denaturation of the polypeptide to inhibit laccase enzyme activity relative to a lower mole ratio of less than 10:1. In some specific embodiments, the mole ratio of at least 84:1 for the norpsilocin and the oxidized ylidene dimers of norpsilocin and psilocin is indicative of effective denaturation of the polypeptide to inhibit laccase enzyme activity relative to a lower mole ratio of less than 84:1. In some specific embodiments, the mole ratio of at least 756:1 for the norpsilocin and the oxidized ylidene dimers of norpsilocin and psilocin is indicative of effective denaturation of the polypeptide to inhibit laccase enzyme activity relative to a lower mole ratio of less than 756:1.

In some embodiments, each of the one or more oxidized ylidene dimers of norpsilocin and psilocin is a dication that comprises two monocationic azaniumyl groups such that each of the one or more oxidized ylidene dimers of norpsilocin and psilocin has an approximate molecular weight of 392 atomic mass units.

In some embodiments, the one or more oxidized ylidene dimers of norpsilocin and psilocin are selected from 3-[2-(dimethylazaniumyl)ethyl]-2-{3-[2-(methylazaniumyl) ethyl]-4-oxo-1H-indol-2-ylidene}-1H-indol-4-one; 3-[2-(dimethylazaniumyl)ethyl]-2-{3-[2-(methylazaniumyl)ethyl]-4-oxo-1H-indol-5-ylidene}-1H-indol-4-one; 3-[2-(methylazaniumyl)ethyl]-2-{3-[2-(dimethylazaniumyl) ethyl]-4-oxo-1H-indol-5-ylidene}-1H-indol-4-one; 3-[2-(dimethylazaniumyl)ethyl]-2-{3-[2-(methylazaniumyl) ethyl]-4-oxo-1H-indol-7-ylidene}-1H-indol-4-one; 3-[2-(methylazaniumyl)ethyl]-2-{3-[2-(dimethylazaniumyl) ethyl]-4-oxo-1H-indol-7-ylidene}-1H-indol-4-one; 3-[2-(dimethylazaniumyl)ethyl]-5-{3-[2-(methylazaniumyl) ethyl]-4-oxo-1H-indol-5-ylidene}-1H-indol-4-one; 3-[2-(dimethylazaniumyl)ethyl]-5-{3-[2-(methylazaniumyl) ethyl]-4-oxo-1H-indol-7-ylidene}-1H-indol-4-one; 3-[2-(methylazaniumyl)ethyl]-5-{3-[2-(dimethylazaniumyl) ethyl]-4-oxo-1H-indol-7-ylidene}-1H-indol-4-one; 3-[2-(dimethylazaniumyl)ethyl]-7-{3-[2-(methylazaniumyl) ethyl]-4-oxo-1H-indol-7-ylidene}-1H-indol-4-one; and tautomers of the foregoing.

The tautomers of 3-[2-(dimethylazaniumyl)ethyl]-2-{3-[2-(methylazaniumyl)ethyl]-4-oxo-1H-indol-2-ylidene}-1H-indol-4-one include 3-[2-(dimethylazaniumyl)ethyl]-2-{3-[2-(methylazaniumyl)ethyl]-4-hydroxyindol-2-ylidene}indol-4-ol. In some embodiments, the oxidized ylidene dimers of norpsilocin and psilocin comprise 3-[2-(dimethylazaniumyl)ethyl]-2-{3-[2-(methylazaniumyl) ethyl]-4-hydroxyindol-2-ylidene}indol-4-ol or a tautomer thereof.

The tautomers of 3-[2-(dimethylazaniumyl)ethyl]-5-{3-[2-(methylazaniumyl)ethyl]-4-oxo-1H-indol-5-ylidene}-1H-indol-4-one include 3-[2-(dimethylazaniumyl)ethyl]-5-{3-[2-(methylazaniumyl)ethyl]-4-hydroxyindol-5-ylidene}indol-4-ol. In some embodiments, the oxidized ylidene dimers of norpsilocin and psilocin comprise 3-[2-(dimethylazaniumyl)ethyl]-5-{3-[2-(methylazaniumyl) ethyl]-4-hydroxyindol-5-ylidene}indol-4-ol or a tautomer thereof.

The tautomers of 3-[2-(dimethylazaniumyl)ethyl]-7-{3-[2-(methylazaniumyl)ethyl]-4-oxo-1H-indol-7-ylidene}-1H-indol-4-one include 3-[2-(dimethylazaniumyl)ethyl]-7-{3-[2-(methylazaniumyl)ethyl]-4-hydroxyindol-7-ylidene}indol-4-ol. In some embodiments, the oxidized ylidene dimers of norpsilocin and psilocin comprise 3-[2-(dimethylazaniumyl)ethyl]-7-{3-[2-(methylazaniumyl) ethyl]-4-hydroxyindol-7-ylidene}indol-4-ol or a tautomer thereof.

Either (i) the laccase enzyme is capable of oxidizing the one or more oxidized diol dimers of 4-HT and psilocin into one or more oxidized ylidene dimers of 4-HT and psilocin, (ii) the one or more oxidized diol dimers of 4-HT and psilocin can undergo spontaneous oxidation into one or more oxidized ylidene dimers of 4-HT and psilocin, or (iii) both (i) and (ii).

In some embodiments, the laccase enzyme is capable of catalyzing at least one reaction that oxidizes the 4-HT into the one or more oxidized ylidene dimers of 4-HT and psilocin. For example, the laccase enzyme may be capable of oxidizing the 4-HT into the one or more oxidized diol dimers of 4-HT and psilocin, which can then undergo further enzymatic or spontaneous oxidation into the one or more oxidized ylidene dimers of 4-HT and psilocin.

In some embodiments, the composition comprises the 4-HT and the one or more oxidized ylidene dimers of 4-HT and psilocin at a mole ratio of at least 5:1 (4-HT:oxidized ylidene dimers of 4-HT and psilocin). In some specific embodiments, the composition comprises the 4-HT and the one or more oxidized ylidene dimers of 4-HT and psilocin at a mole ratio of at least 10:1. In some even more specific embodiments, the composition comprises the 4-HT and the one or more oxidized ylidene dimers of 4-HT and psilocin at a mole ratio of at least 84:1. In some very specific embodiments, the composition comprises the 4-HT and the one or more oxidized ylidene dimers of 4-HT and psilocin at a mole ratio of at least 756:1.

In some embodiments, the mole ratio for the 4-HT and the oxidized ylidene dimers of 4-HT and psilocin in the composition is indicative of effective denaturation of the polypeptide to inhibit laccase enzyme activity relative to a lower mole ratio. In some specific embodiments, the mole ratio of at least 5:1 for the 4-HT and the oxidized ylidene dimers of 4-HT and psilocin is indicative of effective denaturation of the polypeptide to inhibit laccase enzyme activity relative to a lower mole ratio of less than 5:1. In some specific embodiments, the mole ratio of at least 10:1 for the 4-HT and the oxidized ylidene dimers of 4-HT and psilocin is indicative of effective denaturation of the polypeptide to inhibit laccase enzyme activity relative to a lower mole ratio of less than 10:1. In some specific embodiments, the mole ratio of at least 84:1 for the 4-HT and the oxidized ylidene dimers of 4-HT and psilocin is indicative of effective denaturation of the polypeptide to inhibit laccase enzyme activity relative to a lower mole ratio of less than 84:1. In some specific embodiments, the mole ratio of at least 756:1 for the 4-HT and the oxidized ylidene dimers of 4-HT and psilocin is indicative of effective denaturation of the polypeptide to inhibit laccase enzyme activity relative to a lower mole ratio of less than 756:1.

In some embodiments, each of the one or more oxidized ylidene dimers of 4-HT and psilocin is a dication that comprises two monocationic azaniumyl groups such that each of the one or more oxidized ylidene dimers of 4-HT and psilocin has an approximate molecular weight of 378 atomic mass units.

In some embodiments, the one or more oxidized ylidene dimers of 4-HT and psilocin are selected from 3-[2-(dimethylazaniumyl)ethyl]-2-[3-(2-azaniumylethyl)-4-oxo-1H-indol-2-ylidene]-1H-indol-4-one; 3-[2-(dimethylazaniumyl)ethyl]-2-[3-(2-azaniumylethyl)-4-oxo-1H-indol-5-ylidene]-1H-indol-4-one; 3-(2-azaniumylethyl)-2-{3-[2-(dimethylazaniumyl)ethyl]-4-oxo-1H-indol-5-ylidene}-1H-indol-4-one; 3-[2-(dimethylazaniumyl)ethyl]-2-[3-(2-azaniumylethyl)-4-oxo-1H-indol-7-ylidene]-1H-indol-4-one; 3-(2-azaniumylethyl)-2-{3-[2-(dimethylazaniumyl)ethyl]-4-oxo-1H-indol-7-ylidene}-1H-indol-4-one; 3-[2-(dimethylazaniumyl)ethyl]-5-[3-(2-azaniumylethyl)-4-oxo-1H-indol-5-ylidene]-1H-indol-4-one; 3-[2-(dimethylazaniumyl)ethyl]-5-[3-(2-azaniumylethyl)-4-oxo-1H-indol-7-ylidene]-1H-indol-4-one; 3-(2-azaniumylethyl)-5-{3-[2-(dimethylazaniumyl)ethyl]-4-oxo-1H-indol-7-ylidene}-1H-indol-4-one; 3-[2-(dimethylazaniumyl)ethyl]-7-[3-(2-azaniumylethyl)-4-oxo-1H-indol-7-ylidene]-1H-indol-4-one; and tautomers of the foregoing.

The tautomers of 3-[2-(dimethylazaniumyl)ethyl]-2-[3-(2-azaniumylethyl)-4-oxo-1H-indol-2-ylidene]-1H-indol-4-one include 3-[2-(dimethylazaniumyl)ethyl]-2-[3-(2-azaniumylethyl)-4-hydroxyindol-2-ylidene]indol-4-ol. In some embodiments, the oxidized ylidene dimers of 4-HT and psilocin comprise 3-[2-(dimethylazaniumyl)ethyl]-2-[3-(2-azaniumylethyl)-4-hydroxyindol-2-ylidene]indol-4-ol or a tautomer thereof.

The tautomers of 3-[2-(dimethylazaniumyl)ethyl]-5-[3-(2-azaniumylethyl)-4-oxo-1H-indol-5-ylidene]-1H-indol-4-one include 3-[2-(dimethylazaniumyl)ethyl]-5-[3-(2-azaniumylethyl)-4-hydroxyindol-5-ylidene]indol-4-ol. In some embodiments, the oxidized ylidene dimers of 4-HT and psilocin comprise 3-[2-(dimethylazaniumyl)ethyl]-5-[3-(2-azaniumylethyl)-4-hydroxyindol-5-ylidene]indol-4-ol or a tautomer thereof.

The tautomers of 3-[2-(dimethylazaniumyl)ethyl]-7-[3-(2-azaniumylethyl)-4-oxo-1H-indol-7-ylidene]-1H-indol-4-one include 3-[2-(dimethylazaniumyl)ethyl]-7-[3-(2-azaniumylethyl)-4-hydroxyindol-7-ylidene]indol-4-ol. In some embodiments, the oxidized ylidene dimers of 4-HT and psilocin comprise 3-[2-(dimethylazaniumyl)ethyl]-7-[3-(2-azaniumylethyl)-4-hydroxyindol-7-ylidene]indol-4-ol or a tautomer thereof.

Either (i) the laccase enzyme is capable of oxidizing the one or more oxidized diol dimers of 4-hydroxy-TMT and psilocin into one or more oxidized ylidene dimers of 4-hydroxy-TMT and psilocin, (ii) the one or more oxidized diol dimers of 4-hydroxy-TMT and psilocin can undergo spontaneous oxidation into one or more oxidized ylidene dimers of 4-hydroxy-TMT and psilocin, or (iii) both (i) and (ii).

In some embodiments, the laccase enzyme is capable of catalyzing at least one reaction that oxidizes the 4-hydroxy-TMT into the one or more oxidized ylidene dimers of 4-hydroxy-TMT and psilocin. For example, the laccase enzyme may be capable of oxidizing the 4-hydroxy-TMT into the one or more oxidized diol dimers of 4-hydroxy-TMT and psilocin, which can then undergo further enzymatic or spontaneous oxidation into the one or more oxidized ylidene dimers of 4-hydroxy-TMT and psilocin.

In some embodiments, the composition comprises the 4-hydroxy-TMT and the one or more oxidized ylidene dimers of 4-hydroxy-TMT and psilocin at a mole ratio of at least 5:1 (4-hydroxy-TMT:oxidized ylidene dimers of 4-hydroxy-TMT and psilocin). In some specific embodiments, the composition comprises the 4-hydroxy-TMT and the one or more oxidized ylidene dimers of 4-hydroxy-TMT and psilocin at a mole ratio of at least 10:1. In some even more specific embodiments, the composition comprises the 4-hydroxy-TMT and the one or more oxidized ylidene dimers of 4-hydroxy-TMT and psilocin at a mole ratio of at least 84:1. In some very specific embodiments, the composition comprises the 4-hydroxy-TMT and the one or more oxidized ylidene dimers of 4-hydroxy-TMT and psilocin at a mole ratio of at least 756:1.

In some embodiments, the mole ratio for the 4-hydroxy-TMT and the oxidized ylidene dimers of 4-hydroxy-TMT and psilocin in the composition is indicative of effective denaturation of the polypeptide to inhibit laccase enzyme activity relative to a lower mole ratio. In some specific embodiments, the mole ratio of at least 5:1 for the 4-hydroxy-TMT and the oxidized ylidene dimers of 4-hydroxy-TMT and psilocin is indicative of effective denaturation of the polypeptide to inhibit laccase enzyme activity relative to a lower mole ratio of less than 5:1. In some specific embodiments, the mole ratio of at least 10:1 for the 4-hydroxy-TMT and the oxidized ylidene dimers of 4-hydroxy- TMT and psilocin is indicative of effective denaturation of the polypeptide to inhibit laccase enzyme activity relative to a lower mole ratio of less than 10:1. In some specific embodiments, the mole ratio of at least 84:1 for the 4-hydroxy-TMT and the oxidized ylidene dimers of 4-hydroxy-TMT and psilocin is indicative of effective denaturation of the polypeptide to inhibit laccase enzyme activity relative to a lower mole ratio of less than 84:1. In some specific embodiments, the mole ratio of at least 756:1 for the 4-hydroxy-TMT and the oxidized ylidene dimers of 4-hydroxy-TMT and psilocin is indicative of effective denaturation of the polypeptide to inhibit laccase enzyme activity relative to a lower mole ratio of less than 756:1.

In some embodiments, each of the one or more oxidized ylidene dimers of 4-hydroxy-TMT and psilocin is a dication that comprises two monocationic azaniumyl groups such that each of the one or more oxidized ylidene dimers of 4-hydroxy-TMT and psilocin has an approximate molecular weight of 421 atomic mass units.

In some embodiments, the one or more oxidized ylidene dimers of 4-hydroxy-TMT and psilocin are selected from 3-[2-(dimethylazaniumyl)ethyl]-2-{3-[2-(trimethylazaniumyl)ethyl]-4-oxo-1H-indol-2-ylidene}-1H-indol-4-one; 3-[2-(dimethylazaniumyl)ethyl]-2-{3-[2-(trimethylazaniumyl)ethyl]-4-oxo-1H-indol-5-ylidene}-1H-indol-4-one; 3-[2-(trimethylazaniumyl)ethyl]-2-{3-[2-(dimethylazaniumyl)ethyl]-4-oxo-1H-indol-5-ylidene}-1H-indol-4-one; 3-[2-(dimethylazaniumyl)ethyl]-2-{3-[2-(trimethylazaniumyl)ethyl]-4-oxo-1H-indol-7-ylidene}-1H-indol-4-one; 3-[2-(trimethylazaniumyl)ethyl]-2-{3-[2-(dimethylazaniumyl)ethyl]-4-oxo-1H-indol-7-ylidene}-1H-indol-4-one; 3-[2-(dimethylazaniumyl)ethyl]-5-{3-[2-(trimethylazaniumyl)ethyl]-4-oxo-1H-indol-5-ylidene}-1H-indol-4-one; 3-[2-(dimethylazaniumyl)ethyl]-5-{3-[2-(trimethylazaniumyl)ethyl]-4-oxo-1H-indol-7-ylidene}-1H-indol-4-one; 3-[2-(trimethylazaniumyl)ethyl]-5-{3-[2-(dimethylazaniumyl)ethyl]-4-oxo-1H-indol-7-ylidene}-1H-indol-4-one; 3-[2-(dimethylazaniumyl)ethyl]-7-{3-[2-(trimethylazaniumyl)ethyl]-4-oxo-1H-indol-7-ylidene}-1H-indol-4-one; and tautomers of the foregoing.

The tautomers of 3-[2-(dimethylazaniumyl)ethyl]-2-{3-[2-(trimethylazaniumyl)ethyl]-4-oxo-1H-indol-2-ylidene}-1H-indol-4-one include 3-[2-(dimethylazaniumyl)ethyl]-2-{3-[2-(trimethylazaniumyl)ethyl]-4-hydroxyindol-2-ylidene}indol-4-ol. In some embodiments, the oxidized ylidene dimers of 4-hydroxy-TMT and psilocin comprise 3-[2-(dimethylazaniumyl)ethyl]-2-{3-[2-(trimethylazaniumyl)ethyl]-4-hydroxyindol-2-ylidene}indol-4-ol or a tautomer thereof.

The tautomers of 3-[2-(dimethylazaniumyl)ethyl]-5-{3-[2-(trimethylazaniumyl)ethyl]-4-oxo-1H-indol-5-ylidene}-1H-indol-4-one include 3-[2-(dimethylazaniumyl)ethyl]-5-{3-[2-(trimethylazaniumyl)ethyl]-4-hydroxyindol-5-ylidene}indol-4-ol. In some embodiments, the oxidized ylidene dimers of 4-hydroxy-TMT and psilocin comprise 3-[2-(dimethylazaniumyl)ethyl]-5-{3-[2-(trimethylazaniumyl)ethyl]-4-hydroxyindol-5-ylidene}indol-4-ol or a tautomer thereof.

The tautomers of 3-[2-(dimethylazaniumyl)ethyl]-7-{3-[2-(trimethylazaniumyl)ethyl]-4-oxo-1H-indol-7-ylidene}-1H-indol-4-one include 3-[2-(dimethylazaniumyl)ethyl]-7-{3-[2-(trimethylazaniumyl)ethyl]-4-hydroxyindol-7-ylidene}indol-4-ol. In some embodiments, the oxidized ylidene dimers of 4-hydroxy-TMT and psilocin comprise 3-[2-(dimethylazaniumyl)ethyl]-7-{3-[2-(trimethylazaniumyl)ethyl]-4-hydroxyindol-7-ylidene}indol-4-ol or a tautomer thereof.

In some embodiments, the composition is a product that is produced by a process that comprises providing a starting composition that comprises the tryptamines. In some specific embodiments, the composition is a product that is produced by a process that comprises providing a starting composition that comprises the psilocybin and the psilocin. In some very specific embodiments, the starting composition comprises the baeocystin and the norpsilocin. In some very specific embodiments, the starting composition comprises the norbaeocystin and the 4-HT. In some very specific embodiments, the starting composition comprises the aeruginascin and the 4-hydroxy-TMT.

In some embodiments, the starting composition is fungal material. In some specific embodiments, the starting composition is wet fungal material. In some embodiments the starting composition is dried fungal material. In some very specific embodiments, the process comprises drying wet fungal material with a desiccant (e.g., silica gel, calcium oxide, calcium sulfate, calcium chloride, phosphorus pentoxide, molecular sieves) to produce the starting composition. In some very specific embodiments, the process comprises drying wet fungal material under vacuum to produce the starting composition. In some specific embodiments, the starting composition is lyophilized fungal material. In some very specific embodiments the process comprises lyophilizing wet fungal material to produce the starting composition.

In some embodiments, the process comprises denaturing the laccase enzyme. In some specific embodiments, the process comprises denaturing the laccase enzyme to produce the denatured polypeptide. In some very specific embodiments, the process comprises heating the starting composition to denature the laccase enzyme. In some very specific embodiments, the process comprises combining the starting composition with a chaotrope selected from guanidinium, urea, and ammonium sulfate to denature the laccase enzyme. In some very specific embodiments, the process comprises combining the starting composition with a surfactant such as dodecyl sulfate to denature the laccase enzyme.

In some embodiments, the process comprises denaturing the laccase enzyme to produce an intermediate composition that comprises the denatured polypeptide and the tryptamines. In some specific embodiments, the process comprises denaturing the laccase enzyme to produce an intermediate composition that comprises the denatured polypeptide, the psilocybin, and the psilocin. In some very specific embodiments, the process comprises denaturing the laccase enzyme to produce an intermediate composition that comprises the denatured polypeptide, the psilocybin, the psilocin, the baeocystin, and the norpsilocin. In some very specific embodiments, the process comprises denaturing the laccase enzyme to produce an intermediate composition that comprises the denatured polypeptide, the psilocybin, the psilocin, the norbaeocystin, and the 4-HT. In some very specific embodiments, the process comprises denaturing the laccase enzyme to produce an intermediate composition that comprises the denatured polypeptide, the psilocybin, the psilocin, the aeruginascin, and the 4-hydroxy-TMT.

In some embodiments, the process comprises denaturing the phosphatase enzyme. In some specific embodiments, the process comprises denaturing the phosphatase enzyme to produce the denatured polypeptide. In some very specific embodiments, the process comprises heating the starting composition to denature the phosphatase enzyme. In some very specific embodiments, the process comprises combining the starting composition with a chaotrope selected from guanidinium, urea, and ammonium sulfate to denature the phosphatase enzyme. In some very specific embodiments, the process comprises combining the starting composition with a surfactant such as dodecyl sulfate to denature the phosphatase enzyme.

In some embodiments, the process comprises denaturing the phosphatase enzyme to produce an intermediate composition that comprises the denatured polypeptide and the tryptamines. In some specific embodiments, the process comprises denaturing the phosphatase enzyme to produce an intermediate composition that comprises the denatured polypeptide, the psilocybin, and the psilocin. In some very specific embodiments, the process comprises denaturing the phosphatase enzyme to produce an intermediate composition that comprises the denatured polypeptide, the psilocybin, the psilocin, the baeocystin, and the norpsilocin. In some very specific embodiments, the process comprises denaturing the phosphatase enzyme to produce an intermediate composition that comprises the denatured polypeptide, the psilocybin, the psilocin, the norbaeocystin, and the 4-HT. In some very specific embodiments, the process comprises denaturing the phosphatase enzyme to produce an intermediate composition that comprises the denatured polypeptide, the psilocybin, the psilocin, the aeruginascin, and the 4-hydroxy-TMT.

In some embodiments, the process comprises heating the starting composition to produce the intermediate composition.

In some embodiments, the process comprises combining the starting composition with a chaotrope selected from guanidinium, urea, and ammonium sulfate to produce the intermediate composition.

In some embodiments, the process comprises combining the starting composition with a surfactant such as dodecyl sulfate to produce the intermediate composition.

In some embodiments, the process comprises contacting the starting composition with a Brønsted acid.

In some embodiments, the process comprises combining the intermediate composition with a Brønsted acid.

In some embodiments, the Brønsted acid is selected from formic acid, acetic acid, propionic acid, butyric acid, valeric acid, caproic acid, caprylic acid, sorbic acid, ascorbic acid, erythorbic acid, lactic acid, pyruvic acid, malonic acid, monohydrogen malonate, succinic acid, monohydrogen succinate, adipic acid, monohydrogen adipate, fumaric acid, monohydrogen fumarate, malic acid, monohydrogen malate, tartaric acid, monohydrogen tartrate, citric acid, dihydrogen citrate, monohydrogen citrate, aconitic acid, dihydrogen aconitate, monohydrogen aconitate, thiodipropionic acid, monohydrogen thiodipropionate, cinnamic acid, hydrocinnamic acid, aspartic acid, glutamic acid, aminoacetic acid, hydrochloric acid, sulfuric acid, monohydrogen sulfate, carbonic acid, bicarbonate, phosphoric acid, dihydrogen phosphate, and dihydrogen diphosphate. In some embodiments, the Brønsted acid is selected from orthoboric acid, ammonium, 2-azaniumylethyl(trimethyl)azanium, zwitterionic glycine, 2-azaniumylacetamide, (2-azaniumylacetamido)acetate, 2-[bis(2-hydroxyethyl)]azaniumylacetate, 2-[tris(hydroxymethyl)methyl]azaniumylacetate, [tris(hydroxymethyl)methyl]azanium, 2,2'-[(2-amino-2-oxoethyl)azaniumdiyl]diacetate, 2-[(2-amino-2-oxoethyl)azaniumyl]ethylsulfonate, 2-[bis(2-hydroxyethyl)azaniumyl]ethylsulfonate), 3-[bis(2-hydroxyethyl)azaniumyl]-2-hydroxypropanesulfonate, 2-{[tris(hydroxymethyl)methyl]azaniumyl}ethylsulfonate, 3-{[tris(hydroxymethyl)methyl]azaniumyl}propylsulfonate, 3-{[tris(hydroxymethyl)methyl]azaniumyl}-2-hydroxypropylsulfonate, 2-(morpholinium-4-yl)ethylsulfonate, 3-(morpholinium-4-yl)propylsulfonate, 2-hydroxy-3-(morpholinium-4-yl)propylsulfonate, 2-[4-(2-hydroxyethyl)piperazinium-1-yl]ethylsulfonate, 3-[4-(2-hydroxyethyl)piperazinium-1-yl]propylsulfonate, 3-[4-(2-hydroxyethyl)piperazinium-1-yl]-2-hydroxypropylsulfonate, 1,4-bis(2-sulfonatoethyl)piperazinium, and 1,4-bis(2-hydroxy-3-sulfonatopropyl)piperazinium.

In some embodiments, the starting composition comprises an initial amount of the zwitterionic psilocybin, and the process comprises converting some of the psilocybin of the starting composition into the zwitterionic psilocybin such that the composition comprises a final amount of the zwitterionic psilocybin that is greater than the initial amount of the zwitterionic psilocybin. In some specific embodiments, the starting composition comprises an initial amount of the zwitterionic psilocybin and an initial amount of the anionic psilocybin, and the process comprises converting some of the anionic psilocybin of the starting composition into the zwitterionic psilocybin such that the composition comprises (i) a final amount of the zwitterionic psilocybin that is greater than the initial amount of the zwitterionic psilocybin and (ii) a final amount of the anionic psilocybin that is less than the initial amount of the anionic psilocybin. In some very specific embodiments, converting some of the anionic psilocybin of the starting composition into the zwitterionic psilocybin comprises contacting the anionic psilocybin of the starting composition with a Brønsted acid (such as by contacting an intermediate composition that is produced from the starting composition with the Brønsted acid).

In some embodiments, the process comprises combining the starting composition with a Brønsted acid to convert some of the psilocybin of the starting composition into the zwitterionic psilocybin such that the composition comprises a final amount of the zwitterionic psilocybin that is greater than the initial amount. In some specific embodiments, the process comprises combining the starting composition with a Brønsted acid to convert some of the anionic psilocybin of the starting composition into the zwitterionic psilocybin such that the composition comprises a final amount of the zwitterionic psilocybin that is greater than the initial amount.

In some embodiments, the process comprises concurrently performing (i) denaturing the laccase enzyme, and (ii) converting some of the psilocybin of the starting composition into the zwitterionic psilocybin. In some specific embodiments, the process comprises concurrently performing (i) denaturing the laccase enzyme, and (ii) converting some of the anionic psilocybin of the starting composition into the zwitterionic psilocybin.

In some embodiments, the process comprises concurrently performing (i) denaturing the phosphatase enzyme, and (ii) converting some of the psilocybin of the starting composition into the zwitterionic psilocybin. In some specific embodiments, the process comprises concurrently performing (i) denaturing the phosphatase enzyme, and (ii) converting some of the anionic psilocybin of the starting composition into the zwitterionic psilocybin.

In some embodiments, the process comprises combining the intermediate composition with a Brønsted acid to convert some of the psilocybin of the starting composition into the zwitterionic psilocybin such that the composition comprises a final amount of the zwitterionic psilocybin that is greater than the initial amount. In some specific embodiments, the process comprises combining the intermediate composition with a Brønsted acid to convert some of the anionic psilocybin of the starting composition into the zwitterionic psilocybin such that the composition comprises a final amount of the zwitterionic psilocybin that is greater than the initial amount.

In some embodiments, the psilocybin of the starting composition and/or intermediate composition comprises initial zwitterionic psilocybin. In some specific embodiments, the psilocybin of the starting composition and/or intermediate composition comprises initial zwitterionic psilocybin and initial anionic psilocybin. In some specific embodiments, the psilocybin of the starting composition and/or intermediate composition comprises initial zwitterionic psilocybin and initial cationic psilocybin. In some very specific embodiments, the psilocybin of the starting composition and/or intermediate composition comprises initial zwitterionic psilocybin, initial anionic psilocybin, and initial cationic psilocybin.

In some embodiments, the initial zwitterionic psilocybin has a rate of spontaneous dephosphorylation per mole.

In some embodiments, the initial anionic psilocybin has a rate of spontaneous dephosphorylation per mole.

In some embodiments, the rate of spontaneous dephosphorylation for the initial anionic psilocybin per mole of the initial anionic psilocybin is greater than the rate of spontaneous dephosphorylation for the initial zwitterionic psilocybin per mole of the initial zwitterionic psilocybin.

In some embodiments, the starting composition and/or intermediate composition comprises the initial zwitterionic psilocybin and the initial anionic psilocybin at an initial mole ratio of less than 1:2 (initial zwitterionic psilocybin: initial anionic psilocybin); combining the starting composition and/or intermediate composition with the Brønsted acid converts a portion of the initial anionic psilocybin of the starting composition and/or intermediate composition into a portion of the zwitterionic psilocybin of the composition; and the portion of the initial anionic psilocybin that is converted into the portion of the zwitterionic psilocybin is sufficient to result in the mole ratio of the zwitterionic psilocybin and the anionic psilocybin in the composition of at least 1:2 (zwitterionic psilocybin:anionic psilocybin). Ensuring that the mole ratio of zwitterionic psilocybin and anionic psilocybin remains at or above 1:2 inhibits spontaneous dephosphorylation.

In some embodiments, the starting composition and/or intermediate composition comprises the initial zwitterionic psilocybin and the initial anionic psilocybin at an initial mole ratio of less than 1:1; combining the starting composition and/or intermediate composition with the Brønsted acid converts a portion of the initial anionic psilocybin of the starting composition and/or intermediate composition into a portion of the zwitterionic psilocybin of the composition; and the portion of the initial anionic psilocybin that is converted into the portion of the zwitterionic psilocybin is sufficient to result in the mole ratio of the zwitterionic psilocybin and the anionic psilocybin in the composition of at least 1:1.

In some embodiments, the starting composition and/or intermediate composition comprises the initial zwitterionic psilocybin and the initial anionic psilocybin at an initial mole ratio of less than 3:1; combining the starting composition and/or intermediate composition with the Brønsted acid converts a portion of the initial anionic psilocybin of the starting composition and/or intermediate composition into a portion of the zwitterionic psilocybin of the composition; and the portion of the initial anionic psilocybin that is converted into the portion of the zwitterionic psilocybin is sufficient to result in the mole ratio of the zwitterionic psilocybin and the anionic psilocybin in the composition of at least 3:1.

In some embodiments, the starting composition and/or intermediate composition comprises the initial zwitterionic psilocybin and the initial anionic psilocybin at an initial mole ratio of less than 16:1; combining the starting composition and/or intermediate composition with the Brønsted acid converts a portion of the initial anionic psilocybin of the starting composition and/or intermediate composition into a portion of the zwitterionic psilocybin of the composition; and the portion of the initial anionic psilocybin that is converted into the portion of the zwitterionic psilocybin is sufficient to result in the mole ratio of the zwitterionic psilocybin and the anionic psilocybin in the composition of at least 16:1.

In some embodiments, the initial cationic psilocybin has a rate of spontaneous dephosphorylation per mole.

In some embodiments, the rate of spontaneous dephosphorylation for the initial cationic psilocybin per mole of the initial cationic psilocybin is greater than the rate of spontaneous dephosphorylation for the initial zwitterionic psilocybin per mole of the initial zwitterionic psilocybin.

In some embodiments, the starting composition and/or intermediate composition comprises the initial zwitterionic psilocybin and the initial cationic psilocybin at a mole ratio of at least 15:1 (initial zwitterionic psilocybin:initial cationic psilocybin); combining the starting composition and/or intermediate composition with the Brønsted acid converts a portion of the initial zwitterionic psilocybin of the starting composition and/or intermediate composition into a portion of the cationic psilocybin of the composition; and the portion of the initial zwitterionic psilocybin that is converted into the portion of the cationic psilocybin is insufficient to result in a lower mole ratio of the zwitterionic psilocybin and the cationic psilocybin in the composition that is less than 15:1 (zwitterionic psilocybin:cationic psilocybin). Ensuring that the mole ratio of zwitterionic psilocybin and cationic psilocybin remains at or above 15:1 inhibits spontaneous dephosphorylation.

In some embodiments, the starting composition and/or intermediate composition comprises the initial zwitterionic psilocybin and the initial cationic psilocybin at a mole ratio of at least 240:1; combining the starting composition and/or intermediate composition with the Brønsted acid converts a portion of the initial zwitterionic psilocybin of the starting composition and/or intermediate composition into a portion of the cationic psilocybin of the composition; and the portion of the initial zwitterionic psilocybin that is converted into the portion of the cationic psilocybin is insufficient to result in a lower mole ratio of the zwitterionic psilocybin and the cationic psilocybin in the composition that is less than 240:1.

In some embodiments, the starting composition and/or intermediate composition comprises the initial zwitterionic psilocybin and the initial cationic psilocybin at a mole ratio of at least 3200:1; combining the starting composition and/or intermediate composition with the Brønsted acid converts a portion of the initial zwitterionic psilocybin of the starting composition and/or intermediate composition into a portion of the cationic psilocybin of the composition; and the portion of the initial zwitterionic psilocybin that is converted into the portion of the cationic psilocybin is insufficient to result in a lower mole ratio of the zwitterionic psilocybin and the cationic psilocybin in the composition that is less than 3200:1.

In some embodiments, the starting composition and/or intermediate composition comprises the initial zwitterionic psilocybin and the initial cationic psilocybin at a mole ratio of at least 38,000:1; combining the starting composition and/or intermediate composition with the Brønsted acid converts a portion of the initial zwitterionic psilocybin of the starting composition and/or intermediate composition into a portion of the cationic psilocybin of the composition; and the portion of the initial zwitterionic psilocybin that is converted into the portion of the cationic psilocybin is insufficient to result in a lower mole ratio of the zwitterionic psilocybin and the cationic psilocybin in the composition that is less than 38,000:1.

In some embodiments, the starting composition comprises an initial amount of the zwitterionic baeocystin, and the process comprises converting some of the baeocystin of the starting composition into the zwitterionic baeocystin such that the composition comprises a final amount of the zwitterionic baeocystin that is greater than the initial amount of the zwitterionic baeocystin. In some specific embodiments, the starting composition comprises an initial amount of the zwitterionic baeocystin and an initial amount of the anionic baeocystin, and the process comprises converting some of the anionic baeocystin of the starting composition into the zwitterionic baeocystin such that the composition comprises (i) a final amount of the zwitterionic baeocystin that is greater than the initial amount of the zwitterionic baeocystin and (ii) a final amount of the anionic baeocystin that is less than the initial amount of the anionic baeocystin. In some very specific embodiments, converting some of the anionic baeocystin of the starting composition into the zwitterionic baeocystin comprises contacting the anionic baeocystin of the starting composition with a Brønsted acid (such as by contacting an intermediate composition that is produced from the starting composition with the Brønsted acid).

In some embodiments, the process comprises combining the starting composition with a Brønsted acid to convert some of the baeocystin of the starting composition into the zwitterionic baeocystin such that the composition comprises a final amount of the zwitterionic baeocystin that is greater than the initial amount. In some specific embodiments, the process comprises combining the starting composition with a Brønsted acid to convert some of the anionic baeocystin of the starting composition into the zwitterionic baeocystin such that the composition comprises a final amount of the zwitterionic baeocystin that is greater than the initial amount.

In some embodiments, the process comprises concurrently performing (i) denaturing the laccase enzyme, (ii) converting some of the psilocybin of the starting composition into the zwitterionic psilocybin, and (iii) converting some of the baeocystin of the starting composition into the zwitterionic baeocystin. In some specific embodiments, the process comprises concurrently performing (i) denaturing the laccase enzyme, (ii) converting some of the anionic psilocybin of the starting composition into the zwitterionic psilocybin, and (iii) converting some of the anionic baeocystin of the starting composition into the zwitterionic baeocystin.

In some embodiments, the process comprises concurrently performing (i) denaturing the phosphatase enzyme, (ii) converting some of the psilocybin of the starting composition into the zwitterionic psilocybin, and (iii) converting some of the baeocystin of the starting composition into the zwitterionic baeocystin. In some specific embodiments, the process comprises concurrently performing (i) denaturing the phosphatase enzyme, (ii) converting some of the anionic psilocybin of the starting composition into the zwitterionic psilocybin, and (iii) converting some of the anionic baeocystin of the starting composition into the zwitterionic baeocystin.

In some embodiments, the process comprises combining the intermediate composition with a Brønsted acid to convert some of the baeocystin of the starting composition into the zwitterionic baeocystin such that the composition comprises a final amount of the zwitterionic baeocystin that is greater than the initial amount. In some specific embodiments, the process comprises combining the intermediate composition with a Brønsted acid to convert some of the anionic baeocystin of the starting composition into the zwitterionic baeocystin such that the composition comprises a final amount of the zwitterionic baeocystin that is greater than the initial amount.

In some embodiments, the baeocystin of the starting composition and/or intermediate composition comprises initial zwitterionic baeocystin. In some specific embodiments, the baeocystin of the starting composition and/or intermediate composition comprises initial zwitterionic baeocystin and initial anionic baeocystin. In some specific embodiments, the baeocystin of the starting composition and/or intermediate composition comprises initial zwitterionic baeocystin and initial cationic baeocystin. In some very specific embodiments, the baeocystin of the starting composition and/or intermediate composition comprises initial zwitterionic baeocystin, initial anionic baeocystin, and initial cationic baeocystin.

In some embodiments, the initial zwitterionic baeocystin has a rate of spontaneous dephosphorylation per mole.

In some embodiments, the initial anionic baeocystin has a rate of spontaneous dephosphorylation per mole.

In some embodiments, the rate of spontaneous dephosphorylation for the initial anionic baeocystin per mole of the initial anionic baeocystin is greater than the rate of spontaneous dephosphorylation for the initial zwitterionic baeocystin per mole of the initial zwitterionic baeocystin.

In some embodiments, the starting composition and/or intermediate composition comprises the initial zwitterionic baeocystin and the initial anionic baeocystin at an initial mole ratio of less than 1:2 (initial zwitterionic baeocystin: initial anionic baeocystin); combining the starting composition and/or intermediate composition with the Brønsted acid converts a portion of the initial anionic baeocystin of the starting composition and/or intermediate composition into a portion of the zwitterionic baeocystin of the composition; and the portion of the initial anionic baeocystin that is converted into the portion of the zwitterionic baeocystin is sufficient to result in the mole ratio of the zwitterionic baeocystin and the anionic baeocystin in the composition of at least 1:2 (zwitterionic baeocystin:anionic baeocystin). Ensuring that the mole ratio of zwitterionic baeocystin and anionic baeocystin remains at or above 1:2 inhibits spontaneous dephosphorylation.

In some embodiments, the starting composition and/or intermediate composition comprises the initial zwitterionic baeocystin and the initial anionic baeocystin at an initial mole ratio of less than 1:1; combining the starting composition and/or intermediate composition with the Brønsted acid converts a portion of the initial anionic baeocystin of the starting composition and/or intermediate composition into a portion of the zwitterionic baeocystin of the composition; and the portion of the initial anionic baeocystin that is converted into the portion of the zwitterionic baeocystin is sufficient to result in the mole ratio of the zwitterionic baeocystin and the anionic baeocystin in the composition of at least 1:1.

In some embodiments, the starting composition and/or intermediate composition comprises the initial zwitterionic baeocystin and the initial anionic baeocystin at an initial mole ratio of less than 3:1; combining the starting composition and/or intermediate composition with the Brønsted acid converts a portion of the initial anionic baeocystin of the starting composition and/or intermediate composition into a portion of the zwitterionic baeocystin of the composition; and the portion of the initial anionic baeocystin that is converted into the portion of the zwitterionic baeocystin is sufficient to result in the mole ratio of the zwitterionic baeocystin and the anionic baeocystin in the composition of at least 3:1.

In some embodiments, the starting composition and/or intermediate composition comprises the initial zwitterionic baeocystin and the initial anionic baeocystin at an initial mole ratio of less than 16:1; combining the starting composition and/or intermediate composition with the Brønsted acid converts a portion of the initial anionic baeocystin of the starting composition and/or intermediate composition into a portion of the zwitterionic baeocystin of the composition; and the portion of the initial anionic baeocystin that is converted into the portion of the zwitterionic baeocystin is sufficient to result in the mole ratio of the zwitterionic baeocystin and the anionic baeocystin in the composition of at least 16:1.

In some embodiments, the initial cationic baeocystin has a rate of spontaneous dephosphorylation per mole.

In some embodiments, the rate of spontaneous dephosphorylation for the initial cationic baeocystin per mole of the initial cationic baeocystin is greater than the rate of spontaneous dephosphorylation for the initial zwitterionic baeocystin per mole of the initial zwitterionic baeocystin.

In some embodiments, the starting composition and/or intermediate composition comprises the initial zwitterionic baeocystin and the initial cationic baeocystin at a mole ratio of at least 15:1 (initial zwitterionic baeocystin:initial cationic baeocystin); combining the starting composition and/or intermediate composition with the Brønsted acid converts a portion of the initial zwitterionic baeocystin of the starting composition and/or intermediate composition into a portion of the cationic baeocystin of the composition; and the portion of the initial zwitterionic baeocystin that is converted into the portion of the cationic baeocystin is insufficient to result in a lower mole ratio of the zwitterionic baeocystin and the cationic baeocystin in the composition that is less than 15:1 (zwitterionic baeocystin:cationic baeocystin). Ensuring that the mole ratio of zwitterionic baeocystin and cationic baeocystin remains at or above 15:1 inhibits spontaneous dephosphorylation.

In some embodiments, the starting composition and/or intermediate composition comprises the initial zwitterionic baeocystin and the initial cationic baeocystin at a mole ratio of at least 240:1; combining the starting composition and/or intermediate composition with the Brønsted acid converts a portion of the initial zwitterionic baeocystin of the starting composition and/or intermediate composition into a portion of the cationic baeocystin of the composition; and the portion of the initial zwitterionic baeocystin that is converted into the portion of the cationic baeocystin is insufficient to result in a lower mole ratio of the zwitterionic baeocystin and the cationic baeocystin in the composition that is less than 240:1.

In some embodiments, the starting composition and/or intermediate composition comprises the initial zwitterionic baeocystin and the initial cationic baeocystin at a mole ratio of at least 3200:1; combining the starting composition and/or intermediate composition with the Brønsted acid converts a portion of the initial zwitterionic baeocystin of the starting composition and/or intermediate composition into a portion of the cationic baeocystin of the composition; and the portion of the initial zwitterionic baeocystin that is converted into the portion of the cationic baeocystin is insufficient to result in a lower mole ratio of the zwitterionic baeocystin and the cationic baeocystin in the composition that is less than 3200:1.

In some embodiments, the starting composition and/or intermediate composition comprises the initial zwitterionic baeocystin and the initial cationic baeocystin at a mole ratio of at least 38,000:1; combining the starting composition and/or intermediate composition with the Brønsted acid converts a portion of the initial zwitterionic baeocystin of the starting composition and/or intermediate composition into a portion of the cationic baeocystin of the composition; and the portion of the initial zwitterionic baeocystin that is converted into the portion of the cationic baeocystin is insufficient to result in a lower mole ratio of the zwitterionic baeocystin and the cationic baeocystin in the composition that is less than 38,000:1.

In some embodiments, the starting composition comprises an initial amount of the zwitterionic norbaeocystin, and the process comprises converting some of the norbaeocystin of the starting composition into the zwitterionic norbaeocystin such that the composition comprises a final amount of the zwitterionic norbaeocystin that is greater than the initial amount of the zwitterionic norbaeocystin. In some specific embodiments, the starting composition comprises an initial amount of the zwitterionic norbaeocystin and an initial amount of the anionic norbaeocystin, and the process comprises converting some of the anionic norbaeocystin of the starting composition into the zwitterionic norbaeocystin such that the composition comprises (i) a final amount of the zwitterionic norbaeocystin that is greater than the initial amount of the zwitterionic norbaeocystin and (ii) a final amount of the anionic norbaeocystin that is less than the initial amount of the anionic norbaeocystin. In some very specific embodiments, converting some of the anionic norbaeocystin of the starting composition into the zwitterionic norbaeocystin comprises contacting the anionic norbaeocystin of the starting composition with a Brønsted acid (such as by contacting an intermediate composition that is produced from the starting composition with the Brønsted acid).

In some embodiments, the process comprises combining the starting composition with a Brønsted acid to convert some of the norbaeocystin of the starting composition into the zwitterionic norbaeocystin such that the composition comprises a final amount of the zwitterionic norbaeocystin that is greater than the initial amount. In some specific embodiments, the process comprises combining the starting composition with a Brønsted acid to convert some of the anionic norbaeocystin of the starting composition into the zwitterionic norbaeocystin such that the composition comprises a final amount of the zwitterionic norbaeocystin that is greater than the initial amount.

In some embodiments, the process comprises concurrently performing (i) denaturing the laccase enzyme, (ii) converting some of the psilocybin of the starting composition into the zwitterionic psilocybin, and (iii) converting some of the norbaeocystin of the starting composition into the zwitterionic norbaeocystin. In some specific embodiments, the process comprises concurrently performing (i) denaturing the laccase enzyme, (ii) converting some of the anionic psilocybin of the starting composition into the zwitterionic psilocybin, and (iii) converting some of the anionic norbaeocystin of the starting composition into the zwitterionic norbaeocystin.

In some embodiments, the process comprises concurrently performing (i) denaturing the phosphatase enzyme, (ii) converting some of the psilocybin of the starting composition into the zwitterionic psilocybin, and (iii) converting some of the norbaeocystin of the starting composition into the zwitterionic norbaeocystin. In some specific embodiments, the process comprises concurrently performing (i) denaturing the phosphatase enzyme, (ii) converting some of the anionic psilocybin of the starting composition into the zwitterionic psilocybin, and (iii) converting some of the anionic norbaeocystin of the starting composition into the zwitterionic norbaeocystin.

In some embodiments, the process comprises combining the intermediate composition with a Brønsted acid to convert some of the norbaeocystin of the starting composition into the zwitterionic norbaeocystin such that the composition comprises a final amount of the zwitterionic norbaeocystin that is greater than the initial amount. In some specific embodiments, the process comprises combining the intermediate composition with a Brønsted acid to convert some of the anionic norbaeocystin of the starting composition into the zwitterionic norbaeocystin such that the composition comprises a final amount of the zwitterionic norbaeocystin that is greater than the initial amount.

In some embodiments, the norbaeocystin of the starting composition and/or intermediate composition comprises initial zwitterionic norbaeocystin. In some specific embodiments, the norbaeocystin of the starting composition and/or intermediate composition comprises initial zwitterionic norbaeocystin and initial anionic norbaeocystin. In some specific embodiments, the norbaeocystin of the starting composition and/or intermediate composition comprises initial zwitterionic norbaeocystin and initial cationic norbaeocystin. In some very specific embodiments, the norbaeocystin of the starting composition and/or intermediate composition comprises initial zwitterionic norbaeocystin, initial anionic norbaeocystin, and initial cationic norbaeocystin.

In some embodiments, the initial zwitterionic norbaeocystin has a rate of spontaneous dephosphorylation per mole.

In some embodiments, the initial anionic norbaeocystin has a rate of spontaneous dephosphorylation per mole.

In some embodiments, the rate of spontaneous dephosphorylation for the initial anionic norbaeocystin per mole of the initial anionic norbaeocystin is greater than the rate of spontaneous dephosphorylation for the initial zwitterionic norbaeocystin per mole of the initial zwitterionic norbaeocystin.

In some embodiments, the starting composition and/or intermediate composition comprises the initial zwitterionic norbaeocystin and the initial anionic norbaeocystin at an initial mole ratio of less than 1:2 (initial zwitterionic norbaeocystin:initial anionic norbaeocystin); combining the starting composition and/or intermediate composition with the Brønsted acid converts a portion of the initial anionic norbaeocystin of the starting composition and/or intermediate composition into a portion of the zwitterionic norbaeocystin of the composition; and the portion of the initial anionic norbaeocystin that is converted into the portion of the zwitterionic norbaeocystin is sufficient to result in the mole ratio of the zwitterionic norbaeocystin and the anionic norbaeocystin in the composition of at least 1:2 (zwitterionic norbaeocystin:anionic norbaeocystin). Ensuring that the mole ratio of zwitterionic norbaeocystin and anionic norbaeocystin remains at or above 1:2 inhibits spontaneous dephosphorylation.

In some embodiments, the starting composition and/or intermediate composition comprises the initial zwitterionic norbaeocystin and the initial anionic norbaeocystin at an initial mole ratio of less than 1:1; combining the starting composition and/or intermediate composition with the Brønsted acid converts a portion of the initial anionic norbaeocystin of the starting composition and/or intermediate composition into a portion of the zwitterionic norbaeocystin of the composition; and the portion of the initial anionic norbaeocystin that is converted into the portion of the zwitterionic norbaeocystin is sufficient to result in the mole ratio of the zwitterionic norbaeocystin and the anionic norbaeocystin in the composition of at least 1:1.

In some embodiments, the starting composition and/or intermediate composition comprises the initial zwitterionic norbaeocystin and the initial anionic norbaeocystin at an initial mole ratio of less than 3:1; combining the starting composition and/or intermediate composition with the Brønsted acid converts a portion of the initial anionic norbaeocystin of the starting composition and/or intermediate composition into a portion of the zwitterionic norbaeocystin of the composition; and the portion of the initial anionic norbaeocystin that is converted into the portion of the zwitterionic norbaeocystin is sufficient to result in the mole ratio of the zwitterionic norbaeocystin and the anionic norbaeocystin in the composition of at least 3:1.

In some embodiments, the starting composition and/or intermediate composition comprises the initial zwitterionic norbaeocystin and the initial anionic norbaeocystin at an initial mole ratio of less than 16:1; combining the starting composition and/or intermediate composition with the Brønsted acid converts a portion of the initial anionic norbaeocystin of the starting composition and/or intermediate composition into a portion of the zwitterionic norbaeocystin of the composition; and the portion of the initial anionic norbaeocystin that is converted into the portion of the zwitterionic norbaeocystin is sufficient to result in the mole ratio of the zwitterionic norbaeocystin and the anionic norbaeocystin in the composition of at least 16:1.

In some embodiments, the initial cationic norbaeocystin has a rate of spontaneous dephosphorylation per mole.

In some embodiments, the rate of spontaneous dephosphorylation for the initial cationic norbaeocystin per mole of the initial cationic norbaeocystin is greater than the rate of spontaneous dephosphorylation for the initial zwitterionic norbaeocystin per mole of the initial zwitterionic norbaeocystin.

In some embodiments, the starting composition and/or intermediate composition comprises the initial zwitterionic norbaeocystin and the initial cationic norbaeocystin at a mole ratio of at least 15:1 (initial zwitterionic norbaeocystin: initial cationic norbaeocystin); combining the starting composition and/or intermediate composition with the Brønsted acid converts a portion of the initial zwitterionic norbaeocystin of the starting composition and/or intermediate composition into a portion of the cationic norbaeocystin of the composition; and the portion of the initial zwitterionic norbaeocystin that is converted into the portion of the cationic norbaeocystin is insufficient to result in a lower mole ratio of the zwitterionic norbaeocystin and the cationic norbaeocystin in the composition that is less than 15:1 (zwitterionic norbaeocystin:cationic norbaeocystin). Ensuring that the mole ratio of zwitterionic norbaeocystin and cationic norbaeocystin remains at or above 15:1 inhibits spontaneous dephosphorylation.

In some embodiments, the starting composition and/or intermediate composition comprises the initial zwitterionic norbaeocystin and the initial cationic norbaeocystin at a mole ratio of at least 240:1; combining the starting composition and/or intermediate composition with the Brønsted acid converts a portion of the initial zwitterionic norbaeocystin of the starting composition and/or intermediate composition into a portion of the cationic norbaeocystin of the composition; and the portion of the initial zwitterionic norbaeocystin that is converted into the portion of the cationic norbaeocystin is insufficient to result in a lower mole ratio of the zwitterionic norbaeocystin and the cationic norbaeocystin in the composition that is less than 240:1.

In some embodiments, the starting composition and/or intermediate composition comprises the initial zwitterionic norbaeocystin and the initial cationic norbaeocystin at a mole ratio of at least 3200:1; combining the starting composition and/or intermediate composition with the Brønsted acid converts a portion of the initial zwitterionic norbaeocystin of the starting composition and/or intermediate composition into a portion of the cationic norbaeocystin of the composition; and the portion of the initial zwitterionic norbaeocystin that is converted into the portion of the cationic norbaeocystin is insufficient to result in a lower mole ratio of the zwitterionic norbaeocystin and the cationic norbaeocystin in the composition that is less than 3200:1.

In some embodiments, the starting composition and/or intermediate composition comprises the initial zwitterionic norbaeocystin and the initial cationic norbaeocystin at a mole ratio of at least 38,000:1; combining the starting composition and/or intermediate composition with the Brønsted acid converts a portion of the initial zwitterionic norbaeocystin of the starting composition and/or intermediate composition into a portion of the cationic norbaeocystin of the composition; and the portion of the initial zwitterionic norbaeocystin that is converted into the portion of the cationic norbaeocystin is insufficient to result in a lower mole ratio of the zwitterionic norbaeocystin and the cationic norbaeocystin in the composition that is less than 38,000:1.

In some embodiments, the starting composition comprises an initial amount of the zwitterionic aeruginascin, and the process comprises converting some of the aeruginascin of the starting composition into the zwitterionic aeruginascin such that the composition comprises a final amount of the zwitterionic aeruginascin that is greater than the initial amount of the zwitterionic aeruginascin. In some specific embodiments, the starting composition comprises an initial amount of the zwitterionic aeruginascin and an initial amount of the anionic aeruginascin, and the process comprises converting some of the anionic aeruginascin of the starting composition into the zwitterionic aeruginascin such that the composition comprises (i) a final amount of the zwitterionic aeruginascin that is greater than the initial amount of the zwitterionic aeruginascin and (ii) a final amount of the anionic aeruginascin that is less than the initial amount of the anionic aeruginascin. In some very specific embodiments, converting some of the anionic aeruginascin of the starting composition into the zwitterionic aeruginascin comprises contacting the anionic aeruginascin of the starting composition with a Brønsted acid (such as by contacting an intermediate composition that is produced from the starting composition with the Brønsted acid).

In some embodiments, the process comprises combining the starting composition with a Brønsted acid to convert some of the aeruginascin of the starting composition into the zwitterionic aeruginascin such that the composition comprises a final amount of the zwitterionic aeruginascin that is greater than the initial amount. In some specific embodiments, the process comprises combining the starting composition with a Brønsted acid to convert some of the anionic aeruginascin of the starting composition into the zwitterionic aeruginascin such that the composition comprises a final amount of the zwitterionic aeruginascin that is greater than the initial amount.

In some embodiments, the process comprises concurrently performing (i) denaturing the laccase enzyme, (ii) converting some of the psilocybin of the starting composition into the zwitterionic psilocybin, and (iii) converting some of the aeruginascin of the starting composition into the zwitterionic aeruginascin. In some specific embodiments, the process comprises concurrently performing (i) denaturing the laccase enzyme, (ii) converting some of the anionic psilocybin of the starting composition into the zwitterionic psilocybin, and (iii) converting some of the anionic aeruginascin of the starting composition into the zwitterionic aeruginascin.

In some embodiments, the process comprises concurrently performing (i) denaturing the phosphatase enzyme, (ii) converting some of the psilocybin of the starting composition into the zwitterionic psilocybin, and (iii) converting some of the aeruginascin of the starting composition into the zwitterionic aeruginascin. In some specific embodiments, the process comprises concurrently performing (i) denaturing the phosphatase enzyme, (ii) converting some of the anionic psilocybin of the starting composition into the zwitterionic psilocybin, and (iii) converting some of the anionic aeruginascin of the starting composition into the zwitterionic aeruginascin.

In some embodiments, the process comprises combining the intermediate composition with a Brønsted acid to convert some of the aeruginascin of the starting composition into the zwitterionic aeruginascin such that the composition comprises a final amount of the zwitterionic aeruginascin that is greater than the initial amount. In some specific embodiments, the process comprises combining the intermediate composition with a Brønsted acid to convert some of the anionic aeruginascin of the starting composition into the zwitterionic aeruginascin such that the composition comprises a final amount of the zwitterionic aeruginascin that is greater than the initial amount.

In some embodiments, the aeruginascin of the starting composition and/or intermediate composition comprises initial zwitterionic aeruginascin. In some specific embodiments, the aeruginascin of the starting composition and/or intermediate composition comprises initial zwitterionic aeruginascin and initial anionic aeruginascin. In some specific embodiments, the aeruginascin of the starting composition and/or intermediate composition comprises initial zwitterionic aeruginascin and initial cationic aeruginascin. In some very specific embodiments, the aeruginascin of the starting composition and/or intermediate composition comprises initial zwitterionic aeruginascin, initial anionic aeruginascin, and initial cationic aeruginascin.

In some embodiments, the initial zwitterionic aeruginascin has a rate of spontaneous dephosphorylation per mole.

In some embodiments, the initial anionic aeruginascin has a rate of spontaneous dephosphorylation per mole.

In some embodiments, the rate of spontaneous dephosphorylation for the initial anionic aeruginascin per mole of the initial anionic aeruginascin is greater than the rate of spontaneous dephosphorylation for the initial zwitterionic aeruginascin per mole of the initial zwitterionic aeruginascin.

In some embodiments, the starting composition and/or intermediate composition comprises the initial zwitterionic aeruginascin and the initial anionic aeruginascin at an initial mole ratio of less than 1:2 (initial zwitterionic aeruginascin: initial anionic aeruginascin); combining the starting composition and/or intermediate composition with the Brønsted acid converts a portion of the initial anionic aeruginascin of the starting composition and/or intermediate composition into a portion of the zwitterionic aeruginascin of the composition; and the portion of the initial anionic aeruginascin that is converted into the portion of the zwitterionic aeruginascin is sufficient to result in the mole ratio of the zwitterionic aeruginascin and the anionic aeruginascin in the composition of at least 1:2 (zwitterionic aeruginascin:anionic aeruginascin). Ensuring that the mole ratio of zwitterionic aeruginascin and anionic aeruginascin remains at or above 1:2 inhibits spontaneous dephosphorylation.

In some embodiments, the starting composition and/or intermediate composition comprises the initial zwitterionic aeruginascin and the initial anionic aeruginascin at an initial mole ratio of less than 1:1; combining the starting composition and/or intermediate composition with the Brønsted acid converts a portion of the initial anionic aeruginascin of the starting composition and/or intermediate composition into a portion of the zwitterionic aeruginascin of the composition; and the portion of the initial anionic aeruginascin that is converted into the portion of the zwitterionic aeruginascin is sufficient to result in the mole ratio of the zwitterionic aeruginascin and the anionic aeruginascin in the composition of at least 1:1.

In some embodiments, the starting composition and/or intermediate composition comprises the initial zwitterionic aeruginascin and the initial anionic aeruginascin at an initial mole ratio of less than 3:1; combining the starting composition and/or intermediate composition with the Brønsted acid converts a portion of the initial anionic aeruginascin of the starting composition and/or intermediate composition into a portion of the zwitterionic aeruginascin of the composition; and the portion of the initial anionic aeruginascin that is converted into the portion of the zwitterionic aeruginascin is sufficient to result in the mole ratio of the zwitterionic aeruginascin and the anionic aeruginascin in the composition of at least 3:1.

In some embodiments, the starting composition and/or intermediate composition comprises the initial zwitterionic aeruginascin and the initial anionic aeruginascin at an initial mole ratio of less than 16:1; combining the starting composition and/or intermediate composition with the Brønsted acid converts a portion of the initial anionic aeruginascin of the starting composition and/or intermediate composition into a portion of the zwitterionic aeruginascin of the composition; and the portion of the initial anionic aeruginascin that is converted into the portion of the zwitterionic aeruginascin is sufficient to result in the mole ratio of the zwitterionic aeruginascin and the anionic aeruginascin in the composition of at least 16:1.

In some embodiments, the initial cationic aeruginascin has a rate of spontaneous dephosphorylation per mole.

In some embodiments, the rate of spontaneous dephosphorylation for the initial cationic aeruginascin per mole of the initial cationic aeruginascin is greater than the rate of spontaneous dephosphorylation for the initial zwitterionic aeruginascin per mole of the initial zwitterionic aeruginascin.

In some embodiments, the starting composition and/or intermediate composition comprises the initial zwitterionic aeruginascin and the initial cationic aeruginascin at a mole ratio of at least 15:1 (initial zwitterionic aeruginascin:initial cationic aeruginascin); combining the starting composition and/or intermediate composition with the Brønsted acid converts a portion of the initial zwitterionic aeruginascin of the starting composition and/or intermediate composition into a portion of the cationic aeruginascin of the composition; and the portion of the initial zwitterionic aeruginascin that is converted into the portion of the cationic aeruginascin is insufficient to result in a lower mole ratio of the zwitterionic aeruginascin and the cationic aeruginascin in the composition that is less than 15:1 (zwitterionic aeruginascin: cationic aeruginascin). Ensuring that the mole ratio of zwitterionic aeruginascin and cationic aeruginascin remains at or above 15:1 inhibits spontaneous dephosphorylation.

In some embodiments, the starting composition and/or intermediate composition comprises the initial zwitterionic aeruginascin and the initial cationic aeruginascin at a mole ratio of at least 240:1; combining the starting composition and/or intermediate composition with the Brønsted acid converts a portion of the initial zwitterionic aeruginascin of the starting composition and/or intermediate composition into a portion of the cationic aeruginascin of the composition; and the portion of the initial zwitterionic aeruginascin that is converted into the portion of the cationic aeruginascin is insufficient to result in a lower mole ratio of the zwitterionic aeruginascin and the cationic aeruginascin in the composition that is less than 240:1.

In some embodiments, the starting composition and/or intermediate composition comprises the initial zwitterionic aeruginascin and the initial cationic aeruginascin at a mole ratio of at least 3200:1; combining the starting composition and/or intermediate composition with the Brønsted acid converts a portion of the initial zwitterionic aeruginascin of the starting composition and/or intermediate composition into a portion of the cationic aeruginascin of the composition; and the portion of the initial zwitterionic aeruginascin that is converted into the portion of the cationic aeruginascin is insufficient to result in a lower mole ratio of the zwitterionic aeruginascin and the cationic aeruginascin in the composition that is less than 3200:1.

In some embodiments, the starting composition and/or intermediate composition comprises the initial zwitterionic aeruginascin and the initial cationic aeruginascin at a mole ratio of at least 38,000:1; combining the starting composition and/or intermediate composition with the Brønsted acid converts a portion of the initial zwitterionic aeruginascin of the starting composition and/or intermediate composition into a portion of the cationic aeruginascin of the composition; and the portion of the initial zwitterionic aeruginascin that is converted into the portion of the cationic aeruginascin is insufficient to result in a lower mole ratio of the zwitterionic aeruginascin and the cationic aeruginascin in the composition that is less than 38,000:1.

In some embodiments, the starting composition comprises the one or more oxidized diol dimers of psilocin. In some specific embodiments, the starting composition comprises the one or more oxidized diol dimers of psilocin at the mole ratio of the psilocin and the one or more oxidized diol dimers of psilocin, and the process comprises denaturing the laccase enzyme to inhibit further oxidation of the psilocin into the one or more oxidized diol dimers of psilocin.

In some embodiments, the starting composition comprises the one or more oxidized diol dimers of norpsilocin and psilocin. In some specific embodiments, the starting composition comprises the one or more oxidized diol dimers of norpsilocin and psilocin at the mole ratio of the norpsilocin to the one or more oxidized diol dimers of norpsilocin and psilocin, and the process comprises denaturing the laccase enzyme to inhibit further oxidation of the norpsilocin into the one or more oxidized diol dimers of norpsilocin and psilocin.

In some embodiments, the starting composition comprises the one or more oxidized diol dimers of 4-HT and psilocin. In some specific embodiments, the starting composition comprises the one or more oxidized diol dimers of 4-HT and psilocin at the mole ratio of the 4-HT to the one or more oxidized diol dimers of 4-HT and psilocin, and the process comprises denaturing the laccase enzyme to inhibit further oxidation of the 4-HT into the one or more oxidized diol dimers of 4-HT and psilocin.

In some embodiments, the starting composition comprises the one or more oxidized diol dimers of 4-hydroxy-TMT and psilocin. In some specific embodiments, the starting composition comprises the one or more oxidized diol dimers of 4-hydroxy-TMT and psilocin at the mole ratio of the 4-hydroxy-TMT to the one or more oxidized diol dimers of 4-hydroxy-TMT and psilocin, and the process comprises denaturing the laccase enzyme to inhibit further oxidation of the 4-hydroxy-TMT into the one or more oxidized diol dimers of 4-hydroxy-TMT and psilocin.

In some embodiments, the starting composition comprises the one or more oxidized ylidene dimers of psilocin. In some specific embodiments, the starting composition comprises the one or more oxidized ylidene dimers of psilocin at the mole ratio of the psilocin and the one or more oxidized ylidene dimers of psilocin, and the process comprises denaturing the laccase enzyme to inhibit further oxidation of the psilocin into the one or more oxidized ylidene dimers of psilocin.

In some embodiments, the starting composition comprises the one or more oxidized ylidene dimers of norpsilocin and psilocin. In some specific embodiments, the starting composition comprises the one or more oxidized ylidene dimers of norpsilocin and psilocin at the mole ratio of the norpsilocin to the one or more oxidized ylidene dimers of norpsilocin and psilocin, and the process comprises denaturing the laccase enzyme to inhibit further oxidation of the norpsilocin into the one or more oxidized ylidene dimers of norpsilocin and psilocin.

In some embodiments, the starting composition comprises the one or more oxidized ylidene dimers of 4-HT and psilocin. In some specific embodiments, the starting composition comprises the one or more oxidized ylidene dimers of 4-HT and psilocin at the mole ratio of the 4-HT to the one or more oxidized ylidene dimers of 4-HT and psilocin, and the process comprises denaturing the laccase enzyme to inhibit further oxidation of the 4-HT into the one or more oxidized ylidene dimers of 4-HT and psilocin.

In some embodiments, the starting composition comprises the one or more oxidized ylidene dimers of 4-hydroxy-TMT and psilocin. In some specific embodiments, the starting composition comprises the one or more oxidized ylidene dimers of 4-hydroxy-TMT and psilocin at the mole ratio of the 4-hydroxy-TMT to the one or more oxidized ylidene dimers of 4-hydroxy-TMT and psilocin, and the process comprises denaturing the laccase enzyme to inhibit further oxidation of the 4-hydroxy-TMT into the one or more oxidized ylidene dimers of 4-hydroxy-TMT and psilocin.

Various combinations of the features disclosed herein will be evident to those of ordinary skill, and these combinations are expressly contemplated by the inventors. This disclosure discloses each linguistic and grammatical combination of different features disclosed anywhere in the disclosure as though any specific combination were disclosed in the same sentence. The language and grammar of this disclosure is intentionally selected to explicitly clarify the combinations contemplated by the inventors.

The words "comprising," "comprises," and "comprise" refer to open-ended sets. For example, a composition comprising water can also comprise ethanol.

The phrases "consisting of," "consists of," and "consist of" refer to closed sets. For example, a composition consisting of water cannot also comprise ethanol.

The phrases "some embodiments," "some specific embodiments, "some even more specific embodiments," and "some very specific embodiments" differentiate more generic embodiments from more specific embodiments, and no other meaning shall be ascribed to the four foregoing phrases.

The following examples provide a framework to implement certain aspects of the disclosure, and these examples do not limit the scope of this disclosure or any claim that matures from this disclosure.

EXEMPLIFICATION

Example 1. Anionic and Cationic Phosphoryloxytryptamines Display a Greater Rate of Spontaneous Dephosphorylation than Zwitterionic Phosphoryloxytryptamines Phosphate buffers are prepared by dissolving (A) phosphoric acid and sodium dihydrogen phosphate in distilled, deionized water to a final concentration of 100 millimolar and a pH of 2.0 or 3.0, and (B) sodium dihydrogen phosphate and sodium monohydrogen phosphate in distilled, deionized water to a final concentration of 100 millimolar and a pH of 6.0 or 7.0. 450 microliters of each buffer are added to each of twelve different 1.5 milliliter opaque, polypropylene microcentrifuge tubes (48 different samples).

A fresh stock solution of 100 millimolar psilocybin is prepared by dissolving 57 milligrams of zwitterionic psilocybin in 2 milliliters of distilled, deionized water. 50 microliters of the stock solution is added to three microcentrifuge tubes for each different pH (three replicates for each pH). The microcentrifuge tubes are simultaneously placed in a hot water bath at a temperature of 85 degrees Celsius. After one hour in the hot water bath, the microcentrifuge tubes are placed on ice.

A fresh stock solution of 100 millimolar baeocystin is prepared by dissolving 54 milligrams of zwitterionic baeocystin in 2 milliliters of distilled, deionized water. 50 microliters of the stock solution is added to three microcentrifuge tubes for each different pH (three replicates for each pH). The microcentrifuge tubes are simultaneously placed in a hot water bath at a temperature of 85 degrees Celsius. After one hour in the hot water bath, the microcentrifuge tubes are placed on ice.

A fresh stock solution of 100 millimolar norbaeocystin is prepared by dissolving 51 milligrams of zwitterionic norbaeocystin in 2 milliliters of distilled, deionized water. 50 microliters of the stock solution is added to three microcentrifuge tubes for each different pH (three replicates for each pH). The microcentrifuge tubes are simultaneously placed in a hot water bath at a temperature of 85 degrees Celsius. After one hour in the hot water bath, the microcentrifuge tubes are placed on ice.

A fresh stock solution of 100 millimolar aeruginascin is prepared by dissolving 60 milligrams of zwitterionic aeruginascin in 2 milliliters of distilled, deionized water. 50 microliters of the stock solution is added to three microcentrifuge tubes for each different pH (three replicates for each pH). The microcentrifuge tubes are simultaneously placed in a hot water bath at a temperature of 85 degrees Celsius. After one hour in the hot water bath, the microcentrifuge tubes are placed on ice.

The samples are analyzed on a C18 HPLC column comprising type B silica with a water/acetonitrile gradient buffered with 10 millimolar ammonium formate and formic acid to a pH of about 5.0, and tryptamines are detected by measuring absorbance at 220 nanometers.

Greater absorbance is detected for psilocybin, baeocystin, norbaeocystin, and aeruginascin from the samples at the pH of 6.0 relative to the pH of 7.0, and greater absorbance is detected for psilocin, norpsilocin, 4-HT, and 4-hydroxy-TMT at the pH of 7.0 relative to the pH of 6.0, which indicates that anionic phosphoryloxytryptamines display a greater rate of spontaneous dephosphorylation relative to zwitterionic phosphoryloxytryptamines.

Greater absorbance is detected for psilocybin, baeocystin, norbaeocystin, and aeruginascin from the samples at the pH of 3.0 relative to the pH of 2.0, and greater absorbance is detected for psilocin, norpsilocin, 4-HT, and 4-hydroxy-TMT at the pH of 2.0 relative to the pH of 3.0, which indicates that cationic phosphoryloxytryptamines display a greater rate of spontaneous dephosphorylation relative to zwitterionic phosphoryloxytryptamines.

The sample comprising psilocybin at a pH of 2.0 is a composition that comprises (1) the zwitterionic psilocybin and the cationic psilocybin at a mole ratio of less than 15:1, (2) the zwitterionic psilocybin and the anionic psilocybin at a mole ratio of greater than 25,000:1, and (3) the psilocybin and psilocin at a mole ratio of less than 9:1. An aliquot of the sample is dried under vacuum to produce (4) a salt that comprises zwitterionic psilocybin, dihydrogen phosphate, and sodium cation, and (5) a greater amount of a salt that comprises cationic psilocybin and dihydrogen phosphate. The samples comprising baeocystin, norbaeocystin, and aeruginascin at a pH of 2.0 each comprise (1) a zwitterionic tryptamine to corresponding cationic tryptamine mole ratio of less than 15:1, (2) a zwitterionic tryptamine to corresponding anionic tryptamine mole ratio of greater than 25,000:1, and (3) a phosphoryloxytryptamine to corresponding hydroxytryptamine mole ratio of less than 9:1. Aliquots of these samples are dried under vacuum to produce (4) salts that comprise a zwitterionic phosphoryloxytryptamine, dihydrogen phosphate, and sodium cation, and (5) a greater amount of salts that comprise the corresponding cationic phosphoryloxytryptamine and dihydrogen phosphate. The experiment is repeated with potassium dihydrogen phosphate instead of sodium dihydrogen phosphate to produce salts that comprise potassium cation instead of sodium cation.

The sample comprising psilocybin at a pH of 3.0 is a composition that comprises (1) the zwitterionic psilocybin and the cationic psilocybin at a mole ratio of greater than 15:1 and less than 50,000:1, (2) the zwitterionic psilocybin and the anionic psilocybin at a mole ratio of greater than 16:1 and less than 25,000:1, and (3) the psilocybin and psilocin at a mole ratio of greater than 1:1 and less than 120:1. An aliquot of the sample is dried under vacuum to produce (4) a salt that comprises zwitterionic psilocybin, dihydrogen phosphate, and sodium cation, and (5) a lesser amount of a salt that comprises cationic psilocybin and dihydrogen phosphate. The samples comprising baeocystin, norbaeocystin, and aeruginascin at a pH of 3.0 each comprise (1) a zwitterionic tryptamine to corresponding cationic tryptamine mole ratio of greater than 15:1 and less than 50,000:1, (2) a zwitterionic tryptamine to corresponding anionic tryptamine mole ratio of greater than 16:1 and less than 25,000:1, and (3) a phosphoryloxytryptamine to corresponding hydroxytryptamine mole ratio of greater than 1:1 and less than 120:1. Aliquots of these samples are dried under vacuum to produce (4) salts that comprise a zwitterionic phosphoryloxytryptamine, dihydrogen phosphate, and sodium cation, and (5) a lesser amount of a salts that comprise the corresponding cationic phosphoryloxytryptamine and dihydrogen phosphate. The experiment is repeated with potassium dihydrogen phosphate instead of sodium dihydrogen phosphate to produce salts that comprise potassium cation instead of sodium cation.

The sample comprising psilocybin at a pH of 6.0 is a composition that comprises (1) the zwitterionic psilocybin and the anionic psilocybin at a mole ratio of greater than 1:1 and less than 500:1 (2) the zwitterionic psilocybin and the cationic psilocybin at a mole ratio of greater than 38,000:1 and less than 50,000:1, and (3) the psilocybin and psilocin at a mole ratio of greater than 1:1 and less than 120:1. An aliquot of the sample is dried under vacuum to produce (4) a salt that comprises zwitterionic psilocybin, dihydrogen phosphate, and sodium cation, and (5) a lesser amount of a salt that comprises anionic psilocybin, dihydrogen phosphate, and sodium cation. The samples comprising baeocystin, norbaeocystin, and aeruginascin at a pH of 6.0 each comprise (1) a zwitterionic tryptamine to corresponding anionic tryptamine mole ratio of greater than 1:1 and less than 500:1, (2) a zwitterionic tryptamine to corresponding cationic tryptamine mole ratio of greater than 38,000:1 and less than 50,000:1, and (3) a phosphoryloxytryptamine to corresponding hydroxytryptamine mole ratio of greater than 1:1 and less than 120:1. Aliquots of these samples are dried under vacuum to produce (4) salts that comprise a zwitterionic phosphoryloxytryptamine, dihydrogen phosphate, and sodium cation, and (5) a lesser amount of salts that comprise the corresponding anionic phosphoryloxytryptamine, dihydrogen phosphate, and sodium cation. The experiment is repeated with potassium dihydrogen phosphate instead of sodium dihydrogen phosphate and potassium monohydrogen phosphate instead of sodium monohydrogen phosphate to produce salts that comprise potassium cation instead of sodium cation.

The sample comprising psilocybin at a pH of 7.0 is a composition that comprises (1) the zwitterionic psilocybin and the anionic psilocybin at a mole ratio of less than 1:2 (2) the zwitterionic psilocybin and the cationic psilocybin at a mole ratio of greater than 100,000:1, and (3) the psilocybin and psilocin at a mole ratio of less than 9:1. An aliquot of the sample is dried under vacuum to produce (4) a salt that comprises zwitterionic psilocybin, dihydrogen phosphate, and sodium cation, and (5) a greater amount of a salt that comprises anionic psilocybin, dihydrogen phosphate, and sodium cation. The samples comprising baeocystin, norbaeocystin, and aeruginascin at a pH of 7.0 each comprise (1) a zwitterionic tryptamine to corresponding anionic tryptamine mole ratio of less than 1:2, (2) a zwitterionic tryptamine to corresponding cationic tryptamine mole ratio of greater than 100,000:1, and (3) a phosphoryloxytryptamine to corresponding hydroxytryptamine mole ratio of less than 9:1. Aliquots of these samples are dried under vacuum to produce (4) salts that comprise a zwitterionic phosphoryloxytryptamine, dihydrogen phosphate, and sodium cation, and (5) a greater amount of salts that comprise the corresponding anionic phosphoryloxytryptamine, dihydrogen phosphate, and sodium cation. The experiment is repeated with potassium dihydrogen phosphate instead of sodium dihydrogen phosphate and potassium monohydrogen phosphate instead of sodium monohydrogen phosphate to produce salts that comprise potassium cation instead of sodium cation.

Example 2. Denaturing Proteins with Chaotropes and Surfactants Improves Yields of Phosphoryloxytryptamines from *Psilocybe cubensis*

20 milliliters of 6 molar guanidinium chloride in distilled, deionized water and buffered to a pH of 6.0 with 50 millimolar phosphate buffer is added to each of three opaque 50-milliliter polypropylene centrifuge tubes. 20 milliliters of 8 molar urea in distilled, deionized water and buffered to a pH of 6.0 with 50 millimolar phosphate buffer is added to each of three opaque 50-milliliter polypropylene centrifuge tubes. 20 milliliters of 4 molar ammonium sulfate in distilled, deionized water and buffered to a pH of 6.0 with 50 millimolar MES buffer is added to each of three opaque 50-milliliter polypropylene centrifuge tubes. 20 milliliters of 2 percent sodium dodecyl sulfate (w/v) in distilled, deionized water and buffered to a pH of 6.0 with 50 millimolar phosphate buffer is added to each of three opaque 50-milliliter polypropylene centrifuge tubes. 20 milliliters of 1 percent Triton X-100 (v/v) in distilled, deionized water and buffered to a pH of 6.0 with 50 millimolar phosphate buffer is added to each of three opaque 50-milliliter polypropylene centrifuge tubes. 20 milliliters of 2 percent octyl glucoside (w/v) in distilled, deionized water and buffered to a pH of 6.0 with 50 millimolar phosphate buffer is added to each of three opaque 50-milliliter polypropylene centrifuge tubes. 20 milliliters of distilled, deionized water is buffered to a pH of 6.0 with 50 millimolar phosphate buffer and added to each of three opaque 50-milliliter polypropylene centrifuge tubes. Each of the centrifuge tubes is placed on ice.

The stipes of three freshly-harvested *Psilocybe cubensis* fruiting bodies are each cut into seven sections of approximately 1 gram each, weighed, and immediately placed into one of the polypropylene tubes such that a section of each stipe is placed in each of the guanidinium, urea, ammonium sulfate, sodium dodecyl sulfate, Triton X-100, and octyl glucoside solutions as well as the water control. Each of the samples is homogenized and then sonicated within the polypropylene tubes. The polypropylene tubes are then loaded onto an orbital shaker in a cold room at 4 degrees Celsius and mixed at 450 revolutions per minute for four hours. After mixing, the samples are placed on ice.

The samples are centrifuged, and the supernatants are analyzed by HPLC as described in Example 1. The molecular weights of the analytes are determined by electrospray ionization mass spectroscopy (ESI-MS) operating in positive ion mode. The supernatants are also used for a colorimetric assay with a para-nitrophenyl phosphate substrate to identify residual phosphatase enzyme activity and for a colorimetric assay with a syringaldazine substrate to identify any residual laccase enzyme activity.

Each of the guanidinium, urea, and ammonium sulfate samples display significantly greater concentrations of phosphoryloxytryptamines per weight of the stipe sections than the water control. Each of the guanidinium, urea, and ammonium sulfate samples display significantly less phosphatase enzyme activity in the colorimetric assay than the water control. These two findings suggest that guanidinium, urea, and ammonium sulfate can attenuate endogenous phosphatase enzyme activity to increase the yields of phosphoryloxytryptamines obtained from mushrooms. These two findings also suggest that chaotropes can generally attenuate endogenous phosphatase enzyme activity to increase the yields of phosphoryloxytryptamines obtained from mushrooms. Guanidinium, urea, ammonium sulfate, and other chaotropes may therefore improve the accuracy of protocols used to measure the tryptamine content of mushrooms, the tryptamine content of manufacturing intermediates derived from mushrooms, and the tryptamine content of products derived from mushrooms.

Each of the guanidinium, urea, and ammonium sulfate samples display significantly less laccase enzyme activity in the colorimetric assay than the water control, which suggests that guanidinium, urea, ammonium sulfate, and other chaotropes can inhibit the oxidation of tryptamines generally (and hydroxytryptamines specifically) to increase the yields of tryptamines obtained from mushrooms. The inhibition of laccase enzyme activity also provides an additional reason why guanidinium, urea, ammonium sulfate, and other chaotropes may improve the accuracy of protocols used to measure the tryptamine content of mushrooms, to measure the tryptamine content of manufacturing intermediates derived from mushrooms, and to measure the tryptamine content of products derived from mushrooms.

Each of the sodium dodecyl sulfate, Triton X-100, and octyl glucoside samples display significantly greater concentrations of phosphoryloxytryptamines per weight of the stipe sections than the water control. Each of the sodium dodecyl sulfate, Triton X-100, and octyl glucoside samples display significantly less phosphatase enzyme activity in the colorimetric assay than the water control. These two findings suggest that sodium dodecyl sulfate, Triton X-100, and octyl glucoside can attenuate endogenous phosphatase enzyme activity to increase the yields of phosphoryloxytryptamines obtained from mushrooms. These two findings also suggest that surfactants can generally attenuate endogenous phosphatase enzyme activity to increase the yields of phosphoryloxytryptamines obtained from mushrooms. Sodium dodecyl sulfate, Triton X-100, octyl glucoside, and other surfactants may therefore improve the accuracy of protocols used to measure the tryptamine content of mushrooms, the tryptamine content of manufacturing intermediates derived from mushrooms, and the tryptamine content of products derived from mushrooms.

Each of the sodium dodecyl sulfate, Triton X-100, and octyl glucoside samples display significantly less laccase enzyme activity in the colorimetric assay than the water control, which suggests that sodium dodecyl sulfate, Triton X-100, octyl glucoside, and other surfactants can inhibit the oxidation of tryptamines generally (and hydroxytryptamines specifically) to increase the yields of tryptamines obtained from mushrooms. The inhibition of laccase enzyme activity also provides an additional reason why sodium dodecyl sulfate, Triton X-100, octyl glucoside, and other surfactants may improve the accuracy of protocols used to measure the tryptamine content of mushrooms, to measure the tryptamine content of manufacturing intermediates derived from mushrooms, and to measure the tryptamine content of products derived from mushrooms.

Ions with a mass-to-charge ratio of 221 are identified by ESI-MS in the water controls, and these ions are identified by nuclear magnetic resonance spectroscopy (NMR) as 3-[2-(dimethylazaniumyl)ethyl]-1H-indol-2,4-diol, 3-[2-(dimethylazaniumyl)ethyl]-1H-indol-4,5-diol, and 3-[2-(dimethylazaniumyl)ethyl]-1H-indol-4,7-diol, which have an approximate molecular weight of 221 atomic mass units. The water control comprises psilocin and the foregoing ions at a mole ratio of less than 10:1, and all other samples comprise psilocin and the foregoing ions at a mole ratio of greater than 10:1.

Ions with a mass-to-charge ratio of 219 are identified by ESI-MS in the water controls, and these ions are identified by NMR as 3-[2-(dimethylazaniumyl)ethyl]-1H-indol-2,4-dione, 3-[2-(dimethylazaniumyl)ethyl]-1H-indol-4,5-dione, and 3-[2-(dimethylazaniumyl)ethyl]-1H-indol-4,7-dione, which have an approximate molecular weight of 219 atomic mass units. The water control comprises psilocin and the foregoing ions at a mole ratio of less than 10:1, and all other samples comprise psilocin and the foregoing ions at a mole ratio of greater than 10:1.

Ions with a mass-to-charge ratio of 204 are identified by ESI-MS in the water controls, and these ions are identified by NMR as including 3-[2-(dimethylazaniumyl)ethyl]-5-{3-[2-(dimethylazaniumyl)ethyl]-4-hydroxy-1H-indol-5-yl}-1H-indol-4-ol and 3-[2-(dimethylazaniumyl)ethyl]-7-{3-[2-(dimethylazaniumyl)ethyl]-4-hydroxy-1H-indol-7-yl}-1H-indol-4-ol, which have an approximate molecular weight of 409 atomic mass units. The water control comprises psilocin and the foregoing ions at a mole ratio of less than 10:1, and all other samples comprise psilocin and the foregoing ions at a mole ratio of greater than 10:1.

Ions with a mass-to-charge ratio of 203 are identified by ESI-MS in the water controls, and these ions are identified by NMR as including 3-[2-(dimethylazaniumyl)ethyl]-5-{3-[2-(dimethylazaniumyl)ethyl]-4-oxo-1H-indol-5-ylidene}-1H-indol-4-one and 3-[2-(dimethylazaniumyl)ethyl]-7-{3-[2-(dimethylazaniumyl)ethyl]-4-oxo-1H-indol-7-ylidene}-1H-indol-4-one, which have an approximate molecular weight of 407 atomic mass units. The water control comprises psilocin and the foregoing ions at a mole ratio of less than 10:1, and all other samples comprise psilocin and the foregoing ions at a mole ratio of greater than 10:1.

What is claimed is:

1. A composition, comprising trimethylglycine, tryptamines, and a polypeptide, wherein:

the tryptamines comprise phosphoryloxytryptamines and hydroxytryptamines;

the phosphoryloxytryptamines comprise psilocybin;

the psilocybin comprises both of (a) zwitterionic psilocybin, which comprises a monoanionic phosphonate ester and a cationic azanium, and (b) anionic psilocybin, which comprises a dianionic phosphonate ester and a second cationic azanium;

the zwitterionic psilocybin has the chemical formula [2-(4-phosphonooxy-1H-indol-3-yl)ethyl]-dimethylazanium, in which the phosphonooxy is the monoanionic phosphonate ester;

the anionic psilocybin has the chemical formula [2-(4-phosphonatooxy-1H-indol-3-yl)ethyl]-dimethylazanium, in which the phosphonatooxy is the dianionic phosphonate ester;

the hydroxytryptamines comprise psilocin;

the psilocin comprises cationic psilocin, which lacks a phosphonate ester and comprises a third cationic azanium;

the cationic psilocin has the chemical formula [2-(4-hydroxy-1H-indol-3-yl)ethyl]-dimethylazanium;

the zwitterionic psilocybin and the anionic psilocybin each have a rate of spontaneous dephosphorylation per mole in the composition, which converts the psilocybin into additional psilocin;

the rate of spontaneous dephosphorylation for the zwitterionic psilocybin per mole of the zwitterionic psilocybin is less than the rate of spontaneous dephosphorylation for the anionic psilocybin per mole of the anionic psilocybin in the composition;

the composition comprises the zwitterionic psilocybin and the anionic psilocybin at a mole ratio of at least 1:1 (zwitterionic psilocybin:anionic psilocybin);

the mole ratio of at least 1:1 for the zwitterionic psilocybin and the anionic psilocybin in the composition results in a lower rate of spontaneous dephosphorylation for the psilocybin of the composition per mole of the psilocybin relative to a lower mole ratio of less than 1:1;

the psilocybin and the psilocin each have a different rate of spontaneous oxidation per mole in the composition;

the rate of spontaneous oxidation for the psilocybin per mole of the psilocybin is less than the rate of spontaneous oxidation for the psilocin per mole of the psilocin in the composition;

the composition comprises the psilocybin and the psilocin at a mole ratio of at least 3:2 (psilocybin:psilocin);

the mole ratio of at least 3:2 for the psilocybin and the psilocin in the composition results in a lower rate of spontaneous oxidation for the tryptamines per mole of the tryptamines of the composition relative to a lower mole ratio of less than 3:2;

the polypeptide encodes a laccase enzyme, wherein the laccase enzyme is encoded by an amino acid sequence having at least 90 percent sequence identity with the sequence set forth in SEQ ID NO: 1, SEQ ID NO: 2, or SEQ ID NO: 3;

the laccase enzyme is denatured in the composition such that the polypeptide lacks laccase enzyme activity;

the composition is a product that is produced by a process that comprises:

(i) providing a starting composition that comprises the psilocybin, the psilocin, and the laccase enzyme, wherein the psilocybin of the starting composition comprises an initial amount of the zwitterionic psilocybin and an initial amount of the anionic psilocybin;

(ii) heating the starting composition to denature the laccase enzyme and thereby produce an intermediate composition that comprises the psilocybin, the psilocin, and the denatured polypeptide, and (iii) combining the intermediate composition with a Bronsted acid to convert some of the anionic psilocybin of the starting composition into the zwitterionic psilocybin such that the composition comprises (I) a final amount of the zwitterionic psilocybin that is greater than the initial amount of the zwitterionic psilocybin and (II) a final amount of the anionic psilocybin that is less than the initial amount of the anionic psilocybin; and the Bronsted acid is selected from formic acid, acetic acid, propionic acid, butyric acid, valeric acid, caproic acid, caprylic acid, sorbic acid, ascorbic acid, erythorbic acid, lactic acid, pyruvic acid, malonic acid, monohydrogen malonate, succinic acid, monohydrogen succinate, adipic acid, monohydrogen adipate, fumaric acid, monohydrogen fumarate, malic acid, monohydrogen malate, tartaric acid, monohydrogen tartrate, citric acid, dihydrogen citrate, monohydrogen citrate, aconitic acid, dihydrogen aconitate, monohydrogen aconitate, thiodipropionic acid, monohydrogen thiodipropionate, cinnamic acid, hydrocinnamic acid, aspartic acid, glutamic acid, aminoacetic acid, hydrochloric acid, sulfuric acid, monohydrogen sulfate, carbonic acid, bicarbonate, phosphoric acid, dihydrogen phosphate, and dihydrogen diphosphate.

2. A composition, comprising tryptamines and a polypeptide, wherein:

the tryptamines comprise phosphoryloxytryptamines and hydroxytryptamines;

the phosphoryloxytryptamines comprise psilocybin and norbaeocystin;

the psilocybin comprises both of (a) zwitterionic psilocybin, which comprises a monoanionic phosphonate ester and a cationic azanium, and (b) anionic psilocybin, which comprises a dianionic phosphonate ester and a second cationic azanium;

the zwitterionic psilocybin has the chemical formula [2-(4-phosphonooxy-1H-indol-3-yl)ethyl]-dimethylazanium, in which phosphonooxy is the monoanionic phosphonate ester;

the anionic psilocybin has the chemical formula [2-(4-phosphonatooxy-1H-indol-3-yl)ethyl]-dimethylazanium, in which phosphonatooxy is the dianionic phosphonate ester;

the norbaeocystin comprises both of (c) zwitterionic norbaeocystin, which comprises a second monoanionic phosphonate ester and a third cationic azanium, and (d) anionic norbaeocystin, which comprises a second dianionic phosphonate ester and a fourth cationic azanium;

the zwitterionic norbaeocystin has the chemical formula 2-(4-phosphonooxy-1H-indol-3-yl)ethylazanium, in which phosphonooxy is the second monoanionic phosphonate ester;

the anionic norbaeocystin has the chemical formula 2-(4-phosphonatooxy-1H-indol-3-yl)ethylazanium, in which phosphonatooxy is the second dianionic phosphonate ester;

the hydroxytryptamines comprise psilocin and 4-hydroxytryptamine;

the psilocin comprises cationic psilocin, which lacks a phosphonate ester and comprises a fifth cationic azanium;

the cationic psilocin has the chemical formula [2-(4-hydroxy-1H-indol-3-yl)ethyl]-dimethylazanium;

the 4-hydroxytryptamine comprises cationic 4-hydroxytryptamine, which lacks a phosphonate ester and comprises a sixth cationic azanium;

the cationic 4-hydroxytryptamine has the chemical formula 2-(4-hydroxy-1H-indol-3-yl)ethylazanium;

the zwitterionic psilocybin and the anionic psilocybin each have a rate of spontaneous dephosphorylation per mole in the composition, which converts the psilocybin into additional psilocin;

the rate of spontaneous dephosphorylation for the zwitterionic psilocybin per mole of the zwitterionic psilocybin is less than the rate of spontaneous dephosphorylation for the anionic psilocybin per mole of the anionic psilocybin in the composition;

the composition comprises the zwitterionic psilocybin and the anionic psilocybin at a mole ratio of at least 1:1 (zwitterionic psilocybin:anionic psilocybin);

the mole ratio of at least 1:1 for the zwitterionic psilocybin and the anionic psilocybin in the composition results in a lower rate of spontaneous dephosphorylation for the psilocybin of the composition per mole of the psilocybin relative to a lower mole ratio of less than 1:1;

the zwitterionic norbaeocystin and the anionic norbaeocystin each have a rate of spontaneous dephosphorylation per mole in the composition, which converts the norbaeocystin into additional 4-hydroxytryptamine;

the rate of spontaneous dephosphorylation for the zwitterionic norbaeocystin per mole of the zwitterionic norbaeocystin is less than the rate of spontaneous dephosphorylation for the anionic norbaeocystin per mole of the anionic norbaeocystin in the composition;

the composition comprises the zwitterionic norbaeocystin and the anionic norbaeocystin at a mole ratio of at least 1:1 (zwitterionic norbaeocystin:anionic norbaeocystin);

the mole ratio of at least 1:1 for the zwitterionic norbaeocystin and the anionic norbaeocystin in the composition results in a lower rate of spontaneous dephosphorylation for the norbaeocystin of the composition per mole of the norbaeocystin relative to a lower mole ratio of less than 1:1;

the psilocybin and the psilocin each have a different rate of spontaneous oxidation per mole in the composition;

the rate of spontaneous oxidation for the psilocybin per mole of the psilocybin is less than the rate of spontaneous oxidation for the psilocin per mole of the psilocin in the composition;

the composition comprises the psilocybin and the psilocin at a mole ratio of at least 3:2 (psilocybin:psilocin);

the mole ratio of at least 3:2 for the psilocybin and the psilocin in the composition results in a lower rate of spontaneous oxidation for the tryptamines per mole of the tryptamines of the composition relative to a lower mole ratio of less than 3:2;

the norbaeocystin and the 4-hydroxytryptamine each have a different rate of spontaneous oxidation per mole in the composition;

the rate of spontaneous oxidation for the norbaeocystin per mole of the norbaeocystin is less than the rate of spontaneous oxidation for the 4-hydroxytryptamine per mole of the 4-hydroxytryptamine in the composition;

the composition comprises the norbaeocystin and the 4-hydroxytryptamine at a mole ratio of at least 3:2 (norbaeocystin:4-hydroxytryptamine);

the mole ratio of at least 3:2 for the norbaeocystin and the 4-hydroxytryptamine in the composition correlates with a lower rate of spontaneous oxidation for the tryptamines per mole of the tryptamines of the composition relative to a lower mole ratio of less than 3:2;

the polypeptide encodes a laccase enzyme, wherein the laccase enzyme is encoded by an amino acid sequence having at least 90 percent sequence identity with the sequence set forth in SEQ ID NO: 3;

the laccase enzyme, which is capable of oxidizing the psilocin into one or more oxidized diol dimers of psilocin, is denatured in the composition such that the polypeptide lacks laccase enzyme activity;

the composition comprises the psilocin and the one or more oxidized diol dimers of psilocin at a mole ratio of at least 10:1 (psilocin:oxidized diol dimers);

the mole ratio of at least 10:1 for the psilocybin and the oxidized diol dimers of psilocin in the composition is indicative of effective denaturation of the polypeptide to inhibit laccase enzyme activity relative to a lower mole ratio of less than 10:1;

each of the one or more oxidized diol dimers of psilocin is a dication that comprises two monocationic azaniumyl groups such that each of the one or more oxidized diol dimers of psilocin has an approximate molecular weight of 409 atomic mass units;

the one or more oxidized diol dimers of psilocin comprise 3-[2-(dimethylazaniumyl)ethyl]-2-{3-[2-(dimethylazaniumyl)ethyl]-4-hydroxy-1H-indol-2-yl}-1H-indol-4-ol;

either (i) the laccase enzyme is capable of oxidizing the one or more oxidized diol dimers of psilocin into one or more oxidized ylidene dimers of psilocin, (ii) the one or more oxidized diol dimers of psilocin can undergo spontaneous oxidation into one or more oxidized ylidene dimers of psilocin, or (iii) both (i) and (ii);

the composition comprises the psilocin and the oxidized ylidene dimers of psilocin at a mole ratio of at least 10:1 (psilocin:oxidized ylidene dimers);

the mole ratio of at least 10:1 for the psilocin and the oxidized ylidene dimers of psilocin in the composition is indicative of effective denaturation of the polypeptide to inhibit laccase enzyme activity relative to a lower mole ratio of less than 10:1;

each of the one or more oxidized ylidene dimers of psilocin is a dication that comprises two monocationic azaniumyl groups such that each of the one or more oxidized ylidene dimers of psilocin has an approximate molecular weight of 407 atomic mass units;

the oxidized ylidene dimers of psilocin comprise 3-[2-(dimethylazaniumyl)ethyl]-2-{3-[2-(dimethylazaniumyl)ethyl]-4-hydroxyindol-2-ylidene}indol-4-ol or a tautomer thereof;

the laccase enzyme is capable of oxidizing the 4-hydroxytryptamine into one or more oxidized diol dimers of 4-hydroxytryptamine and psilocin;

the composition comprises the 4-hydroxytryptamine and the one or more oxidized diol dimers of 4-hydroxytryptamine and psilocin at a mole ratio of at least 10:1 (4-hydroxytryptamine:oxidized diol dimers of 4-hydroxytryptamine and psilocin);

the mole ratio of at least 10:1 for the 4-hydroxytryptamine and the oxidized diol dimers of 4-hydroxytryptamine and psilocin in the composition is indicative of effective denaturation of the polypeptide to inhibit laccase enzyme activity relative to a lower mole ratio of less than 10:1;

each of the one or more oxidized diol dimers of 4-hydroxytryptamine and psilocin is a dication that comprises two monocationic azaniumyl groups such that each of the one or more oxidized diol dimers of 4-hydroxytryptamine and psilocin has an approximate molecular weight of 380 atomic mass units;

the one or more oxidized diol dimers of 4-hydroxytryptamine and psilocin comprise 3-(2-azaniumylethyl)-2-{3-[2-(dimethylazaniumyl)ethyl]-4-hydroxy-1H-indol-2-yl}-1H-indol-4-ol;

either (iv) the laccase enzyme is capable of oxidizing the one or more oxidized diol dimers of 4-hydroxytryptamine and psilocin into one or more oxidized ylidene dimers of 4-hydroxytryptamine and psilocin, (v) the one or more oxidized diol dimers of 4-hydroxytryptamine and psilocin can undergo spontaneous oxidation into one or more oxidized ylidene dimers of 4-hydroxytryptamine and psilocin, or (vi) both (iv) and (v);

the composition comprises the 4-hydroxytryptamine and the oxidized ylidene dimers of 4-hydroxytryptamine and psilocin at a mole ratio of at least 10:1 (4-hydroxytryptamine:oxidized ylidene dimers of 4-hydroxytryptamine and psilocin);

the mole ratio of at least 10:1 for the 4-hydroxytryptamine and the oxidized ylidene dimers of 4-hydroxytryptamine and psilocin in the composition is indicative of effective denaturation of the polypeptide to inhibit laccase enzyme activity relative to a lower mole ratio of less than 10:1;

each of the one or more oxidized ylidene dimers of 4-hydroxytryptamine and psilocin is a dication that comprises two monocationic azaniumyl groups such that each of the one or more oxidized ylidene dimers of 4-hydroxytryptamine and psilocin has an approximate molecular weight of 378 atomic mass units;

the oxidized ylidene dimers of 4-hydroxytryptamine and psilocin comprise 3-(2-azaniumylethyl)-2-{3-[2-(dimethylazaniumyl)ethyl]-4-hydroxyindol-2-ylidene}indol-4-ol or a tautomer thereof;

the composition is a product that is produced by a process that comprises:

(i) providing a starting composition that comprises the psilocybin, the norbaeocystin, the psilocin, the 4-hydroxytryptamine, and the laccase enzyme, wherein the psilocybin of the starting composition comprises an initial amount of the zwitterionic psilocybin and an initial amount of the anionic psilocybin, and the norbaeocystin of the starting composition comprises an initial amount of the zwitterionic norbaeocystin and an initial amount of the anionic norbaeocystin;

(ii) denaturing the laccase enzyme to produce the denatured polypeptide;

(iii) converting some of the anionic psilocybin of the starting composition into the zwitterionic psilocybin such that the composition comprises (I) a final amount of the zwitterionic psilocybin that is greater than the initial amount of the zwitterionic psilocybin and (II) a final amount of the anionic psilocybin that is less than the initial amount of the anionic psilocybin; and (iv) converting some of the anionic norbaeocystin of the starting composition into the zwitterionic norbaeocystin such that the composition comprises (III) a final amount of the zwitterionic norbaeocystin that is greater than the initial amount of the zwitterionic norbaeocystin and (IV) a final amount of the anionic norbaeocystin that is less than the initial amount of the anionic norbaeocystin; and optionally the process comprises concurrently performing denaturing the laccase enzyme to produce the denatured polypeptide; converting some of the anionic psilocybin of the starting composition into the zwitterionic psilocybin; and converting some of the anionic norbaeocystin of the starting composition into the zwitterionic norbaeocystin.

3. A composition, comprising tryptamines and a polypeptide, wherein:

the tryptamines comprise phosphoryloxytryptamines and hydroxytryptamines;

the phosphoryloxytryptamines comprise psilocybin;

the psilocybin comprises both of (a) zwitterionic psilocybin, which comprises a monoanionic phosphonate ester and a cationic azanium, and (b) anionic psilocybin, which comprises a dianionic phosphonate ester and a second cationic azanium;

the zwitterionic psilocybin has the chemical formula [2-(4-phosphonooxy-1H-indol-3-yl)ethyl]-dimethylazanium, in which the phosphonooxy is the monoanionic phosphonate ester;

the anionic psilocybin has the chemical formula [2-(4-phosphonatooxy-1H-indol-3-yl)ethyl]-dimethylazanium, in which the phosphonatooxy is the dianionic phosphonate ester;

the hydroxytryptamines comprise psilocin;

the psilocin comprises cationic psilocin, which lacks a phosphonate ester and comprises a third cationic azanium;

the cationic psilocin has the chemical formula [2-(4-hydroxy-1H-indol-3-yl)ethyl]-dimethylazanium;

the zwitterionic psilocybin and the anionic psilocybin each have a rate of spontaneous dephosphorylation per mole in the composition, which converts the psilocybin into additional psilocin;

the composition comprises the zwitterionic psilocybin and the anionic psilocybin at a mole ratio of at least 1:1 (zwitterionic psilocybin:anionic psilocybin);

the polypeptide encodes a laccase enzyme, wherein the laccase enzyme is encoded by an amino acid sequence having at least 90 percent sequence identity with the sequence set forth in SEQ ID NO: 1, SEQ ID NO: 2, or SEQ ID NO: 3;

the laccase enzyme is denatured in the composition such that the polypeptide lacks laccase enzyme activity;

the psilocybin and the psilocin each have a different rate of spontaneous oxidation per mole in the composition;

the composition comprises the psilocybin and the psilocin at a mole ratio of at least 3:2 (psilocybin:psilocin); and the composition is a product that is produced by a process that comprises (i) providing a starting composition that comprises the psilocybin, the psilocin, and the laccase enzyme, wherein the psilocybin of the starting composition comprises an initial amount of the zwitterionic psilocybin and an initial amount of the anionic psilocybin;

(ii) (a) heating the starting composition to denature the laccase enzyme and thereby produce an intermediate composition that comprises the psilocybin, the psilocin, and the denatured polypeptide, or (ii) (b) combining the starting composition with a chaotrope selected from guanidinium, urea, and ammonium sulfate to denature the laccase enzyme and thereby produce an intermediate composition, and (iii) combining the intermediate composition with a Bronsted acid to convert some of the anionic psilocybin of the starting composition into the zwitterionic psilocybin such that the composition comprises (I) a final amount of the zwitterionic psilocybin that is greater than the initial amount of the zwitterionic psilocybin and (II) a final amount of the anionic psilocybin that is less than the initial amount of the anionic psilocybin.

4. The composition of claim 3, further comprising trimethylglycine, wherein:

the rate of spontaneous dephosphorylation for the zwitterionic psilocybin per mole of the zwitterionic psilocybin is less than the rate of spontaneous dephosphorylation for the anionic psilocybin per mole of the anionic psilocybin in the composition;

the mole ratio of at least 1:1 for the zwitterionic psilocybin and the anionic psilocybin in the composition results in a lower rate of spontaneous dephosphorylation for the psilocybin of the composition per mole of the psilocybin relative to a lower mole ratio of less than 1:1;

the rate of spontaneous oxidation for the psilocybin per mole of the psilocybin is less than the rate of spontaneous oxidation for the psilocin per mole of the psilocin in the composition;

the mole ratio of at least 3:2 for the psilocybin and the psilocin in the composition results in a lower rate of spontaneous oxidation for the tryptamines per mole of the tryptamines of the composition relative to a lower mole ratio of less than 3:2; and the Bronsted acid is selected from formic acid, acetic acid, propionic acid, butyric acid, valeric acid, caproic acid, caprylic acid, sorbic acid, ascorbic acid, erythorbic acid, lactic acid, pyruvic acid, malonic acid, monohydrogen malonate, succinic acid, monohydrogen succinate, adipic acid, monohydrogen adipate, fumaric acid, monohydrogen fumarate, malic acid, monohydrogen malate, tartaric acid, monohydrogen tartrate, citric acid, dihydrogen citrate, monohydrogen citrate, aconitic acid, dihydrogen aconitate, monohydrogen aconitate, thiodipropionic acid, monohydrogen thiodipropionate, cinnamic acid, hydrocinnamic acid, aspartic acid, glutamic acid, aminoacetic acid, hydrochloric acid, sulfuric acid, monohydrogen sulfate, carbonic acid, bicarbonate, phosphoric acid, dihydrogen phosphate, and dihydrogen diphosphate.

5. The composition of claim 3, wherein:

the mole ratio of at least 1:1 for the zwitterionic psilocybin and the anionic psilocybin in the composition results in a lower rate of spontaneous dephosphorylation for the psilocybin of the composition per mole of the psilocybin relative to a lower mole ratio of less than 1:1; and the mole ratio of at least 3:2 for the psilocybin and the psilocin in the composition results in a lower rate of spontaneous oxidation for the tryptamines per mole of the tryptamines of the composition relative to a lower mole ratio of less than 3:2.

6. The composition of claim 3, wherein:

the Bronsted acid is selected from formic acid, acetic acid, propionic acid, butyric acid, valeric acid, caproic acid, caprylic acid, sorbic acid, ascorbic acid, erythorbic acid, lactic acid, pyruvic acid, malonic acid, monohydrogen malonate, succinic acid, monohydrogen succinate, adipic acid, monohydrogen adipate, fumaric acid, monohydrogen fumarate, malic acid, monohydrogen malate, tartaric acid, monohydrogen tartrate, citric acid, dihydrogen citrate, monohydrogen citrate, aconitic acid, dihydrogen aconitate, monohydrogen aconitate, thiodipropionic acid, monohydrogen thiodipropionate, cinnamic acid, hydrocinnamic acid, aspartic acid, glutamic acid, aminoacetic acid, hydrochloric acid, sulfuric acid, monohydrogen sulfate, carbonic acid, bicarbonate, phosphoric acid, dihydrogen phosphate, and dihydrogen diphosphate;

the psilocybin of the intermediate composition comprises initial zwitterionic psilocybin and initial anionic psilocybin;

the initial zwitterionic psilocybin and the initial anionic psilocybin each have a rate of spontaneous dephosphorylation per mole in the intermediate composition;

the rate of spontaneous dephosphorylation for the anionic psilocybin per mole of the anionic psilocybin is greater than the rate of spontaneous dephosphorylation for the zwitterionic psilocybin per mole of the zwitterionic psilocybin in the composition, and the rate of spontaneous dephosphorylation for the initial anionic psilocybin per mole of the initial anionic psilocybin is greater than the rate of spontaneous dephosphorylation for the initial zwitterionic psilocybin per mole of the initial zwitterionic psilocybin in the intermediate composition;

the intermediate composition comprises the initial zwitterionic psilocybin and the initial anionic psilocybin at an initial mole ratio of less than 1:1 (initial zwitterionic psilocybin:initial anionic psilocybin); and combining the intermediate composition with the Bronsted acid converts a portion of the initial anionic psilocybin of the intermediate composition into a portion of the zwitterionic psilocybin of the composition; and the portion of the initial anionic psilocybin that is converted into the portion of the zwitterionic psilocybin is sufficient to result in the mole ratio of the zwitterionic psilocybin and the anionic psilocybin in the composition of at least 1:1 (zwitterionic psilocybin:anionic psilocybin).

7. The composition of claim 3, wherein:

the Bronsted acid is selected from formic acid, acetic acid, propionic acid, butyric acid, valeric acid, caproic acid, caprylic acid, sorbic acid, ascorbic acid, erythorbic acid, lactic acid, pyruvic acid, malonic acid, monohydrogen malonate, succinic acid, monohydrogen succinate, adipic acid, monohydrogen adipate, fumaric acid, monohydrogen fumarate, malic acid, monohydrogen malate, tartaric acid, monohydrogen tartrate, citric acid, dihydrogen citrate, monohydrogen citrate, aconitic acid, dihydrogen aconitate, monohydrogen aconitate, thiodipropionic acid, monohydrogen thiodipropionate, cinnamic acid, hydrocinnamic acid, aspartic acid, glutamic acid, aminoacetic acid, hydrochloric acid, sulfuric acid, monohydrogen sulfate, carbonic acid, bicarbonate, phosphoric acid, dihydrogen phosphate, and dihydrogen diphosphate;

the psilocybin of the intermediate composition comprises initial zwitterionic psilocybin and initial anionic psilocybin;

the intermediate composition comprises the initial zwitterionic psilocybin and the initial anionic psilocybin at an initial mole ratio of less than 1:1 (initial zwitterionic psilocybin:initial anionic psilocybin);

combining the intermediate composition with the Bronsted acid converts a portion of the initial anionic psilocybin of the intermediate composition into a portion of the zwitterionic psilocybin of the composition; and the portion of the initial anionic psilocybin that is converted into the portion of the zwitterionic psilocybin is sufficient to result in the mole ratio of the zwitterionic psilocybin and the anionic psilocybin in the composition of at least 1:1 (zwitterionic psilocybin:anionic psilocybin).

8. The composition of claim 3, comprising the psilocin and one or more oxidized diol dimers of psilocin at a mole ratio of at least 10:1 (psilocin:oxidized diol dimers), wherein:

the mole ratio of at least 10:1 for the psilocybin and the oxidized diol dimers of psilocin in the composition is indicative of effective denaturation of the polypeptide to inhibit laccase enzyme activity relative to a lower mole ratio of less than 10:1;

the one or more oxidized diol dimers of psilocin are selected from 3-[2-(dimethylazaniumyl)ethyl]-2-{3-[2-(dimethylazaniumyl)ethyl]-4-hydroxy-1H-indol-2-yl}-1H-indol-4-ol; 3-[2-(dimethylazaniumyl)ethyl]-2-{3-[2-(dimethylazaniumyl)ethyl]-4-hydroxy-1H-indol-5-yl}-1H-indol-4-ol; 3-[2-(dimethylazaniumyl)ethyl]-2-{3-[2-(dimethylazaniumyl)ethyl]-4-hydroxy-1H-indol-7-yl}-1H-indol-4-ol; 3-[2-(dimethylazaniumyl)ethyl]-5-{3-[2-(dimethylazaniumyl)ethyl]-4-hydroxy-1H-indol-5-yl}-1H-indol-4-ol; 3-[2-(dimethylazaniumyl)ethyl]-5-{3-[2-(dimethylazaniumyl)ethyl]-4-hydroxy-1H-indol-7-yl}-1H-indol-4-ol; and 3-[2-(dimethylazaniumyl)ethyl]-7-{3-[2-(dimethylazaniumyl)ethyl]-4-hydroxy-1H-indol-7-yl}-1H-indol-4-ol.

9. The composition of claim 3, comprising the psilocin and one or more oxidized diol dimers of psilocin at a mole ratio of at least 10:1 (psilocin:oxidized diol dimers), wherein:

the mole ratio of at least 10:1 for the psilocybin and the oxidized diol dimers of psilocin in the composition is indicative of effective denaturation of the polypeptide to inhibit laccase enzyme activity relative to a lower mole ratio of less than 10:1;

each of the one or more oxidized diol dimers of psilocin is a dication that comprises two monocationic azaniumyl groups such that each of the one or more oxidized diol dimers of psilocin has an approximate molecular weight of 409 atomic mass units; and the one or more oxidized diol dimers of psilocin comprise 3-[2-(dimethylazaniumyl)ethyl]-2-{3-[2-(dimethylazaniumyl)ethyl]-4-hydroxy-1H-indol-2-yl}-1H-indol-4-ol.

10. The composition of claim 3, comprising the psilocin and one or more oxidized ylidene dimers of psilocin at a mole ratio of at least 10:1 (psilocin:oxidized ylidene dimers), wherein:

the mole ratio of at least 10:1 for the psilocybin and the oxidized ylidene dimers of psilocin in the composition is indicative of effective denaturation of the polypeptide to inhibit laccase enzyme activity relative to a lower mole ratio of less than 10:1;

the one or more oxidized ylidene dimers of psilocin are selected from 3-[2-(dimethylazaniumyl)ethyl]-2-{3-[2-(dimethylazaniumyl)ethyl]-4-oxo-1H-indol-2-ylidene}-1H-indol-4-one; 3-[2-(dimethylazaniumyl)ethyl]-2-{3-[2-(dimethylazaniumyl)ethyl]-4-oxo-1H-indol-5-ylidene}-1H-indol-4-one; 3-[2-(dimethylazaniumyl)ethyl]-2-{3-[2-(dimethylazaniumyl)ethyl]-4-oxo-1H-indol-7-ylidene}-1H-indol-4-one; 3-[2-(dimethylazaniumyl)ethyl]-5-{3-[2-(dimethylazaniumyl)ethyl]-4-oxo-1H-indol-5-ylidene}-1H-indol-4-one; 3-[2-(dimethylazaniumyl)ethyl]-5-{3-[2-(dimethylazaniumyl)ethyl]-4-oxo-1H-indol-7-ylidene}-1H-indol-4-one; 3-[2-(dimethylazaniumyl)ethyl]-7-{3-[2-(dimethylazaniumyl)ethyl]-4-oxo-1H-indol-7-ylidene}-1H-indol-4-one; and tautomers of the foregoing; and the tautomers consist of 3-[2-(dimethylazaniumyl)ethyl]-2-{3-[2-(dimethylazaniumyl)ethyl]-4-hydroxyindol-2-ylidene}-1H-indol-4-one; 3-[2-(dimethylazaniumyl)ethyl]-2-{3-[2-(dimethylazaniumyl)ethyl]-4-hydroxy-1H-indol-2-yl}indol-4-one; 3-[2-(dimethylazaniumyl)ethyl]-2-{3-[2-(dimethylazaniumyl)ethyl]-4-hydroxyindol-2-ylidene} indol-4-ol; 3-[2-(dimethylazaniumyl)ethyl]-2-{3-[2-(dimethylazaniumyl)ethyl]-4-hydroxyindol-5-ylidene}-1H-indol-4-one; 3-[2-(dimethylazaniumyl)ethyl]-5-{3-[2-(dimethylazaniumyl)ethyl]-4-hydroxyindol-2-ylidene}-1H-indol-4-one; 3-[2-(dimethylazaniumyl)ethyl]-2-{3-[2-(dimethylazaniumyl)ethyl]-4-hydroxy-1H-indol-5-yl} indol-4-one; 3-[2-(dimethylazaniumyl)ethyl]-5-{3-[2-(dimethylazaniumyl)ethyl]-4-hydroxy-1H-indol-2-yl}indol-4-one; 3-[2-(dimethylazaniumyl)ethyl]-2-{3-[2-(dimethylazaniumyl)ethyl]-4-hydroxyindol-5-ylidene}indol-4-ol; 3-[2-(dimethylazaniumyl)ethyl]-2-{3-[2-(dimethylazaniumyl)ethyl]-4-hydroxyindol-7-ylidene}-1H-indol-4-one; 3-[2-(dimethylazaniumyl)ethyl]-7-{3-[2-(dimethylazaniumyl)ethyl]-4-hydroxyindol-2-ylidene}-1H-indol-4-one; 3-[2-(dimethylazaniumyl)ethyl]-2-{3-[2-(dimethylazaniumyl)ethyl]-4-hydroxy-1H-indol-7-yl}indol-4-one; 3-[2-(dimethylazaniumyl)ethyl]-7-{3-[2-(dimethylazaniumyl)ethyl]-4-hydroxy-1H-indol-2-yl}indol-4-one; 3-[2-(dimethylazaniumyl)ethyl]-2-{3-[2-(dimethylazaniumyl)ethyl]-4-hydroxyindol-7-ylidene}indol-4-ol; 3-[2-(dimethylazaniumyl)ethyl]-5-{3-[2-(dimethylazaniumyl)ethyl]-4-hydroxyindol-5-ylidene}-1H-indol-4-one; 3-[2-(dimethylazaniumyl)ethyl]-5-{3-[2-(dimethylazaniumyl)ethyl]-4-hydroxy-1H-indol-5-yl}indol-4-one; 3-[2-(dimethylazaniumyl)ethyl]-5-{3-[2-(dimethylazaniumyl)ethyl]-4-hydroxyindol-5-ylidene}indol-4-ol; 3-[2-(dimethylazaniumyl)ethyl]-5-{3-[2-(dimethylazaniumyl)ethyl]-4-hydroxyindol-7-ylidene}-1H-indol-4-one; 3-[2-(dimethylazaniumyl)ethyl]-7-{3-[2-(dimethylazaniumyl)ethyl]-4-hydroxyindol-5-ylidene}-1H-indol-4-one; 3-[2-(dimethylazaniumyl)ethyl]-5-{3-[2-(dimethylazaniumyl)ethyl]-4-hydroxy-1H-indol-7-yl}indol-4-one; 3-[2-(dimethylazaniumyl)ethyl]-7-{3-[2-(dimethylazaniumyl)ethyl]-4-hydroxy-1H-indol-5-yl}indol-4-one; 3-[2-(dimethylazaniumyl)ethyl]-5-{3-[2-(dimethylazaniumyl)ethyl]-4-hydroxyindol-7-ylidene}indol-4-ol; 3-[2-(dimethylazaniumyl)ethyl]-7-{3-[2-(dimethylazaniumyl)ethyl]-4-hydroxyindol-7-ylidene}-1H-indol-4-one; 3-[2-(dimethylazaniumyl)ethyl]-7-{3-[2-(dimethylazaniumyl)ethyl]-4-hydroxy-1H-indol-7-yl}indol-4-one; and 3-[2-(dimethylazaniumyl)ethyl]-7-{3-[2-(dimethylazaniumyl)ethyl]-4-hydroxyindol-7-ylidene}indol-4-ol.

11. The composition of claim 3, comprising the psilocin and one or more oxidized ylidene dimers of psilocin at a mole ratio of at least 10:1 (psilocin:oxidized ylidene dimers), wherein:

the mole ratio of at least 10:1 for the psilocybin and the oxidized ylidene dimers of psilocin in the composition is indicative of effective denaturation of the polypeptide to inhibit laccase enzyme activity relative to a lower mole ratio of less than 10:1;

each of the one or more oxidized ylidene dimers of psilocin is a dication that comprises two monocationic azaniumyl groups such that each of the one or more oxidized ylidene dimers of psilocin has an approximate molecular weight of 407 atomic mass units; and the one or more oxidized ylidene dimers of psilocin comprise 3-[2-(dimethylazaniumyl)ethyl]-2-{3-[2-(dimethylazaniumyl)ethyl]-4-hydroxyindol-2-ylidene}indol-4-ol or a tautomer thereof.

12. The composition of claim 3, wherein:

the phosphoryloxytryptamines further comprise norbaeocystin;

the norbaeocystin comprises both of (c) zwitterionic norbaeocystin, which comprises a second monoanionic phosphonate ester and a fourth cationic azanium, and (d) anionic norbaeocystin, which comprises a second dianionic phosphonate ester and a fifth cationic azanium;

the zwitterionic norbaeocystin has the chemical formula 2-(4-phosphonooxy-1H-indol-3-yl)ethylazanium, in which phosphonooxy is the second monoanionic phosphonate ester;

the anionic norbaeocystin has the chemical formula 2-(4-phosphonatooxy-1H-indol-3-yl)ethylazanium, in which phosphonatooxy is the second dianionic phosphonate ester;

the hydroxytryptamines comprise 4-hydroxytryptamine;

the 4-hydroxytryptamine comprises cationic 4-hydroxytryptamine, which lacks a phosphonate ester and comprises a sixth cationic azanium;

the cationic 4-hydroxytryptamine has the chemical formula 2-(4-hydroxy-1H-indol-3-yl)ethylazanium;

the composition comprises the zwitterionic norbaeocystin and the anionic norbaeocystin at a mole ratio of at least 1:1 (zwitterionic norbaeocystin:anionic norbaeocystin);

the mole ratio of at least 1:1 for the zwitterionic norbaeocystin and the anionic norbaeocystin in the composition results in a lower rate of spontaneous dephosphorylation for the norbaeocystin of the composition per mole of the norbaeocystin relative to a lower mole ratio of less than 1:1;

the norbaeocystin and the 4-hydroxytryptamine each have a different rate of spontaneous oxidation per mole in the composition;

the rate of spontaneous oxidation for the norbaeocystin per mole of the norbaeocystin is less than the rate of spontaneous oxidation for the 4-hydroxytryptamine per mole of the 4-hydroxytryptamine in the composition; and the composition comprises the norbaeocystin and the 4-hydroxytryptamine at a mole ratio of at least 3:2 (norbaeocystin:4-hydroxytryptamine).

* * * * *

SEQUENCE LISTING

```
Sequence total quantity: 90
SEQ ID NO: 1           moltype = AA  length = 243
FEATURE                Location/Qualifiers
source                 1..243
                       mol_type = protein
                       organism = Psilocybe cubensis
SEQUENCE: 1
MTVIEADSQS VQPLTVNEIT IFAGQRYSFI LYANNPVGNY WIRSQPTYPD DGIQGYAGGI  60
NSAILRYSGA PAVNPTTKKA SITIPLVEAD LRPLYSPAAP GLPSPGAADV NIKLDISYNS  120
PSETFFVNNF TFPEVPVPVL LQILSGAQSA NDLLPAGSVY TLPPNKVIEI SMPGGRPGSP  180
HPMHLHGHDF SVVRSAGSNR YNYANPVRRD VVNIGREDTD NVTIRFKTDN SGPWILHCHI  240
FMP                                                               243

SEQ ID NO: 2           moltype = AA  length = 383
FEATURE                Location/Qualifiers
source                 1..383
                       mol_type = protein
                       organism = Psilocybe cubensis
SEQUENCE: 2
MILKTLKERY MTTFPKADST LINGKGRYPK GKPAALSVVN VEYGKRYRLR LISITCDGSY  60
TIFIDKHPFT VIEADGQSVV PVRAIDALTI FAGQRYSVVI VANQPIGNYW IRAQRGVVQG  120
NVDPFEGGLN SAILRYKGAE EVEPVPIPYI PPNRVLRETE LHALIDPEAP GKPEQDGGDV  180
NLHFSITYDE KTKMFLTNGK YFQPPKVPVL LQLLSGTPPE ELLPEGSIFT LPRNKTISIS  240
MLPGEFDTPH PFHLHGHTFS VVRSANTTDD PAPKYNYRDP VRRDTVNLGK VDSGSNVTIR  300
FRTDNPGPWI FHCHVDWHLE RGMAIVFAEA PEEARKEIHP PEEWHYLCPV FDNLPESLTS  360
ISTVAIPPPT ATTIEPTPFI NLL                                         383

SEQ ID NO: 3           moltype = AA  length = 528
FEATURE                Location/Qualifiers
source                 1..528
                       mol_type = protein
                       organism = Psilocybe cubensis
SEQUENCE: 3
MNFLLSIATL GLGLQAYAVM IGPSATLVIG NKNIAPDGIK RSAVLAGTSL DTLSFPGPVI  60
RATKGDTLSL NVVNQLTDAT MLMGTSIHWH GFHQKGTSWA DGVVGVTQCP IAPGHSFLYQ  120
FPTANQAGTF WYHSHYSTQY CDGLRGALIV YDPTDPYRTW YDIDDESTII TLADWYHKAA  180
PLQTLRTAKE DSVLINGQGR VPGDKTTDST PLSVINIIPQ KRYRFRLISI SCDPAFSFSI  240
DGHSMTVIEA DSQSVQPLTV NEITIFAGQR YSFILYANNP VGNYWIRSQP TYPDDGIQGY  300
AGGINSAILR YSGAPAVNPT TKKASITIPL VEADLRPLYS PAAPGLPSPG AADVNIKLDI  360
SYNSPSETFF VNNSTFPEVP VPVLLQILSG AQSANDLLPA GSVYTLPPNK VIEISMPGGR  420
PGSPHPMHLH GHDFSVVRSA GSNRYNYANP VRRDVVNIGM EDTDNVTIRF KTDNSGPWIL  480
HCHIDWHIEA GLAVVFTEDI PSIQFSNPPP AWDQLCPIFN AIPPQKFH              528

SEQ ID NO: 4           moltype = AA  length = 4
FEATURE                Location/Qualifiers
source                 1..4
                       mol_type = protein
                       organism = Psilocybe cubensis
SEQUENCE: 4
VLAG                                                              4

SEQ ID NO: 5           moltype = AA  length = 4
FEATURE                Location/Qualifiers
source                 1..4
```

```
                        mol_type = protein
                        organism = Psilocybe cubensis
SEQUENCE: 5
FPGP                                                                4

SEQ ID NO: 6            moltype = AA  length = 5
FEATURE                 Location/Qualifiers
source                  1..5
                        mol_type = protein
                        organism = Psilocybe cubensis
SEQUENCE: 6
IHWHG                                                               5

SEQ ID NO: 7            moltype = AA  length = 4
FEATURE                 Location/Qualifiers
source                  1..4
                        mol_type = protein
                        organism = Psilocybe cubensis
SEQUENCE: 7
WADG                                                                4

SEQ ID NO: 8            moltype = AA  length = 4
FEATURE                 Location/Qualifiers
source                  1..4
                        mol_type = protein
                        organism = Psilocybe cubensis
SEQUENCE: 8
QCPI                                                                4

SEQ ID NO: 9            moltype = AA  length = 5
FEATURE                 Location/Qualifiers
source                  1..5
                        mol_type = protein
                        organism = Psilocybe cubensis
SEQUENCE: 9
WYHSH                                                               5

SEQ ID NO: 10           moltype = AA  length = 8
FEATURE                 Location/Qualifiers
source                  1..8
                        mol_type = protein
                        organism = Psilocybe cubensis
SEQUENCE: 10
QYCDGLRG                                                            8

SEQ ID NO: 11           moltype = AA  length = 8
FEATURE                 Location/Qualifiers
source                  1..8
                        mol_type = protein
                        organism = Psilocybe cubensis
SEQUENCE: 11
ITLADWYH                                                            8

SEQ ID NO: 12           moltype = AA  length = 4
FEATURE                 Location/Qualifiers
source                  1..4
                        mol_type = protein
                        organism = Psilocybe cubensis
SEQUENCE: 12
LING                                                                4

SEQ ID NO: 13           moltype = AA  length = 5
FEATURE                 Location/Qualifiers
source                  1..5
                        mol_type = protein
                        organism = Psilocybe cubensis
SEQUENCE: 13
RYRFR                                                               5

SEQ ID NO: 14           moltype = AA  length = 6
FEATURE                 Location/Qualifiers
source                  1..6
                        mol_type = protein
                        organism = Psilocybe cubensis
SEQUENCE: 14
FSIDGH                                                              6

SEQ ID NO: 15           moltype = AA  length = 4
FEATURE                 Location/Qualifiers
```

```
source                  1..4
                        mol_type = protein
                        organism = Psilocybe cubensis
SEQUENCE: 15
QRYS                                                                        4

SEQ ID NO: 16           moltype = AA  length = 7
FEATURE                 Location/Qualifiers
source                  1..7
                        mol_type = protein
                        organism = Psilocybe cubensis
SEQUENCE: 16
NSAILRY                                                                     7

SEQ ID NO: 17           moltype = AA  length = 4
FEATURE                 Location/Qualifiers
source                  1..4
                        mol_type = protein
                        organism = Psilocybe cubensis
SEQUENCE: 17
AAPG                                                                        4

SEQ ID NO: 18           moltype = AA  length = 5
FEATURE                 Location/Qualifiers
source                  1..5
                        mol_type = protein
                        organism = Psilocybe cubensis
SEQUENCE: 18
PVLLQ                                                                       5

SEQ ID NO: 19           moltype = AA  length = 5
FEATURE                 Location/Qualifiers
source                  1..5
                        mol_type = protein
                        organism = Psilocybe cubensis
SEQUENCE: 19
GSPHP                                                                       5

SEQ ID NO: 20           moltype = AA  length = 5
FEATURE                 Location/Qualifiers
source                  1..5
                        mol_type = protein
                        organism = Psilocybe cubensis
SEQUENCE: 20
HLHGH                                                                       5

SEQ ID NO: 21           moltype = AA  length = 4
FEATURE                 Location/Qualifiers
source                  1..4
                        mol_type = protein
                        organism = Psilocybe cubensis
SEQUENCE: 21
RDVV                                                                        4

SEQ ID NO: 22           moltype = AA  length = 4
FEATURE                 Location/Qualifiers
source                  1..4
                        mol_type = protein
                        organism = Psilocybe cubensis
SEQUENCE: 22
TIRF                                                                        4

SEQ ID NO: 23           moltype = AA  length = 4
FEATURE                 Location/Qualifiers
source                  1..4
                        mol_type = protein
                        organism = Psilocybe cubensis
SEQUENCE: 23
GPWI                                                                        4

SEQ ID NO: 24           moltype = AA  length = 7
FEATURE                 Location/Qualifiers
source                  1..7
                        mol_type = protein
                        organism = Psilocybe cubensis
SEQUENCE: 24
HCHIDWH                                                                     7

SEQ ID NO: 25           moltype = AA  length = 324
```

```
FEATURE                 Location/Qualifiers
source                  1..324
                        mol_type = protein
                        organism = Psilocybe cubensis
SEQUENCE: 25
MTVGQTIVPI FDLPEDLQIH VVQYQHTERP IEDRYSVNLS DDGRRLLIGV YDGHGGPETA  60
DHISQILPSR LLAHPSSQHA EQFELLDNSM ISNFKKDHSI FRRRSSNWVH NAQLMKSGSA  120
ALVLDVDLSN LSASYANLGD CRLVLCDSNS SQKAVSFCTT DLNMNTPSER ERLIQEHPKE  180
DYLNVGGRLF GRLMCTRGFG DGYYKLPKGI FGSSLHRKYI DTISSIERKG KIPMNAQYAS  240
LFYAYKTPPY ITAWPDTGNL QLKKGDVVIL ATDGLWDLVS TEDATRIVLQ GMAEQENNLA  300
KFLLEMVKAT ISIGDDVTIL VYRA                                        324

SEQ ID NO: 26           moltype = AA  length = 475
FEATURE                 Location/Qualifiers
source                  1..475
                        mol_type = protein
                        organism = Psilocybe cubensis
SEQUENCE: 26
MPFSPPFPPH DPTDKNGYET VIKRWPIILT GVVDTVHNAC HRLTVQLSEI GDEDAEKKKV  60
LQEKTTEGTA IIEKLSKLKY EMARDRVLVE IPQDGEASAD LYNTELEALK QDNRNTWFTA  120
PWLFAEYRLL RSFFVQTQHW KTYDPFEDQK LKTFKHSGKA IFQIAKTIHE LGSDVEGVKS  180
DPEKLKILFN EMIQMCLWGN ATDLSLLTQM TEADIQNLQT VGKDARIARQ QFILKDDEEA  240
VWSYIETLKD AQVDFVLDNS GFELFTDLVF ADFLVSYTPY VSKVVFHPKL IPWFVSDVTP  300
PDFKATLSIL SDVTFFPEEV VNSPDVNTDY LKEMVGRWKK YVDEGVFALS VPLDTPLGGD  360
AGSEVGEFWT TPRPYWDMKT EAPVTFSQLA ESGLVIFKGD LNYRKLTGDI KWPAWTPFEE  420
AIGPLAGSFP ILSLRTNKAD VVVGVEREVA DRLDARGEKW RVDGRYALVS FLPKA       475

SEQ ID NO: 27           moltype = AA  length = 624
FEATURE                 Location/Qualifiers
source                  1..624
                        mol_type = protein
                        organism = Psilocybe cubensis
SEQUENCE: 27
MSGKTPAKAS SPAPTHSRET SYQNGVTHDL DVQSLKQRFL TNDVTPGLQG KDVYDSTLSW  60
WRAGIRRKLV ATVQWESWII AAMQEKIRTP WLDAYFVYSS ILGTHTFFMI LLPALFFFGY  120
DETGRALLAI LGLGIYGSSV IKDLFCSPRP FAPPVTRLTI GSHHLEYGFP STHSTNSVSI  180
ALIFFAHVHR LASTPIPSSQ TIISTITNGT STIINSSDTT EYMISPRLYY FINFILFIYA  240
FSVVFGRLYT AMHSFTDCIT GILLGAGIWW AHTDWAGAPY LLEPSNPLNA LCAFLGFGTL  300
QPSGALLVFM GQGLAAGKWI EKWIQYGGWE VPLILIPLCL FAVHVHPQPV DDCPCFEDAI  360
AILSVVLGSL VSRWAVCYSQ AGMDLVKNVI MPGSGWILEA GQWVQVEREW NDVLVWWTFA  420
AIKMSFGILV IFVWRLLAKS ALHIILPPTF RLLARAFQLP HRRFYTPATE YKSVPSEFHS  480
SADGGGFELH PIPSVIDLPS AGNVGIEIGG IGSGVEGHSG SRTVMAKDLK MRSGNGHRNA  540
NGAANGNAHP SNEKAFNGKA GVGAHRTDKE STGKDGQPDD VRHYDADVLT KVIVYAGIAV  600
IACEVLPLAF DLFGWGVGSH VTIL                                        624

SEQ ID NO: 28           moltype = AA  length = 670
FEATURE                 Location/Qualifiers
source                  1..670
                        mol_type = protein
                        organism = Psilocybe cubensis
SEQUENCE: 28
MAPNCEPLCV FGDRLYFTTF PHPPPPPHAL NKQDSEHGNQ PRIRSRPKGS SSASTSDHYA  60
SYYYFTIDDQ LLYLSFFQDW GPLNLAMVYK ACILIHELLE DKDLASHRLV LYSSDDPKRK  120
ANAALLMALY VMIVQRRAPW EAFHPIAELE FMPFRDAGRG PSDFNLSIQD CLWGLWKAMQ  180
HGLCDMNEFS VEDYEYYEKV ENGDWNWLTP NFIAFASPVD TNWIKREKEA KESTNSSNPG  240
SISRTPSSSG SNLALQRKLP TPYLNCLDYF EKRNIKLVVR LNTELYDRNT FLDRGIDHME  300
LYFDDGTNPT DEIVRTFLDV ADRIVESGGV VAVHCKAGLG RTGTLIGAYL IWKYGFTANE  360
AIAFMRIVRP GTVVGPQQQY MYLKQLEWAK WAAVDEIKKA QAQAQAATSP VPIPIVTPAT  420
PPAEADDDAV MQTTPKSQKI ALPPVTPSRH VAAAAAQAKA IAPPGQPRKT PNAKRVAQDS  480
DDEDEDESSD VLPALGIAPP TRKVKTVPSR GVTASDQRPS RVTRSTANAS VIQKAGTGAA  540
APDSPIKASR QGPNKIPRLA TTKTTSAARA LAAANVQQIQ PRTLRNNANA VPPTPSRLPT  600
LAGKRAHTQN SSSLTDVAAI KPSADKKANA EGWVPNNVAS VVVPASKSER PGLRSVRRRR  660
SSFSAADVVA                                                        670

SEQ ID NO: 29           moltype = AA  length = 438
FEATURE                 Location/Qualifiers
source                  1..438
                        mol_type = protein
                        organism = Psilocybe cubensis
SEQUENCE: 29
MSLSRPTSSS ISSLLKCYTP ALARHISRKA RPTPALRNRF FARLNAAVNT NSPSSSSSSA  60
SSSSSATSTD DSNILFARGN GRGTVPVRPY TFHIGASWAG KPEDPRGMKK VPFPPDTLIG  120
AWRDNTLMRS RGGQTLDAGE DFFFVQEVLV PIYPALPLLS PLKAHVLTRI FLILQMRNRS  180
GVSFGVADGV GGWIDSGVDP ALFSQALMYH AHRYSRNAWA GEPEIDPTMD YEEREQVEGW  240
EMTPYECLDL AYGGVLREKF VLAGSSTACI ISLNASSGVL RSANLGDSGY SILRNTQIVY  300
RQRSQTHFFN CPKQLTKLPT NNGRKFSRAC VDSPNEADTY ETKLRDGDIV VAYTDGFSDN  360
VFPSEMVTIC SLVARAGGTE EEQVQAMADR LVEYSRQCMK SKLRVSPFER EASRVGQYFR  420
GGKPDDVTVI VALIRETS                                               438
```

-continued

```
SEQ ID NO: 30          moltype = AA  length = 631
FEATURE                Location/Qualifiers
source                 1..631
                       mol_type = protein
                       organism = Psilocybe cubensis
SEQUENCE: 30
MDAKLKALKV VDLRNILATA RVQVPAKATK NDLIAKILAS NAALDTYAAL YPPDDLLAPP  60
EEVDWNEDQI DTPPPQQQQQ QQQQKVAPAP APAPEPAPQS APTPAPAPVA PSDTTQSSAE  120
DIELEKRKQR AARFGIPLVE PHQKKTRPAA KSAAVAASID PKVLEQRAAR FGLNTQAPDA  180
KANSNGKKRS APTTQDVDPE ELERRRKRAE RFGTGIPRIQ PNMTPELVKK TTDMGWSQTD  240
ALWVYTSLPE PLLSSELERL SFAHTKCDTD VVGFQPCPNP EETSQDRFVI NDWPLPNGTW  300
IFRAIFDGHA GHETADYASS ALPDIIKGAL TAVVEKDAHP SSSAVSEALS NAISSFDKGI  360
GQAIVDLFPD EQALAEMPIE DIQRIINDNG PNSATILKGM RGTTALVSLA DPAKANIWVA  420
SLGDCAAVLG LKEISGEWNA QVLSKAHNGE NDVEEERVRQ EHPGEEECMM DNRVLGAIAV  480
TRAIGDFSFK LPAIYTERVF LNSNPGFLVP DKVRGYIGRS KTPPYMTGVP EVEHINLKAL  540
NATSTFLIMC SDGLTDLYDD RLKLNEVLAS RWVGIVGEQY GLKDRKNLAL TLLRDGLGAD  600
EENKGEKISR MITVEMAFKW MDDTTILVVP L                                 631

SEQ ID NO: 31          moltype = AA  length = 486
FEATURE                Location/Qualifiers
source                 1..486
                       mol_type = protein
                       organism = Psilocybe cubensis
SEQUENCE: 31
MAYRCLLKLP SHSATKPRSI ARYHDYIRAA TPGRTERPYI TFTTHVQPAG SIRVPLSSPK  60
VIGVVNSRGN RRQILNQVHQ EDFYGFATLS LPPEELRLSL KRDHGVDWDP SQVGDVLARQ  120
VLFVGIYDGH GGSAVAQYLR QELHGLFESV DKSLIPELFG WIKEIGGYFK RFKGGAIAPW  180
IDGTNKEEMT LEARATLTFF EVDKNLSADN AAQACGATAS VAVLQSLDAP ATPFFSAEKL  240
ALTVAHCGDT RVLLCSTLNG QVFPMTENHY PDARIESIRL RRMMGSSLIT DSYGESRWMG  300
SLANTRWYVL NTILQNLGDL NYKKFGITPE PEVRSKLLNG REWAFLVLVS DGISSILSDA  360
EIVDLARGCN DPKTAAERIL AFSEELGGED NATAIVVPLA GWGKITGPDA TKDLRAYRQK  420
QAVGSERQRL SCEIPSSKYT SLLISPAAPV SLLSTSGVPA EIQKRGESSA VWGVKPRMNT  480
LPQIRR                                                             486

SEQ ID NO: 32          moltype = AA  length = 508
FEATURE                Location/Qualifiers
source                 1..508
                       mol_type = protein
                       organism = Psilocybe cubensis
SEQUENCE: 32
MAAPTQNGNG VQHSSGAAPS RVTLHLGHLP SKKDIKAPWP RTPTRVDPNN PPWPAYRGYH  60
EYSFAHATMQ SRLPTILGKA IEDATRTLNS QSSEERVVDL VQCIDRMGDL MIDLSGNAKL  120
RPIIDDDEAD VALWNKEIAK YFQGKDFMNA PWLFAEAYKY RRLHEAFSIS KFWRDYDVFY  180
RQKCDTFSRS SDAVFELSLR FAEPFKINES LSPKEKLEAE RLMFLELTQV CLWGNSTDLS  240
LLINMTEDQI KSLQSTGGDS LAATEKNILG NDMHRLWDRV RQLREKTGGR IDFVLDNAGF  300
ELYCDCVYAD FLIQSGLANQ IRFHGKRYPW FVSDVTKKDW EWLLNTMVYG QLFPKASDAE  360
RESLRRLGLR WKQYEKEGKW VYEQHPFWCT GYTFWDLHSE APDLFLHLSR SDLVIFKGDL  420
NHRKLTYDCA APASTQFEDA IGPMASSAGA PVIASLRTIK SDVVVGLGPQ GDEISDELTK  480
NEPGWKISGK YAVVLLSEGR PGEPVRFA                                     508

SEQ ID NO: 33          moltype = AA  length = 486
FEATURE                Location/Qualifiers
source                 1..486
                       mol_type = protein
                       organism = Psilocybe cubensis
SEQUENCE: 33
MAYRCLLKLP SHSATKPRSI ARYHDYIRAA TPGRTERPYI TFTTHVQPAG SIRVPLSSPK  60
VIGVVNSRGN RRQILNQVHQ EDFYGFATLS LPPEELRLSL KRDHGVDWDP SQVGDVLARQ  120
VLFVGIYDGH GGSAVAQYLR QELHGLFESV DKSLIPELFG WIKEIGGYFK RFKGGAIAPW  180
IDGTNKEEMT LEARATLTFF EVDKNLSADN AAQACGATAS VAVLQSLDAP ATPFFSAEKL  240
ALTVAHCGDT RVLLCSTLNG QVFPMTENHY PDARIESIRL RRMMGSSLIT DSYGESRWMG  300
SLANTRWYVL NTILQNLGDL NYKKFGITPE PEVRSKLLNG REWAFLVLVS DGISSILSDA  360
EIVDLARGCN DPKTAAERIL AFSEELGGED NATAIVVPLA GWGKITGPDA TKDLRAYRQK  420
QAVGSERQRL SCEIPSSKYT SLLISPAAPV SLLSTSGVPA EIQKRGESSA VWGVKPRMNT  480
LPQIRR                                                             486

SEQ ID NO: 34          moltype = AA  length = 379
FEATURE                Location/Qualifiers
source                 1..379
                       mol_type = protein
                       organism = Psilocybe cubensis
SEQUENCE: 34
MHLAKICFSA ALLSTTVHGL PTAPQGRGIL DEVGILDDIL VFDSPAYPDP ANAGNTLIDL  60
QTFVSLRQID LGGLAAALSA ALTTLGVNVG DKLGNLQERV KLIGAIGLPG KSTTVSIAGC  120
SAKAKTGETS GSDLGMSLKT GVSLGACNAG REFEATATLG GLFNSRTVKA SVFSSPDSGF  180
GVISDIDDTV KISNTLDKLA LLRSTLLDDP KPVPGMPELY SSLSQSLDDP QFVYITASPF  240
QLYPFLNDFL DTTYSSAKGP IFTSNLTIAD PSEIIQFVTS SNTEAFKLAS IDRLNGMYPN  300
KKWLAIGDST QKDPEVYAQS IRKHGDWIAC AWIRRVEGAN NTDARFAAAF ADIPASRFRI  360
YTDADIPGLA DIDVAGGEC                                               379
```

```
SEQ ID NO: 35          moltype = AA  length = 391
FEATURE                Location/Qualifiers
source                 1..391
                       mol_type = protein
                       organism = Psilocybe cubensis
SEQUENCE: 35
MLLSTLLSAT VILGVVAAPP PDHDHQPPKH NKIVPGIVFD RFISIWLENT DSTDAQADPN  60
FAALTQQSLR LTNYFAVTHP SEPNYVASVG GEYFGMQNDN LNRIPANIST IVDLLEEKGI  120
SWAEYQEDMP ETGFQGFQQL APSGANDYVR KHNPLIIYDS VANSTTRSAN IKNFTLFEQD  180
LASNNIPQWL FITPNMTNDG HDTNITFASS WARGFLEPLL KNPHFNGPKT LILLTFDESG  240
SDGIQNRVDS ILLGNAVPKH LIGTEDSSFY THYSGIATIE ANWNLHTLGR YDVGANVFSF  300
VAEKTGDKLR TLENPPLSET FLNASYPGVF NTGPKAPLPI PNTRLVVNGR FVHPKVVEIW  360
GSPALQSCTT YTDSVQVPSL ANPPVLPAGC L                                391

SEQ ID NO: 36          moltype = AA  length = 591
FEATURE                Location/Qualifiers
source                 1..591
                       mol_type = protein
                       organism = Psilocybe cubensis
SEQUENCE: 36
MSGSTNRHHH SGSFSGHTAG PTQQQPSASH HALESHEGKD FSKRPVPQVP PPATHKPSDH  60
DFYVYDGGER KVNHEYLKKH FYREGRLTEA QALYIIEHVT NIFSREPNMV PLKSPVTICG  120
DIHGQYYDLM KMFEVGGNLQ DSLYLFLGDY VDRGDFGIEC LLYLYALKIS SPSRIVLLRG  180
NHECRHLTEY FTFKRECLHK YSEKVYEACL RSFCALPISA LVDGKFFCVH GGISPELIKL  240
SDLDHINRFT EPGSHGLLCD LLWSDPIVNF GHENEPAPTG QGVTPGTTFM HNNTRGCSYF  300
YTYEAVCQFL ERNNLLTVIR GHEAQDAGYT MHRKTPKRNF PSVITIFSAP NYLDVYHNRG  360
AILKYANKNI TIRQYNSTAH PFWLPNFMDA FTWSLPFVGQ KITEMLLAIL SICSNDELAE  420
SDSDGEEAQA APADLAARRQ LIKNKILAVG RMQKVFQLLR EEAENATELD GVTATSTAVS  480
KPGADALSVQ GARLNKSIRT FADARRSDMA NERLPEFNEQ QKPTIFPVPS MRNTSRRSSA  540
EGLDMEDLIK RALEDDSVVD DGGVVEMLAE KIARGRSVTG RPGALKRHET T           591

SEQ ID NO: 37          moltype = AA  length = 468
FEATURE                Location/Qualifiers
source                 1..468
                       mol_type = protein
                       organism = Psilocybe cubensis
SEQUENCE: 37
MRNTVTCFFV CFAISTAAGT VIHYPPIASN INNLTFALNG FGSPGIFTTS KTPDSQYGVY  60
NWCNMPHVRQ REYIMPGKNY TLQYVEIIQR HHKRTPYASN TFFKEDVPWS CDGAGATFGS  120
ISPNGPGSSV SPVQWRGYID QQNPWTTSVG PGFAGSSCQF PQITSQGLED SITHGSDLRA  180
VYASRLGLGP TFEPTKAIIR VTNNVITSQV ASGLVAGLFP LSKSHDVAVL IQSSTIDSLE  240
PTYSCNAASK LLSDYTTGSS GELWKDHLAQ AAPLYSRLDN ISGIATLDTA GWHSSLDHYY  300
DNLSAKQCHG KTLPCNLNDT SECVTQKDAN TVYRLGNWEY SYRFRDAPAS AEYSSLRYGA  360
WVLELKSHLQ NNINGTSNVA HDGSVSALLG FLQIDQMVWP GMGSEIVFEL YSSADQPNEH  420
FIRVLWGGQP MKTSTPLGLL DMIPVTIFFD YIDSMIGTSK DLFTNCNQ                468

SEQ ID NO: 38          moltype = AA  length = 880
FEATURE                Location/Qualifiers
source                 1..880
                       mol_type = protein
                       organism = Psilocybe cubensis
SEQUENCE: 38
METPLAEAAT QETASLSDSL HDNPASSSAS TQAQELQPPT ESVYSEPKGP RVHTPQVRLP  60
PAFNKFILYE NRLRFFIIAS NASDSRHRII KIDRTTQDEE LNIIEDEVEY TGKQMTAMLK  120
MLDDGNRASG GLGKAKMFFG IAGFIRFTAG WYMILITKRS VVALLGGHYL YHCENSDIVP  180
VPFNHKIEKP AEEQRLMNIF KQVDMSKNFY FSYTYDLTST LQHNLTGEVR SGENDWPIND  240
RFAWNFHMLT APFSKQATPP LNHYWLLPLV HGHVDQAKLT VLGRVIFVTL IARRSRHFAG  300
ARYLKRGAND EGNVANEVET EQIVCEALTT PFYYPDRGKG DAHRHRRPSP NYTSYVQYRG  360
SIPIYWTQET TSMSPKPPIE ISVVDPFYTA ASRHFDDLFK RYGAPITILN LIKRREPVPR  420
ESKLLDEYTQ CVRYLNQFLP RGKKMVYRAW DMSRAYKEKT QDVISYLEDI AEESIQMTKF  480
FHSGPEPYSH YLNSEGEEAK ASWRGTISLQ NGICRTNCVD CLDRTNAAQF VFGKRALGHQ  540
LYALGVVDSP NLAFDSDAVN MLTEMYHDHG DTIALQYTGS ALVNRVETYR RMPHWNSHSR  600
DIIENIRRFY TNSLLDADKQ TAINLFLGVQ NERAITHPPV RSGYRKWFHE EYLGPSRDVN  660
DFQESLRRFV QQRGDYWVEY YRPLLFTSLG KHFAYSMNST LKLPGKTAKD MNVSPFQPHG  720
YRPAQGDPSS RVVQGVRRWI GSHHPSREIL RAGKPIVRQE AKRPPPKPQV QDNKSTEALA  780
LASLDPAVPE KEEKEYTKYI VQIEDTPGMI PYNGLSDLKH YVEVVQIARG QLDYYPDDET  840
CDHYSKYVER NSTRYPGGKG REAFHVSFNY GRWLDGWQEM                        880

SEQ ID NO: 39          moltype = AA  length = 841
FEATURE                Location/Qualifiers
source                 1..841
                       mol_type = protein
                       organism = Psilocybe cubensis
SEQUENCE: 39
MLHHQRPPVH NDTSTTSEDD DDDDDNDVFE DTLQLSDSDS SNPSSPTGRA GPSIKLDEPL  60
PDDITKDLEA LQQLRQSVKK NLRLRPIRSR TDLRKLDLDL DSIISRSASF TAAASPAAPP  120
LTALSPTSSI ASSYFTPSSD TPQSALFSAI QAPRPSPMSP PVSLAAQTLA SRLIQPKRPL  180
LIDTRPLAAH QSYHLRHSIN IAIPSLILKR CRRPGGGLQS LDALRQFTTT ELGKIQWDAL  240
```

-continued

```
MCPGGPWDGD VVVYDDEMDP KDKDNLGITA WAIIPVISPL LTYGSVAYLE GGLSIAGHHP  300
ELQALVTTAD ELDSISDMHN NSIPPPLSTT SSRGGMKRSA GLLQLDTQAA TRLKKLPEIE  360
LASTTSSKPP SPLPISPLPI MSSMMTSSSS SSSSQSISTA DAQPMDVVDA SPSPPPSSIG  420
FRRPAPPRRP NLRRIDTKSA ERLGPPKLSV RTKQMRSATL AVPPTLSLSI QAPPQSPSHL  480
NLLYSTHSPP PSARYPMTPS TDPANYLTPY YTPPHTPGTP KPVLPPSPIT ARPDLDPPTT  540
EDAFPVFTIS TILPNFLFLG PELTAPEHVA ELQALGVKRI LNIAAECDDD HGLRLREVFD  600
KYYKIPMRDT VEEDNISRGV REVCDILDDA RLHSAATYVH CKAGKSRSVT AVMAYLIHAN  660
HWTLSSAYAF VLERRKGISP NIGFVSELMN FEEQELGGKS VGVQPTLSNP SHHGHGHGAN  720
GAGTGGEGGG GGGGIGLPES YVLASGASRR SGAHVRESLP PMDTHSGQLN GLGGGVGGAG  780
GGGPMSAGGI MDRVLGDSGQ EMEIKDSYGR YRHARRAPVD ETTLQPMRRV SKAGLESASW  840
S                                                                  841

SEQ ID NO: 40          moltype = AA  length = 290
FEATURE                Location/Qualifiers
source                 1..290
                       mol_type = protein
                       organism = Psilocybe cubensis
SEQUENCE: 40
MSLLIGCYAD TNIVLTNDDG WAVAQLRSEY SALKSAGYNV ILSAPAINKS GTGSSTTTPK  60
QLEVPCQFET CPVGSPAYGY ESFDRNINYV NGYPVDAVKY GIKTLAPSIF GSIPTLVISG  120
TNIGTNLGSI SGSGTVGAAA AAALEGIPSI AFSGSSGSTV SYTTLTSNPS SSSSKSAKIY  180
TDLVLKFSAA LLNNSGTLLP KGVSLNVNFA STSSCSSASN YKFVLTRVKS SSSATDVTTC  240
GTNKLTDEST AIKKGCIATV SVFNATTKAD VGSSTQSIVL GKLKPILECL             290

SEQ ID NO: 41          moltype = AA  length = 297
FEATURE                Location/Qualifiers
source                 1..297
                       mol_type = protein
                       organism = Psilocybe cubensis
SEQUENCE: 41
MRLTPSLLAL SLISTCAAQK KVVLTNDDGW ATAQIRAEYA ALQAAGFNVI LSAPAINKSG  60
TGSSTTTPTT LTTACEFNTC PSGSPATGAN STDPRINYVN AFPVDAVRFG IQTLAPKFFG  120
SKPDFVISGS NIGTNLGSIG GSGTVGAASE AALEGIPSIA FSGSSGSQVS YTTLSDTTTT  180
STMAANIYTS LILKLTNQLL NNTSPILPAG ISLNVNFASI SSCPSASSFK FVLTRLESSS  240
ATDVTTCGTN KLTPESTAIK EGCIATVSVF NASTKADVNS ATQGVVLNKL QPILGCL     297

SEQ ID NO: 42          moltype = AA  length = 324
FEATURE                Location/Qualifiers
source                 1..324
                       mol_type = protein
                       organism = Psilocybe cubensis
SEQUENCE: 42
MSTSASSPSS PSSSSISDPD RWIAQLKTCT HLSEPDMKKL CAMVRNILLE ESNIQPVSSP  60
VTICGDIHGQ FWDLLELLRK GGDVPGTSYI FMGDFVDRGH YSLETVSLLF ALKARYPDRV  120
TLLRGNHESR QITQIIDGHT LCVHGGLSPD IRTLDSIRTL SRAQEIPHEG AFCDLMWSDP  180
DDIENWAVSP RGAGWLFGGS VVKEFNHVNA LSLIARAHQL VQEGYKYMFD KQLVTVWSAP  240
NYCYRCGNMA GIMTVRDDGG QTFEVFEAAA ENERDAMGAG GLGGMGGGMG MGGGFGARRG  300
GVSVFVFTIR SLFREFLLCE FSLT                                         324

SEQ ID NO: 43          moltype = AA  length = 225
FEATURE                Location/Qualifiers
source                 1..225
                       mol_type = protein
                       organism = Psilocybe cubensis
SEQUENCE: 43
MAESTYPTTQ YLAGDFVLSA GSVLFRRRPR LGTSTSTSTS TSNPTNTLEP ELEICILHYL  60
THDEWLLPKG RKDRGEPIER TAVRETYEET GYVCALWPQR MPTLATVPVP APGQGAGQQS  120
HGLEVPMEDG YGLIEPIAVT VREIARGRVK IIYWYITVVE EGVEKVEGSQ MENENFESMF  180
VDVREAEERL TFRGDRDVVR VAIDIVCGRG VVQGADTHSG TLSAV                  225

SEQ ID NO: 44          moltype = AA  length = 194
FEATURE                Location/Qualifiers
source                 1..194
                       mol_type = protein
                       organism = Psilocybe cubensis
SEQUENCE: 44
MAAPRHPTTQ YLAGSFVLSA GSVLFRRRAS TNTLEICILH QLTRDEWLLP KGRKDRGETI  60
EQAAVRETYE ETGYVCALWP QRMPTRATVP GVSNVHVVEI AGGLVEPIAV TVRDLGSSNS  120
KIIFWYITVV EEGVEKVEGS QMENENFESV FVDVEDAVER LTFQVDREVV NLAIDIVVGG  180
RIVESTSSGT LNAV                                                    194

SEQ ID NO: 45          moltype = AA  length = 531
FEATURE                Location/Qualifiers
source                 1..531
                       mol_type = protein
                       organism = Psilocybe cubensis
SEQUENCE: 45
MQAQPGSRSP RFHLLLSFLI VLSLPHLIGA ESILGDNNTC DNAHILERNA DCDPQRAAMT  60
WNTTKETTAN TGAKMYGYRY PQVPLEVDNY PVGPEGLQLE QVHVYVRHGE RTPVGVRLTD  120
```

```
PPASIPEYWM MCKTARRFRA AVSSALGPSP NQAPHLSVRN DELEETLQTQ KVVERKDGTL  180
VEGECLLGEL TDLGRQSTYS FGQNLRRLYV ERLGFIPDTL PSSDIVYFRS TNMPRTIESL  240
QQVVHGLYPT NKCLDGAQPP LRIRNGKDEN LIGNTYACKR LEILQAGFAN AAAQAYNRSL  300
ERLDKKVSKY LNGNPIRVDG KPRASGIMDT IRASIAHGIK VPPEFEDKTI VDVIDVCSTL  360
FLPYGHPLRT IYALDKTEEV RRLAMGRLLD DMSRKMQTKI QQREADPLKI LVHSTHDTAI  420
AGLCSTFDVF DDKWPAFTAS ITFELFKTRE PESDQTRSQS ILTRMGSPSS SSQYYVRMRH  480
QNKDMTLPIC AQSGNHLEGH PEFCTFSAFK ARVKELTPTE WDDECLPAGK P           531

SEQ ID NO: 46          moltype = AA  length = 382
FEATURE                Location/Qualifiers
source                 1..382
                       mol_type = protein
                       organism = Psilocybe cubensis
SEQUENCE: 46
MWALVSLLSL LALYARGIVI PSLQSHDVSV PPDSINPYPG KPRLLFKKDG TFKITVFSDL  60
HFGENPWDDW GPEQDVNSTI LMNAVLADEK PDYVVLNGDL ITGENTFREN STSLIDEIMK  120
PLNAAKIPFS STHGNHDNQA NITHEEEIQR ELKVAPLSYT RMAPKGVGGT EGPGNYWVPI  180
YRDAKDLAPI LVLWFFDSRG GFSPNPDSVP VPDWVDESVA GWIESESQAM EKAWGPAELR  240
GALAFVHIPP HAIQVLQTNL DSDKNPGLND DILGDGSVQD SSAQGEDIPF WDALNSNVKN  300
LHAIISGHDH GNEWCAREFT KDVIFCFDKH SGYGGYSSAG WGHGVRNLVF HTPDPKAGVE  360
TWIRLQEGDT RARITLDDNY GR                                          382

SEQ ID NO: 47          moltype = AA  length = 561
FEATURE                Location/Qualifiers
source                 1..561
                       mol_type = protein
                       organism = Psilocybe cubensis
SEQUENCE: 47
MPLVAREMDA WLSGSPDRVA VLHCKAGKGR SGTMACTYLL SLGDVPQPPQ LERNQTSKER  60
AKRRIEDALD VLPPDEENQP PVASRPTSPP FVTPAIGISD TAGIFDAESG GRPSIPTAGA  120
EKSFTDSLKG VLDLHTARRM KPPSEQDGKA KQGVSIPSQR RFLYYWALIL AHEAPSHLWG  180
LGSLKSTNIN LQSSCLDKNA IQRPKVLLTQ LNIRMRETSN MKMNFVKAAN MVIERTNMAK  240
APENTSTQLW ASMARYDDKM VNLLEEWEAY TRDSSGNMGK RRPGSDHLPR GESTEDEVLS  300
HIFKTGKWDK GKMVRSFARL GVTDSKKNEG SVVIDEKHGK IRVYALRPLS DKRWEGLKHD  360
LHKHSAQNND EHQTIEANAT TLGVSRSEAN SINEVVPKDA KVDHKIENGI ILDAAREVRI  420
KLYMGQVFMG WFWFIPTFHM SQPPPSSTST EKVDPTILKA NMTLSRKDID FPLGVGSAII  480
DIDIQMEWAM PSPPSPSAVD ISNLEPPLRT RTEDSKIGTD PEPEQSGLAA ALQAIVGSDG  540
MEGMGNVGVR ETVEAKQGAD E                                           561

SEQ ID NO: 48          moltype = AA  length = 508
FEATURE                Location/Qualifiers
source                 1..508
                       mol_type = protein
                       organism = Psilocybe cubensis
SEQUENCE: 48
MDEIIPGLWI GDLASALDVE ELKSHSIFSI LSAMRGRVTI HETFIRHQIK LDDTEDEDIL  60
THFLPSINFI QEELDKGRGV LVHCQAGISR SSTIVAAYLM YSQKIDPNAA LALIKQKRPN  120
VEPNQGFLYQ LELFHTARYK ISRREKSVRR FYMERTVGEV MNGDGSLPET GMFARYPSDS  180
VPATPSETSA PAFPIPRRRI RCKKCRQELA TREHMLDHGQ LGPATPAIGT PASVSPAVSR  240
RPSGSSGQGS LRPLIRPSIS SGLTDSLAMS SIQEHPSTEQ KLDLSSSQQE SNSTSASTFA  300
LETEEDADEP TAVGSPLSLK VNADGTAAAD ISIHKSEILG RQLSDAVIST IDDRNAHLSR  360
RNSHHKVPSD AAVVESPMEL PDTTIEQPSR LISPSDLSAQ LFSNPKLAGL RSPTLPSQST  420
LSNNSVKGST PVSAPILVNP QCSGYFVEPM GWMEHFLEGG QLAGKITCPN KKCGAKLGNY  480
DWAGVCCGCK EWVTPGFCIN RSKVDEVL                                    508

SEQ ID NO: 49          moltype = AA  length = 443
FEATURE                Location/Qualifiers
source                 1..443
                       mol_type = protein
                       organism = Psilocybe cubensis
SEQUENCE: 49
MADTATEIDL DSVIDRLLEG ELAWSYLCSG KTEAVGRVGC EEGLGRCCLS TVGVAGQWDI  60
SASLQYPIVW LFQTHVARDD SPPTKTFPAK SNVHPQTLHG LLISVPIAKI ARLLLARKAL  120
HHRRHHQTVI MRGNRPGKPV QLAEYEIKYL CTKAREIFIN QPILLELEAP IKICGDIHGQ  180
YYDLLRLFEY GGFPPEANYL FLGDYVDRGK QSLETICLLL AYKIKYPENF FILRGNHECA  240
SINRIYGFYD ECKRRYNIKL WKTFTDCFNC LPIAAIIDEK IFTMHGGLSP DLQSMEQIRR  300
VMRPTDVPDT GLLCDLLWSD PDKDITGWSE NDRGVSFTFG PDVVSRFLQK HDMDLICRAH  360
QVVEDGYEFF AKRHLVTLFS APNYCGEFDN AGAMMSVDET LLCSFQILKP AEKKAKYPYG  420
GINMGGRGPV TPPRKPKKSN KMG                                         443

SEQ ID NO: 50          moltype = AA  length = 810
FEATURE                Location/Qualifiers
source                 1..810
                       mol_type = protein
                       organism = Psilocybe cubensis
SEQUENCE: 50
MSEDMPSSWR YLTSAGNRIS SFKGYLSGRE PGAGWRSGRT TPNASQAPRD EPRQSWRAWA  60
GQKIRVRRRG QYDATESNEL INIFPGWAAR RYASQQDEYG RGPRPFELEV FVSGYAISYR  120
SPENASRSQR AFIRLAKGFA SLPKIVDSAA DVRPNSSSFA QLTPSTEALL AQVKLPPRPT  180
```

-continued

```
DIADDYDIDA LERQLRLAKT TDDPLKDDSA SLSSSSSASS STNDLPSTGR ETADSVVNSV  240
AENTADVIKR LHANLERRLQ PFWSSTLPNR VVRLHLFSAP HNDSSSTSVG PGNTDDVDEL  300
ATDAQNGPLA SQDVMTGVDG SFQVKFNIPW EDLCHHPRAL HIAFGEAEVE HELLIVAQLL  360
PLNPSSSSLS VDSSPTSTPL TSLTRIPVTY SPIRVISDID DTVKFSGVLS GARAVFHNVF  420
VKDLRDNVIP GMGEWYAAMW SRGVRFHYVS NGPFEILPVL NEFFEVSQLP PGSIKLKSYA  480
GRSLFTGLLS APAARKRAGI VDILDSFPDS RFFLIGDSGE QDLELYADIA RERPDRILAV  540
FVRDADANTF GGPPALEDPT GWKAMGAAGT RPIERPLVSR SESGMTNGSF SPSISSYSKY  600
SSFFSSNSGS STPNVRTGDA NETPRPNTFG FDSGRQPSTS ASVDDKALAK ARDQSYLGVG  660
ALTAEPESMR SGDAVTPPRL SAVTGPAIYV NSPNNSSREP QDVMQSPGKF VDQPPKATPP  720
PSIRSSMSSL GPASAAASFR SQRTGSSTSS GSSNTTGKRI SSISEAEKKR NDLQMRVYRA  780
RTQMPSHIPL RIFRDPSECV EAQEILDQER                                   810

SEQ ID NO: 51          moltype = AA  length = 213
FEATURE                Location/Qualifiers
source                 1..213
                       mol_type = protein
                       organism = Psilocybe cubensis
SEQUENCE: 51
MLSFPAANWQ KALGSTSALG KNLKYGRVAS PIIPGRLYLS DLYTATDEEK IRELGITHII  60
TVMEYKPALP DFIEEGKRMH IPIADSSQSD ILQYLDATTN FIKRALEENE MNKVLVHCFQ  120
GISRSATVVC AYLVATTSMT AESSITHVQS LRGIVSPNDG FRRQLNQYGD QYVKLKAKPK  180
PNQAITEDVL KFGGGIAARI RRLKGIDTAE KSP                               213

SEQ ID NO: 52          moltype = AA  length = 609
FEATURE                Location/Qualifiers
source                 1..609
                       mol_type = protein
                       organism = Psilocybe cubensis
SEQUENCE: 52
MGWQSWDVVT ITDQSTPSEV PTKPSIGGDL ETSVDWWNVT KPEEKVDFSS LPLDTWSPTL  60
PHDTGLSEIA VTRCVINPEV GGDLCAPDTT SEQDAIKGKW VRVPRNLNLE AGYLSGWLNI  120
YYRRTRRQDI NLITEIRLYP QNEQPPTLDG WHKAQTSLRA GIRGLPPLFL WYKTGKTSGD  180
MSPEEKMNII TELDVLYGED TPWYGFEKLD PPTIAQQSKV EATWITYRRG VKIPPRAPPL  240
HFSHSGKFKV LQVADLHFSV SQGFCRDTIL SPCEHSDNLT NTLISHVIDQ EKPDLIVFTG  300
DQLNGQGSSW DPKSVLAKFS KAVTAKGVPW AAVFGNHDEE DGMAKEQQVT LMKSLPYSLV  360
ERGPKDVHGV GNYVLKVFSP DPSKTHTLTL YFLDSGSYSK GVLDWFGFFK PTEYDWIHVS  420
KASIRQIERP FTPDTGKDLG SVWGRQDDQV IPGTRRLAKP NALMFFHMPL PETYLKADIN  480
PNTGKALDVG VSGQEPPGNA KSNDGFFEKG ILKAMESNHV SNRNALEVKA IGNGHCHITE  540
NCRRVKGVWF CFGGGGSYSG YGKIGFDRRF RIYDVSDFGE TIKTYKRTEK DEIIDEMILT  600
GKGAPPLPS                                                          609

SEQ ID NO: 53          moltype = AA  length = 295
FEATURE                Location/Qualifiers
source                 1..295
                       mol_type = protein
                       organism = Psilocybe cubensis
SEQUENCE: 53
MLRSKQYCGE DALEWANRPF FVDWAVTGVI WLLSYFVSAS PVYQRDFTLS DPDISHPHRK  60
DQIESWLNNL ISLFCPLLVF VGVGCIKRSM LVIHHSAIGL FTARGVARLI TEAFKHSVGR  120
LRPDFLARCR WDEALKKCTG ERDKILAGRK SFPSGHSSTA FAGMLFLSLW IAGQTAAWCF  180
AVPKSGHNFR SSRMLSFALS LLPIFWAAHV AVTRIQDYRH HTEDVIIGSL LGCISALLSY  240
LLFWPNPLSQ DSYEPSVYGE PRLLYTYTGR NHQRTRTTEF ELGRFEAEDV DSTYV       295

SEQ ID NO: 54          moltype = AA  length = 196
FEATURE                Location/Qualifiers
source                 1..196
                       mol_type = protein
                       organism = Psilocybe cubensis
SEQUENCE: 54
MVKRHKAATS LRHPSDTVSV VLSSALYLGP CSAASSESFL STKSITQVLS VGSTPSPKVE  60
GVVYHRLSLS DSTTSSISNT IDAATEIIKA ALQSNKGRGR ILVHCSAGVS RSPTIVCGYL  120
MKEHNMSLKN ALGLIVRARP QVSPNPGFLN QLKDLEVALF GSSSLDIDEL PRREIDRLAL  180
FNDDGDNVQL SHTVNN                                                  196

SEQ ID NO: 55          moltype = AA  length = 349
FEATURE                Location/Qualifiers
source                 1..349
                       mol_type = protein
                       organism = Psilocybe cubensis
SEQUENCE: 55
MYSPPSKTFV ADAVLFDMDG TLTDSIAAVE AAWAKVASEI GQDPEHVIAA THGKRAVDNL  60
SQFKPHLAEE EMEREVERFE NTILYYADAH HLHGPNSGSV TPPSDVSYAS SAHDTPDLTP  120
GPSAPASRRS SVSAFESRRP SFGSRLLNML SQAARLRAHN EDVVVVDEDG SEKDNLIQPG  180
YPAVEKKNAL NATLEAWQME AASVDRSIRI LPGVRKMIDS LPEGRYAVAT SGAKTYAYGC  240
MKRVGIVPPP VTITADDKRL KAGKPAPDPF LLAAECLGYD PKRCVVFEDS PSGIKAGVAS  300
GATVVAVCTS HERSKIENCG AHYIIEDMES ISCHVGDDDR LVFTITSSG              349

SEQ ID NO: 56          moltype = AA  length = 151
FEATURE                Location/Qualifiers
```

```
source                1..151
                      mol_type = protein
                      organism = Psilocybe cubensis
SEQUENCE: 56
MGTNTISHIK ASLFSAPAGT ILVHACNTHG AWGSGIALAF RDIYPAAYGV YRAHCQAHGE  60
SLVGTCLLIP GDDAHDIACL FTSRAYGRRK DAPAQILAAT RAAVMDLLEK NVSNKPLHAC  120
RFNSGKFGVP WQETEAVLKD LKVTMTVYST D                                151

SEQ ID NO: 57         moltype = AA  length = 138
FEATURE               Location/Qualifiers
source                1..138
                      mol_type = protein
                      organism = Psilocybe cubensis
SEQUENCE: 57
MAQTLRYMNG DELADIMKSG KVPQKDFVVV DVRDDDYAGG NIKGSVNYPS AEFLGNVDQL  60
VKVTKEVPLV IFHCTLSQVR GPKAARIYSE TRKNILSNDI PHEVAILRDG FSQFQVKYKD  120
DADLVEKWDK NVWASDWS                                               138

SEQ ID NO: 58         moltype = AA  length = 180
FEATURE               Location/Qualifiers
source                1..180
                      mol_type = protein
                      organism = Psilocybe cubensis
SEQUENCE: 58
MIRFDNLPPE VMQAMCTPMH NILPPTNQSP GSLYLGSLSA IQDTSLLRQH NITHLVQVLD  60
VPWLPVSEKD GFECYKIPIQ DEGSVDLRPY LEAVCAWIAR ALAQGRSVLV HCQQGISRSP  120
AIIIAYLMRV HHMSYSNAHS FVLKKRACIK PNSGFVRALQ DWESSLGTAV RPGMTRRFTS  180

SEQ ID NO: 59         moltype = AA  length = 521
FEATURE               Location/Qualifiers
source                1..521
                      mol_type = protein
                      organism = Psilocybe cubensis
SEQUENCE: 59
MDFMDKSSKD WGILNGVKLQ KPKLSFPELS SYKPLRTLSP NEFPIDDPTK RVLIVGDIHG  60
QMTYLEKLMQ KVKYSPSQDV LLHVGDIVSK GPLEGSLAVL QFMVSNNVTG VRGNHDQLVV  120
EWRNWYDWVT DSLGGKEWLD GLQARWEKAV SKDPDTELEA WLKREKKAST RREKAWWKLI  180
PKGWVILDDH YYVAKEMSDQ HFQYLLDLPL RLYIPSAHTF IVHAGLLPCD PRYPVEDEAR  240
QPLARIPTLT RRPSGNQTGV NTTLLHDVDA NSTSTSLMSN KSIDALRNLQ ETGILTQIPQ  300
NSDPWVVLNM RNVLPDGRIS KQFGEGMPWS KLWKQHMQSC LGYTRFPRIA SRDADDDIDA  360
SGNETTVDDS DDDEQGVKKY NLLCYPSTTV YGHAAGRGLD AKRWSFGLDT GCIYRRRLSA  420
LMIKGQSKDL KDVDSTENGT MPRYEDDEED EDEDEGEDDD RDEGDGNDED EDEDEDEDED  480
DEDHSDLAAK NKHKNKAKTP WLPFGDNHRA TVASVRCKPR S                      521

SEQ ID NO: 60         moltype = AA  length = 304
FEATURE               Location/Qualifiers
source                1..304
                      mol_type = protein
                      organism = Psilocybe cubensis
SEQUENCE: 60
MEHEIDGWIE QLSQCKQLSE ADVKKLCDKT REILMEESNV QPVRCPVTVC GDIHGQFHDL  60
SELFRIGGNS PDTNYLFMGD YVDRGYYSVE TVTLLVAMKL RYRDRVTILR GNHESRQITQ  120
VYGFYDECLR KYGNASVWRY FTDLFDFLPL TALIDNQIFC LHGGLSPSID TLDHVRSIDR  180
VQEVPHEGPM CDLLWSDPDD RCGWGISPRG AGYTFGQDIS EAFNHNNGLT LVARAHQLVM  240
EGYSWGQDRN VVTIFSAPNY CYRCGNQAAI MEIDEKLSYS FLQFDPAPRA GEPLVSRRVP  300
DYFL                                                              304

SEQ ID NO: 61         moltype = AA  length = 660
FEATURE               Location/Qualifiers
source                1..660
                      mol_type = protein
                      organism = Psilocybe cubensis
SEQUENCE: 61
MPPRTSILFL ALAGAGIVSA QTFQRLGTCP TLGCVFPPDQ TDFLAGQLFD IRLEVHAPVN  60
GSEAYNGGIV NEKFSFCIQS GKGSCQDVTT FFKLRDPALE KWSFSYFEDL FARDAGEITV  120
VNVASKAYRA PGTYKAKLTY NGGSTTVATW TVREPATQRK AKNVLLFIGD GMTQPMITAA  180
RLIAHKSING KYQSLMQMDQ MDNLGHQMTH SVDSFITDSA NSATALYTGK KSSVNALNVY  240
ADSSKNSFDD PKIETIAELF RRRIGGALGI VSTAFIADAT PAALCAHTRD RGQYAAVVTE  300
YLYGASAVNA SYAWPTSCDA PDVIFGGGAE QFIAGKGSPN GTDFYKAFET KGYNVIYSNT  360
ELKSAPVKEK TLGIFSTGNM AKWIDRNVLT ENLNGLKNSP TGDGSDATDQ PGLKDMTLKA  420
IDILQARTKR NSGWFMMSEA ASIDKMMHAL DYDRALGELL ELDDTIRASI AHLKKIGEYE  480
NTLIVVTADH GHGFDVFGGA DTKYIAAQRD DRSKRGGVGT YGESGLSGYT VSEGSLPNNN  540
TIVYGSQGPN FPVQWNPRYT YAAGFGANPD HRESYVLNTE GPRVATVSSP EGIVVNPTDN  600
VDGFNVGGTI GTTESQGVHS LQDVSVFANG PGSEAFRGVY SAVDIFFKMA DALALGRANN  660

SEQ ID NO: 62         moltype = AA  length = 2032
FEATURE               Location/Qualifiers
source                1..2032
                      mol_type = protein
```

```
                        organism = Psilocybe cubensis
SEQUENCE: 62
MDVDHPHGLV YPNGLLAALP VLHPPPDNDP HTLNTNTPHH HHNHPRPRPR TRSPRHTASP  60
PIRALSAPQF ADLHLQHTLA HPPDNTLFPF LHGLEGDNHA QNTFFASSFA NNTTTNSNGN  120
QRHHYQHQHQ HGAEPPPRIT PRVPHYRGLV WVVCEDDLER ARDWASLRVL RRKPVGPTST  180
ATATANANAN VSTNAAGGIA GEDDTDHNPH APSSSDSSSS ASSSSSDSSS LYDDEDEDLD  240
LDLDLDPAHA HAHSQPERGV DTDAQDILLM LEATNEAAVA AKAAAVAVAA KDLDTDKGAL  300
EDKEKERERM GYRDRPLDAE LDLDTDPDEE DADADEDEDG SHTSASAAQV RLPSTQTQTQ  360
PQVISLEEVF TVDTGNAKGT QNYEGAHMHP VAHRPALVLA PPVAVPGVGV GVGGGKGLGI  420
DTNTIANGHA VSSIANGNVV SSYANGHANA NSNSNSNGKG GTTTTTTNAT ANAQITTSTT  480
THATHTSLSP LTFATISPSS SLSATSASAS TSTSSSPSSS VSSSSSFVDS PPHSVSVSPS  540
ASVSASPSLT GSPSMSMSGD TEGEGEGEWS PATSISHIAG SPLSKEVDVD VDANAELGVE  600
GEGGQGRPMS LLEIELDAKR VGRLQSRQES GHPHEHEQQS QSQSQHEHQE LIPTTSPASA  660
SPLPLPLPLP LPLSSPSSSS LPLPLPTTLL QPDSNPKPKP KPKERRATDP TKPPLLTSTF  720
RPKELLRRVK GQGRKHSHGH GLGHGRHREK GRLRVDVGGN GNGVVGGGEG EGEGEQDEDV  780
DVDEDEEDGR WEFVPARVPD GISLRNFGIQ VLESRWRVVG SYTWRSAAGL VCALQALSDG  840
SGAKVGKERN GWWDRQAPYP IYATLSDIVI YSPHGATPAA LALARRFRAA IKAKRAERLR  900
AAGLDDESIR GAERALKARE AVQNKLDMME REGSGDSGSS GSNFGPVYED DNTAQQQQHQ  960
MPELQTEKDS AMHPHIAALH RRRAEFLEYN VFVLDADEDE MRRAMPHMMM RVCGAGVPGG  1020
LGLGVSVEAS AVGSAATATA TATATVFGAD TALMDGGAHT DRSDGHVIEL KREEELAAAE  1080
ARRVRMEAEA EGMGMVVDTV EAGVDVDAMD VDEVVDIVAA AASRVAAEQA QAEKTEEKDT  1140
KKEEEEEDIL PNTVDFALRE REEMRDLTKA SEIISLPPIT SASSRGQTKT PVEYSDLGPS  1200
PVWDPRVGQV YLGNSGDVPL TPDVPTQFRH AASVARAAAA ATTTTDANAE ENAKWNWKTL  1260
TRHLRGVDGL MKEYNGELGL EYQHGFEEED AEGTLPADDP FNYAATNDPA HGFGYDICVE  1320
CHDLAPFPSA AHLRAAEEHL GMLDVMWRER WERAWTARLV RLCAGKSAEE QARIRNMHAP  1380
PTPPRPPPHA NAVIHLPFPS SPPNSQGTMV ALMPVVRFLE KWIQPVPVPV IVPPPPPPPV  1440
APVQESQKGE SPPATTGGAG SRRWSSVTAL MPSFPVFPGS GSSNNNTTKA APTPPPSSPL  1500
PPAPARMRSM TSPSSSMSHH PPTPVQARSR PLKILLYSSD GYTESSVPAL CLLMAIKSLM  1560
LPEAYLELQV EKRRSFFVYQ TDLGLLRRVE NRLREERERE KEKERERERE RERLATGVYL  1620
SSSSSSTGGG SINANGKRTA GGPVVVPARG GYWSGSSSSA GNANSNQNPG TTSNPTPSAF  1680
TGRPAAKSVS FAHAPGYMQQ QSSSHQVATS SISGASSASS PSMAQLVPHA RVVSSQQSTS  1740
ASQFSQKPQF EFGSLPATPP AGMTTTQQPQ PQPPMMGVVK GRPRASTSPW LPSLFGGDHQ  1800
SWFNDPRFDG SFPSRVLPFL YLGNLNHASN VYMLHALGIT HVVSVGECAL VPPPHHMSMH  1860
GGAGDACARP GPGAHFVPGK GPGGHGSLWI EEREGRIKVL DIKGVCDDGI DTLEPQLEPI  1920
CDWIDKARQE GGQVLVHCRV GVSRSATVTI AYVMKHLNLP LVDAYLIVRS RRLSVLIQPN  1980
MRLLYNLCGW EIKLAKERAG GDERKLKKEL ARTLTWPYLS KEVHALNEKY LH          2032

SEQ ID NO: 63           moltype = AA  length = 391
FEATURE                 Location/Qualifiers
source                  1..391
                        mol_type = protein
                        organism = Psilocybe cubensis
SEQUENCE: 63
MNTLGYVARQ FDVLASPTSE KKSDDKPRLP RVSTWSTKSF LLPPPTVPTT RTTPKRSHSS  60
PSFRPQPQQP LPPDVTMAPS CKPHIDSVID RIFVIRVFLL VWDHLKSAWS SLVRIVQDRQ  120
SVRLIQDSKP LQALKDKTEE VALTVVDSVS SSSSSLSPTP PPQVASVLEN VSASRAATPP  180
IPPRKTPFHL PKTLVLDLDE TLIHSTSRPI PFETSTGSGI LSLGSFGRSN KGAGHMVEVV  240
LGGRSTIYHV YKRPFVDFFL RTVSSWYTLV IFTASMQEYA DPVIDWLDAG RGILEHRFFR  300
DSCTQLPNGS YTKDLSLIEA DLSRVCLVDN SPISYTVNEA NGIPIEGWTH DPSDEALLDL  360
LPVLDSLRFT SDVRRVLGLR SAGVMHRHHD S                                391

SEQ ID NO: 64           moltype = AA  length = 174
FEATURE                 Location/Qualifiers
source                  1..174
                        mol_type = protein
                        organism = Psilocybe cubensis
SEQUENCE: 64
MVWKNINAVE NRLFLGNIMA ARSTRSLAEN RITHILSVCP DPIPAELPEA GIVHQRINIE  60
DVDYADLLIH LPAACRFIEQ ALASGGVVLV HCVQGISRSA AVVAAYLMYS RRINSTQALN  120
IVRTARDHIW PNPGFQEQLV LFELCQYAPS RSNGIYVNWR TQLERRLRAA GLPY        174

SEQ ID NO: 65           moltype = AA  length = 236
FEATURE                 Location/Qualifiers
source                  1..236
                        mol_type = protein
                        organism = Psilocybe cubensis
SEQUENCE: 65
MPHTTLHVDA ILFDMDGTLV DSTAGVVGAW ELFRQTYPTI DVHNILSSAH GVRTVDNLRK  60
YCGIEDPEIL EAESARFEQA IVTSSTQGGR QGIVLLPGVK PIMEEIAPGR YGPKPCWAIC  120
TSATRDYATS ALNTAGIPIP DVFVASEDVS QGKPFPDPYL LGAKLSGVKP ENCIVFEDAP  180
NGVRSGRDAG CKTVALLTTH SREQLEAAKP DYIVKDLSSV SITRTATGVS VTLQTL      236

SEQ ID NO: 66           moltype = AA  length = 280
FEATURE                 Location/Qualifiers
source                  1..280
                        mol_type = protein
                        organism = Psilocybe cubensis
SEQUENCE: 66
MRDLDPLDPD YVQDVLSKPP FVTIPGVINV RDLGNYPSTT EKGLITRPGY LFRSAELSGI  60
```

-continued

```
TEDGKVKLRE LGVTKAFDLR SDTEIRKYNT PLPQIDGVEV VHTPVFQTAD YSPEMMAKRY  120
QLYASGKTEA FLELYSQILD NGGRAFGAIL RHVRDRPNEG CVFHCTAGKD RTGIMAAIFL  180
KLAGVDNELI SRDYALTRVG REPAREMIMA RLSKEPLFAS NNEAALNMFT CRHETMQAFL  240
QHFDEKYGGA VTYLKEYVGF SDEDIVTIRR NILTPGLPRL                        280

SEQ ID NO: 67          moltype = AA  length = 398
FEATURE                Location/Qualifiers
source                 1..398
                       mol_type = protein
                       organism = Psilocybe cubensis
SEQUENCE: 67
MTRNAPASLS EVLKDQLYVG NLSAALSVEQ RKKHGITHIL SVCPEYPTTG ATQDHLNISI  60
EDSEYADLLI HLPETCRFID DALRKGGRVL VHCVMGISRS PAVVAAYLMK TRGYLAPEAI  120
TFVRQRRPQV HLNYGFAVQL DTFRKCGFAP SLANPIYRSW KRRNEQDVTA FLNHLVDTVS  180
IIPDKLFLSS EFPSDPQQTW SLLMDLGITH LLSISPTEIA TTTTAGAVTH HHHVNVDSRA  240
PDALLSTLPD ICAYVDGAIK RGGRVLVHSM VESRACAAVC AYLMSIRQYT ATEAFGVINE  300
ALPLFNPTRN FIRTLEVFEE CGYAPGPNLS SSARSSAKSE NFSCELESSK ESGMIYDDTR  360
RDFGLGFSEN FGNVGANVNM NKRSSKIAPS QHAPISVR                          398

SEQ ID NO: 68          moltype = AA  length = 305
FEATURE                Location/Qualifiers
source                 1..305
                       mol_type = protein
                       organism = Psilocybe cubensis
SEQUENCE: 68
MPSDLDKQIE QLTRCEPISE EQVKRLCLKA REILIEEGNV QVVDSPVTIC GDIHGQFFDL  60
MELFKVGGFC PETNYLFMGD FVDRGFYSVE TFLLLLALKV RYPERITLIR GNHESRQITQ  120
VYGFYDECQR KYGSSNVWRW CCEVFDYLAL GAIVDGRVFC VHGGLSPNLN SIDQIRAIDR  180
KQEVPHDGPM CDLLWSDPDD IQGWGLSPRG AGFLFGADTT KIFAHNNAID LIARAHQLAM  240
EGFKLMFDQT IVTVWSAPNY CYRCGNVASI LELDEHLAQE YKVFNHAPVD VKSIPAKRPP  300
ADYFL                                                              305

SEQ ID NO: 69          moltype = AA  length = 211
FEATURE                Location/Qualifiers
source                 1..211
                       mol_type = protein
                       organism = Psilocybe cubensis
SEQUENCE: 69
MSFHRGGSGH NTHHSQYPQP WTLAPTNPTV SPPSASPFSP SYHARPARNV SEIIPRLYIS  60
DLAFAENPAL LTSYRITHIL STLSDTIFRP PPTLLPVQPI RMQVRIEDLP FAELAGHLPS  120
TTAFIRDALN SSPNAHVLVH CAEGVSRSVS VVAAYLMAAY GWTPTEAVHF IKSKRRVANP  180
NFGFIQQLHE YSRDSLGRMI PNPTPPFSTP H                                 211

SEQ ID NO: 70          moltype = AA  length = 1062
FEATURE                Location/Qualifiers
source                 1..1062
                       mol_type = protein
                       organism = Psilocybe cubensis
SEQUENCE: 70
MKRFFERASK PFSLPNASKA NDAAETASAP APAPATAATS ASTGPSAKLP SSNHANLPGT  60
TGTTGLHPRY TLPAVAHPCP HSHLALLATK DGLLIRPHVK GQATIAQSAY IKISWGKTIR  120
IEEIETVVGD GAEETVDWKD GVVVYGIVGI LELYSCSYLL VITSRTEVGH IIDPRHEVYG  180
VKGVTDIPLV EDRAKMALNT LAARNVALTR PSLIPRRQGT DVSVDVDDDQ NSKPDPESST  240
KPSPRVQFLS NPAIKFLTPK ALSSTNLDAG NSIARPSSAQ STVSDISTPS SEASVATSPV  300
IKTLASRLSF WSRLSKRTNS PIDANFPPIE PMSLTEEQEV LDNLMQDGKE EPAAVIESIL  360
SSTAPPPVTT EERHSELETK VIRETIREFT KGDMYFAYTF DLTRSLQHKQ EQFLKAQKQH  420
DLLAGLGALP SPENQSHVPL SPMDGKFLAL VEPYPSLPLW RRVDKQFWWN EWMSKPFIDA  480
GLHTYVLPIM QGYCQVTKFN IPSSPVTVEE DVDVDYILVS RRSRYRPGLR YQRRGIDEGA  540
HVANFVETET IMRVDTVVNL AEQAGKEGAI TQAYRNYMHE LNLKEATYCE YDFHTETKGM  600
KYENISTLIE SMERTFESQG YFWVSDNVVF SQQKGVFRVN CIDCLDRTNV VQSAFARYML  660
NKQLGAVALL NPSNSGRTDA DLAFNDVWAN NGDAISRAYA GTSALKGDFT RTGKRDLTGM  720
LNDGVNSLAR MYTSTFSDWF SQAVIDFMLG NRTTSVFSEF LLQLKSTDPR DLIRLSKIRA  780
EAIATSVSRV LPEGERLLSG WTLFSPEELN TKVGMKFEEK VLLLSVKALY IVSYDYTLEK  840
VKLYTRVPLG DIISITKGAY ILSPLEESSC DPEQNAGFVV TWLSSNQESR VTSYSVRNSL  900
DFSNRNGPPS PLGPPSPSSP GFPLGNKPAR GRSNTMPTAS LSNILTGNVS FSTAGASGTV  960
NFGAFKVLPI DPGRVRRHSS YGSEASDGGG GMSDEMRGAA TCREAVDLIV ERIERACGDV  1020
GGAQGKNFIV LEDVVSLAEA QRMTSVYAKM EYGVKRLLWL GG                     1062

SEQ ID NO: 71          moltype = AA  length = 519
FEATURE                Location/Qualifiers
source                 1..519
                       mol_type = protein
                       organism = Psilocybe cubensis
SEQUENCE: 71
MRLLAFAHII CLSVNLISAN HNVYERNLAY KSPFVDHPQL AHNTRNLHDT NIQRRQTIDA  60
ASFKDEHYIT FYGSDFSNGD PFDTSVLLWT RAVPISSTGA LPDQSVPVCL SFKIATTSDL  120
SGKIIDSGEA FTSYDVDWTV KVEASGLKPD TKYFYQFSDC ASKTSSPIGS TRTIASANNL  180
MFPEQGWFNA YGFAAHNTTA DIFIHLGDYI YESLGSGAKI GRQTLGRELA TIHDYRQRLN  240
QYRTDQSLVT AHQNAPWITV WYVADNSWKA GTADSNDTTI GCAFSPSGAC FTDRKLAAVR  300
```

-continued

```
AYHEWMPIRQ VDPQDKLRIW RNFQIGKLLD LTMLDTRQYD RDLTDVYYNT VDLDAWDGYR  360
ANRARVLDHL YNNKISNTII LSGDSHANWV SDLAHPNDTV TYNPTTGAGA IGVEFAGTAV  420
TSGSAFGSGI TPEKADVISR TLVDVNADLQ WSEGSYRGFF TLSIDSDHLN ATYYAMRNVS  480
FANLDGFASA QFTVKAGQNR LSRPVAGGSV NAGVLKSQL                         519

SEQ ID NO: 72           moltype = AA  length = 744
FEATURE                 Location/Qualifiers
source                  1..744
                        mol_type = protein
                        organism = Psilocybe cubensis
SEQUENCE: 72
MTTSAMSTPF LDRLIESSTR RSYKRQKRSH SPPQKSSMAF LASPSGQFLS APLAPSRKKS  60
QRFLATNNEI DEFLSSDLEV SFASNVSLNS PPREHQSLAA SDCEPMDISP APAKHSSRLS  120
ASGHRPRAFT SGARLFGNDL SNSNSQLLSS PQLAIGQATK SSSGTQGTKK TQRSALPFEW  180
LATSRVPEPP TPEGFRQPSS PMDDAMDVDT SYIADSAIEP ADFDPVPESA APTITDFNQL  240
FHDTMSPRRS FESPAGPELR KRRSFSPESA RAPKYQSSSP IPPSSPSESK LERMAAGAAA  300
SRLGKPGLQG LGAPSASFLR RPRRPVLSAM VQPYDQHAQS AYPTLESPPS ISRDSEEDPS  360
PRGSAPVRRA FSAFLPPSVY TELEEDETSF EGQDMSSPAQ AYSKRQQVKT IRRCDGTEDF  420
RPLTGVTALV QNESPSAKFM AAGLPGFGDN EAHGKLLPCH RVTEDGLMRI TCDTLNDLLD  480
GKYDEDIIAY HIIDCRFDYE YNGGHIPGAV NINTTAAVEE LLLGPSLTKP KASVSGDKAR  540
KTILVFHCEF SAKRGPTFAK HLRAKDRAMN NHVYPKIHYP EVYILEGGYC QYFKDSAHRC  600
EPCGYVTMDD PNHATSRRED LDQFRKAKFG RHKSYAYGDA NGKSLSFGQQ QQQQPKRNTA  660
PSAPPSLFAA ATAARSRRGG NGTGSGLMTL AEDGNVTADA DDTDTDLGDS PCPPPIKATT  720
LKAKKGVRTS IVRSETYGPI RMPY                                         744

SEQ ID NO: 73           moltype = AA  length = 359
FEATURE                 Location/Qualifiers
source                  1..359
                        mol_type = protein
                        organism = Psilocybe cubensis
SEQUENCE: 73
MPKAAPMTPI RRRKLIYSYA PDWALTIVLA AFFFSLDKVD GYRRVFSLED SSIRHPYAVH  60
ERVPNVALYF ICFVAPFLIM PIVNFITVRS WWDFHNSSLG LILGLSMTGS LTQIVKITVG  120
RPRPDLLDRC KPPPGLTDPP YGSTDWTVCT QTDNGILRDG FRSFFSGHSS MSFAGLGFLA  180
YYLAGKVHLF DNRGHASKAW LALSPFMAAS LVAISRTMDY RHHWQDVLVG SLVGTFFAFF  240
TYRQYYPPLS SELSHRPYSP RIKREDNDRA VLPTHIDQFN GQTNIGNRHQ YSDSTDDHFE  300
LAGTVPRPPG PGRLENVWKQ GAGSPDLSQE DVVAGGSANI QSTSGGAFVP LRNPGTTMT   359

SEQ ID NO: 74           moltype = AA  length = 318
FEATURE                 Location/Qualifiers
source                  1..318
                        mol_type = protein
                        organism = Psilocybe cubensis
SEQUENCE: 74
MELGENGTIK SPEISHELAE EHWTKLQFTW ISKSYKVEIA DSDRLYDLKA AIYSLTKVPN  60
ERQKILGLVK GKLPPDEVRI SELTILPTKK FTLIGTPEGD EIKDPSQLES LPDVVNDLDV  120
DFTENMVASN RYQHDTRNIR KVQEAIRNLN INIIHPLRQG KKLLVLDIDY TILDTKPLTS  180
GSLPPAECAR PGLHEFLEAI YPYYDILDKT SMFTVFTERD SKPWTHSVKA LQIIWSHFPQ  240
FNATNTIHVD DLSRNFALNP KEGLKISAFK NAHTPQAWED RELYKLARYM VYIANIDDFT  300
TLSHKNWKNV VKRLPGPS                                                318

SEQ ID NO: 75           moltype = AA  length = 262
FEATURE                 Location/Qualifiers
source                  1..262
                        mol_type = protein
                        organism = Psilocybe cubensis
SEQUENCE: 75
MPLNIPALLV PFQLSIFPRL VIPALVVHDI RQVDFQALRR AGYRGAIFDK DNCLTLPHKD  60
TLIPELQEAW KSCKETFGER NVLIVSNSAG THLDAGGIQA ESVSHHLGVP VLSHKAMKPA  120
YSCITAIRGY FKSLPDPVED NELIVVGDRV FTDLVLANRM RMQYQRRSSK TRPLPDASNE  180
NQESCPVPQG PLSIWTKGVW ERESMLMRKM EYGLISLMEG LTVPPKEEFV NVGAFVKPFP  240
VRKDAKPTGL LAFLKFMYKR EI                                           262

SEQ ID NO: 76           moltype = AA  length = 540
FEATURE                 Location/Qualifiers
source                  1..540
                        mol_type = protein
                        organism = Psilocybe cubensis
SEQUENCE: 76
MSDQSTPSPS LAASSPPTSL PPSPELQKLN LSSEVSEQDK QEALRLKAAA NKAFTSHEFN  60
DAARLYSESI QKNPNEPTVW CNRAYARMKL EEYGYALTDA SQAITLDPKY AKAYYRRATC  120
YMQVMKYQAA VADFKKVLAL EPNNDTVRGQ LVSTQKLIRK IEFEKAIEVE GEKDPVVRCR  180
EIIQEGGCEV DSNYTGPKLP QSEDGKFYMT QEFLQEMIEW FKQGKTLPKR YAWEIVMGAH  240
EQFIKEESLV SVDIPDGVTC DVIGDVHGQF YDVLHLFSLT GPPSEKHYLL MNGDLVDRGS  300
WSIEVILLAF SYKWLYPKYM YINRGNHEAK DMNRTYGFEG EAKHKHGEQA YKLFAHVFTT  360
LPLSTLVNAT KPPPSKDNAI LSPEGFKRFF VVHGGLFSKD GVTLEDIRKI DRVGRQPGQE  420
GIMCELLWTD PQEAPGRGPS KRGVGIAFGP DVTKRWCTLN GVTGVIRSHE VRQNGYEIEH  480
EGLCTTVFSA PNYVDQSGNK GAFIRIDSAG NRKYTQFEAS PHPPMKPMAY IQGGLGSLMM  540
```

```
SEQ ID NO: 77          moltype = AA  length = 242
FEATURE                Location/Qualifiers
source                 1..242
                       mol_type = protein
                       organism = Psilocybe cubensis
SEQUENCE: 77
MASPKRQLVV FDFDWSMSDQ DTDRWIFEVL APDLRRKMKT LKDQVQWTDL VGQSLREAFA  60
RGITKEQIIH TLQIMPFHPA MVRAVTELKN RGETTFLCLS NANSVFIKTI LESKGLSNLF  120
HEIITNPAEW DPSGLLKVSR RVDPSGPQHS CKVGCSPNMC KGEELEAFLS RQGIEYDHIA  180
YVGDGTNDFC PILRLRSQDT IFCRTGRGLQ KRIEKEGEQE GLKCNIQYWG GAWEIEEKFS  240
KL                                                                242

SEQ ID NO: 78          moltype = AA  length = 314
FEATURE                Location/Qualifiers
source                 1..314
                       mol_type = protein
                       organism = Psilocybe cubensis
SEQUENCE: 78
MAPFDLDACI QQLLRKQLLH EVLLREICEK TKEVLMRESN VVHVSAPVTV VGDIHGQFYD  60
LIEIFRIGGY APNTNYLFLG DYVDRGLFSV ETISLLTCLK LRYPDRVQLI RGNHESRAVT  120
QTYGFYTECV RKYGSSHVWT YFTDMFDFLT LSVVIDDRIF CVHGGLSPSI HSIDQIKVVD  180
RFREIPHEGP MADLVWSDPD PEKEDFAISP RGAGYTFGSG VVYKFLDQNN MSHILRAHQL  240
CMEGYSSLFD KHLSTVWSAP NYCYRCGNSA SILEVGPGGS MYFNVFDAAP ENDRDGPNQQ  300
AAQNAAGKLP EYFL                                                   314

SEQ ID NO: 79          moltype = AA  length = 249
FEATURE                Location/Qualifiers
source                 1..249
                       mol_type = protein
                       organism = Psilocybe cubensis
SEQUENCE: 79
MTSNYRLGPG SSSPQTTTCP TASTSTAAAS DHPDDLQHSQ RKLQALFIED IPRPLTAVCA  60
RPIPNSYWAT PLLLACEYPW TPKNPNKPKL DALLRAGVRT FIDLTECGEL LPYSSILSQR  120
SALLGIDPAT IEYHRFAIRD RCLPESINHM YRVLDTLRDN QERGRISAVH CRGGIGRTGM  180
VIGCWLVESG IARDGKEALA IIAREWKTVE KCKRYPHSPE TGAQFDFVAK FHPSPKQLHA  240
TLELESEDA                                                         249

SEQ ID NO: 80          moltype = AA  length = 540
FEATURE                Location/Qualifiers
source                 1..540
                       mol_type = protein
                       organism = Psilocybe cubensis
SEQUENCE: 80
MMGVVLVELG GIKSTAAIYK TLSPVTSSSE LKLAPTLLSV FTSRLSKSRP QSPQPPGASM  60
GQQPSKKSKK AGKDKDRESP ADGATSEAHH DPNDDNTPQS SISRATAPST AHSSDSSSLP  120
NGNPSINVSD PAGSTVPSSA TSARAHGSPY PPQATIPSIE TAQLSESLPS PLPSPMTASL  180
PLDIPVTQTI LSNGNALSPS SMTSNGNAPT SESVGNGGAK DRLKQFDVDD MIQRLLDVGY  240
TGKVSKSLCL KNTEITAICL AARDVFLSQP TLVELSPPVK IVGDVHGQYS DLIRLFEMCG  300
FPPAANYLFL GDYVDRGKQS LETILLLLCY KIKYPENFFL LRGNHECANV TRVYGFYDEC  360
KRRCNIKTWK TFIDVFNCLP IAAIVASKIF CVHGGLSPSL HSMEDIKRIQ RPTDVPDYGL  420
LNDLLWSDPS DTALDWEDNE RGVSYCFGKA IINEFLVRYD MDLICRAHMV VEDGYEFWND  480
RTLVTVFSAP NYCGEFDNYG ACMSVSEDLL CAFELLKPLD GAALRKEMTK AKRKSVMTTA  540

SEQ ID NO: 81          moltype = AA  length = 690
FEATURE                Location/Qualifiers
source                 1..690
                       mol_type = protein
                       organism = Psilocybe cubensis
SEQUENCE: 81
MAAPHRRRRA PASLRIDAPS LALPLAIALA DEDSSTTLSS ADSDYPPFHA QPEDRSSRKN  60
MKKLSLTLRS SPAPLDPPLP VSPVPADTRR RPSVISLPAP TPTPASLIHR KDEDGPSDAA  120
PYANGPIQII PGIWIGSEDN ARDWKCLVER GIRSILNVAK EVLLPFDTPI PATPLRLAAS  180
TPNFRNRPPK DDPTYYPAHL PSGRPAMHYL KLQWSHGQQN LVDDGFKAGM AFADAALSRG  240
EGCLIHCQCG ISRSATMVIA LVMRAAAERH TSVPPEVWSL QGMQGAYTFV KEKSPHVGPN  300
MSLIYQLLEY EKKLRGDKAS PSDSDGSSDD EEEWGRRRQM LDDASDNEAD ERESHIVMQE  360
AKALDKAMED RIVARKSSAS SMSSTGSGIG MGPAWRSRYG SRKRTGSVAS NQTNQSFWSE  420
DLVEEDEEQE LLGTGGAFDS ESRLDRASLT ATSSPEDEQH DSTPRNESLM ALHGPATARP  480
PPSAPVWKSS FNIPPPPKTA VRSTFDIPPR PKPRGKPRPM GLSLLPVVPS SPVTLVIETE  540
SSDENDHQPG PPPTQQPPPA KPTLPLPPVR QRAESRKLVP PPLHLRSSVL RRASSSSTST  600
TGSADVAGLS TPSQTLFVFP PSPTLTTRTP STMTLTSNFA GPVPFPSLST PRVSTFHSKG  660
RTRSFIGLGA PPTPTVAFSK VDVRGYVGLE                                  690

SEQ ID NO: 82          moltype = AA  length = 1185
FEATURE                Location/Qualifiers
source                 1..1185
                       mol_type = protein
                       organism = Psilocybe cubensis
SEQUENCE: 82
MDSFAQAIAD RFKQSAILSV PPPPDPARPN VFPAIDPASL DDWLTDPTAL ILDIRPHAAF  60
```

```
SAARIPHAIS LSVPSTLLKR PLFSLQRLSA MLPSSAARNR FSAWAAASRI LVYDADSSSV  120
PDSSNIAGLL RKFKADGFQR DLVWLKGGFH ALWRDRRDLI DTSPPTPDNE HDDDDDESAS  180
SDPKSSLLKT RHLPMAAFSL SSTTVHSSPR FNTSAAGAPS APKFVQPSSG LLPAAISAPT  240
NSHPAFNPFF DTIRQNTELS HGITDRIPLR LPKRVRRRIH ELPFPWLQDI ARRAANAPHH  300
HGSYSDSTSS ESEDDEGATQ ADIEEGKEAL AMQFFKIELS EQRRMMGIME HHSRESGQVS  360
QMASSSHTSN PFPYSITAGV EKGAKNRYRH IWPFEHARVR LHQKKETDDD YINASYIQPL  420
GTTKRYIATQ GPLPATFTDF WTLCWEQNVH VIVMLTREVE GAMVKCGAYW SDTVFGPLRL  480
RLVSTEGLPS VDERPTTAGF FSQHSSLSVQ PPSRVTSQRR FPHSAGSQRR YRHHHYHNKS  540
SETVKRIFEL THTGYPEAKP RRIVHLQYLE WPDMNVPEDP RGVLGLVKQV EEAVRETQMD  600
DQPSEPKKRR KGSNQVSLTD IDEKTGVAMH TLGGNNPVLL HCSAGVGRTG GFIAVDAILD  660
AIRREVRNAR TGDAMDVAPD SHKATTISEK TATLDLTNRQ GSGEPTTEES RTIHVRMATP  720
MQVDHPDQFE NEAADATMSS SGTMQWAENV RDETGIVGSS NGPSQTTEEC RFPSSSNLSF  780
STPESSNLAG ASETPHKHGS YYYNPSSSLG TSVSGSSSYF KAHPQHQFTS DLLQASFNHQ  840
KPSASEQRHR TISAPPVHST SATLGRYHRD IVRSLVSSPS PLHLKKGSSD LPDLSNSRVE  900
TVVKPFALSL DLMSSPSKSL SSLHPPMSSD AESPPSRSQS PSADEASFKF KSSKKASSPV  960
NGSTSTCKVT PPDGQPKTFD YKEPRPLHED YTPPPLTTFD DPIWEVVQDM REQRMSLCQS  1020
LRQYVFVHAA IIEGSLMVLD EEKEAAEGLI PPSRKTSKPA TPTATSSSAD VPQTPRSSTS  1080
ASRSPKSSPS RRQNSHPYSH ELASIASSSS ISIGKRGASP TELPKENKEG DLMLSKRPSV  1140
KRKQRSGDDL NVVDDARYHP VPVRVTSSVL HMGGVSAPSA RAMPP                  1185

SEQ ID NO: 83          moltype = AA  length = 217
FEATURE                Location/Qualifiers
source                 1..217
                       mol_type = protein
                       organism = Psilocybe cubensis
SEQUENCE: 83
MDGTLIDSTP GVLRAWRIFS DDYKLGDSES VAHETHGRRL YDTLKEYCGI TDEERLLQEI  60
DRFEEEVIEG GPMALPGAID LLRKLNSDPS TSSKWTIVTS ASNKYAPRAL ERSGVPLPSV  120
GIITSNDVSE GKPHPAPYLA GSLRCSINPE NCLVVEDAIS GLKSGRAAGC RTLAVCTSTL  180
RSKILDSGVQ PDFIVSDLTK VSVAVVDNKL QVTVDQS                           217

SEQ ID NO: 84          moltype = AA  length = 219
FEATURE                Location/Qualifiers
source                 1..219
                       mol_type = protein
                       organism = Psilocybe cubensis
SEQUENCE: 84
MAEHRPAPRL FVVRHGQTEW SQNGQTGRSD IPLTDVGVEQ VKKMAPLLVG EGRLLDPKNI  60
CTAQVSPRQR AATTFHLLFD HTVEPDYVLT EEVREWDYGE YEGLKPAEIQ KINPGWKIWN  120
DGCPGGESVE DMQARVDGVI KKVRQYHKEY KEEGKHTRDV LIVAHGHFSR VLISRWINFP  180
LCLGTHFNVE PGSVSILSYN HNSLDEPALN GLNLVASGA                         219

SEQ ID NO: 85          moltype = AA  length = 137
FEATURE                Location/Qualifiers
source                 1..137
                       mol_type = protein
                       organism = Psilocybe cubensis
SEQUENCE: 85
MGEAVLKEVA RKRGIEIVVD SCGTAGYHVG ESPDERTVAI CQKHNVPIDS YARQVATSDF  60
VRFTHILASD ESNLQNLNRI KPSNTTADVR LWGSYLDNKP IPDPYYGGMS DFEKVYQQCV  120
RLSNAFLDEV TTKDSKS                                                 137

SEQ ID NO: 86          moltype = AA  length = 839
FEATURE                Location/Qualifiers
source                 1..839
                       mol_type = protein
                       organism = Psilocybe cubensis
SEQUENCE: 86
MDDSEPTPLH LPQNLPYPLK ITSLNAAQNA TVDRKSRLLE YSFVYSPPGP EQLPETRFGT  60
WDSTLDGVVK AWNLKVGDVV TRKKAAESPA IFVVEPCKHE IQISGLCALC AKDMTIADYL  120
DVSDTSRANI QMTHSAHGPT VSLEYAKRLE RESADHLLKS RKLSLIVDLD QTIVHATVDP  180
TVGEWINEGL AWEARQAKKA STTPPDDGAP TANDADDDDE CNPNWEALKD VKSFRLGPES  240
FGPLAVRSAH RGKGKNKMVE TEGCMYYIKP RPGWKEFLRE TATKYEMHVY TMGTRAYAEE  300
VCAAIDPDGN IFGGRLLSRD ESGNDFFVGI GDINSSFLPK IEPLTPVLNV PQATPTASIN  360
GSSTSPIPNN NANPVTPDVP TTVAADGEIS ELENAMFTQN NAALDAQLEE RPLAKKEKEL  420
QEHEIQEQQA AEKTPTPPET PASVEKLPTP TPSPKPEKMH KKALLKNDDY ELERIGKLLN  480
EVHTRFFTAY DTRRANENAK AKAAAAKAYD VTRIIPRIRS EVFEGVHILF SSVIPLDTKP  540
ETTEIWRMAH MFGAQCSTEL TSNITHVVAA KRGTVKVDMA RRRGGIKIVW LAWFTDSIAL  600
WRRQDEKPYL LDDPPVVIPA SSPTTEYHQL SSDLDIDSDD WDQEPPEMKE TGPLHLEAIN  660
WDDINDEVEA AMNESDDEYD EYYAAFKSGN VSEDDTTDGG ANNTSQTMTT RKRFRSATPS  720
DGGGGNDEYL GTGSRKRMRS KTPSDAGSDY GSPLARRKKA AAGRTGYSKL KEGITADDIE  780
GGDAVTNDVN ESGNGTALPD AQGSSPAAYD EEEDGEDDDE EEEEEEDDFL ARELEEEWG   839

SEQ ID NO: 87          moltype = AA  length = 442
FEATURE                Location/Qualifiers
source                 1..442
                       mol_type = protein
                       organism = Psilocybe cubensis
SEQUENCE: 87
```

-continued

```
MPSFLKSKQT TAKTTTIPPW LILANTDKHI YKVERLLSSR EATRYAARDA SHQIALKASE  60
STQHDKSPVF KRSSQRKEGS AVDFVEYYGI TAGLHEDNRD LNRYTDIIPY DRTRIIVHDG  120
SPPAVGDESE GKRHERYLNA NWVLEKFGHK WWIATQAPLR HTAHAFLSVM LQPSVRPPHV  180
DLPLKDSKTR RVRTVVQLAR NVENGRKKAD AYFPSEVGRS VVVLAEHGWR APPLKVTLLA  240
KKAIDEAHCI QSTVSVAPIK NATSHLAEGR HGTGVQDEDN HGQAIVFNHL LYLSWPDHGV  300
PSPEDRLSLV HFIQLVDRIN RDTSQCPIHS AATTNHICEE LDPDPPIIVG CSAGIGRTGA  360
FVALSSLLRK YGFLLPAAHP TIAPHVYTSP LGPIPSDPDL QDDLVLQEVD SLREQRPGMV  420
ERKVQMSLIY EVLASVLASE SN                                          442

SEQ ID NO: 88          moltype = AA  length = 875
FEATURE                Location/Qualifiers
source                 1..875
                       mol_type = protein
                       organism = Psilocybe cubensis
SEQUENCE: 88
MATIKLENFR GCLALAGQAV DNFVNTDPSF ANLIRSGALK PSQKLYHITV ITKDELRMIS  60
SEQIQKITST EVDPKSLFSL GIGGKEQAGI YWVVIIWAAG QKLRKQAGLP PKHFHITLSS  120
NDIHDVDKGI NSLISRDLPE VSGVEALDHT IFTLQQFAQY NEATEYSSRL ILTDPNSHKG  180
FLRMGDACFA NGSHKIAMLS YACAYQRSGD QKVQSYCMKK LTECSKETEW GLVFQEHEKE  240
QIENLSEISS LLLKPWSQDL QERLSDQGNT PSLLLEPRQP LYIPSTKNMG AKLHFYRLPR  300
FFRWLIPYHL AIMSTPKNED DITALASAPL GIRHVLTLTE EEPLRPAWFQ GKSISNTFLP  360
VPNYYPPSIE QMDLVMRLFD DQDKLPLLVH CGGGKGRAGT VAACYLAAFG FNKPRHDQDH  420
PELAATEAIS SLRALRPGSL ETSRQEEFVS RWCSTIWKRQ SVYPDIPSEP SPSPMEVEGK  480
LSADNDLFVL VGLPGSGKSW FSKSLISRDP SKWTHISQDD SRSKEACETE IGRSPKGKHV  540
LLDRCNTSAA DRKIWLDLAS NWCVSPVCIL FDYSQELCTS RAQMRAGHPT LPPGSRVRNA  600
VDQMQKIFMK PTLKEGFKAV ITVRSFAAAE EAVLRFSSPV SILKFPRTPH LINTGAASAD  660
DVHTDLAVFT NTAAGHTVIT EKIDGANMGF SLSSDRSRII VQNRSHYVNS STHEQFRKLG  720
LWVERHDQEL RRVLDRDPYF PERYILYGEW VYATHSIPYT SLPDYFIAYD LFDRSTKTWA  780
DTATLRHLLG ETSIATAPIV HEGTMPTESQ LLRMVQQPSM FYDGRVEGVY VKLEVNKCVK  840
LRGKVVRSDF ISGNEHWTRG GVRVNGLRLD QTGVE                            875

SEQ ID NO: 89          moltype = AA  length = 552
FEATURE                Location/Qualifiers
source                 1..552
                       mol_type = protein
                       organism = Psilocybe cubensis
SEQUENCE: 89
MHSLGLFALI SLLPYLVVAQ RASTFAGATT TAVFPPPNAG IAATDTNFPD GSKVGFPGPT  60
RTGDEAAAIE TAPVAAKVDS FFPLINGGAE DSTPMDPFDV LVHLGNLSPF QSVPSSAFGL  120
PGASPLIPEG CDIVQAHLLH RHGARYPTAD SGPPGFAAKV NAAANSGSGF SAKGDLSFLN  180
TWTYKLGGDI LTPFGRSQLF NLGVGFRVKY GQLLKGFKNL PVFRTTSEAR MLDSALHFAT  240
GFFGVQKYQD SYHQLITIEH GGKQNNTLAP YESCTNGLNA VAAFGDIQSQ KWAQIYLAPA  300
VKRLNANLRG LQLNVTDLFA MQQLCAFETV ALGYSSFCDL FTEEEWRGFE YQSDLQFWYS  360
FGPGNPASSA MGIGYVQELV SRLTKTRITT FDTTVNASIV TSDILFPLDQ PIYVDATHDT  420
ILTAIFAAMN LTTLAANGPL PTDHIPKGQT FFANQLAPFA ANVVGQVLSC PASSKPTHIR  480
WIINDGVVPL TGIKGCKPDK NGMCEINTFI AGMKQRMQEI DFNFDCFANY TVPVPDNIVN  540
GQYPQNLKPK KK                                                     552

SEQ ID NO: 90          moltype = AA  length = 886
FEATURE                Location/Qualifiers
source                 1..886
                       mol_type = protein
                       organism = Panaeolus cyanescens
SEQUENCE: 90
MEPAEIDQWI EQLSQCKQLS EADVKKLCDK TREILMEESN VQIVKCPVTV CGDIHGQFHD  60
LSELFRIGGN SPDTNYLFMG DYVDRGYYSV ETVTLLVALK LRYRHRVTIL RGNHESRQIT  120
QVYGFYDECL RKYGNASVWR FFTDLFDFLP LTALIDNQIF CLHGGLSPSI DTLDHVRSID  180
RVQEVPHEGP MCDLLWSDPD DRCGWGISPR GAGYTFGQDI SEAFNHNNGL TLVARAHQLV  240
MEGYSWGQDR NVVTIFSAPN YCYRCGNQAA IMEIDEKLSY SFLQFDPAPR AGEPLVSRRV  300
PDYFLRDLGG SGLLRLNFWT TMIFLYGVPA GFALLGTAFL WSRLKQYRRT RCLGYIPGPP  360
SESFLTGVLN RFYHPIDGWK FHDKLMKTYG GVVRLKGVLG ANELYVYDPK ALHHILVKDL  420
DIYGETDAFY AGNKVIFGEG ILSSEGEQHR RHKKMLNPVF SAAHFRGMVP LFHEITHKAR  480
QSLEKKVANG PVEIDMLSWM TRVALELIAQ SGLGYSFDTL EDDSIPHPYS RASKDLVPLS  540
SGSMLLRNII MPPLVKIGYK WKRFSRFFLE VFPWRTLSKI KGLVDVLHST SVEIFQAKKK  600
ALEAGDEAML EQLGQGKDII SILMKANTRA SAEDRMSDTE LIGQVTSLTF AATDTTSGAL  660
ASTLQQLARH PEVQDKLREE IRTAREVHGD LDYDQLFALP YLDAVCRETL RLYPPVLNAQ  720
RTQVVPNALY DLRIDEFSSV LQDVVLPLHA PLKGYKGEDI REIFIPQGTA VHVSILSANR  780
NPALWGPDYA EWKPERWLNP LPNELVNAKM PGIYSHILSF LGGGRACLGV KFAQLELKTV  840
LTVIVDSLRF EPAKRDAVWQ MNMLLTPNVD PEGKFPNLPL KVSLAK                 886
```